United States Patent

Brito et al.

(10) Patent No.: US 10,059,655 B2
(45) Date of Patent: Aug. 28, 2018

(54) LIPIDS AND LIPID COMPOSITIONS FOR THE DELIVERY OF ACTIVE AGENTS

(71) Applicants: Luis Brito, Cambridge, MA (US); Delai Chen, Cambridge, MA (US); Gabriel Grant Gamber, Cambridge, MA (US); Andrew Geall, Cambridge, MA (US); Kevin Love, Somerville, MA (US); Thomas Zabawa, Cambridge, MA (US); Frederic Zecri, Cambridge, MA (US)

(72) Inventors: Luis Brito, Cambridge, MA (US); Delai Chen, Cambridge, MA (US); Gabriel Grant Gamber, Cambridge, MA (US); Andrew Geall, Cambridge, MA (US); Kevin Love, Somerville, MA (US); Thomas Zabawa, Cambridge, MA (US); Frederic Zecri, Cambridge, MA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/104,736

(22) PCT Filed: Dec. 17, 2014

(86) PCT No.: PCT/US2014/070882
§ 371 (c)(1),
(2) Date: Jun. 15, 2016

(87) PCT Pub. No.: WO2015/095340
PCT Pub. Date: Jun. 25, 2015

(65) Prior Publication Data
US 2016/0311759 A1  Oct. 27, 2016

Related U.S. Application Data

(60) Provisional application No. 61/918,175, filed on Dec. 19, 2013, provisional application No. 61/918,927, filed on Dec. 20, 2013.

(51) Int. Cl.
*C07C 229/12* (2006.01)
*C07C 229/38* (2006.01)
*C07D 205/04* (2006.01)
*C07D 265/30* (2006.01)
*C07D 207/12* (2006.01)
(Continued)

(52) U.S. Cl.
CPC .......... *C07C 229/12* (2013.01); *A61K 9/1272* (2013.01); *A61K 9/5123* (2013.01); *A61K 31/713* (2013.01); *A61K 31/7105* (2013.01); *A61K 39/39* (2013.01); *A61K 47/18* (2013.01); *C07C 219/04* (2013.01); *C07C 229/38* (2013.01); *C07C 271/20* (2013.01); *C07C 271/22* (2013.01); *C07D 205/04* (2013.01); *C07D 207/12* (2013.01); *C07D 207/16* (2013.01); *C07D 211/06* (2013.01); *C07D 211/22* (2013.01); *C07D 211/34* (2013.01); *C07D 211/44* (2013.01); *C07D 211/46* (2013.01); *C07D 211/60* (2013.01); *C07D 211/62* (2013.01); *C07D 265/30* (2013.01);
(Continued)

(58) Field of Classification Search
CPC ... C07C 271/20; C07C 229/38; C07D 211/62; C07D 211/60; C07D 295/15; C07D 295/088; C07D 211/22; C07D 207/16; C07D 207/12; C07D 265/30; C07D 205/04; C07D 211/46
See application file for complete search history.

(56) References Cited

U.S. PATENT DOCUMENTS 4,987,071 A   1/1991  Cech et al.
5,589,332 A  12/1996  Shih et al.
(Continued)

FOREIGN PATENT DOCUMENTS

WO   WO 1995/008986   4/1995
WO   WO 1998/027104   6/1998
(Continued)

OTHER PUBLICATIONS

Akhtar, S. et al., "Cellular Uptake and Intracellular Fate of Antisense Ologonucleotides," *Trends in Cell Biology*, vol. 2, (1992) pp. 139-144.
(Continued)

*Primary Examiner* — Jafar F Parsa
*Assistant Examiner* — Amy C Bonaparte
(74) *Attorney, Agent, or Firm* — Brinks Gilson & Lione

(57) ABSTRACT

This invention provides for a compound of formula (I): or a pharmaceutically acceptable salt thereof, wherein $R^1$-$R^4$, n and p are defined herein. The compounds of formula (I) and pharmaceutically acceptable salts thereof are cationic lipids useful in the delivery of biologically active agents to cells and tissues.

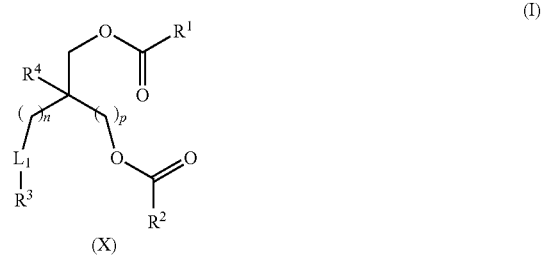

15 Claims, No Drawings
Specification includes a Sequence Listing.

(51) Int. Cl.

| | | |
|---|---|---|
| C07D 207/16 | (2006.01) | |
| C07D 211/22 | (2006.01) | |
| C07D 295/088 | (2006.01) | |
| C07D 211/46 | (2006.01) | |
| C07D 211/60 | (2006.01) | |
| C07D 211/62 | (2006.01) | |
| C07D 295/15 | (2006.01) | |
| C07C 271/20 | (2006.01) | |
| C07C 219/04 | (2006.01) | |
| A61K 47/18 | (2017.01) | |
| A61K 9/127 | (2006.01) | |
| A61K 9/51 | (2006.01) | |
| A61K 31/7105 | (2006.01) | |
| A61K 31/713 | (2006.01) | |
| A61K 39/39 | (2006.01) | |
| C07C 271/22 | (2006.01) | |
| C07D 211/06 | (2006.01) | |
| C07D 211/34 | (2006.01) | |
| C07D 211/44 | (2006.01) | |

(52) U.S. Cl.
CPC ....... *C07D 295/088* (2013.01); *C07D 295/15* (2013.01)

(56) References Cited

U.S. PATENT DOCUMENTS

| | | | |
|---|---|---|---|
| 5,705,188 A * | 1/1998 | Junichi | A61K 9/1272 424/450 |
| 5,741,679 A | 4/1998 | George et al. | |
| 5,834,186 A | 11/1998 | George et al. | |
| 5,837,282 A | 11/1998 | Fenske et al. | |
| 5,849,902 A | 12/1998 | Arrow et al. | |
| 5,871,914 A | 2/1999 | Nathan | |
| 7,811,602 B2 | 10/2010 | Cullis et al. | |
| 8,455,666 B1 * | 6/2013 | Laszlo | C07D 339/04 549/39 |
| 2004/0043952 A1 * | 3/2004 | Niedzinski | A61K 9/1272 514/44 R |
| 2009/0048197 A1 | 2/2009 | Chen et al. | |

FOREIGN PATENT DOCUMENTS

| | | |
|---|---|---|
| WO | WO 1999/029842 | 6/1999 |
| WO | WO 1999/032619 | 7/1999 |
| WO | WO 2000/024931 | 5/2000 |
| WO | WO 2000/026226 | 5/2000 |
| WO | WO 2000/044895 | 8/2000 |
| WO | WO 2001/029058 A1 | 4/2001 |
| WO | WO 2002/002606 A2 | 1/2002 |
| WO | WO 2002/034771 A2 | 5/2002 |
| WO | WO 2003/018054 A1 | 3/2003 |
| WO | WO 2005/002619 A2 | 1/2005 |
| WO | WO 2005/032582 A2 | 4/2005 |
| WO | WO 2005/111066 A2 | 11/2005 |
| WO | WO 2006/007712 A1 | 1/2006 |
| WO | WO 2006/089264 A2 | 8/2006 |
| WO | WO 2006/091517 A2 | 8/2006 |
| WO | WO 2006/110413 A2 | 10/2006 |
| WO | WO 2006/138004 A2 | 12/2006 |
| WO | WO 2007/049155 A2 | 5/2007 |
| WO | WO 2008/020330 A2 | 2/2008 |
| WO | WO 2009/016515 A2 | 2/2009 |
| WO | WO 2009/031043 A2 | 3/2009 |
| WO | WO 2009/104092 A2 | 8/2009 |
| WO | WO 2009/109860 A2 | 9/2009 |
| WO | WO 2009/129395 A1 | 10/2009 |
| WO | WO 2010/119343 A2 | 10/2010 |
| WO | WO 2011/005799 A2 | 1/2011 |
| WO | WO 2011/076807 A2 | 6/2011 |
| WO | WO 2012/006372 A1 | 1/2012 |
| WO | WO 2013/086354 A1 | 6/2013 |
| WO | WO 2015/095351 | 6/2015 |

OTHER PUBLICATIONS

Allen, T.M. et al., "Liposomal Drug Delivery Systems: From Concept to Clinical Applications," *Advanced Drug Delivery Reviews*, 65 (2013) pp. 36-48.

Bangham, A.D. et al., "Diffusion of Univalent Ions Across the Lamellae of Swollen Phospholipids," *Journal of Molecular Biology*, vol. 13, Issue 1, (1965) pp. 238-252. Abstract Only.

Brighham, K.L. et al., "Rapid Communication: In vivo Transfection of Murine Lungs with a Functioning Prokaryotic Gene Using a Liposome Vehicle," *The American Journal of the Medical Sciences*, vol. 298, No. 4, (1989) pp. 278-281.

Cech, T.R., PhD., "Ribozymes and Their Medical Implications," *JAMA*, vol. 260, No. 20, (1988) pp. 3030-3034.

Duval-Valentin, G. et al., "Specific Inhibiition of Transcription by Triple Helix-Forming Oligonucleotides," Proc. Natl. Acad. Sci. USA, Biochemistry, vol. 89, (1992) pp. 504-508.

Egholm, M. et al., "PNA Hybridizes to Complementary Oligonucleotides Obeying the Watson-Crick Hydrogen-Bonding Rules," *Nature*, vol. 365 (1993) pp. 566-568.

Elbashir, S.M. et al., "Duplexes of 21-Nucleotide RNAs Mediate RNA Interference in Cultured Mammalian Cells," *Nature*, vol. 411, (2001) pp. 494-498.

Falsini, S. et al., "Advances in Lipid-Based Platforms for RNAi Therapeutics," *J. Med. Chem.*, (2013) pp. A-I.

Feigner, P.L., "Particulate Systems and Polymers for In Vitro and In Vitvo Delivery of Polynucleotides," *Advanced Drug Delivery Reviews*, vol. 5, Issue 3, (1990) pp. 163-187, Abstract Only.

Feigner, P.L. PhD., "Cationic Lipid/Polynucleotide Condensates for In Vitro and In Vivo Polynucleotide Delivery — the Cytofectins," Journal of Liposome Research, 3 (1), (1993) pp. 3-16.

Feigner, P.L., "Lipofection: A Highly Efficient, Lipid-Mediated DNA-Transfection Procedure," *Proc. Natl. Acad. Sci. USA*, Biochemistry, vol. 84, (1987) pp. 7413-7417.

Fox, K.R., "Targeting DNA with Triplexes," *Current Medicinal Chemistry*, 7, (2000), pp. 17-37.

Gallas, A. et al., "Chemistry and Formulations for siRNA Therapeutics," *Chem. Soc. Rev.*, 42, (2013) pp. 7983-7997.

Geall, A.J. et al., "Nonviral Delivery of Self-Amplifying RNA Vaccines," *PNAS*, vol. 109, No. 36, (2012) pp. 14604-14609.

Giuliani, M.M. et al., "A Universal Vaccine for Serogroup B Meningococcus," *PNAS*, vol. 103, No. 29, (2006) pp. 10834-10839.

Hammann, C. et al., "Length Variation of Helix III in a Hammerhead Ribozyme and Its Influence on Cleavage Activity," *Antisense & Nucleic Acid Drug Development*, 9 (1999) pp. 25-31.

International Search Report and Written Opinion for International Patent Application No. PCT/US2014/070882, dated May 7, 2015, 10 pages.

Janowski, B.A. et al., "Inhibiting Gene Expression at Transcription Start Sites in Chromosomal DNA with Antigene RNAs," *Nature Chemical Biology*, vol. 1, No. 4, (2005) pp. 216-222.

Jayaraman, M. et al., "Maximizing the Potency of siRNA Lipid Nanoparticles for Hepatic Gene Silencing In Vivo," *Angew. Chem. Int. Ed.*, 51, (2012) pp. 8529-8533.

Jeffs, L.B. et al., "A Scalable, Extrusion—Free Method for Efficient Liposomal Encapsulation of Plasmid DNA," *Pharmaceutical Research*, vol. 22, No. 3, (2005) pp. 362-372.

Leung, A.K.K. et al., Lipid Nanoparticles Containing siRNA Synthesized by Microfluidic Mixing Exhibit an Electron-Dense Nanostructured Core, *J. Phys. Chem. C*. 116, (2012) pp. 18440-18450.

Maier, M.A. et al., "Biodegradable Lipids Enabling Rapidly Eliminated Lipid Nanoparticles for Systemic Delivery of RNAi Therapeutics," *Molecular Therapy*, vol. 21, No. 8, (2013) pp. 1570-1578.

Maurer, N. et al., "Spontaneous Entrapment of Polynucleotides Upon Electrostatic Interaction with Ethanol-Destabilized Cationic Liposomes," *Biophysical Journal*, vol. 80, (2001) pp. 2310-2326.

Morrissey, D. V. et al., "Potent and Persistent In Vivo Anti-HBV Activity of Chemically Modified siRNAs," *Nature Biotechnology*, vol. 23, No. 8, (2005) pp. 1002-1007.

(56) References Cited

OTHER PUBLICATIONS

Obika, S. et al., "Symmetrical Cationic Triglycerides: An Efficient Synthesis and Application to Gene Transfer," *Bioorganic & Medicinal Chemistry*, 9 (2001) pp. 245-254.

Player, M.R. et al., "The 2-5A System: Modulation of Viral and Cellular Processes Through Acceleration of RNA Degradation," *Pharmacol. Ther.*, vol. 78, No. 2 (1998) pp. 55-113.

Praseuth, D. et al., "Triple Helix Formation and the Antigene Strategy for Sequence-Specific Control of Gene Expression," *Biochimica et Biophysica Acta*, 1489, (1999) pp. 181-206.

Rejman, J. et al., "Characterization and Transfection Properties of Lipoplexes Stabilized with Novel Exchangeable Polyethylene Glycol-Lipid Conjugates," *Biochimica et Biophysica Acta*, 1660 (2004) pp. 41-52.

Romberg, B. et al., "Sheddable Coatings for Long-Circulating Nanoparticles," *Pharmaceutical Research*, vol. 25, No. 1., (2008) pp. 55-71.

Semple, S.C. et al. "Rational Design of Cationic Lipids for siRNA Delivery," *Nature Biotechnology*, vol. 28, No. 2., (2010) pp. 172-178.

Silverman, R.H. et al., "Selective RNA Cleavage by Isolated RNase L Activated with 2-5A Antisense Chimeric Oligonucleotides," *Methods of Enzymology*, vol. 313, (1999) pp. 522-533.

Stein, C.A. et al., "Antisense Oligonucleotides as Therapeutic Agents—Is the Bullet Really Magical," *Science*, vol. 261 (1993) pp. 1004-1012.

Torrence, P.F. et al., "Targeting RNA for Degradation with a (2'-5') Oligoadenylate-Antisense Chimera," *Proc. Natl. Acad. Sci. USA*, Biochemistry, vol. 90, (1993) pp. 1300-1304.

Werner, M. et al., "The Effect of Base Mismatches in the Substrate Recognition Helices of Hammerhead Ribozymes on Binding and Catalysis," *Nucleic Acids Research*, vol. 23, No. 12 (1995) pp. 2092-2096.

Xu, Y. et al., "Mechanism of DNA Release from Cationic Liposome/DNA Complexes Used in Cell Transfection," *Biochemistry*, 35, (1996) pp. 5616-5623.

Zamore, P.D. et al., "Ribo-gnome: The Big World of Small RNAs," *Science*, 309 (2005) pp. 1519-1534.

Zamore, P.D. et al., "RNAi: Double-Stranded RNA Directs the ATP-Dependent Cleavage of mRNA at 21 to 23 Nucleotide Intervals," *CELL*, vol. 101, (2000), pp. 25-33.

Zhang, J. et al., "Interaction of Cholesterol-Conjugated Ionizable Amino Lipids with Biomembranes: Lipid Polymorphism, Structure-Activity Relationship, and Implications for siRNA Delivery," *Langmuir*, 27, (2011) pp. 9473-9483.

Zimmermann, T.S. et al., "RNAi-Mediated Gene Silencing in Non-Human Primates," *Nature*, vol. 441, 4, (2006) pp. 111-114.

\* cited by examiner

LIPIDS AND LIPID COMPOSITIONS FOR THE DELIVERY OF ACTIVE AGENTS

RELATED APPLICATIONS

This application is the U.S. National Phase under 35 U.S.C. § 371 of International Patent Application No. PCT/US2014/070882, filed Dec. 17, 2014, which claims priority to and the benefit of U.S. Provisional Application Ser. No. 61/918,927, filed Dec. 20, 2013, and U.S. Provisional Application Ser. No. 61/918,175, filed Dec. 19, 2013. The entire disclosures of these applications are hereby incorporated by reference.

SEQUENCE LISTING

The instant application contains a Sequence Listing which has been submitted electronically in ASCII format and is hereby incorporated by reference in its entirety. Said ASCII copy, created on Jun. 14, 2016, is named PAT055893-US-PCT_ST25.txt and is 27 KB in size.

FIELD OF THE INVENTION

This invention relates to cationic lipid compounds and to compositions comprising such compounds. This invention also relates to processes for making such compounds and compositions, and to methods and uses of such compounds and compositions, e.g., to deliver biologically active agents, such as RNA agents, to cells and tissues.

BACKGROUND OF THE INVENTION

The delivery of biologically active agents (including therapeutically relevant compounds) to subjects is often hindered by difficulties in the compounds reaching the target cell or tissue. In particular, the trafficking of many biologically active agents into living cells is highly restricted by the complex membrane systems of the cells. These restrictions can result in the need to use much higher concentrations of biologically active agents than is desirable to achieve a result, which increases the risk of toxic effects and side effects. One solution to this problem is to utilize specific carrier molecules and carrier compositions which are allowed selective entry into the cell. Lipid carriers, biodegradable polymers and various conjugate systems can be used to improve delivery of biologically active agents to cells.

One class of biologically active agents that is particularly difficult to deliver to cells is a bio therapeutic (including nucleosides, nucleotides, polynucleotides, nucleic acids and derivatives, such as mRNA, RNAi, and self-replicating RNA agents). In general, nucleic acids are stable for only a limited duration in cells or plasma. The development of RNA interference, RNAi therapy, mRNA therapy, RNA drugs, antisense therapy, gene therapy, and nucleic acid vaccines (e.g., RNA vaccines), among others, has increased the need for an effective means of introducing active nucleic acid agents into cells. For these reasons, compositions that can stabilize and deliver nucleic acid-based agents into cells are of particular interest.

The most well-studied approaches for improving the transport of foreign nucleic acids into cells involve the use of viral vectors or formulations with cationic lipids. Viral vectors can be used to transfer genes efficiently into some cell types, but they generally cannot be used to introduce chemically synthesized molecules into cells.

An alternative approach is to use delivery compositions incorporating cationic lipids which interact with a biologically active agent at one part and interact with a membrane system at another part. Such compositions are reported to provide liposomes, micelles, lipoplexes, or lipid nanoparticles, depending on the composition and method of preparation (for reviews, see Feigner, 1990, Advanced Drug Delivery Reviews, 5, 162-187; Feigner, 1993, J. Liposome Res., 3, 3-16; Gallas, 2013, Chem. Soc. Rev., 42, 7983-7997; Falsini, 2013, J. Med. Chem. dx.doi.org/10.1021/jm400791q; and references therein).

Since the first description of liposomes in 1965 by Bangham (J. Mol. Biol. 13, 238-252), there has been a sustained interest and effort in developing lipid-based carrier systems for the delivery of biologically active agents (Allen, 2013, Advanced Drug Delivery Reviews, 65, 36-48). The process of introducing functional nucleic acids into cultured cells by using positively charged liposomes was first described by Philip Feigner et al. Proc. Natl. Acad. Sci., USA, 84, 7413-7417 (1987). The process was later demonstrated in vivo by K. L. Brigham et al., Am. J. Med. Sci., 298, 278-281 (1989). More recently, lipid nanoparticle formulations have been developed with demonstrated efficacy in vitro and in vivo. (Falsini, 2013, J. Med. Chem. dx.doi.org/10.1021/jm400791q; Morrissey, 2005, Nat. Biotech., 23, 1002-1007; Zimmerman, 2006, Nature, 441, 111-114.; Jayaraman, 2012, Angew. Chem. Int. Ed., 51, 8529-8533.)

Lipid formulations are attractive carriers since they can protect biological molecules from degradation while improving their cellular uptake. Out of the various classes of lipid formulations, formulations which contain cationic lipids are commonly used for delivering polyanions (e.g. nucleic acids). Such formulations can be formed using cationic lipids alone and optionally including other lipids and amphiphiles such as phosphatidylethanolamine. It is well known in the art that both the composition of the lipid formulation as well as its method of preparation affect the structure and size of the resultant aggregate (Leung, 2012, J. Phys Chem. C, 116, 18440-18450).

The encapsulation of anionic compounds using cationic lipids is essentially quantitative due to electrostatic interaction. In addition, it is believed that the cationic lipids interact with the negatively charged cell membranes initiating cellular membrane transport (Akhtar et al., 1992, Trends Cell Bio., 2, 139; Xu et al., 1996, Biochemistry 35, 5616). Further, it is believed that the molecular shape, conformation, and properties of the cationic lipids provide enhanced delivery efficiency from endosomal compartments to the cytosol (Semple, 2010, Nat. Biotech, 28, 172-176; Zhang, 2011, 27, 9473-9483).

Although the use of cationic lipids for cellular delivery of biologically active agents has been shown to have several advantages, there still remains a need for further cationic lipids that facilitate the systemic and local delivery of biologically active agents such as mRNA and RNAi agents to cells. There is also a need for cationic lipids that, relative to those cationic lipids that are known in the art, improve the systemic and local delivery of biologically active agents to cells. There is a further need for lipid formulations that have optimized physical characteristics for improved systemic and local delivery of biologically active agents to specific organs and to tumors, especially tumors outside the liver.

In addition, there is a need for further cationic lipids that provide decreased toxicity (or improved therapeutic index), relative to those cationic lipids that are known in the art. Traditional cationic lipids have been employed for RNA and DNA delivery to the liver or tumors but suffer from nonoptimal delivery efficiency along with tissue and organ toxicity at higher doses. One method of reducing exposure and increasing biocompatability of cationic lipids is to incorporate chemically or biochemically degradable functionalities, (such as ester, amide, acetal, imine, etc.), which can lead to enhanced in vivo clearance (Maier, 2013, 21, 1570-1578).

SUMMARY OF THE INVENTION

The present invention provides a cationic lipid scaffold that demonstrates enhanced efficacy along with lower toxicity (improved therapeutic index) as a result of lower sustained lipid levels in the relavent tissues, and for local delivery applications (eye, ear, skin, lung); delivery to muscle (i.m.), fat, or sub cutaneous cells (s.c. dosing).

In one aspect, this invention provides for a compound of formula (X):

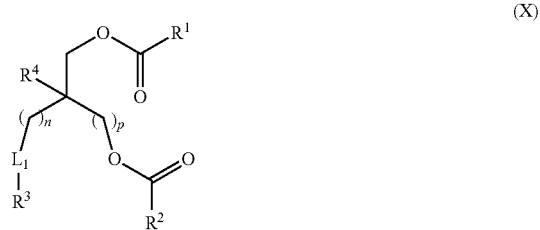

or a pharmaceutically acceptable salt thereof, wherein $R^1$-$R^4$, $L_1$, n and p are defined herein. The compounds of formula (X) and pharmaceutically acceptable salts thereof are cationic lipids useful in the delivery of biologically active agents to cells and tissues.

In a second aspect, this invention provides for a lipid composition comprising a compound according to formula (X) (i.e. a lipid composition of the invention), or a pharmaceutically acceptable salt thereof. In one embodiment, the lipid composition further comprises at least one other lipid component. In another embodiment, the lipid composition further comprises a biologically active agent, optionally in combination with one or more other lipid components. In another embodiment the lipid composition is in the form of a liposome. In another embodiment the lipid composition is in the form of a lipid nanoparticle (LNP). In another embodiment the lipid composition is suitable for delivery to the liver. In another embodiment the lipid composition is suitable for delivery to a tumor. In another embodiment the lipid composition is suitable for immunization purposes. In another embodiment the lipid composition is suitable for local delivery applications (eye, ear, skin, lung); delivery to muscle (i.m.), fat, or sub cutaneous cells (s.c. dosing).

In a third aspect, this invention provides for a pharmaceutical composition (i.e. formulation) comprising a lipid composition of the invention and a pharmaceutically acceptable carrier or excipient. In one embodiment, the pharmaceutical composition comprises at least one other lipid component in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the lipid composition is suitable for local delivery applications (eye, ear, skin, lung); delivery to muscle (i.m.), fat, or sub cutaneous cells (s.c. dosing). In another embodiment the biologically active agent is an RNA or DNA. In another embodiment the lipid composition is suitable for immunization purposes, and the biologically active agent is a RNA or DNA which encodes an immunogen.

In a fourth aspect, this invention provides a method for the treatment of a disease or condition comprising the step of administering a therapeutically effective amount of a lipid composition of the invention to a patient in need of treatment thereof. In one embodiment, the disease or condition is treatable by administering an RNA or DNA agent. In another embodiment the lipid composition is suitable for immunization purposes, and the biologically active agent is an RNA or DNA which encodes an immunogen.

In a fifth aspect, this invention provides for the use of a lipid composition of the invention in treating a disease or condition in a patient. In one embodiment, the disease or condition is treatable by administering an RNA or DNA agent.

In a sixth aspect, this invention provides a method for inducing an immune response in a subject against an immunogen of interest comprising administering an immunologically effective amount of a lipid composition of the invention to the subject, in combination with a RNA or DNA that encodes the immunogen.

In a seventh aspect, this invention provides for the use of a lipid composition of the invention in inducing an immune response in a subject against an immunogen of interest (e.g., in the preparation or manufacture of a medicament). The lipid is used in combination with a RNA which encodes the immunogen.

DETAILED DESCRIPTION OF THE INVENTION

In a first embodiment, the invention is a compound, or salt thereof, of formula (X) (a "lipid provided by the invention"):

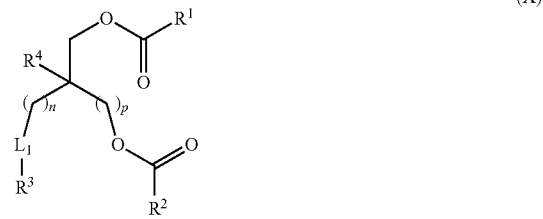

wherein n and p are each, independently, 0, 1 or 2; $L_1$ is —OC(O)—, —C(O)O— or a bond; $R^1$ is heterocyclyl, heterocyclyl-$C_{1-8}$-alkyl or heterocyclyl-$C_{1-8}$-alkoxyl, each of which may be optionally substituted with 1, 2, 3, 4 or 5 groups, independently selected from halogen, formidamidine, $C_{1-8}$-alkyl, $C_{3-7}$-cycloalkyl, heterocyclyl, —[($C_1$-$C_4$)alkylene]$_v$-N(R')R", —O—[($C_1$-$C_4$)alkylene]$_v$-N(R)R" or —N(H)—[($C_1$-$C_4$)alkylene]$_v$-N(R)R", where said ($C_1$-$C_4$) alkylene is optionally substituted with one or more R groups; v is 0, 1, 2, 3 or 4; R is hydrogen or —$C_{1-8}$-alkyl or when v is 0 R is absent; R' and R", are each, independently, hydrogen, —$C_{1-8}$-alkyl; or R' and R" combine with the nitrogen to which they are bound, and optionally including another heteroatom selected from N, O and S, to form a 5-8 membered heterocycle or heteroaryl, optionally substituted with an —$C_{1-8}$-alkyl, hydroxy or cycloalkyl-$C_{1-8}$—; $R^2$ and $R^3$ are each, independently, $C_{7-22}$ alkyl, $C_{12-22}$ alkenyl, $C_{3-8}$ cycloalkyl optionally substituted with 1, 2, or 3 $C_{1-8}$ alkyl groups,

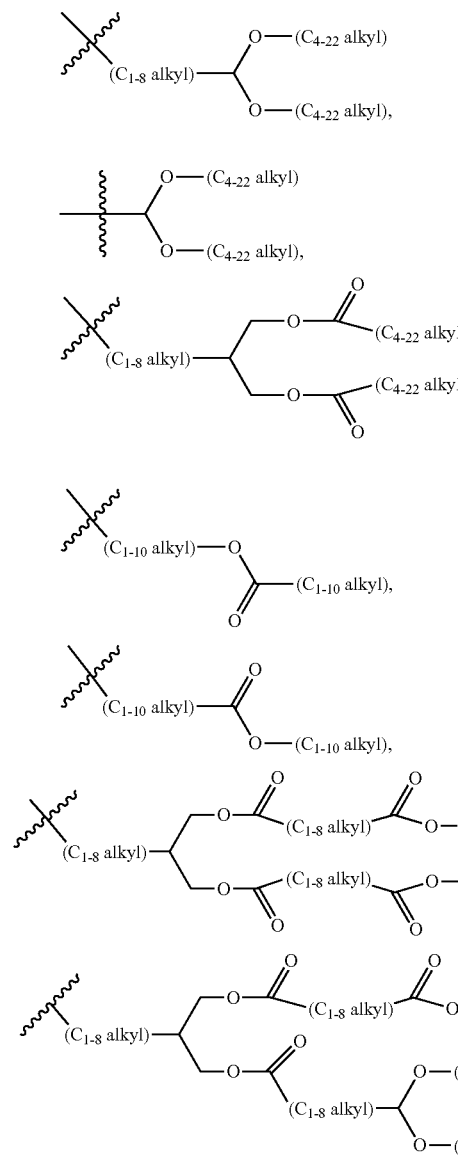

$R^4$ is selected from hydrogen, $C_{1-14}$ alkyl,

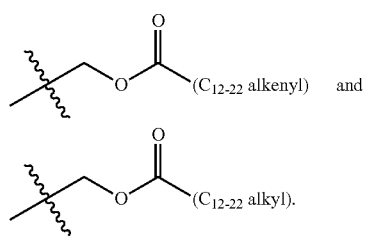

In a second embodiment, the invention is a compound, or salt thereof, according to the first embodiment, wherein the compound is of formula (I):

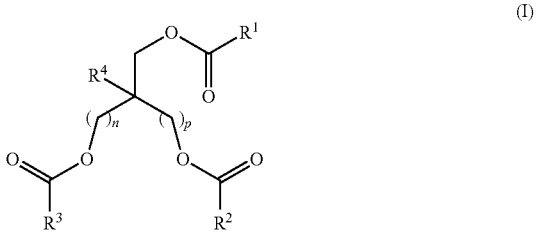

wherein n and p are each, independently, 1 or 2; $R^1$ is heterocyclyl, heterocyclyl-$C_{1-8}$-alkyl or heterocyclyl-$C_{1-8}$-alkoxyl, each of which may be optionally substituted with 1, 2 or 3 groups, independently selected from $C_{1-8}$-alkyl, $C_{3-7}$-cycloalkyl, heterocyclyl, —[($C_1$-$C_4$)alkylene]$_v$-N(R')R", —O—[($C_1$-$C_4$)alkylene]$_v$-N(R)R" or —N(H)—[($C_1$-$C_4$)alkylene]$_v$-N(R')R", where said ($C_1$-$C_4$)alkylene is optionally substituted with one or more R groups; v is 0, 1, 2, 3 or 4; R is hydrogen or —$C_{1-8}$-alkyl or when v is 0 R is absent; R' and R", are each, independently, hydrogen, —$C_{1-8}$-alkyl; or R' and R" combine with the nitrogen to which they are bound, and optionally including another heteroatom selected from N, O and S, to form a 5-8 membered heterocycle or heteroaryl, optionally substituted with an —$C_{1-8}$-alkyl, hydroxy or cycloalkyl-$C_{1-8}$—; $R^2$ and $R^3$ are each, independently, $C_{12-22}$ alkyl, $C_{12-22}$ alkenyl,

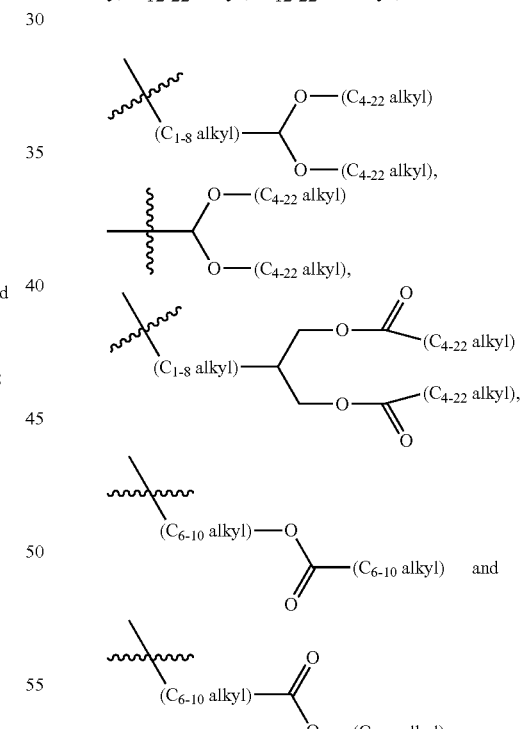

$R^4$ is selected from hydrogen, $C_{1-14}$ alkyl,

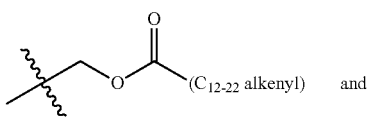

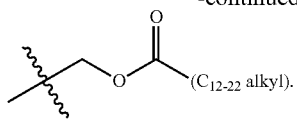

In a third embodiment, the invention is the the compound, or salt thereof, according to any one of the first or second embodiments, wherein the compound is of formula (II):

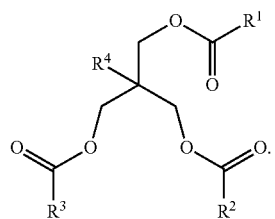

In a fourth embodiment, the invention is the compound, or salt thereof, according to any one of the first through third embodiments, wherein $R^4$ is hydrogen.

In a fifth embodiment, the invention is the compound, or salt thereof, according to any one of the first through third embodiments, wherein $R^4$ is

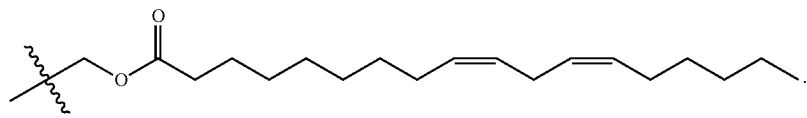 [SMILES: *COC(=O)CCCCCCC/C=C\C/C=C\CCCCC]

In a sixth embodiment, the invention is the compound, or salt thereof, according to any one of the first or third through fifth embodiments, wherein $R^1$ is selected from:

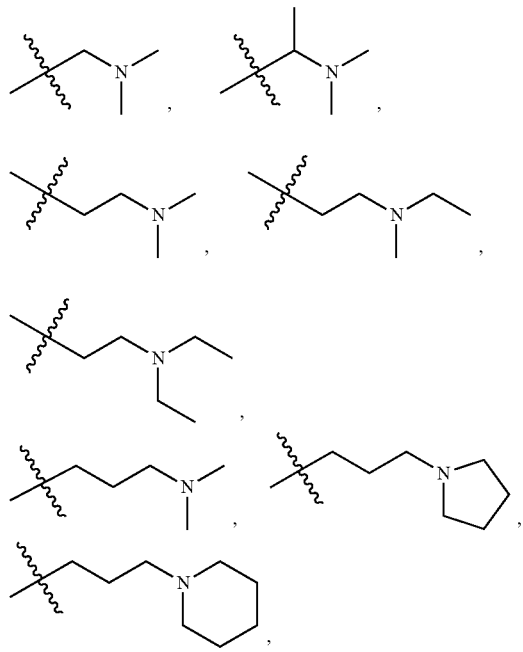

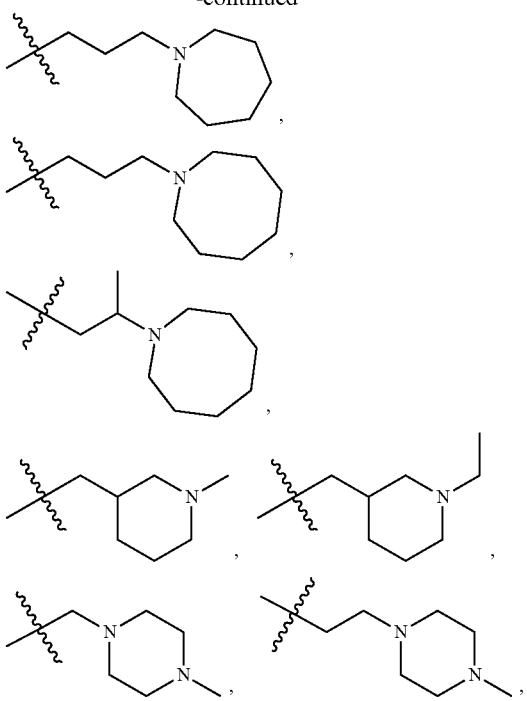

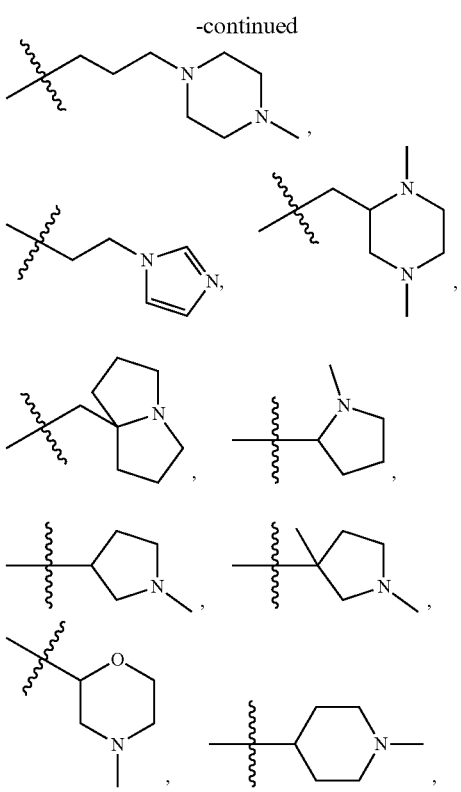

-continued
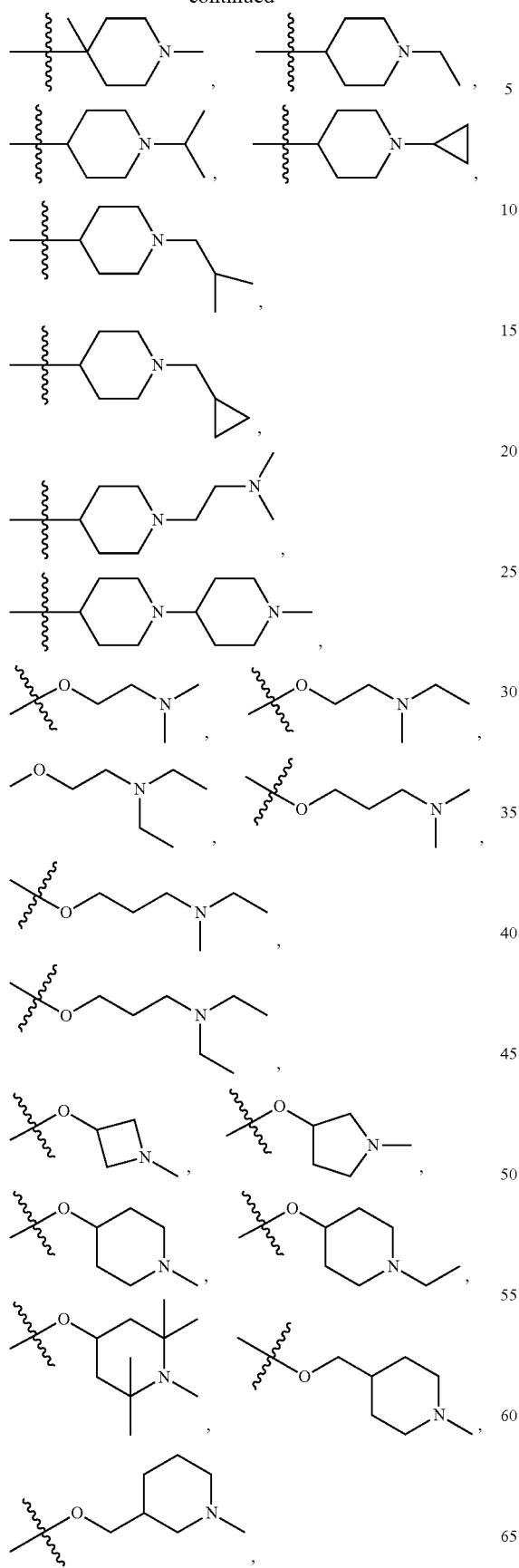
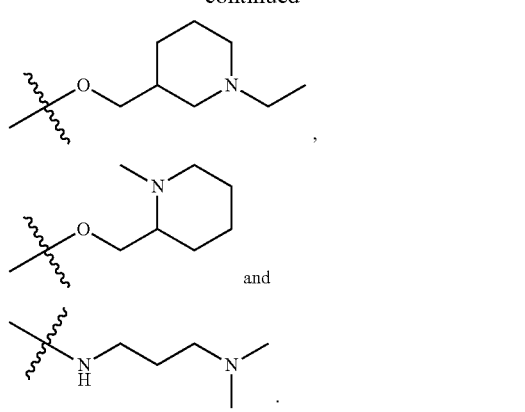
and
In a seventh embodiment, the invention is the compound, or salt thereof, according to any one of the first through sixth embodiments, wherein $R^1$ is selected from:

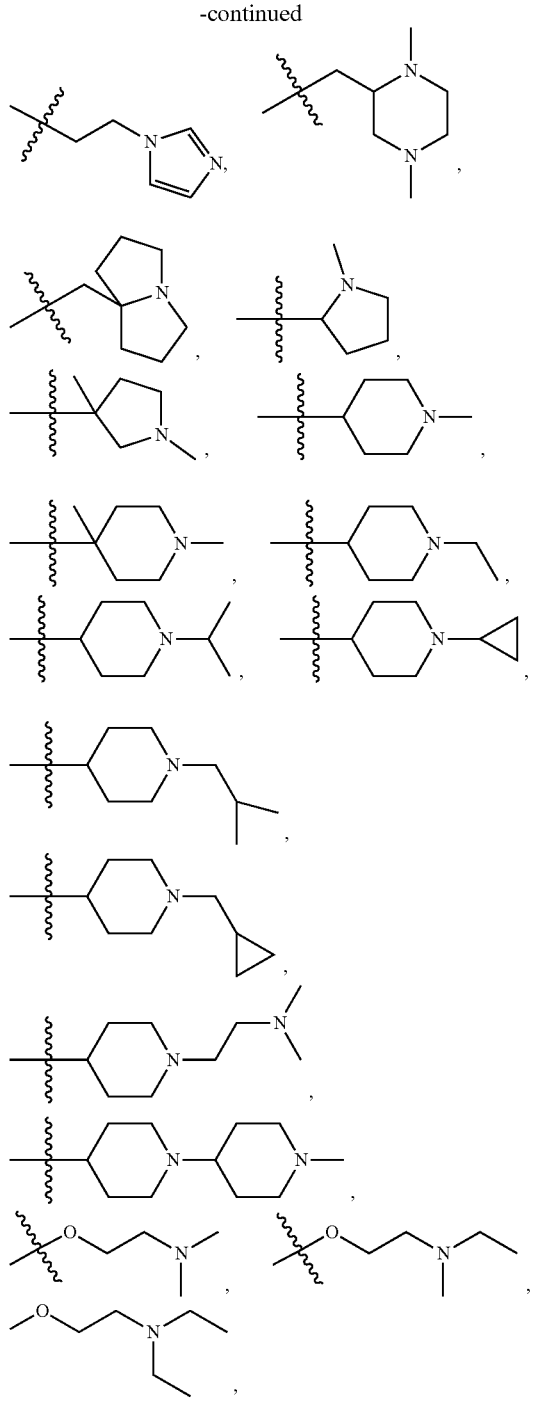
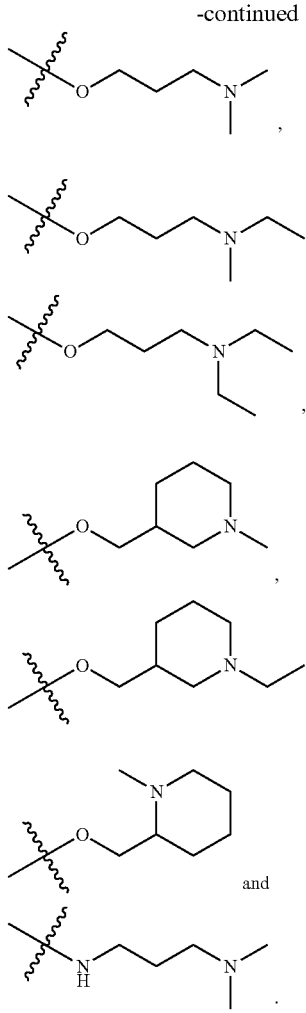
In a seventh embodiment, the invention is the compound, or salt thereof, according to any one of the first through seventh embodiments, wherein $R^1$ is
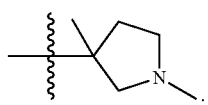 [SMILES: *C1(C)CCN(C)C1]
In a ninth embodiment, the invention is the compound, or salt thereof, according to any one of the first or third through eighth embodiments, wherein $R^2$ is selected from:
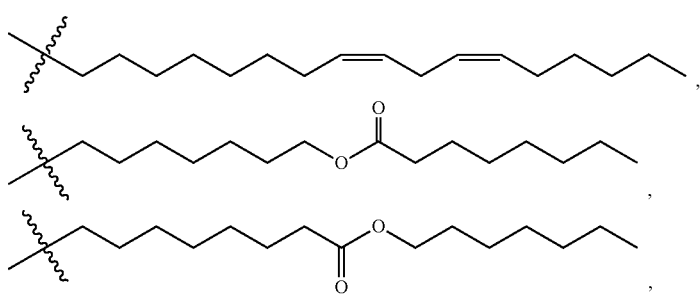

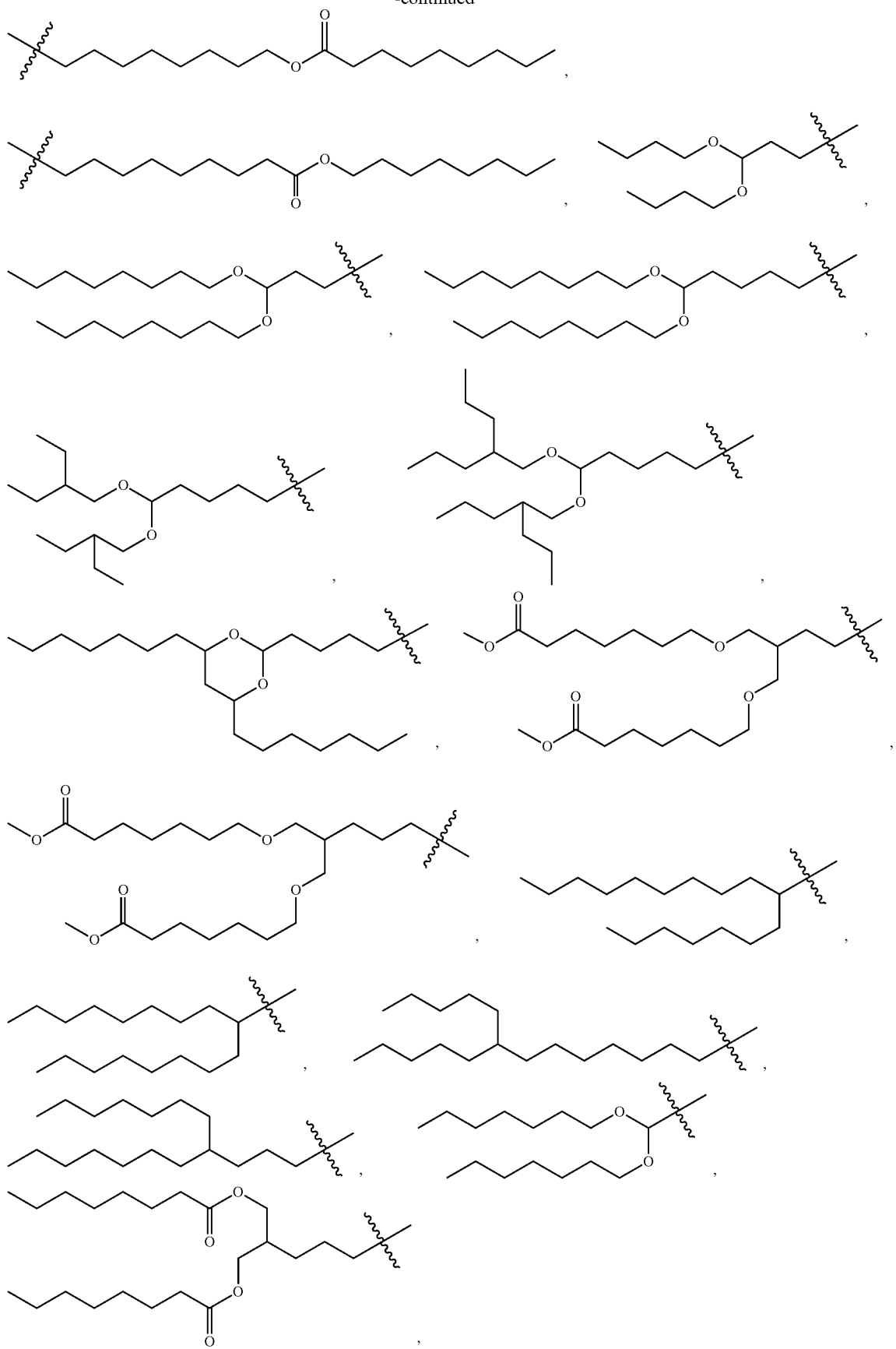

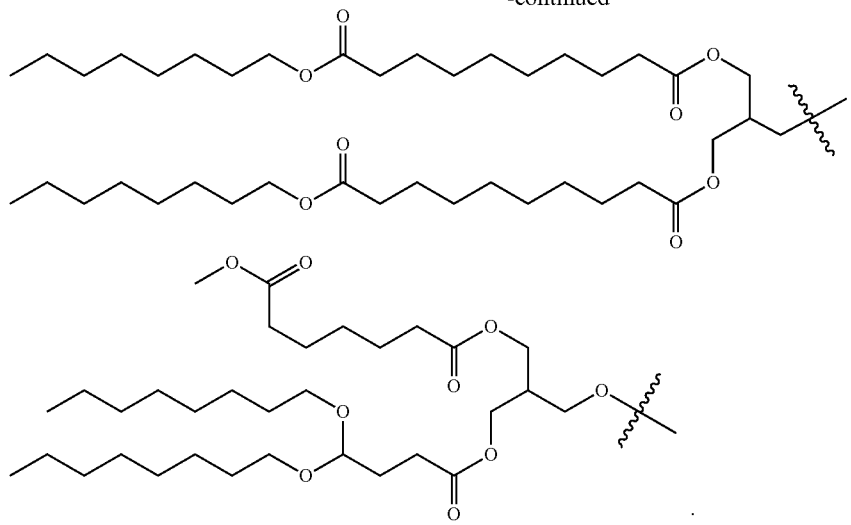

In a tenth embodiment, the invention is the compound, or salt thereof, according to any one of the first through ninth embodiments, wherein $R^2$ is selected from:

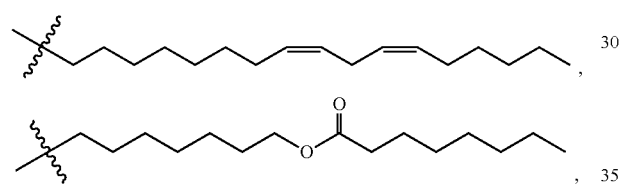

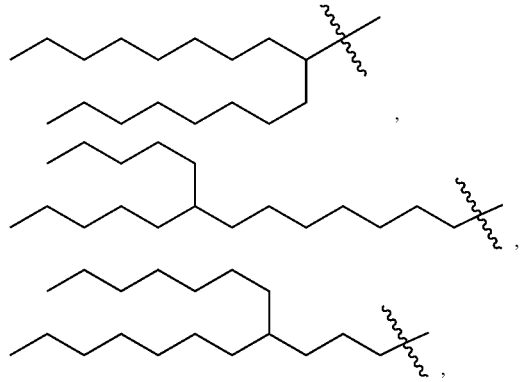

and

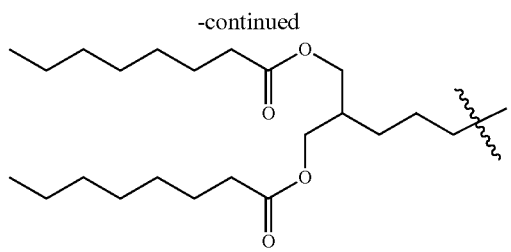

In an eleventh embodiment, the invention is the compound, or salt thereof, according to any one of the first through tenth embodiments, wherein $R^2$ is

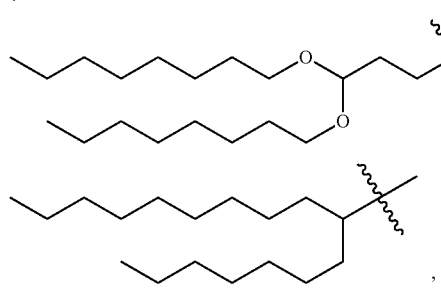

In a twelfth embodiment, the invention is the compound, or salt thereof, according to any one of the first and third through eleventh embodiments, wherein $R^3$ is selected from

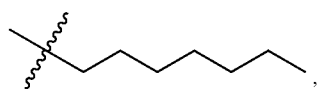

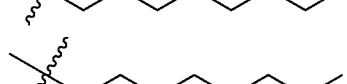

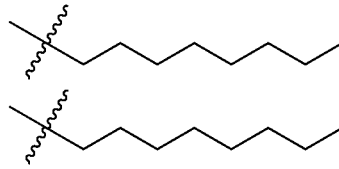

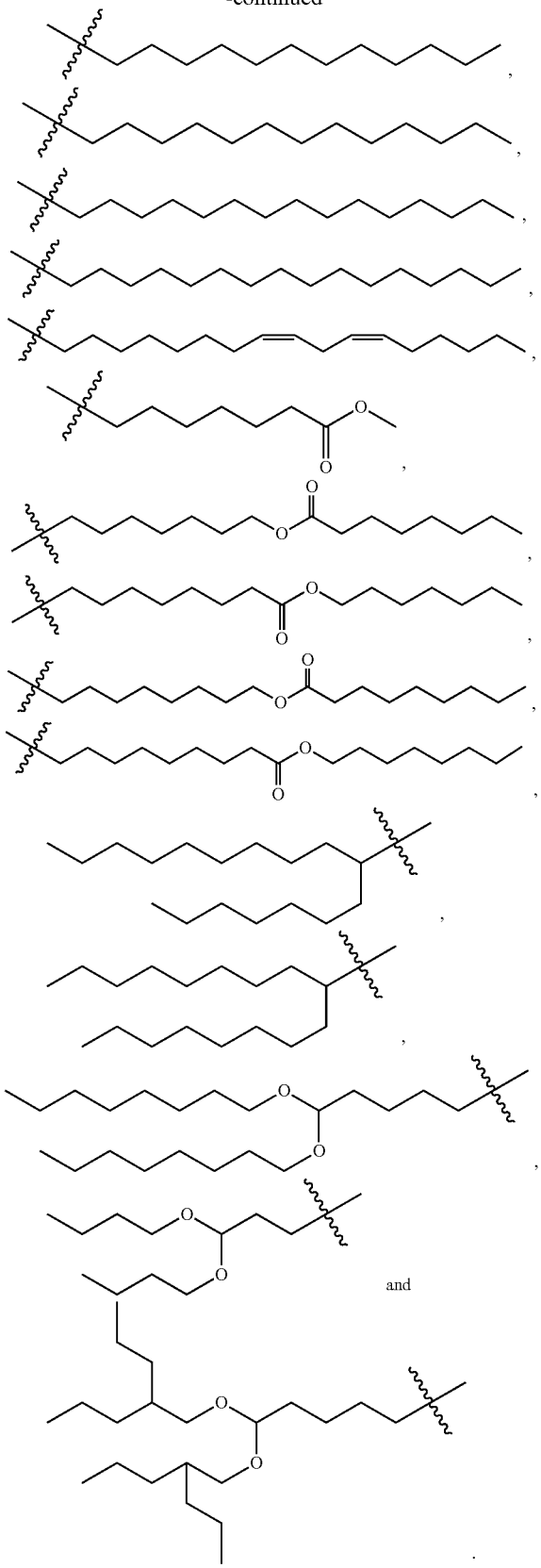

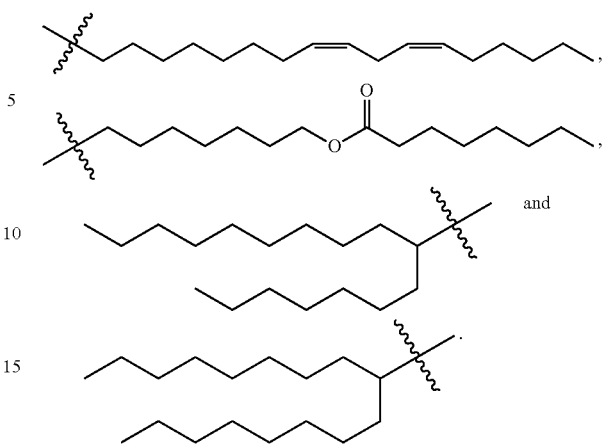

In a thirteenth embodiment, the invention is the compound, or salt thereof, according to any one of the first through twelfth embodiments, wherein $R^3$ is selected from In a fourteenth embodiment, the invention is the compound, or salt thereof, according to any one of the first through thirteenth embodiments, wherein $R^2$ and $R^3$ are identical.

In a fifteenth embodiment, the invention is the compound, or salt thereof, according to any one of the first and third through fourteenth embodiments, wherein the compound is selected from the group consisting of:

(9Z,9'Z,12Z,12'Z)-2-(((1,3-dimethylpyrrolidine-3-carbonyl)oxy)methyl)propane-1,3-diyl bis(octadeca-9,12-dienoate;

(9Z,9'Z,12Z,12'Z)-2-(((3-(4-methylpiperazin-1-yl)propanoyl)oxy)methyl)propane-1,3-diyl bis(octadeca-9,12-dienoate);

(9Z,9'Z,12Z,12'Z)-2-(((4-(pyrrolidin-1-yl)butanoyl)oxy)methyl)propane-1,3-diyl bis(octadeca-9,12-dienoate);

(9Z,9'Z,12Z,12'Z)-2-(((4-(piperidin-1-yl)butanoyl)oxy)methyl)propane-1,3-diyl bis(octadeca-9,12-dienoate);

(9Z,9'Z,12Z,12'Z)-2-(((3-(dimethylamino)propanoyl)oxy)methyl)propane-1,3-diyl bis(octadeca-9,12-dienoate);

(9Z,9'Z,12Z,12'Z)-2-((2-(dimethylamino)acetoxy)methyl)propane-1,3-diyl bis(octadeca-9,12-dienoate);

(9Z,9'Z,12Z,12'Z)-2-(((3-(diethylamino)propanoyl)oxy)methyl) propane-1,3-diyl bis(octadeca-9,12-dienoate);

(9Z,9'Z,12Z,12'Z)-2-(((1,4-dimethylpiperidine-4-carbonyl)oxy)methyl)propane-1,3-diyl bis(octadeca-9,12-dienoate);

(9Z,9'Z,12Z,12'Z)-2-(((1-(cyclopropylmethyl)piperidine-4-carbonyl)oxy)methyl)propane-1,3-diyl bis(octadeca-9,12-dienoate);

(9Z,9'Z,12Z,12'Z)-2-(((3-morpholinopropanoyl)oxy)methyl)propane-1,3-diyl bis(octadeca-9,12-dienoate);

(9Z,9'Z,12Z,12'Z)-2-(((4-(dimethylamino)butanoyl)oxy)methyl)propane-1,3-diyl bis(octadeca-9,12-dienoate);

2-(((1,3-dimethylpyrrolidine-3-carbonyl)oxy)methyl)propane-1,3-diyl bis(8-(octanoyloxy)octanoate);

(9Z,12Z)-3-((4,4-bis(octyloxy)butanoyl)oxy)-2-((((3-(diethylamino)propoxy)carbonyl)oxy)methyl)propyl octadeca-9,12-dienoate;

(9Z,12Z)-3-((4,4-bis(octyloxy)butanoyl)oxy)-2-((((3-(dimethylamino)propoxy)carbonyl)oxy)methyl)propyl octadeca-9,12-dienoate;

(9Z,12Z)-3-((4,4-bis(octyloxy)butanoyl)oxy)-2-(((((1-ethylpiperidin-3-yl)methoxy)carbonyl)oxy)methyl)propyl octadeca-9,12-dienoate;

2-(((((2-(diethylamino)ethoxy)carbonyl)oxy)methyl)propane-1,3-diyl bis(2-heptylundecanoate);

(9Z,12Z)-3-(((2-(diethylamino)ethoxy)carbonyl)oxy)-2-(((2-heptylundecanoyl)oxy)methyl)propyl octadeca-9,12-dienoate;

2-((((3-(dimethylamino)propoxy)carbonyl)oxy)methyl)propane-1,3-diyl bis(2-heptylundecanoate);

(9Z,12Z)-3-(((3-(diethylamino)propoxy)carbonyl)oxy)-2-(((2-heptylundecanoyl)oxy)methyl)propyl octadeca-9,12-dienoate;

(9Z,12Z)-3-(((2-(dimethylamino)ethoxy)carbonyl)oxy)-2-(((3-octylundecanoyl)oxy)methyl)propyl octadeca-9,12-dienoate;

2-((((3-(diethylamino)propoxy)carbonyl)oxy)methyl)propane-1,3-diyl bis(3-octylundecanoate);

(9Z,12Z)-3-(((3-(diethylamino)propoxy)carbonyl)oxy)-2-(((3-octylundecanoyl)oxy)methyl)propyl octadeca-9,12-dienoate;

(9Z,12Z)-3-(((3-(diethylamino)propoxy)carbonyl)oxy)-2-(((9-pentyltetradecanoyl)oxy)methyl)propyl octadeca-9,12-dienoate;

(9Z,12Z)-3-(((3-(diethylamino)propoxy)carbonyl)oxy)-2-(((5-heptyldodecanoyl)oxy)methyl)propyl octadeca-9,12-dienoate;

(9Z,12Z)-3-(2,2-bis(heptyloxy)acetoxy)-2-((((2-(dimethylamino)ethoxy)carbonyl)oxy)methyl)propyl octadeca-9,12-dienoate;

(9Z,12Z)-3-((6,6-bis(octyloxy)hexanoyl)oxy)-2-((((3-(diethylamino)propoxy)carbonyl)oxy)methyl)propyl octadeca-9,12-dienoate;

2-(3-ethyl-11-(((9Z,12Z)-octadeca-9,12-dienoyloxy)methyl)-8,14-dioxo-7,9,13-trioxa-3-azaheptadecan-17-yl)propane-1,3-diyl dioctanoate;

(9Z,9'Z,12Z,12'Z)-2-((((3-(dimethylamino)propoxy)carbonyl)oxy)methyl)propane-1,3-diyl bis(octadeca-9,12-dienoate);

(9Z,9'Z,12Z,12'Z)-2-((((3-(diethylamino)propoxy)carbonyl)oxy)methyl)propane-1,3-diyl bis(octadeca-9,12-dienoate);

(9Z,9'Z,12Z,12'Z)-2-((((2-(dimethylamino)ethoxy)carbonyl)oxy)methyl)propane-1,3-diyl bis(octadeca-9,12-dienoate);

(9Z,12Z)-3-((4,4-bis(octyloxy)butanoyl)oxy)-2-(((3-(dimethylamino)propanoyl)oxy)methyl)propyl octadeca-9,12-dienoate;

3-((4,4-bis(octyloxy)butanoyl)oxy)-2-(((9Z,12Z)-octadeca-9,12-dienoyloxy)methyl)propyl 1-isopropylpiperidine-4-carboxylate;

3-((4,4-bis(octyloxy)butanoyl)oxy)-2-(((9Z,12Z)-octadeca-9,12-dienoyloxy)methyl)propyl 1-(cyclopropylmethyl)piperidine-4-carboxylate;

3-((4,4-bis(octyloxy)butanoyl)oxy)-2-(((9Z,12Z)-octadeca-9,12-dienoyloxy)methyl)propyl 1-methylpyrrolidine-3-carboxylate;

(9Z,9'Z,12Z,12'Z)-2-((((3-(diethylamino)propoxy)carbonyl)oxy)methyl)-2-(((9Z,12Z)-octadeca-9,12-dienoyloxy)methyl)propane-1,3-diylbis(octadeca-9,12-dienoate);

(2S)-3-((4,4-bis(octyloxy)butanoyl)oxy)-2-(((9Z,12Z)-octadeca-9,12-dienoyloxy)methyl)propyl 1-methylpyrrolidine-2-carboxylate;

(2R)-3-((4,4-bis(octyloxy)butanoyl)oxy)-2-(((9Z,12Z)-octadeca-9,12-dienoyloxy)methyl)propyl 1-methylpyrrolidine-2-carboxylate;

3-((4,4-bis(octyloxy)butanoyl)oxy)-2-(((9Z,12Z)-octadeca-9,12-dienoyloxy)methyl)propyl 4-methylmorpholine-2-carboxylate;

3-((4,4-bis(octyloxy)butanoyl)oxy)-2-(((9Z,12Z)-octadeca-9,12-dienoyloxy)methyl)propyl 1,4-dimethylpiperidine-4-carboxylate;

3-((4,4-bis(octyloxy)butanoyl)oxy)-2-(((9Z,12Z)-octadeca-9,12-dienoyloxy)methyl)propyl 1-methylpiperidine-4-carboxylate;

3-((4,4-bis(octyloxy)butanoyl)oxy)-2-(((9Z,12Z)-octadeca-9,12-dienoyloxy)methyl)propyl 1-methylpiperidine-3-carboxylate;

3-((4,4-bis(octyloxy)butanoyl)oxy)-2-(((9Z,12Z)-octadeca-9,12-dienoyloxy)methyl)propyl 3-((dimethylamino)methyl)benzoate;

3-((4,4-bis(octyloxy)butanoyl)oxy)-2-(((9Z,12Z)-octadeca-9,12-dienoyloxy)methyl)propyl 4-((diethylamino)methyl)benzoate;

(9Z,12Z)-3-((4,4-bis(octyloxy)butanoyl)oxy)-2-((((3-(pyrrolidin-1-yl)propoxy)carbonyl)oxy)methyl)propyl octadeca-9,12-dienoate;

(9Z,12Z)-3-((4,4-bis(octyloxy)butanoyl)oxy)-2-((((3-(4-methylpiperazin-1-yl)propoxy)carbonyl)oxy)methyl)propyl octadeca-9,12-dienoate;

(9Z,12Z)-3-((4,4-bis(octyloxy)butanoyl)oxy)-2-(((((1-methylpyrrolidin-3-yl)oxy)carbonyl)oxy)methyl)propyl octadeca-9,12-dienoate;

(9Z,12Z)-3-((4,4-bis(octyloxy)butanoyl)oxy)-2-(((((1-methylpiperidin-4-yl)oxy)carbonyl)oxy)methyl)propyl octadeca-9,12-dienoate;

(9Z,12Z)-3-((4,4-bis(octyloxy)butanoyl)oxy)-2-(((((1-methylazetidin-3-yl)oxy)carbonyl)oxy)methyl)propyl octadeca-9,12-dienoate;

(9Z,12Z)-3-((4,4-bis(octyloxy)butanoyl)oxy)-2-(((((1-ethylpiperidin-4-yl)oxy)carbonyl)oxy)methyl)propyl octadeca-9,12-dienoate;

(9Z,12Z)-3-((4,4-bis(octyloxy)butanoyl)oxy)-2-(((((1-methylpiperidin-4-yl)methoxy)carbonyl)oxy)methyl)propyl octadeca-9,12-dienoate;

(9Z,12Z)-3-((4,4-bis(octyloxy)butanoyl)oxy)-2-((((((1,2,2,6,6-pentamethylpiperidin-4-yl)oxy)carbonyl)oxy)methyl)propyl octadeca-9,12-dienoate;

(9Z,12Z)-3-((4,4-bis(octyloxy)butanoyl)oxy)-2-((((3-(dimethylamino)propyl)carbamoyl)oxy)methyl)propyl octadeca-9,12-dienoate;

3-((4,4-bis((2-propylpentyl)oxy)butanoyl)oxy)-2-(((9Z,12Z)-octadeca-9,12-dienoyloxy)methyl)propyl 1,4-dimethylpiperidine-4-carboxylate;

3-((6,6-bis((2-propylpentyl)oxy)hexanoyl)oxy)-2-(((9Z,12Z)-octadeca-9,12-dienoyloxy)methyl)propyl 1,4-dimethylpiperidine-4-carboxylate;

1-(3-(((1,3-dimethylpyrrolidine-3-carbonyl)oxy)-2-(((9Z,12Z)-octadeca-9,12-dienoyloxy)methyl)propyl) 10-octyl decanedioate;

2-(((1-methylpyrrolidine-3-carbonyl)oxy)methyl)propane-1,3-diyl bis(4,4-bis(octyloxy)butanoate);

2-(((1,3-dimethylpyrrolidine-3-carbonyl)oxy)methyl)propane-1,3-diyl bis(4,4-bis(octyloxy)butanoate);

2-(((3-(dimethylamino)propanoyl)oxy)methyl)propane-1,3-diyl bis(4,4-bis(octyloxy)butanoate);

2-(((1-methylpyrrolidine-3-carbonyl)oxy)methyl)propane-1,3-diyl bis(6,6-bis(octyloxy)hexanoate);

2-(((1-methylpyrrolidine-3-carbonyl)oxy)methyl)propane-1,3-diyl bis(6,6-bis((2-propylpentyl)oxy)hexanoate);

2-(5-(3-(dodecanoyloxy)-2-(((1-methylpyrrolidine-3-carbonyl)oxy)methyl)propoxy)-5-oxopentyl)propane-1,3-diyl dioctanoate;

2-(5-(3-((1-methylpyrrolidine-3-carbonyl)oxy)-2-((palmitoyloxy)methyl)propoxy)-5-oxopentyl)propane-1,3-diyl dioctanoate;

2-(5-(3-((1-methylpyrrolidine-3-carbonyl)oxy)-2-((tetradecanoyloxy)methyl)propoxy)-5-oxopentyl)propane-1,3-diyl dioctanoate;

3-((4,4-bis(octyloxy)butanoyl)oxy)-2-((dodecanoyloxy)
  methyl)propyl 1-methylpyrrolidine-3-carboxylate;
3-((4,4-bis(octyloxy)butanoyl)oxy)-2-((tetradecanoyloxy)
  methyl)propyl 1-methylpyrrolidine-3-carboxylate;
3-((4,4-bis(octyloxy)butanoyl)oxy)-2-((palmitoyloxy)
  methyl)propyl 1-methylpyrrolidine-3-carboxylate;
1-(3-((4,4-bis(octyloxy)butanoyl)oxy)-2-(((1-methylpyrrolidine-3-carbonyl)oxy)methyl)propyl) 8-methyl octanedioate;
1-(3-((4,4-bis(octyloxy)butanoyl)oxy)-2-(((1-methylpyrrolidine-3-carbonyl)oxy)methyl)propyl) 8-methyl octanedioate;
1-(16-(((4,4-bis(octyloxy)butanoyl)oxy)methyl)-9-dodecyl-2-methyl-7,13-dioxo-6,8,12,14-tetraoxa-2-azaheptadecan-17-yl) 8-methyl octanedioate;
1-(3-((6,6-bis((2-propylpentyl)oxy)hexanoyl)oxy)-2-(((1,4-dimethylpiperidine-4-carbonyl)oxy)methyl)propyl) 10-octyl decanedioate;
1-(3-((6,6-bis((2-propylpentyl)oxy)hexanoyl)oxy)-2-(((1,4-dimethylpiperidine-4-carbonyl)oxy)methyl)propyl) 8-methyl octanedioate;
8-dimethyl O'1,O1-(2-(((1-methylpyrrolidine-3-carbonyl)oxy)methyl)propane-1,3-diyl) dioctanedioate;
O'1,O1-(2-(7-dodecyl-14-methyl-3,9-dioxo-2,4,8,10-tetraoxa-14-azapentadecyl)propane-1,3-diyl) 8-dimethyl dioctanedioate;
O'1,O1-(2-(7-dodecyl-14-methyl-3,9-dioxo-2,4,8,10-tetraoxa-14-azapentadecyl)propane-1,3-diyl) 10-dioctyl bis(decanedioate);
O'1,O1-(2-(14-methyl-7-octyl-3,9-dioxo-2,4,8,10-tetraoxa-14-azapentadecyl)propane-1,3-diyl) 10-dioctyl bis(decanedioate); and
O'1,O1-(2-(((1,3-dimethylpyrrolidine-3-carbonyl)oxy)methyl)propane-1,3-diyl) 10-dioctyl bis(decanedioate).

In a sixteenth embodiment, the invention is the compound, or salt thereof, according to any one of the first through fifteenth embodiments, wherein the compound is selected from the group consisting of:
(9Z,9'Z,12Z,12'Z)-2-(((1,3-dimethylpyrrolidine-3-carbonyl)oxy)methyl)propane-1,3-diyl bis(octadeca-9,12-dienoate;
(9Z,9'Z,12Z,12'Z)-2-(((3-(4-methylpiperazin-1-yl)propanoyl)oxy)methyl)propane-1,3-diyl bis(octadeca-9,12-dienoate);
(9Z,9'Z,12Z,12'Z)-2-(((4-(pyrrolidin-1-yl)butanoyl)oxy)methyl)propane-1,3-diyl bis(octadeca-9,12-dienoate);
(9Z,9'Z,12Z,12'Z)-2-(((4-(piperidin-1-yl)butanoyl)oxy)methyl)propane-1,3-diyl bis(octadeca-9,12-dienoate);
(9Z,9'Z,12Z,12'Z)-2-(((3-(dimethylamino)propanoyl)oxy)methyl)propane-1,3-diyl bis(octadeca-9,12-dienoate);
(9Z,9'Z,12Z,12'Z)-2-((2-(dimethylamino)acetoxy)methyl)propane-1,3-diyl bis(octadeca-9,12-dienoate);
(9Z,9'Z,12Z,12'Z)-2-(((3-(diethylamino)propanoyl)oxy)methyl) propane-1,3-diyl bis(octadeca-9,12-dienoate);
(9Z,9'Z,12Z,12'Z)-2-(((1,4-dimethylpiperidine-4-carbonyl)oxy)methyl)propane-1,3-diyl bis(octadeca-9,12-dienoate);
(9Z,9'Z,12Z,12'Z)-2-(((1-(cyclopropylmethyl)piperidine-4-carbonyl)oxy)methyl)propane-1,3-diyl bis(octadeca-9,12-dienoate);
(9Z,9'Z,12Z,12'Z)-2-(((3-morpholinopropanoyl)oxy)methyl)propane-1,3-diyl bis(octadeca-9,12-dienoate);
(9Z,9'Z,12Z,12'Z)-2-(((4-(dimethylamino)butanoyl)oxy)methyl)propane-1,3-diyl bis(octadeca-9,12-dienoate);
2-(((1,3-dimethylpyrrolidine-3-carbonyl)oxy)methyl)propane-1,3-diyl bis(8-(octanoyloxy)octanoate);
(9Z,12Z)-3-((4,4-bis(octyloxy)butanoyl)oxy)-2-((((3-(diethylamino)propoxy)carbonyl)oxy)methyl)propyl octadeca-9,12-dienoate;
(9Z,12Z)-3-((4,4-bis(octyloxy)butanoyl)oxy)-2-((((3-(dimethylamino)propoxy)carbonyl)oxy)methyl)propyl octadeca-9,12-dienoate;
(9Z,12Z)-3-((4,4-bis(octyloxy)butanoyl)oxy)-2-(((((1-ethylpiperidin-3-yl)methoxy)carbonyl)oxy)methyl)propyl octadeca-9,12-dienoate;
2-((((2-(diethylamino)ethoxy)carbonyl)oxy)methyl)propane-1,3-diyl bis(2-heptylundecanoate);
(9Z,12Z)-3-(((2-(diethylamino)ethoxy)carbonyl)oxy)-2-(((2-heptylundecanoyl)oxy)methyl)propyl octadeca-9,12-dienoate;
2-((((3-(dimethylamino)propoxy)carbonyl)oxy)methyl)propane-1,3-diyl bis(2-heptylundecanoate);
(9Z,12Z)-3-(((3-(diethylamino)propoxy)carbonyl)oxy)-2-(((2-heptylundecanoyl)oxy)methyl)propyl octadeca-9,12-dienoate;
(9Z,12Z)-3-(((2-(dimethylamino)ethoxy)carbonyl)oxy)-2-(((3-octylundecanoyl)oxy)methyl)propyl octadeca-9,12-dienoate;
2-((((3-(diethylamino)propoxy)carbonyl)oxy)methyl)propane-1,3-diyl bis(3-octylundecanoate);
(9Z,12Z)-3-(((3-(diethylamino)propoxy)carbonyl)oxy)-2-(((3-octylundecanoyl)oxy)methyl)propyl octadeca-9,12-dienoate;
(9Z,12Z)-3-(((3-(diethylamino)propoxy)carbonyl)oxy)-2-(((9-pentyltetradecanoyl)oxy)methyl)propyl octadeca-9,12-dienoate;
(9Z,12Z)-3-(((3-(diethylamino)propoxy)carbonyl)oxy)-2-(((5-heptyldodecanoyl)oxy)methyl)propyl octadeca-9,12-dienoate;
(9Z,12Z)-3-(2,2-bis(heptyloxy)acetoxy)-2-((((2-(dimethylamino)ethoxy)carbonyl)oxy)methyl)propyl octadeca-9,12-dienoate;
(9Z,12Z)-3-((6,6-bis(octyloxy)hexanoyl)oxy)-2-((((3-(diethylamino)propoxy)carbonyl)oxy)methyl)propyl octadeca-9,12-dienoate;
2-(3-ethyl-11-(((9Z,12Z)-octadeca-9,12-dienoyloxy)methyl)-8,14-dioxo-7,9,13-trioxa-3-azaheptadecan-17-yl)propane-1,3-diyl dioctanoate;
(9Z,9'Z,12Z,12'Z)-2-((((3-(dimethylamino)propoxy)carbonyl)oxy)methyl)propane-1,3-diyl bis(octadeca-9,12-dienoate);
(9Z,9'Z,12Z,12'Z)-2-((((3-(diethylamino)propoxy)carbonyl)oxy)methyl)propane-1,3-diyl bis(octadeca-9,12-dienoate);
(9Z,9'Z,12Z,12'Z)-2-((((2-(dimethylamino)ethoxy)carbonyl)oxy)methyl)propane-1,3-diyl bis(octadeca-9,12-dienoate);
(9Z,12Z)-3-((4,4-bis(octyloxy)butanoyl)oxy)-2-(((3-(dimethylamino)propanoyl)oxy)methyl)propyl octadeca-9,12-dienoate;
3-((4,4-bis(octyloxy)butanoyl)oxy)-2-(((9Z,12Z)-octadeca-9,12-dienoyloxy)methyl)propyl 1-isopropylpiperidine-4-carboxylate;
3-((4,4-bis(octyloxy)butanoyl)oxy)-2-(((9Z,12Z)-octadeca-9,12-dienoyloxy)methyl)propyl 1-(cyclopropylmethyl)piperidine-4-carboxylate;
3-((4,4-bis(octyloxy)butanoyl)oxy)-2-(((9Z,12Z)-octadeca-9,12-dienoyloxy)methyl)propyl 1-methylpyrrolidine-3-carboxylate; and
(9Z,9'Z,12Z,12'Z)-2-((((3-(diethylamino)propoxy)carbonyl)oxy)methyl)-2-(((9Z,12Z)-octadeca-9,12-dienoyloxy)methyl)propane-1,3-diylbis(octadeca-9,12-dienoate).

In a seventeenth embodiment, the invention is a lipid composition comprising a compound according to any one of the first through sixteenth embodiments, or a pharmaceutically acceptable salt thereof.

In an eighteenth embodiment, the invention is the lipid composition according to the seventeenth embodiment, further comprising a biologically active agent.

In a nineteenth embodiment, the invention is the lipid composition according to the eighteenth embodiment, wherein the biologically active agent is a nucleic acid.

In a twentieth embodiment, the invention is the lipid composition according to any one of the eighteenth or nineteenth embodiments, wherein the biologically active agent is a DNA, siRNA or mRNA.

In a twentyfirst embodiment, the invention is the lipid composition according to any one of the eighteenth through twentieth embodiments, wherein the biologically active agent is an mRNA.

In a twentysecond embodiment, the invention is the lipid composition according to any one of the eighteenth through twentieth embodiments, wherein the biologically active agent is a siRNA.

In a twentythrid embodiment, the invention is the lipid composition according to any one of the seventeenth through twentysecond embodiments, further comprising a helper lipid.

In a twentyfourth embodiment, the invention is the lipid composition according to any one of the seventeenth through twentythird embodiments, further comprising a neutral lipid.

In a twentyfifth embodiment, the invention is the lipid composition according to any one of the seventeenth through twentyfourth embodiments, further comprising a stealth lipid.

In a twentysixth embodiment, the invention is the lipid composition according to any one of the seventeenth through twentysixth embodiments, wherein the helper lipid is cholesterol, the neutral lipid is DSPC, and the stealth lipid is S010, S024, S027, S031, or S033.

In a twentyseventh embodiment, the invention is the lipid composition according to any one of the seventeenth through twentysixth embodiments, wherein the lipid composition is in the form of a lipid nanoparticle.

In a twentyeighth embodiment, the invention is the lipid composition according to any one of the seventeenth through twentyseventh embodiments, having 30-60% of a compound of formula (I), 5-10% cholesterol/30-60% DSPC, and 0.1-5% S010, S024, S027, S031, or S033

In a twentyninth embodiment, the invention is the lipid composition according to any one of the seventeenth through twentyeighth embodiments, wherein the pH of said lipid composition is 4-6 at the time of encapsulation and/or formulation.

In a thirtieth embodiment, the invention is the lipid composition according to any one of the seventeenth through twentyninth embodiments, wherein the pH of said lipid composition is 5-6 at the time of encapsulation and/or formulation.

In a thirtyfirst embodiment, the invention is the lipid composition according to any one of the seventeenth through thirtieth embodiments, wherein the pH of said lipid composition is 5.6-6.0 at the time of encapsulation and/or formulation.

In a thirtysecond embodiment, the invention is a pharmaceutical composition comprising a lipid composition according to any one of the seventeenth through thirtyfirst embodiments, and a pharmaceutically acceptable carrier or excipient.

In a thirtythird embodiment, the invention is a method for the treatment of a disease or condition comprising the step of administering a therapeutically effective amount of lipid composition according to any one of the seventeenth through thirtysecond embodiments, to a patient in need of treatment thereof.

In a thirtyfourth embodiment, the invention is a method for the treatment of a disease or condition comprising the step of administering a therapeutically effective amount of pharmaceutical composition according to the thirtythird embodiment.

In a thirtyfifth embodiment, the invention is the composition of any one of the seventeenth through thirtysecond embodiments, wherein the composition comprises a RNA molecule that encodes an immunogen.

In a thirtysixth embodiment, the invention is the composition of the thirtyfifth embodiment, wherein the lipid is in the form of a lipid nanoparticle (LNP) and the RNA is associated with the LNP.

In a thirtyseventh embodiment, the invention is the composition of the thirtysixth embodiment, wherein the LNP is a liposome.

In a thirtyeighth embodiment, the invention is the composition of the thirtyseventh embodiment, wherein the liposome has a diameter in the range of about: 60-180 nm, e.g., about: 80-160 nm.

In a thirtyninth embodiment, the invention is the composition of any one of the thirtyseventh through thirtyeighth embodiments, wherein said liposome further comprises a lipid comprising a zwitterionic head group.

In a fortieth embodiment, the invention is the composition of any one of the thrityseventh through thirtyninth embodiments, wherein said liposome further comprises DlinDMA (1,2-dilinoleyloxy-N,N-dimethyl-3-aminopropane), DSPC (1,2-Diastearoyl-sn-glycero-3-phosphocholine), a cholesterol, a PEGylated lipid, or a combination thereof.

In a fortyfirst embodiment, the invention is a pharmaceutical composition comprising the composition of any one of the thirtyseventh through fortieth embodiments and a pharmaceutical excipient.

In a fortysecond embodiment, the invention is a pharmaceutical composition comprising liposomes and immunogen-encoding RNA molecules, wherein the liposomes comprise the compound of any one of the first through sixteenth embodiments, and wherein at least half of the molar percentage of the RNA molecules are encapsulated in the liposomes.

In a fortythird embodiment, the invention is the pharmaceutical composition of the fortysecond embodiment, wherein (i) at least 80% by number of the liposomes have diameters in the range of about: 60-180 nm, (ii) the average diameter of the liposomes is in the range of about: 60-180 nm, or (iii) the diameters of the liposomes have a polydispersity index of <0.2.

In a fotyfourth embodiment, the invention is the composition of any one of the thirtyseventh through fortythird embodiments, wherein the RNA is a self-replicating RNA.

In a fortyfifth embodiment, the invention is the composition of the fortyfourth embodiment, wherein the self-replicating RNA encodes a RNA-dependent RNA polymerase.

In a fortysixth embodiment, the invention is the composition of the fortyfourth or fotyfifth embodiments, wherein the self-replicating RNA comprises a first open read-frame that encodes an alphavirus replicase and a second open reading frame that encodes the immunogen.

In a fortyseventh embodiment, the invention is the composition of any one of the fortyfouth through fortysixth embodiments, wherein the self-replicating RNA is greater than about 2000 nucleotides, such as greater than about: 9000, 12000, 15000, 18000, 21000, 24000, or more nucleotides long.

In a fortyeighth embodiment, the invention is the composition of any one of the thirtyfifth through fortyseventh embodiments, wherein the immunogen can elicit an immune response in vivo against a bacterium, a virus, a fungus or a parasite.

In a fortyninth embodiment, the invention is a method for inducing an immune response to an immunogen in a vertebrate, comprising administering an effective amount of the composition of any one of the thirtyfifth through fortyeighth embodiments to the vertebrate.

In a fiftieth embodiment, the invention is the composition of any one of the thirtyfifth through fortyninth embodiments for inducing an immune response in a vertebrate to an immunogen.

As used herein, the term "alkyl" refers to a fully saturated branched or unbranched hydrocarbon chain having the specified number of carbon atoms. For example, $C_{1-8}$ alkyl refers to an alkyl group having from 1 to 8 carbon atoms. For example, $C_{4-22}$ alkyl refers to an alkyl group having from 4 to 22 carbon atoms. For example, $C_{6-10}$ alkyl refers to an alkyl group having from 6 to 10 carbon atoms. For example, $C_{12-22}$ alkyl refers to an alkyl group having from 12 to 22 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, n-undecanyl, n-dodecanyl, n-tridecanyl, 9-methylheptadecanyl, 1-heptyldecyl, 2-octyldecyl, 6-hexyldodecyl, 4-heptylundecyl, and the like.

As used herein, the term "alkylene" refers to divalent alkyl group as defined herein above. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene, n-decylene, and the like.

As used herein, the term "alkenyl" refers to an unsaturated branched or unbranched hydrocarbon chain having the specified number of carbon atoms and one or more carbon-carbon double bonds within the chain. For example, $C_{12-22}$ alkenyl refers to an alkenyl group having 12 to 22 carbon atoms with one or more carbon-carbon double bonds within the chain. In certain embodiments alkenyl groups have one carbon-carbon double bond within the chain.

In other embodiments, alkenyl groups have more than one carbon-carbon double bond within the chain. Alkyenyl groups may be optionally substituted with one or more substituents as defined in formula (I). Representative examples of alkenyl include, but are not limited to, ethylenyl, propenyl, butenyl, pentenyl, hexenyl and the like. Other examples of alkenyl include, but are not limited to: Z-octadec-9-enyl, Z-undec-7-enyl, Z-heptadeca-8-enyl, (9Z, 12Z)-octadeca-9,12-dienyl, (8Z,11Z)-heptadeca-8,11-dienyl, (8Z, 11Z, 14Z)-heptadeca-8,11,14-trienyl, linolenyl, 2-octyldeca-1-enyl, linoleyl and olelyl.

As used herein, the term "alkenylene" refers a divalent alkenyl group as defined herein above. Representative examples of alkenylene include, but are not limited to, ethenylene, propenylene, butenylene, pentenylene, hexenylene and the like.

As used herein, the term "alkoxy" refers to refers to any alkyl moiety attached through an oxygen bridge (i.e. a —O—$C_{1-3}$ alkyl group wherein $C_{1-3}$ alkyl is as defined herein). Examples of such groups include, but are not limited to, methoxy, ethoxy, and propoxy.

As used herein, the term "cycloalkyl" refers to a saturated monocyclic, bicyclic or tricyclic hydrocarbon ring having the specified number of carbon atoms. For example, $C_{3-7}$ cycloalkyl refers to a cycloalkyl ring having from 3 to 7 carbon atoms. Cycloalkyl groups may be optionally substituted with one or more substituents as defined in formula (I). Representative examples of cycloalkyl include, but are not limited to, cyclopropyl, cyclobutyl, cyclopentyl, cyclohexyl, bicyclo[2.1.1]hexyl, bicyclo[2.2.1]heptyl, adamantyl and the like.

As used herein, the term "halo" refers to fluoro, chloro, bromo, and iodo.

As used herein, the term "heterocyclic" refers to a 4 to 12 membered saturated or unsaturated monocyclic or bicyclic ring containing from 1 to 4 heteroatoms. Heterocyclic ring systems are not aromatic. Heterocyclic groups containing more than one heteroatom may contain different heteroatoms. Heterocyclic groups are monocyclic, spiro, or fused or bridged bicyclic ring systems. Examples of monocyclic heterocyclic groups include tetrahydrofuranyl, dihydrofuranyl, 1,4-dioxanyl, morpholinyl, 1,4-dithianyl, azetidinyl, piperazinyl, piperidinyl, 1,3-dioxolanyl, imidazolidinyl, imidazolinyl, pyrrolinyl, pyrrolidinyl, tetrahydropyranyl, dihydropyranyl, 1,2,3,6-tetrahydropyridinyl, oxathiolanyl, dithiolanyl, 1,3-dioxanyl, 1,3-dithianyl, oxathianyl, thiomorpholinyl, 1,4,7-trioxa-10-azacyclododecanyl, azapanyl and the like. Examples of spiro heterocyclic rings include, but are not limited to, 1,5-dioxa-9-azaspiro[5.5]undecanyl, 1,4-dioxa-8-azaspiro[4.5]decanyl, 2-oxa-7-azaspiro[3.5]nonanyl, and the like. Fused heterocyclic ring systems have from 8 to 11 ring atoms and include groups wherein a heterocyclic ring is fused to a phenyl ring. Examples of fused heterocyclic rings include, but are not limited to decahydroqunilinyl, (4aS, 8aR)-decahydroisoquinolinyl, (4aS,8aS)-decahydroisoquinolinyl, octahydrocyclopenta[c]pyrrolyl, isoinolinyl, (3aR,7aS)-hexahydro-[1,3]dioxolo[4.5-c]pyridinyl, octahydro-1H-pyrrolo[3,4-b]pyridinyl, tetrahydroisoquinolinyl and the like.

As used herein, the term "heterocyclyl$C_{1-8}$alkyl" refers to a heterocyclic ring as defined above which is attached to the rest of the molecule by a single bond or by a $C_{1-8}$alkyl radical as defined above.

As used herein, the term "heteroaryl" refers to a 5- or 6-membered aromatic monocyclic ring radical which comprises 1, 2, 3 or 4 heteroatoms individually selected from nitrogen, oxygen and sulfur. The heteroaryl radical may be bonded via a carbon atom or heteroatom. Examples of heteroaryl include, but are not limited to, furyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroaryl$C_{1-8}$alkyl" refers to a heteroaryl ring as defined above which is attached to the rest of the molecule by a single bond or by a $C_{1-8}$alkyl radical as defined above. As used herein, the term "an optical isomer" or "a stereoisomer" refers to any of the various stereoisomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis- (Z)- or trans- (E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the terms "salt" or "salts" refers to an acid addition of a compound of the invention. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

General Methods for Synthesizing Cationic Lipids

The present invention also includes processes for the preparation of compounds of formula (I). In the reactions described, it could be necessary to protect reactive functional groups, for example hydroxyl, amino, iminio, thio or carboxy groups, where these are desired in the final product, to avoid their unwanted participation in the reactions.

The compounds and processes of the present invention will be better understood in connection with the following synthetic schemes, which are merely intended to illustrate methods by which the compounds may be generally prepared and are not intended to limit the scope of the invention as defined in the claims.

Final compounds of formula (I) can be prepared as described in Scheme I.

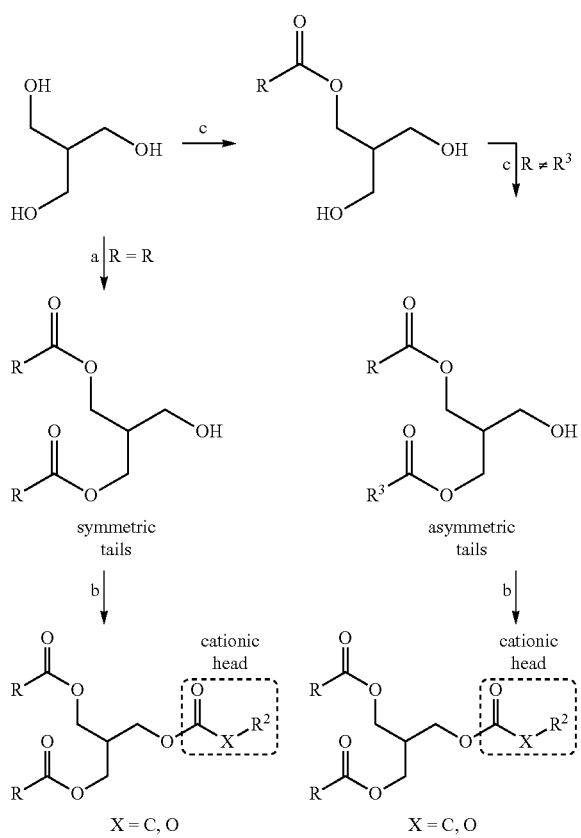

a) Selective bis-acylation for symmetric tail installation. b) Ester or carbonate cationic head coupling. c) Selective mono-acylation for asymmetric tail installation.

Lipid Compositions

The present invention provides for a lipid composition comprising at least one compound of formula (I), i.e. a lipid composition of the invention. In one embodiment, at least one other lipid component is present. Such compositions can also contain a biologically active agent, optionally in combination with one or more other lipid components.

One embodiment of the present invention provides for a lipid composition comprising a compound of formula (I) and another lipid component. Such other lipid components include, but are not limited to, cationic lipids, neutral lipids, anionic lipids, helper lipids, and stealth lipids.

Cationic lipids suitable for use in a lipid composition of the invention include, but are not limited to, N,N-dioleyl-N,N-dimethylammonium chloride (DODAC), N,N-distearyl-N,N-dimethylammonium bromide (DDAB), N-(1-(2,3-dioleoyloxy) propyl)-N,N,N-trimethylammonium chloride (DOTAP), 1,2-Dioleoyl-3-Dimethylammonium-propane (DODAP), N-(1-(2,3-dioleyloxy)propyl)-N,N,N-trimethylammonium chloride (DOTMA), 1,2-Dioleoylcarbamyl-3-Dimethylammonium-propane (DOCDAP), 1,2-Dilineoyl-3-Dimethylammonium-propane (DLINDAP), dilauryl($C_{12:0}$) trimethyl ammonium propane (DLTAP), Dioctadecylamidoglycyl spermine (DOGS), DC-Choi, Dioleoyloxy-N-[2-sperminecarboxamido)ethyl}-N,N-dimethyl-1-propanaminiumtrifluoroacetate (DOSPA), 1,2-Dimyristyloxypropyl-3-dimethyl-hydroxyethyl ammonium bromide (DMRIE), 3-Dimethylamino-2-(Cholest-5-en-3-beta-oxybutan-4-oxy)-1-(cis,cis-9,12-octadecadienoxy)propane (CLinDMA), N,N-dimethyl-2,3-dioleyloxy)propylamine (DODMA), 2-[5'-(cholest-5-en-3[beta]-oxy)-3'-oxapentoxy)-3-dimethyl-1-(cis,cis-9',12'-octadecadienoxy) propane (CpLinDMA) and N,N-Dimethyl-3,4-dioleyloxybenzylamine (DMOBA), and 1,2-N,N'-Dioleylcarbamyl-3-dimethylaminopropane (DOcarbDAP). In one embodiment the cationic lipid is DOTAP or DLTAP.

"Neutral lipids" suitable for use in a lipid composition of the invention include, for example, a variety of neutral, uncharged or zwitterionic lipids. Examples of neutral phospholipids suitable for use in the present invention include, but are not limited to: 5-heptadecylbenzene-1,3-diol (resorcinol), dipalmitoylphosphatidylcholine (DPPC), distearoylphosphatidylcholine (DSPC), phosphocholine (DOPC), dimyristoylphosphatidylcholine (DMPC), phosphatidylcholine (PLPC), 1,2-distearoyl-sn-glycero-3-phosphocholine (DAPC), phosphatidylethanolamine (PE), egg phosphatidylcholine (EPC), dilauryloylphosphatidylcholine (DLPC), dimyristoylphosphatidylcholine (DMPC), 1-myristoyl-2-palmitoyl phosphatidylcholine (MPPC), 1-palmitoyl-2-myristoyl phosphatidylcholine (PMPC), 1-palmitoyl-2-stearoyl phosphatidylcholine (PSPC), 1,2-diarachidoyl-sn-glycero-3-phosphocholine (DBPC), 1-stearoyl-2-palmitoyl phosphatidylcholine (SPPC), 1,2-dieicosenoyl-sn-glycero-3-phosphocholine (DEPC), palmitoyloleoyl phosphatidylcholine (POPC), lysophosphatidyl choline, dioleoyl phosphatidylethanolamine (DOPE), dilinoleoylphosphatidylcholine distearoylphophatidylethanolamine (DSPE), dimyristoyl phosphatidylethanolamine (DMPE), dipalmitoyl phosphatidylethanolamine (DPPE), palmitoyloleoyl phosphatidylethanolamine (POPE), lysophosphatidylethanolamine and combinations thereof. In one embodiment, the neutral phospholipid is selected from the group consisting of distearoylphosphatidylcholine (DSPC) and dimyristoyl phosphatidyl ethanolamine (DMPE).

Anionic lipids suitable for use in the present invention include, but are not limited to, phosphatidylglycerol, cardiolipin, diacylphosphatidylserine, diacylphosphatidic acid, N-dodecanoyl phosphatidyl ethanoloamine, N-succinyl phosphatidylethanolamine, N-glutaryl phosphatidylethanolamine cholesterol hemisuccinate (CHEMS), and lysyl-phosphatidylglycerol.

Suitable neutral and anionic lipids also include those described in US 2009/0048197.

"Helper lipids" are lipids that enhance transfection (e.g. transfection of the nanoparticle including the biologically active agent) to some extent. The mechanism by which the helper lipid enhances transfection may include, e.g., enhancing particle stability and/or enhancing membrane fusogenicity. Helper lipids include steroids and alkyl resorcinols. Helper lipids suitable for use in the present invention include, but are not limited to, cholesterol, 5-heptadecylresorcinol, and cholesterol hemisuccinate.

"Stealth lipids" are lipids that increase the length of time for which the nanoparticles can exist in vivo (e.g. in the blood). Stealth lipids suitable for use in a lipid composition of the invention include, but are not limited to, stealth lipids having a hydrophilic head group linked to a lipid moiety. Examples of such stealth lipids include compounds of formula (XI), as described in WO2011/076807,

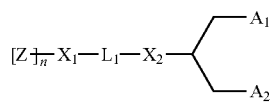

(XI)

or a salt or pharmaceutically acceptable derivative thereof, wherein:

$Z_n$ is a hydrophilic polymer moiety selected from PEG (poly(ethyleneoxide)) or polymers based on poly(oxazoline), poly(vinyl alcohol), poly(glycerol), poly(N-vinylpyrro-lidone), poly[N-(2-hydroxypropyl)methacrylamide], polysaccharides and poly(amino acid)s, or a combination of the foregoing, wherein the polymer may be linear or branched, and wherein each Z is independently and optionally may be optionally substituted;

wherein Z is polymerized by n subunits;

n is a number-averaged degree of polymerization between 10 and 200 units of Z, wherein n is optimized for different polymer types;

$L_1$ is an optionally substituted $C_{1-10}$ alkylene or $C_{1-10}$ heteroalkylene linker including zero, one, two or more of an ether (e.g., —O—), ester (e.g., —C(O)O—), succinate (e.g., —O(O)C—CH$_2$—CH$_2$—C(O)O—)), carbamate (e.g., —OC(O)—NR'—), carbonate (e.g., —OC(O)O—), ketone (e.g., —C—C(O)—C—), carbonyl (e.g., —C(O)—), urea (e.g., —NRC(O)NR'—), amine (e.g., —NR'—), amide (e.g., —C(O)NR'—), imine (e.g., —C(NR')—), thioether (e.g., —S—), xanthate (e.g., —OC(S)S—), and phosphodiester (e.g., —OP(O)$_2$O—); any of which may be substituted by zero, one or more Z groups;

wherein R' is independently selected from —H, NH—, —NH$_2$, —O—, —S—, a phosphate or an optionally substituted $C_{1-10}$ alkylene;

$X_1$ and $X_2$ are independently selected from a carbon or a heteroatom selected from —NH—, —O—, —S— or a phosphate;

$A_1$ and $A_2$ are independently selected from a $C_{6-30}$ alkyl, $C_{6-30}$ alkenyl, and $C_{6-30}$ alkynyl, wherein $A_1$ and $A_2$ may be the same or different, or wherein $A_1$ and $A_2$ together with the carbon atom to which they are attached form an optionally substituted steroid.

Specific stealth lipids include, but are not limited to, those listed in Table 1.

TABLE 1

| Stealth Lipids | |
|---|---|
| Stealth Lipid | Lipid |
| S001 | 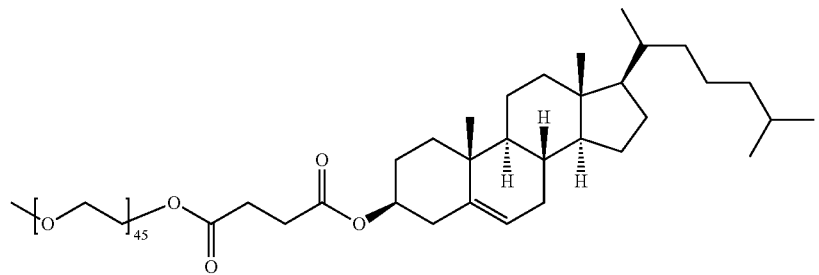 |
| S002 | 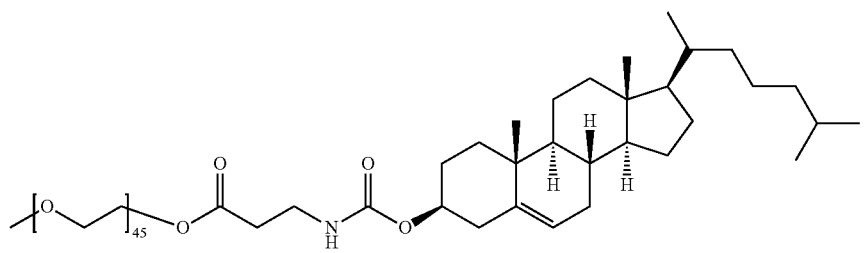 |

TABLE 1-continued

Stealth Lipids

| Stealth Lipid | Lipid |
|---|---|
| S003 | |
| S004 | |
| S005 | |
| S006 | |
| S007 | |
| S008 | |
| S009 | |
| S010 | |
| S011 | |

TABLE 1-continued

Stealth Lipids

| Stealth Lipid | Lipid |
|---|---|
| S012 | |
| S013 | |
| S014 | |
| S015 | |
| S016 | |
| S017 | |
| S018 | |
| S019 | |
| S020 | |
| S021 | |

TABLE 1-continued
Stealth Lipids
| Stealth Lipid | Lipid |
|---|---|
| S022 | 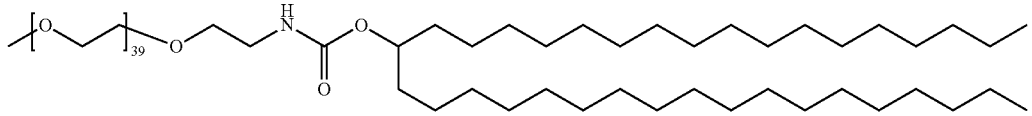 |
| S023 | 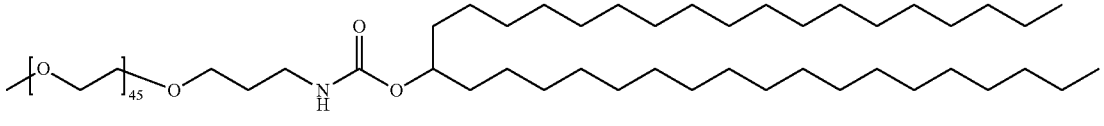 |
| S024 | 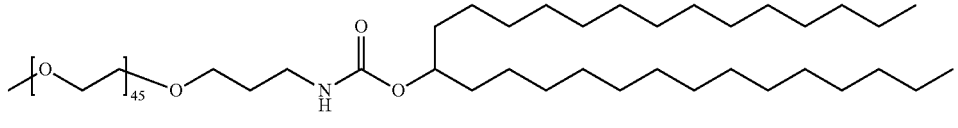 |
| S025 | 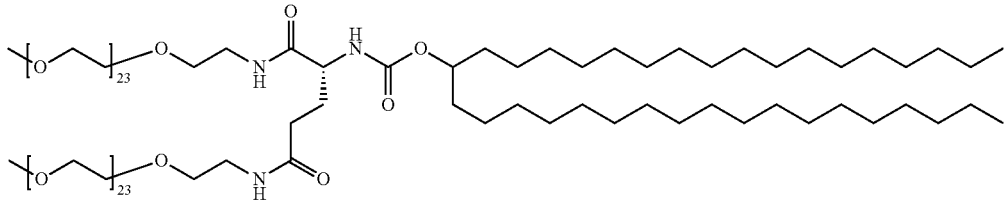 |
| S026 | 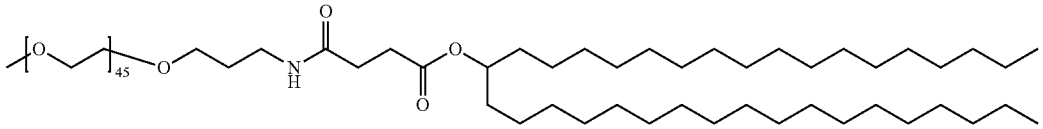 |
| S027 | 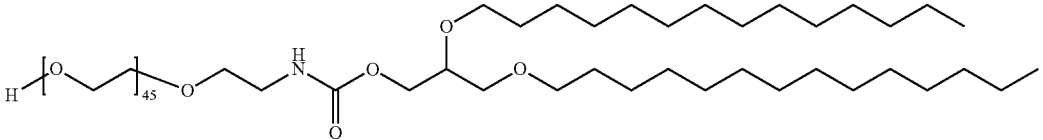 |
| S028 | 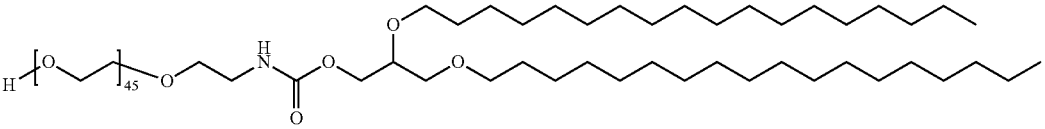 |
| S029 | 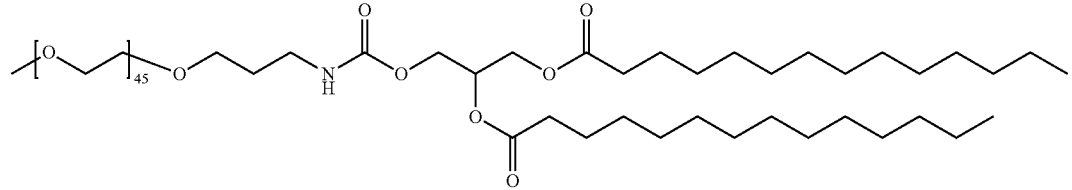 |
| S030 | 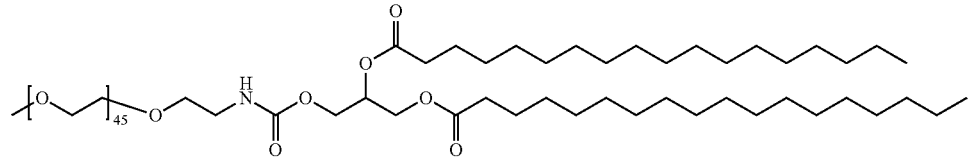 |

TABLE 1-continued

Stealth Lipids

| Stealth Lipid | Lipid |
|---|---|
| S031 | [structure: PEG(45)-glycerol with two ester-linked long alkyl chains] |
| S032 | [structure: PEG(45)-glycerol with two ester-linked long alkyl chains] |
| S033 | [structure: PEG(45)-carbamate-ethyl-phosphate-glycerol with two ester-linked long alkyl chains] |

Other stealth lipids suitable for use in a lipid composition of the present invention and information about the biochemistry of such lipids can be found in Romberg et al., Pharmaceutical Research, Vol. 25, No. 1, 2008, p.55-71 and Hoekstra et al., Biochimica et Biophysica Acta 1660 (2004) 41-52.

In one embodiment, the suitable stealth lipid comprises a group selected from PEG (sometimes referred to as poly (ethylene oxide) and polymers based on poly(oxazoline), poly(vinyl alcohol), poly(glycerol), poly(N-vinylpyrrolidone), polyaminoacids and poly[N-(2-hydroxypropyl) methacrylamide]. Additional suitable PEG lipids are disclosed, e.g., in WO 2006/007712.

Other stealth lipids suitable for use in a lipid composition of the present invention and information about the biochemistry of such lipids can be found in Romberg et al., Pharmaceutical Research, Vol. 25, No. 1, 2008, p.55-71 and Hoekstra et al., Biochimica et Biophysica Acta 1660 (2004) 41-52.

In one embodiment, the suitable stealth lipid comprises a group selected from PEG (sometimes referred to as poly (ethylene oxide) and polymers based on poly(oxazoline), poly(vinyl alcohol), poly(glycerol), poly(N-vinylpyrrolidone), polyaminoacids and poly[N-(2-hydroxypropyl) methacrylamide]. Additional suitable PEG lipids are disclosed, e.g., in WO 2006/007712.

Specific suitable stealth lipids include polyethyleneglycol-diacylglycerol or polyethyleneglycol-diacylglycamide (PEG-DAG) conjugates including those comprising a dialkylglycerol or dialkylglycamide group having alkyl chain length independently comprising from about $C_4$ to about $C_{40}$ saturated or unsaturated carbon atoms. The dialkylglycerol or dialkylglycamide group can further comprise one or more substituted alkyl groups. In any of the embodiments described herein, the PEG conjugate can be selected from PEG-dilaurylglycerol, PEG-dimyristylglycerol (PEG-DMG) (catalog # GM-020 from NOF, Tokyo, Japan), PEG-dipalmitoylglycerol, PEG-disterylglycerol, PEG-dilaurylglycamide, PEG-dimyristylglycamide, PEG-dipalmitoylglycamide, and PEG-disterylglycamide, PEG-cholesterol (1-[8'-(Cholest-5-en-3[beta]-oxy)carboxamido-3',6'-dioxaoctanyl] carbamoyl-[omega]-methyl-poly (ethylene glycol), PEG-DMB (3,4-Ditetradecoxylbenzyl-[omega]-methyl-poly(ethylene glycol) ether), 1,2-dimyristoyl-sn-glycero-3-phosphoethanolamine-N-[methoxy(polyethylene glycol)-2000] (catalog #880150P from Avanti Polar Lipids, Alabaster, Ala., USA).

In one embodiment the stealth lipid is S010, S024, S027, S031, or S033.

In another embodiment the stealth lipid is S024.

Unless otherwise indicated, the term "PEG" as used herein means any polyethylene glycol or other polyalkylene ether polymer. In one embodiment, PEG is an optionally substituted linear or branched polymer of ethylene glycol or ethylene oxide. In one embodiment PEG is unsubstituted. In one embodiment the PEG is substituted, e.g., by one or more alkyl, alkoxy, acyl, hydroxy or aryl groups. In one embodiment, the term includes PEG copolymers such as PEG-polyurethane or PEG-polypropylene (see, e.g., J. Milton Harris, Poly(ethylene glycol) chemistry: biotechnical and biomedical applications (1992)); in another embodiment, the term does not include PEG copolymers. In one embodiment, the PEG has a molecular weight of from about 130 to about 50,000, in a sub-embodiment about 150 to about 30,000, in a sub-embodiment about 150 to about 20,000, in a sub-embodiment about 150 to about 15,000, in a sub-embodiment about 150 to about 10,000, in a sub-embodiment about 150 to about 6000, in a sub-embodiment about 150 to about 5000, in a sub-embodiment about 150 to about 4000, in a sub-embodiment about 150 to about 3000, in a sub-embodiment about 300 to about 3000, in a sub-embodiment about 1000 to about 3000, and in a sub-embodiment about 1500 to about 2500.

In certain embodiments the PEG (e.g., conjugated to a lipid, such as a stealth lipid) is a "PEG-2K", also termed "PEG 2000", which has an average molecular weight of about 2000 daltons. PEG-2K is represented herein by the following formula (XIIa), wherein n is 45, meaning that the number-averaged degree of polymerization comprises about 45 subunits. However, other PEG embodiments known in the art may be used, including, e.g., those where the number-averaged degree of polymerization comprises about 23 subunits (n=23) and/or 68 subunits (n=68).

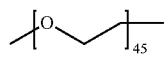
(XIIa)

The lipid compositions of the invention can also include one or more biologically active agents including, but not limited to, antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozyme, decoys and analogs thereof, plasmids and other types of expression vectors, and small nucleic acid molecules, RNAi agents, short interfering nucleic acid (siNA), messenger ribonucleic acid" (messenger RNA, mRNA), short interfering RNA (siRNA), double-stranded RNA (dsRNA), micro-RNA (miRNA), and short hairpin RNA (shRNA) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. Such compounds may be purified or partially purified, and may be naturally occurring or synthetic, and may be chemically modified. In one embodiment the biologically active agent is an RNAi agent, short interfering nucleic acid (siNA), short interfering RNA (siRNA), double-stranded RNA (dsRNA), micro-RNA (miRNA), or a short hairpin RNA (shRNA) molecule. In one embodiment the biologically active agent is a RNAi agent useful for mediating RNA interference (RNAi). In another embodiment the biologically active agent is a mRNA.

Various methods for loading biologically active agents into lipid compositions, such as liposomes and lipid nanoparticles are available in the art, including both passive and active loading methods. The exact method used may be chosen based on multiple factors that include, but are not limited to, e.g., the biologically active agent to be loaded, the storage method to be used once loaded, the size of the resulting particle, and the dosage regimen contemplated. Methods include, e.g., mechanical mixing of the drug and lipids at the time the liposomes are formed or reconstituted, dissolving all components in an organic solvent and concentrating them into a dry film, forming a pH or ion gradient to draw the active agent into the interior of the liposome, creating a transmembrane potential, and ionophore mediated loading. See, e.g., PCT Publication No. WO 95/08986, U.S. Pat. No. 5,837,282, U.S. Pat. No. 5,837,282, and U.S. Pat. No. 7,811,602.

By "lipid nanoparticle" is meant a particle that comprises a plurality of (i.e. more than one) lipid molecules physically associated with each other by intermolecular forces. The lipid nanoparticles may be, e.g., microspheres (including unilamellar and multilamellar vesicles, e.g. "liposomes"—lamellar phase libid bilayers that, in some embodiments are substantially spherical, and, in more particular embodiments can comprise an aqueous core, e.g., comprising a substantial portion of RNA molecules), a dispersed phase in an emulsion, micelles or an internal phase in a suspension.

The lipid nanoparticles have a size of about 1 to about 2,500 nm, about 10 to about 1,500 nm, about 20 to about 1,000 nm, in a sub-embodiment about 50 to about 600 nm, in a sub-embodiment about 50 to about 400 nm, in a sub-embodiment about 50 to about 250 nm, and in a sub-embodiment about 50 to about 150 nm. Unless indicated otherwise, all sizes referred to herein are the average sizes (diameters) of the fully formed nanoparticle, as measured by dynamic light scattering on a Malvern Zetasizer. The nanoparticle sample is diluted in phosphate buffered saline (PBS) so that the count rate is approximately 200-400 kcts. The data is presented as a weighted average of the intensity measure.

One embodiment of the present invention provides for a lipid composition comprising a compound of formula (I) and another lipid component. Another embodiment provides for a lipid composition comprising a compound of formula (I) and a helper lipid, for example cholesterol. Another embodiment provides for a lipid composition comprising a compound of formula (I), a helper lipid, for example cholesterol, and a neutral lipid, for example DSPC. Another embodiment of the present invention provides for a lipid composition comprising a compound of formula (I), a helper lipid, for example cholesterol, a neutral lipid, for example DSPC, and a stealth lipid, for example S010, S024, S027, S031, or S033. Another embodiment of the present invention provides for a lipid composition comprising a compound of formula (I), a helper lipid, for example cholesterol, a neutral lipid, for example DSPC, a stealth lipid, for example S010, S024, S027, S031, or S033, and a biologically active agent, for example a RNA or DNA. Another embodiment of the present invention provides for a lipid nanoparticle comprising a compound of formula (I) a helper lipid, for example cholesterol, a neutral lipid, for example DSPC, and a stealth lipid, for example S010, S024, S027, S031, or S033, and a biologically active agent, for example a mRNA, siRNA or DNA.

Embodiments of the present invention also provide lipid compositions described according to the respective molar ratios of the component lipids in the formulation, wherein a slash ("/") indicates the respective components, as provided herein.

Another embodiment of the present invention is a lipid composition comprising a compound of formula (I) and a helper lipid, for example cholesterol, in a lipid molar ratio of 55-40 compound of formula (I)/55-40 helper lipid. Another embodiment provides for a lipid composition comprising a compound of formula (I), a helper lipid, for example cholesterol, and a neutral lipid, for example DPSC in a lipid molar ratio of 55-40 compound of formula (I)/55-40 helper lipid/15-5 neutral lipid. Another embodiment provides for a lipid composition comprising a compound of formula (I), a helper lipid, for example cholesterol, a neutral lipid, for example DSPC, and a stealth lipid, for example S010, S024, S027, S031, or S033 in a lipid molar ratio of 55-40 compound of formula (I)/55-40 helper lipid/15-5 neutral lipid/ 10-1 stealth lipid.

Another embodiment of the present invention is a lipid composition comprising a compound of formula (I) and a helper lipid, for example cholesterol, in a lipid molar ratio of 50-40 compound of formula (I)/50-40 helper lipid. Another embodiment provides for a lipid composition comprising a compound of formula (I), a helper lipid, for example cholesterol, and a neutral lipid, for example DPSC in a lipid molar ratio of 50-40 compound of formula (I)/50-40 helper lipid/15-5 neutral lipid. Another embodiment provides for a lipid composition comprising a compound of formula (I), a helper lipid, for example cholesterol, a neutral lipid, for example DPSC, a stealth lipid, for example S010, S024, S027, S031, or S033 in a lipid molar ratio of 50-40 compound of formula (I)/50-40 helper lipid/15-5 neutral lipid/ 5-1 stealth lipid.

Another embodiment of the present invention is a lipid composition comprising a compound of formula (I) and a helper lipid, for example cholesterol, in a lipid molar ratio of 47-43 compound of formula (I)/47-43 helper lipid. Another embodiment provides for a lipid composition comprising a compound of formula (I), a helper lipid, for example cholesterol, and a neutral lipid, for example DPSC in a lipid molar ratio of 47-43 compound of formula (I)/47-43 helper lipid/12-7 neutral lipid. Another embodiment provides for a lipid composition comprising a compound of formula (I), a helper lipid, for example cholesterol, a neutral lipid, for example DSPC, a stealth lipid, for example S010, S024, S027, S031, or S033 in a lipid molar ratio of 47-43 compound of formula (I)/47-43 helper lipid/12-7 neutral lipid/ 4-1 stealth lipid.

Another embodiment of the present invention is a lipid composition comprising a compound of formula (I) and a helper lipid, for example cholesterol, in a lipid molar ratio of about 45 compound of formula (I)/about 44 helper lipid. Another embodiment provides for a lipid composition comprising a compound of formula (I), a helper lipid, for example cholesterol, and a neutral lipid, for example DPSC in a lipid molar ratio of about 45 compound of formula (I)/about 44 helper lipid/about 9 neutral lipid. Another embodiment provides for a lipid composition comprising a compound of formula (I), a helper lipid, for example cholesterol, a neutral lipid, for example DSPC, a stealth lipid, for example S010, S024, S027, S031, or S033 in a lipid molar ratio of about 45 compound of formula (I)/about 44 helper lipid/about 9 neutral lipid/about 2 stealth lipid, for example S010, S024, S027, S031, or S033.

Preferred compounds of formula (I) for use in the above lipid compositions are given in Examples 1-36. Particularly preferred compounds are given in Examples 1, 13 and 15. Preferred biologically active agents are RNA's and DNA's.

Lipid compositions of the present invention can be further optimized by one skilled in the art by combining cationic lipids with the desired pKa range, stealth lipids, helper lipids, and neutral lipids into formulations, including, e.g., liposome formulations, lipid nanoparticles (LNP) formulations, and the like for delivery to specific cells and tissues in vivo. In one embodiment, further optimization is obtained by adjusting the lipid molar ratio between these various types of lipids. In one embodiment, further optimization is obtained by adjusting one or more of: the desired particle size, N/P ratio, formulation methods and/or dosing regimen (e.g., number of doses administered over time, actual dose in mg/kg, timing of the doses, combinations with other therapeutics, etc.). The various optimization techniques known to those of skill in the art pertaining to the above listed embodiments are considered as part of this invention.

General Methods for Making Lipid Nanoparticles

The following methods can be used to make lipid nanoparticles of the invention. To achieve size reduction and/or to increase the homogeneity of size in the particles, the skilled person may use the method steps set out below, experimenting with different combinations. Additionally, the skilled person could employ sonication, filtration or other sizing techniques which are used in liposomal formulations.

The process for making a composition of the invention typically comprises providing an aqueous solution, such as citrate buffer, comprising a biologically active agent in a first reservoir, providing a second reservoir comprising an organic solution, such as an organic alcohol, for example ethanol, of the lipid(s) and then mixing the aqueous solution with the organic lipid solution. The first reservoir is optionally in fluid communication with the second reservoir. The mixing step is optionally followed by an incubation step, a filtration or dialysis step, and a dilution and/or concentration step. The incubation step comprises allowing the solution from the mixing step to stand in a vessel for about 0 to about 100 hours (preferably about 0 to about 24 hours) at about room temperature and optionally protected from light. In certain embodiments, the temperature may be about 4° C. during incubation. In one embodiment, a dilution step follows the incubation step. The dilution step may involve dilution with aqueous buffer (e.g. citrate buffer or pure water) e.g., using a pumping apparatus (e.g. a peristaltic pump). The filtration step is ultrafiltration or dialysis. Ultrafiltration comprises concentration of the diluted solution followed by diafiltration, e.g., using a suitable pumping system (e.g. pumping apparatus such as a peristaltic pump or equivalent thereof) in conjunction with a suitable ultrafiltration membrane (e.g. GE Hollow fiber cartridges or equivalent). Dialysis comprises solvent (buffer) exchange through a suitable membrane (e.g. 10,000 mwc snakeskin membrane). Alternatively, in some embodiments, dialysis may be accomplished using buffer exchange columns (e.g., PD-10 columns from GE healthcare).

In one embodiment, the mixing step provides a clear single phase.

In one embodiment, after the mixing step, the organic solvent is removed to provide a suspension of particles, wherein the biologically active agent is encapsulated by the lipid(s).

The selection of an organic solvent will typically involve consideration of solvent polarity and the ease with which the solvent can be removed at the later stages of particle formation. The organic solvent, which is also used as a solubilizing agent, is preferably in an amount sufficient to provide a clear single phase mixture of biologically active agents and lipids. The organic solvent may be selected from one or more (e.g. two) of chloroform, dichloromethane, diethylether, cyclohexane, cyclopentane, benzene, toluene, methanol, and other aliphatic alcohols (e.g. $C_1$ to $C_8$) such as ethanol, propanol, isopropanol, butanol, tert-butanol, isobutanol, pentanol and hexanol.

The mixing step can take place by any number of methods, e.g., by mechanical means such as a vortex mixer.

The methods used to remove the organic solvent will typically involve diafiltration or dialysis or evaporation at reduced pressures or blowing a stream of inert gas (e.g. nitrogen or argon) across the mixture.

In other embodiments, the method further comprises adding nonlipid polycations which are useful to effect the transformation of cells using the present compositions. Examples of suitable nonlipid polycations include, but are limited to, hexadimethrine bromide (sold under the brand-name POLYBRENE®, from Aldrich Chemical Co., Milwaukee, Wis., USA) or other salts of hexadimethrine. Other suitable polycations include, e.g., salts of poly-L-ornithine, poly-L-arginine, poly-L-lysine, poly-D-lysine, polyallylamine and polyethyleneimine. In certain embodiments, the formation of the lipid nanoparticles can be carried out either in a mono-phase system (e.g. a Bligh and Dyer monophase or similar mixture of aqueous and organic solvents) or in a two-phase system with suitable mixing.

The lipid nanoparticle may be formed in a mono- or a bi-phase system. In a mono-phase system, the cationic lipid(s) and biologically active agent are each dissolved in a volume of the mono-phase mixture. Combining the two solutions provides a single mixture in which the complexes form. In a bi-phase system, the cationic lipids bind to the biologically active agent (which is present in the aqueous phase), and "pull" it into the organic phase. In one embodiment, the lipid nanoparticles are prepared by a method which comprises: (a) contacting the biologically active agent with a solution comprising noncationic lipids and a detergent to form a compound-lipid mixture; (b) contacting cationic lipids with the compound-lipid mixture to neutralize a portion of the negative charge of the biologically active agent and form a charge-neutralized mixture of biologically active agent and lipids; and (c) removing the detergent from the charge-neutralized mixture.

In one group of embodiments, the solution of neutral lipids and detergent is an aqueous solution. Contacting the biologically active agent with the solution of neutral lipids and detergent is typically accomplished by mixing together a first solution of the biologically active agent and a second solution of the lipids and detergent. Preferably, the biologically active agent solution is also a detergent solution. The amount of neutral lipid which is used in the present method is typically determined based on the amount of cationic lipid used, and is typically of from about 0.2 to 5 times the amount of cationic lipid, preferably from about 0.5 to about 2 times the amount of cationic lipid used.

The biologically active agent-lipid mixture thus formed is contacted with cationic lipids to neutralize a portion of the negative charge which is associated with the molecule of interest (or other polyanionic materials) present. The amount of cationic lipids used is typically 3-8 fold more than the calculated molar ratio of negative charge (phosphates).

The methods used to remove the detergent typically involve dialysis. When organic solvents are present, removal is typically accomplished by diafiltration or evaporation at reduced pressures or by blowing a stream of inert gas (e.g. nitrogen or argon) across the mixture.

There is herein disclosed an apparatus for making a composition of the present invention. The apparatus typically includes a first reservoir for holding an aqueous solution comprising a biologically active agent and a second reservoir for holding an organic lipid solution. The apparatus also typically includes a pump mechanism configured to pump the aqueous and the organic lipid solutions into a mixing region or mixing chamber at substantially equal flow rates. In one embodiment, the mixing region or mixing chamber comprises a T coupling or equivalent thereof, which allows the aqueous and organic fluid streams to combine as input into the T connector and the resulting combined aqueous and organic solutions to exit out of the T connector into a collection reservoir or equivalent thereof. In other embodiments, a microfluidic device, such as a NANO-ASSEMBLR™, can be used for making a composition provided by the invention.

Methods for Delivering Biologically Active Agents and the Treatment of Disease

The cationic lipids of formula (I) and lipid compostions thereof are useful in pharmaceutical compositions or formulations used for delivery of biologically active agents. Formulations containing cationic lipds of formula (I) or lipid compositions thereof may be in various forms, including, but not limited to, particle forming delivery agents including microparticles, nanoparticles and transfection agents that are useful for delivering various molecules to cells. Specific formulations are effective at transfecting or delivering biologically active agents, such as antibodies (e.g., monoclonal, chimeric, humanized, nanobodies, and fragments thereof etc.), cholesterol, hormones, peptides, proteins, chemotherapeutics and other types of antineoplastic agents, low molecular weight drugs, vitamins, co-factors, nucleosides, nucleotides, oligonucleotides, enzymatic nucleic acids, antisense nucleic acids, triplex forming oligonucleotides, antisense DNA or RNA compositions, chimeric DNA:RNA compositions, allozymes, aptamers, ribozymes, decoys and analogs thereof, plasmids and other types of expression vectors, and small nucleic acid molecules, mRNA, RNAi agents, short interfering nucleic acid (siNA), short interfering RNA (siRNA), double-stranded RNA (dsRNA), micro-RNA (miRNA), short hairpin RNA (shRNA) and "self-replicating RNA" (encoding a replicase enzyme activity and capable of directing its own replication or amplification in vivo) molecules, peptide nucleic acid (PNA), a locked nucleic acid ribonucleotide (LNA), morpholino nucleotide, threose nucleic acid (TNA), glycol nucleic acid (GNA), sisiRNA (small internally segmented interfering RNA), aiRNA (assymetrical interfering RNA), and siRNA with 1, 2 or more mismatches between the sense and anti-sense strand to relevant cells and/or tissues, such as in a cell culture, subject or organism. The above list of biologically active agents is exemplary only, and is not intended to be limiting. Such compounds may be purified or partially purified, and may be naturally occurring or synthetic, and may be chemically modified.

Such formulations containing biologically active agents are useful, e.g., in providing compositions to prevent, inhibit, or treat diseases, conditions, or traits in a cell, subject or organism. Diseases, conditions or traits include, but are not limited to, proliferative diseases, including cancer, inflammatory disease, transplant and/or tissue rejection, autoimmune diseases or conditions, age-related disease, neurological or neurodegenerative disease, respiratory disease, cardiovacular disease, ocular disease, metabolic disease, dermatological disease, auditory disease, a liver disease, a kidney or renal disease, etc.

The amount of active agent administered per dose is an amount above the minimal therapeutic dose but below a toxic dose. The actual amount per dose may be determined by a physician depending on a number of factors, such as the medical history of the patient, the use of other therapies, the biologically active agent to be provided, and the nature of the disease. The amount of biologically active agent administered may be adjusted throughout treatment, depending on the patient's response to treatment and the presence or severity of any treatment-associated side effects. Exemplary dosages and treatment for compounds that have been approved by an appropriate regulatory agency are known and available to those skilled in the art. See, e.g., Physician's Desk Reference, 64th ed., Physician's Desk Reference Inc. (2010), Remington's Pharmaceutical Sciences, Mack Publishing Company, Philadelphia, Pa. (1985), and Remington The Science and Practice of Pharmacy, 21st ed., Lippincott Williams & Williams Publishers (2005).

In one embodiment, a single dose is administered of a biologically active agent to a patient in need thereof. In one embodiment, multiple doses are administered, wherein the multiple doses may be administered concurrently, sequentially or alternating. In one embodiment, the same formulation is administered over multiple doses. In one embodiment, the formulations differ over multiple doses. In various embodiments, the doses may be administered once a day, or for one, two, three, four or more consecutive days. In one embodiment, the doses are administered once a week. In one embodiment, the doses are administered once every other week. In one embodiment, patients receive at least two courses of a treatment regimen, and potentially more, depending on the response of the patient to the treatment. In single agent regimens, total courses of treatment are determined by the patient and physician based on observed responses and toxicity. The above dosage regimens are to be considered as non-limiting examples. Other dosage regimens are contemplated as being within the scope of the invention, and depend on the therapeutic effect desired.

The invention also provides a method for the treatment of a disease or condition comprising the step of administering a therapeutically effective amount of a lipid composition of the invention to a patient in need of treatment thereof. In one embodiment, the disease or condition is treatable by administering a RNA agent.

The invention also provides for use of a lipid composition of the invention in treating a disease or condition, including raising an immune response to an immunogen, in a patient. In one embodiment, the disease or condition is treatable by administering a RNA agent.

The total amount of lipid provided by the invention in the composition being administered is, in one embodiment, from about 5 to about 30 mg lipid per mg biologically active agent (e.g. RNA), in another embodiment from about 5 to about 25 mg lipid per mg biologically active agent (e.g. RNA), in another embodiment from about 7 to about 25 mg lipid per mg biologically active agent (e.g. RNA) and in one embodiment from about 7 to about 15 mg lipid per mg biologically active agent (e.g. RNA).

As used herein, "treatment" includes ameliorative, curative and prophylactic treatment. As used herein, a "patient" means an animal, preferably a mammal, preferably a human, in need of treatment.

The term "therapeutically effective amount" refers to the amount of the compound of the invention and the biologically active agent (e.g. the therapeutic compound) needed to treat or ameliorate a targeted disease or condition.

The term "immunologically effective amount" refers to the amount of the compound of the invention and of RNA which encodes an immunogen needed to elicit an immune response which recognizes the immunogen (e.g. in the context of a pathogen). The term "immunogen" refers to any substance or organism that provokes an immune response when introduced into the body. The phrase "RNA which encodes an immunogen" refers to a polynucleotide, such as a messenger RNA or a replicon (e.g., self-replicating RNA), that when administered to a cell or organism is capable of being translated into a polypeptide according to the codon sequence of such RNA.

By "proliferative disease" as used herein is meant any disease, condition, trait, genotype or phenotype characterized by unregulated cell growth or replication as is known in the art. In one embodiment, the proliferative disease is cancer. In one embodiment, the proliferative disease is a tumor. In one embodiment, the proliferative disease includes, but are not limited to, e.g., liquid tumors such as, e.g., leukemias, e.g., acute myelogenous leukemia (AML), chronic myelogenous leukemia (CML), acute lymphocytic leukemia (ALL), multiple myeloma, and chronic lymphocytic leukemia; and solid tumors, e.g., AIDS related cancers such as Kaposi's sarcoma; breast cancers; bone cancers; brain cancers; cancers of the head and neck, non-Hodgkins lymphoma, adenoma, squamous cell carcinoma, laryngeal carcinoma, gallbladder and bile duct cancers, cancers of the retina, cancers of the esophagus, gastrointestinal cancers, ovarian cancer, uterine cancer, thyroid cancer, testicular cancer, endometrial cancer, melanoma, colorectal cancer, lung cancer, bladder cancer, prostate cancer, lung cancer (including non-small cell lung carcinoma), pancreatic cancer, sarcomas, Wilms' tumor, cervical cancer, head and neck cancer, skin cancers, nasopharyngeal carcinoma, liposarcoma, epithelial carcinoma, renal cell carcinoma, gallbladder adeno carcinoma, endometrial sarcoma, multidrug resistant cancers. In one embodiment, the proliferative disease includes neovascularization associated with tumor angiogenesis, macular degeneration (e.g. wet/dry age related macular degeneration), corneal neovascularization, diabetic retinopathy, neovascular glaucoma, myopic degeneration. In one embodiment, the proliferative disease includes restenosis and polycystic kidney disease.

By "autoimmune disease" as used herein is meant any disease, condition, trait, genotype or phenotype characterized by autoimmunity as is known in the art. Autoimmune diseases include, but are not limited to, e.g., multiple sclerosis, diabetes mellitus, lupus, scleroderms, fibromyalgia, transplantation rejection (e.g. prevention of allograft rejection), pernicious anemia, rheumatoid arthritis, systemic lupus erythematosus, dermatomyositis, myasthenia gravis, lupus erythematosus, multiple sclerosis, and Grave's disease.

By "infectious disease" is meant any disease, disorder or condition associated with an infectious agent, such as a virus, bacteria, fungus, prion or parasite. The invention can be used to immunize against pathogens which cause infectious disease. Examples of such pathogens are given below.

By "neurologic disease" is meant any disease, disorder, or condition affecting the central or peripheral nervous system. Neurologic diseases include, but are not limited to, diseases or disorders of either the peripheral or the central nervous system including, e.g., Alzheimer's Disease, Aneurysm, Brain Injury, Carpal Tunnel Syndrome, Cerebral Aneurysm, Chronic Pain, Creutzfeldt-Jakob Disease, Epilepsy, Huntington's Disease, Meningitis, Seizure Disorders, and other neurologic diseases, disorders and syndromes.

By "respiratory disease" is meant any disease or condition affecting the respiratory tract. Respiratory diseases include, but are not limited to, e.g., asthma, chronic obstructive pulmonary disease (COPD), allergic rhinitis, sinusitis, allergies, impeded respiration, respiratory distress syndrome, cystic fibrosis, pulmonary hypertension or vasoconstriction and emphysema.

By "cardiovascular disease" is meant and disease or condition affecting the heart and vasculature. Cardiovascular diseases include, but are not limited to, e.g., coronary heart disease (CHD), cerebrovascular disease (CVD), aortic stenosis, peripheral vascular disease, myocardial infarction (heart attack), arrhythmia, ischemia, and congestive heart failure.

By "ocular disease" as used herein is meant any disease, condition, trait, genotype or phenotype of the eye and related structures. Ocular diseases include, but are not limited to, e.g., cystoid macular edema, diabetic retinopathy, lattice degeneration, retinal vein occlusion, retinal artery occlusion, macular degeneration (e.g. age related macular degeneration such as wet AMD or dry AMD), toxoplasmosis, retinitis pigmentosa, conjunctival laceration, corneal laceration, glaucoma, and the like.

By "metabolic disease" is meant any disease or condition affecting metabolic pathways. Metabolic disease can result in an abnormal metabolic process, either congenital due to inherited enzyme abnormality (inborn errors of metabolism) or acquired due to disease of an endocrine organ or failure of a metabolically important organ such as the liver. In one embodiment, metabolic disease includes obesity, insulin resistance, and diabetes (e.g. type I and/or type II diabetes).

By "dermatological disease" is meant any disease or condition of the skin, dermis, or any substructure therein such as a hair, a follicle, etc. Dermatological diseases, disorders, conditions, and traits can include psoriasis, ectopic dermatitis, skin cancers such as melanoma and basal cell carcinoma, hair loss, hair removal and alterations in pigmentation.

By "auditory disease" is meant any disease or condition of the auditory system, including the ear, such as the inner ear, middle ear, outer ear, auditory nerve, and any substructures therein. Auditory diseases, disorders, conditions, and traits can include hearing loss, deafness, tinnitus, vertigo, balance and motion disorders.

By "regenerative disease" is meant any disease or condition where insufficient cell or tissue generation or regeneration in vivo or in vitro prevents the establishment or restoration of proper organ function before or after injury, prevents or slows wound healing or resolution of ulcerative lesions, accelerates ageing, or prevents effective cell-based therapy. The term "messenger ribonucleic acid" (messenger RNA, mRNA) refers to a ribonucleic acid (RNA) molecule that mediates the transfer of genetic information to ribosomes in the cytoplasm, where it serves as a template for protein synthesis. It is synthesized from a DNA template during the process of transcription. See, *The American Heritage® Dictionary of the English Language, Fourth Edition* (Updated in 2009). Houghton Mifflin Company.

In eukaryotes, mRNA is transcribed in vivo at the chromosomes by the cellular enzyme RNA polymerase. During or after transcription in vivo, a 5' cap (also termed an RNA cap, an RNA 7-methylguanosine cap, or an RNA m7G cap) is added in vivo to the 5' end of the mRNA. The 5' cap is terminal 7-methylguanosine residue that is linked through a 5'-5'-triphosphate bond to the first transcribed nucleotide. In addition, most eukaryotic mRNA molecules have a polyadenylyl moiety ("poly(A) tail") at the 3' end of the mRNA molecule. In vivo, the eukaryotic cell adds the poly(A) tail after transcription, often at a length of about 250 adenosine residues (SEQ ID NO: 12). Thus, a typical mature eukaryotic mRNA has a structure that begins at the 5' end with an mRNA cap nucleotide followed by a 5' untranslated region (5'UTR) of nucleotides, then an open reading frame that begins with a start codon which is an AUG triplet of nucleotide bases, that is the coding sequence for a protein, and that ends with a stop codon that may be a UAA, UAG, or UGA triplet of nucleotide bases, then a 3' untranslated region (3'UTR) of nucleotides and ending with a polyadenosine tail. While the features of the typical mature eukaryotic mRNA are made naturally in a eukaryotic cell in vivo, the same or structurally and functionally equivalent features can be made in vitro using the methods of molecular biology. Accordingly, any RNA having the structure similar to a typical mature eukaryotic mRNA can function as a mRNA and is within the scope of the term "messenger ribonucleic acid".

The mRNA molecule is generally of a size that it can be encapsulated in a lipid nanoparticle of the invention. While the size of a mRNA molecule varies in nature depending upon the identity of the mRNA species that encodes for a particular protein, an average size for a mRNA molecule is 500-10,000 bases.

DNA can exist in at least two forms, which have different sizes. The first form of DNA is a very large-sized polymer called a chromosome. A chromosome contains the genetic information for many or most of the proteins in a cell and also contains information whereby the cell can control the replication of the DNA molecule. A bacterial cell may contain one or more chromosome. A eukaryotic cell usually contains more than one cell chromosome, each chromosome The second form of DNA is a shorter sized form. Many DNA molecules of the second form are of a size that it can be encapsulated in a lipid nanoparticle of the invention. Some of these shorter forms of DNA can be of a size to usefully encode for proteins. Examples of these second, shorter, useful forms of DNA include plasmids and other vectors. For a fuller description, see, Alberts B et al. (2007) *Molecular Biology of the Cell, Fifth Edition*, Garland Science.

A plasmid is a small DNA molecule that is physically separate from, and can replicate independently of, chromosomal DNA within a cell. Plasmids commonly exist in vivo as small circular, double-stranded DNA molecules. In nature, plasmids carry genes that can be transcribed and translated to proteins that may benefit survival of an organism (e.g. antibiotic resistance). In nature, plasmids can frequently be transmitted from one organism to another by horizontal gene transfer. Artificial or recombinant plasmids are widely used in molecular biology, serving to permit the replication of recombinant DNA sequences and the expression of useful proteins within host organisms. Plasmid sizes can vary from about 1 to over 25 kilobase pairs. A recombinant plasmid can be recombinantly made to be of a size that it can be encapsulated in a lipid nanoparticle of the invention.

In molecular biology, a vector is a DNA molecule used as a vehicle to artificially carry genetic material from one cell or from a biochemical reaction in vitro into another cell, where the DNA can be replicated and/or expressed. A vector containing foreign DNA is termed recombinant. Among the types of useful vectors are plasmids and viral vectors. Insertion of a vector into the target cell is usually called transformation for bacterial cells, transfection for eukaryotic cells, although insertion of a viral vector is often called transduction.

Viral vectors are generally recombinant viruses carrying modified viral DNA or RNA that has been rendered noninfectious, but that still contain viral promoters and also the transgene, thus allowing for translation of the transgene through a viral promoter. Viral vectors, in some embodiments, are designed for permanent incorporation of the insert into the host genome (integrate), and thus leave distinct genetic markers in the host genome after incorporating the transgene. A viral vector can be recombinantly made to be of a size that it can be encapsulated in a lipid nanoparticle of the invention.

The term "short interfering nucleic acid" (siNA) as used herein refers to any nucleic acid molecule capable of inhibiting or down regulating gene expression or viral replication by mediating RNA interference (RNAi) or gene silencing in a sequence-specific manner. It includes short interfering RNA (siRNA), microRNA (miRNA), short interfering oligonucleotides and chemically-modified short interfering nucleic acid molecules. siRNAs are responsible for RNA interference, the process of sequence-specific post-transcriptional gene silencing in animals and plants. siRNAs are generated by ribonuclease III cleavage from longer double-stranded RNA (dsRNA) which are homologous to, or specific to, the silenced gene target.

The term "RNA interference" (RNAi) is a post-transcriptional, targeted gene-silencing technique that uses a RNAi agent to degrade messenger RNA (mRNA) containing a sequence which is the same as or very similar to the RNAi agent. See: Zamore and Haley, 2005, Science, 309, 1519-1524; Zamore et al., 2000, Cell, 101, 25-33; Elbashir et al., 2001, Nature, 411, 494-498; and Kreutzer et al., PCT Publication WO 00/44895; Fire, PCT Publication WO 99/32619; Mello and Fire, PCT Publication WO 01/29058; and the like.

As used herein, RNAi is equivalent to other terms used to describe sequence specific RNA interference, such as post-transcriptional gene silencing, translational inhibition, transcriptional inhibition, or epigenetics. For example, the formulations containing lipids of the invention can be used in conjunction with siNA molecules to epigenetically silence genes at both the post-transcriptional level and/or the pre-transcriptional level. In a non-limiting example, modulation of gene expression by siNA molecules can result from siNA mediated cleavage of RNA (either coding or non-coding RNA) via RISC, or alternately, translational inhibition as is known in the art. In another embodiment, modulation of gene expression by siNA can result from transcriptional inhibition such as is reported e.g., in Janowski et al., 2005, Nature Chemical Biology, 1, 216-222.

The term "RNAi inhibitor" is any molecule that can down modulate (e.g. reduce or inhibit) RNA interference function or activity in a cell or patient. An RNAi inhibitor can down regulate, reduce or inhibit RNAi (e.g. RNAi mediated cleavage of a target polynucleotide, translational inhibition, or transcriptional silencing) by interaction with or interfering with the function of any component of the RNAi pathway, including protein components such as RISC, or nucleic acid components such as miRNAs or siRNAs. An RNAi inhibitor can be a siNA molecule, an antisense molecule, an aptamer, or a small molecule that interacts with or interferes with the function of RISC, a miRNA, or a siRNA or any other component of the RNAi pathway in a cell or patient. By inhibiting RNAi (e.g. RNAi mediated cleavage of a target polynucleotide, translational inhibition, or transcriptional silencing), an RNAi inhibitor can be used to modulate (e.g, up-regulate or down-regulate) the expression of a target gene. In one embodiment, an RNA inhibitor is used to up-regulate gene expression by interfering with (e.g. reducing or preventing) endogenous down-regulation or inhibition of gene expression through translational inhibition, transcriptional silencing, or RISC mediated cleavage of a polynucleotide (e.g. mRNA). By interfering with mechanisms of endogenous repression, silencing, or inhibition of gene expression, RNAi inhibitors of the invention can therefore be used to up-regulate gene expression for the treatment of diseases or conditions resulting from a loss of function. The term "RNAi inhibitor" is used interchangeably with the term "siNA" in various embodiments herein.

The term "enzymatic nucleic acid" as used herein refers to a nucleic acid molecule that has complementarity in a substrate binding region to a specified gene target, and also has an enzymatic activity that acts to specifically cleave a target RNA, thereby inactivating the target RNA molecule. The complementary regions allow sufficient hybridization of the enzymatic nucleic acid molecule to the target RNA and thus permit cleavage. Complementarity of 100% is preferred, but complementarity as low as 50-75% can also be useful in this invention (see e.g., Werner and Uhlenbeck, 1995, Nucleic Acids Research, 23, 2092-2096; Hammann et al., 1999, Antisense and Nucleic Acid Drug Dev., 9, 25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The key features of an enzymatic nucleic acid molecule are that it has a specific substrate binding site that is complementary to one or more of the target nucleic acid regions, and that it has nucleotide sequences within or surrounding that substrate binding site that impart a nucleic acid cleaving and/or ligation activity to the molecule (see, e.g., Cech et al., U.S. Pat. No. 4,987,071; Cech et al., 1988, 260 JAMA 3030). Ribozymes and enzymatic nucleic acid molecules of the invention can be chemically modified, e.g., as described in the art and elsewhere herein.

The term "antisense nucleic acid", as used herein, refers to a non-enzymatic nucleic acid molecule that binds to target RNA by means of RNA-RNA or RNA-DNA or RNA-PNA (protein nucleic acid; Egholm et al., 1993 Nature 365, 566) interactions and alters the activity of the target RNA (for a review, see Stein and Cheng, 1993 Science 261, 1004 and Woolf et al., U.S. Pat. No. 5,849,902). Antisense DNA can be synthesized chemically or expressed via the use of a single stranded DNA expression vector or equivalent thereof. Antisense molecules of the invention can be chemically modified, e.g. as described in the art.

The term "RNase H activating region" as used herein, refers to a region (generally greater than or equal to 4-25 nucleotides in length, preferably from 5-11 nucleotides in length) of a nucleic acid molecule capable of binding to a target RNA to form a non-covalent complex that is recognized by cellular RNase H enzyme (see e.g., Arrow et al., U.S. Pat. No. 5,849,902; Arrow et al., U.S. Pat. No. 5,989,912). The RNase H enzyme binds to the nucleic acid molecule-target RNA complex and cleaves the target RNA sequence.

The term "2-5A antisense chimera" as used herein, refers to an antisense oligonucleotide containing a 5'-phosphorylated 2'-5'-linked adenylate residue. These chimeras bind to target RNA in a sequence-specific manner and activate a cellular 2-5A-dependent ribonuclease that, in turn, cleaves the target RNA (Torrence et al., 1993 Proc. Natl. Acad. Sci. USA 90, 1300; Silverman et al., 2000, Methods Enzymol., 313, 522-533; Player and Torrence, 1998, Pharmacol. Ther., 78, 55-113). 2-5A antisense chimera molecules can be chemically modified, e.g. as described in the art.

The term "triplex forming oligonucleotides" as used herein, refers to an oligonucleotide that can bind to a double-stranded DNA in a sequence-specific manner to form a triple-strand helix. Formation of such triple helix structure has been shown to inhibit transcription of the targeted gene (Duval-Valentin et al., 1992 Proc. Natl. Acad. Sci. USA 89, 504; Fox, 2000, Curr. Med. Chem., 7, 17-37; Praseuth. et. al., 2000, Biochim. Biophys. Acta, 1489, 181-206). Triplex forming oligonucleotide molecules of the invention can be chemically modified, e.g. as described in the art.

The term "decoy RNA" as used herein, refers to an RNA molecule or aptamer that is designed to preferentially bind to a predetermined ligand. Such binding can result in the inhibition or activation of a target molecule. The decoy RNA or aptamer can compete with a naturally occurring binding target for the binding of a specific ligand. Similarly, a decoy RNA can be designed to bind to a receptor and block the binding of an effector molecule, or can be designed to bind to receptor of interest and prevent interaction with the receptor. Decoy molecules of the invention can be chemically modified, e.g. as described in the art.

The term "single stranded DNA" (ssDNA) as used herein refers to a naturally occurring or synthetic deoxyribonucleic acid molecule comprising a linear single strand, e.g., a ssDNA can be a sense or antisense gene sequence or EST (Expressed Sequence Tag).

The term "allozyme" as used herein refers to an allosteric enzymatic nucleic acid molecule, including e.g., U.S. Pat. Nos. 5,834,186; 5,741,679; 5,589,332; 5,871,914; and PCT publication Nos. WO 00/24931, WO 00/26226, WO 98/27104, and WO 99/29842.

The term "aptamer" as used herein is meant a polynucleotide composition that binds specifically to a target molecule, wherein the polynucleotide has a sequence that differs from a sequence normally recognized by the target molecule in a cell. Alternately, an aptamer can be a nucleic acid molecule that binds to a target molecule where the target molecule does not naturally bind to a nucleic acid. The target molecule can be any molecule of interest. Aptamer molecules of the invention can be chemically modified, e.g. as described in the art.

Formulation of Lipid Compositions

For pharmaceutical use, the lipid compositions of the invention may be administered by enteral or parenteral routes, including intravenous, intramuscular, subcutaneous, transdermal, airway (aerosol), oral, intranasal, rectal, vaginal, buccal, nasopharangeal, gastrointestinal or sublingual administration. The administration may be systemic (e.g., IV) or local (e.g., IM, SC, TD, intranasal, or topical). Topical administration may involve, e.g., catheterization, implantation, osmotic pumping, direct injection, dermal/transdermal application, stenting, ear/eye drops or portal vein administration. The compounds of formula (I) should be assessed for their biopharmaceutical properties, such as solubility and solution stability (across pH), permeability, etc., in order to select the most appropriate dosage form and route of administration for treatment of the proposed indication.

The compositions of the invention will generally, but not necessarily, be administered as a formulation in association with one or more pharmaceutically acceptable excipients. The term "excipient" includes any ingredient other than the compound(s) of the invention, the other lipid component(s) and the biologically active agent. An excipient may impart either a functional (e.g drug release rate controlling) and/or a non-functional (e.g. processing aid or diluent) characteristic to the formulations. The choice of excipient will to a large extent depend on factors such as the particular mode of administration, the effect of the excipient on solubility and stability, and the nature of the dosage form.

Typical pharmaceutically acceptable excipients include:
diluents, e.g. lactose, dextrose, sucrose, mannitol, sorbitol, cellulose and/or glycine;
lubricants, e.g. silica, talcum, stearic acid, its magnesium or calcium salt and/or polyethyleneglycol;
binders, e.g. magnesium aluminum silicate, starch paste, gelatin, tragacanth, methylcellulose, sodium carboxymethylcellulose and/or polyvinylpyrrolidone;
disintegrants, e.g. starches, agar, alginic acid or its sodium salt, or effervescent mixtures; and/or
absorbants, colorants, flavors and/or sweeteners.

The excipient may be an aqueous solution carrier which may optionally contain a buffer (e.g. a PBS buffer) and/or a sugar.

A thorough discussion of pharmaceutically acceptable excipients is available in Gennaro, *Remington: The Science and Practice of Pharmacy* 2000, 20th edition (ISBN: 0683306472).

The compositions of the invention may be administered orally. Oral administration may involve swallowing, so that the compound enters the gastrointestinal tract, and/or buccal, lingual, or sublingual administration by which the compound enters the blood stream directly from the mouth.

The compositions of the invention can be administered parenterally. The compounds and compositions of the invention may be administered directly into the blood stream, into subcutaneous tissue, into muscle, or into an internal organ. Suitable means for administration include intravenous, intraarterial, intrathecal, intraventricular, intraurethral, intrasternal, intracranial, intramuscular, intrasynovial and subcutaneous. Suitable devices for administration include needle (including microneedle) injectors, needle-free injectors and infusion techniques.

Parenteral formulations are typically aqueous or oily solutions. Where the solution is aqueous, excipients such as sugars (including but not restricted to glucose, mannitol, sorbitol, etc.) salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water (WFI).

Parenteral formulations may include implants derived from degradable polymers such as polyesters (i.e. polylactic acid, polylactide, polylactide-co-glycolide, polycapro-lactone, polyhydroxybutyrate), polyorthoesters and polyanhydrides. These formulations may be administered via surgical incision into the subcutaneous tissue, muscular tissue or directly into specific organs.

The preparation of parenteral formulations under sterile conditions, e.g., by lyophilisation, may readily be accomplished using standard pharmaceutical techniques well known to the skilled person.

The solubility of the compounds and compositions used in the preparation of parenteral solutions may be increased by the use of appropriate formulation techniques, such as the incorporation of co-solvents and/or solubility-enhancing agents such as surfactants, micelle structures and cyclodextrins.

The compositions of the invention can be administered intranasally or by inhalation, typically in the form of a dry powder (either alone, as a mixture, e.g., in a dry blend with lactose, or as a mixed component particle, e.g., mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, e.g., chitosan or cyclodextrin.

The pressurized container, pump, spray, atomizer, or nebuliser contains a solution or suspension of the compound(s) of the invention comprising, e.g., ethanol, aqueous ethanol, or a suitable alternative agent for dispersing, solubilising, or extending release of the compositions of the invention, a propellant(s) as solvent and an optional surfactant, such as sorbitan trioleate, oleic acid, or an oligolactic acid.

Prior to use in a dry powder or suspension formulation, the composition is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, e.g., from gelatin or hydroxypropylmethylcellulose), blisters and cartridges for use in an inhaler or insufflator may be formulated to contain a powder mix of the compound or composition of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

Formulations for inhaled/intranasal administration may be formulated to be immediate and/or modified release using, e.g., PGLA. Modified release formulations include delayed-, sustained-, pulsed-, controlled-, targeted and programmed release.

Suitable formulations for transdermal application include a therapeutically effective amount of a compound or composition of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin.

Lipid compositions of the invention are administered in any of a number of ways, including parenteral, intravenous, systemic, local, oral, intratumoral, intramuscular, subcutaneous, intraperitoneal, inhalation, or any such method of delivery. In one embodiment, the compositions are administered parenterally, i.e., intraarticularly, intravenously, intraperitoneally, subcutaneously, or intramuscularly. In a specific embodiment, the liposomal compositions are administered by intravenous infusion or intraperitoneally by a bolus injection.

Lipid compositions of the invention can be formulated as pharmaceutical compositions suitable for delivery to a subject. The pharmaceutical compositions of the invention will often further comprise one or more buffers (e.g., neutral buffered saline or phosphate buffered saline), carbohydrates (e.g., glucose, mannose, sucrose, dextrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate.

Suitable formulations for use in the present invention can be found, e.g., in Remington's Pharmaceutical Sciences, Mack Publishing Company, Philadelphia, Pa., 17.sup.th Ed. (1985). Often, compositions will comprise a solution of the lipid nanoparticles suspended in an acceptable carrier, such as an aqueous carrier.

In one embodiment, this invention provides for a pharmaceutical composition (i.e. formulation) comprising a lipid composition of the invention and a pharmaceutically acceptable carrier or excipient. In another embodiment at least one other lipid component is present in the lipid composition. In another embodiment the lipid composition is in the form of a liposome. In another embodiment the lipid composition is in the form of a lipid nanoparticle. In another embodiment the lipid composition is suitable for delivery to the liver. In another embodiment the lipid composition is suitable for delivery to a tumor. In another embodiment the lipid composition is suitable for local delivery applications (eye, ear, skin, lung); delivery to muscle (i.m.), fat, or sub cutaneous cells (s.c. dosing). In another embodiment the biologically active agent is a RNA or DNA.

For immunization purposes a composition will generally be prepared as an injectable, and will be administered by injection (e.g. by intramuscular injection).

The invention also provides a delivery device (e.g. syringe, nebuliser, sprayer, inhaler, dermal patch, etc.) containing a composition of the invention. This device can be used to administer a pharmaceutical composition to a subject e.g. to a human for immunization.

Cells and Organs Targeted by the Invention

The compounds, compositions, methods and uses of the invention can be used to deliver a biologically active agent to one or more of the following in a patient:
    the liver or liver cells (e.g. hepatocytes);
    a kidney or kidney cells;
    a tumor or tumor cells;
    the CNS or CNS cells (Central Nervous System, e.g. brain and/or spinal cord);
    the PNS or PNS cells (Peripheral Nervous System);
    a lung or lung cells;
    the vasculature or vascular cells;
    the skin or skin cells (e.g. dermis cells and/or follicular cells);
    an eye or ocular cells (e.g. macula, fovea, cornea, retina), and
    an ear or cells of the ear (e.g. cells of the inner ear, middle ear and/or outer ear).

The compounds, compositions, methods and uses of the invention can also be used to deliver a biologically active agent (e.g. RNA which encodes an immunogen) to cells of the immune system.

In one embodiment, the compounds, compositions, methods and uses of the invention are for delivering a biologically active agent to liver cells (e.g. hepatocytes). In one embodiment, the compounds, compositions, methods and uses of the invention are for delivering a biologically active agent to a tumor or to tumor cells (e.g. a primary tumor or metastatic cancer cells). In another embodiment, the compounds, compositions, methods and uses are for delivering a biologically active agent to the skin adipose, muscle and lymph nodes (i.e. sc dosing).

For delivery of a biologically active agent to the liver or liver cells, in one embodiment a composition of the invention is contacted with the liver or liver cells of the patient as is generally known in the art, such as via parental administration (e.g. intravenous, intramuscular, subcutaneous administration) or local administration (e.g. direct injection, portal vein injection, catheterization, stenting), to facilitate delivery.

For delivery of a biologically active agent to the kidney or kidney cells, in one embodiment a composition of the invention is contacted with the kidney or kidney cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to a tumor or tumor cells, in one embodiment a composition of the invention is contacted with the tumor or tumor cells of the patient as is generally known in the art, such as via parental administration (e.g. intravenous, intramuscular, subcutaneous administration) or local administration (e.g. direct injection, catheterization, stenting), to facilitate delivery.

For delivery of a biologically active agent to the CNS or CNS cells (e.g. brain cells and/or spinal cord cells), in one embodiment a composition of the invention is contacted with the CNS or CNS cells (e.g. brain cells and/or spinal cord cells) of the patient as is generally known in the art, such as via parental administration (e.g. intravenous, intramuscular, subcutaneous administration) or local administration (e.g. direct injection, catheterization, stenting, osmotic pump administration (e.g. intrathecal or ventricular)), to facilitate delivery.

For delivery of a biologically active agent to the PNS or PNS cells, in one embodiment a composition of the invention is contacted with the PNS or PNS cells of the patient as is generally known in the art, such as via parental administration (e.g. intravenous, intramuscular, subcutaneous administration) or local administration (e.g. direct injection), to facilitate delivery.

For delivery of a biologically active agent to a lung or lung cells, in one embodiment a composition of the invention is contacted with the lung or lung cells of the patient as is generally known in the art, such as via parental administration (e.g. intravenous, intramuscular, subcutaneous administration) or local administration (e.g. pulmonary administration directly to lung tissues and cells), to facilitate delivery.

For delivery of a biologically active agent to the vasculature or vascular cells, in one embodiment a composition of the invention is contacted with the vasculature or vascular cells of the patient as is generally known in the art, such as via parental administration (e.g. intravenous, intramuscular, subcutaneous administration) or local administration (e.g. clamping, catheterization, stenting), to facilitate delivery.

For delivery of a biologically active agent to the skin or skin cells (e.g. dermis cells and/or follicular cells), in one embodiment a composition of the invention is contacted with the skin or skin cells (e.g. dermis cells and/or follicular cells) of the patient as is generally known in the art, such as via parental administration (e.g. intravenous, intramuscular, subcutaneous administration) or local administration (e.g. direct dermal application, iontophoresis), to facilitate delivery.

For delivery of a biologically active agent to an eye or ocular cells (e.g. macula, fovea, cornea, retina), in one embodiment a composition of the invention is contacted with the eye or ocular cells (e.g. macula, fovea, cornea, retina) of the patient as is generally known in the art, such as via parental administration (e.g. intravenous, intramuscular, subcutaneous administration) or local administration (e.g. direct injection, intraocular injection, periocular injection, subretinal, iontophoresis, use of eyedrops, implants), to facilitate delivery.

For delivery of a biologically active agent to an ear or cells of the ear (e.g. cells of the inner ear, middle ear and/or outer ear), in one embodiment a composition of the invention is contacted with the ear or cells of the ear (e.g. cells of the inner ear, middle ear and/or outer ear) of the patient as is generally known in the art, such as via parental administration (e.g. intravenous, intramuscular, subcutaneous administration) or local administration (e.g. direct injection), to facilitate delivery.

For delivery of a biologically active agent (e.g. RNA encoding an immunogen) to cells of the immune system (e.g. antigen-presenting cells, including professional antigen presenting cells), in one embodiment composition of the invention is delivered intramuscularly, after which immune cells can infiltrate the delivery site and process delivered RNA and/or process encoded antigen produced by non-immune cells, such as muscle cells. Such immune cells can include macrophages (e.g. bone marrow derived macrophages), dendritic cells (e.g. bone marrow derived plasmacytoid dendritic cells and/or bone marrow derived myeloid dendritic cells), monocytes (e.g. human peripheral blood monocytes), etc. (e.g. see WO2012/006372).

Immunization According to the Invention

For immunization purposes, in some embodiments, the invention encompasses delivering a RNA that encodes an immunogen. The immunogen elicits an immune response which recognizes the immunogen, and so can be used to provide immunity against a pathogen, or against an allergen, or against a tumor antigen. Immunising against disease and/or infection caused by a pathogen is preferred.

The RNA is delivered with a lipid composition of the invention (e.g. formulated as a liposome or LNP). In some embodiments, the invention utilises liposomes within which immunogen-encoding RNA is encapsulated. Encapsulation within liposomes can protect RNA from RNase digestion. The encapsulation efficiency does not have to be 100%. Presence of external RNA molecules (e.g. on the exterior surface of liposome) or "naked" RNA molecules (RNA molecules not associated with a liposome) is acceptable. Preferably, for a composition comprising liposomes and RNA molecules, at least half of the RNA molecules (e.g., at least 50%, at least 55%, at least 60%, at least 65%, at least 70%, at least 75%, at least 80%, at least 85%, at least 90%, or at least 95% of the RNA molecules) are encapsulated in liposomes.

RNA molecules may also be complexed with LNPs. For example, it is not necessary that the lipid forms liposomes (with aqueous core) only. Some lipid nanoparticles may comprise a lipid core (e.g., the composition may comprise a mixture of liposomes and nanoparticles with a lipid core). In such cases, the RNA molecules may be encapsulated by LNPs that have an aqueous core, and complexed with the LNPs that have a lipid core by non-covalent interactions (e.g., ionic interactions between negatively charged RNA and cationic lipid). Encapsulation and complexation with LNPs (whether with a lipid or aqueous core) can protect RNA from RNase digestion. The encapsulation/complexation efficiency does not have to be 100%. Presence of "naked" RNA molecules (RNA molecules not associated with a liposome) is acceptable. Preferably, for a composition comprising a population of LNPs and a population of RNA molecules, at least half of the population of RNA molecules (e.g., at least 50%, at least 55%, at least 60%, at least 65%, at least 70%, at least 75%, at least 80%, at least 85%, at least 90%, or at least 95% of the RNA molecules) are either encapsulated in LNPs, or complexed with LNPs.

Liposomes and LNPs

Liposomes are usually divided into three groups: multilamellar vesicles (MLV); small unilamellar vesicles (SUV); and large unilamellar vesicles (LUV). MLVs have multiple bilayers in each vesicle, forming several separate aqueous compartments. SUVs and LUVs have a single bilayer encapsulating an aqueous core; SUVs typically have a diameter <50 nm, and LUVs have a diameter >50 nm. For delivery of immunogen-coding RNA, preferred range of diameters is in the range of 60-180 nm, and more preferably in the range of 80-160 nm.

The lipid composition can also be LNPs. The composition can comprise a mixture of nanoparticles having an aqueous core and nanoparticles having a lipid core or, in other embodiments may consist of substantially only aqueous core particles or substantially only fully lipid particles. For delivery of immunogen-coding RNA, preferred range of diameters is in the range of 60-180 nm, and in more particular embodiments, in the range of 80-160 nm.

A liposome or LNP can be part of a composition comprising a population of liposomes or LNPs, and the liposomes or LNPs within the population can have a range of diameters. For a composition comprising a population of liposomes or LNPs with different diameters, it is preferred that (i) at least 80% by number of the liposomes or LNPs have diameters in the range of 60-180 nm, e.g., in the range of 80-160 nm, (ii) the average diameter (by intensity e.g. Z-average) of the population is ideally in the range of 60-180 nm, e.g., in the range of 80-160 nm; and/or (iii) the diameters within the plurality have a polydispersity index <0.2.

To obtain liposomes or LNPs with the desired diameter(s), mixing can be performed using a process in which two feed streams of aqueous RNA solution are combined in a single mixing zone with one stream of an ethanolic lipid solution, all at the same flow rate e.g. in a microfluidic channel.

Useful mixtures of lipids, for forming lipid compositions (e.g., liposomes or LNPs) for immunization uses, comprise: a lipid of formula (I); cholesterol; and a PEGylated lipid, such as PEG-DMG i.e. PEG-conjugated 1,2-dimyristoyl-sn-glycero-3-phosphoethanolamine-N-[methoxy(polyethylene glycol). This mixture may also include a neutral zwitterionic lipid, such as DSPC (1,2-Diastearoyl-sn-glycero-3-phosphocholine) or DPyPE. These (and other) mixtures are used in the examples.

In certain embodiments, the lipid compositions provided by the invention (such as liposomes or LNPs) have adjuvant activity, i.e., in the absence of an immunogen, such as protein antigen or a nucleic acid (DNA or RNA), such as a nucleic acid encoding such an antigen. Therefore the lipids and lipid composition provided by the invention can be formulated with any manner of immunogen, e.g., polypeptide, nucleic acid, small molecule, et cetera. Thus, in some embodiments, compositions provided by the invention can be used in methods of generating an immune response to an immunogen, e.g., by administering a composition comprising a lipid or lipid composition provided by the invention together with an immunogen.

RNA Molecules

After in vivo administration of an immunization composition, the delivered RNA is released and is translated inside a cell to provide the immunogen in situ. In certain embodiments, the RNA is plus ("+") stranded, so it can be translated by cells without needing any intervening replication steps such as reverse transcription. It may also bind to TLR7 receptors expressed by immune cells, thereby initiating an adjuvant effect. Additionally or alternatively, the RNA may bind other receptors such as RIG I, MDA5, or RIG I and MDA5.

In certain embodiments, the RNA is a self-replicating RNA. A self-replicating RNA molecule (replicon) can, when delivered to a vertebrate cell even without any proteins, lead to the production of multiple daughter RNAs by transcription from itself (via an antisense copy which it generates from itself). A self-replicating RNA molecule is thus in certain embodiments, a (+) strand molecule that can be directly translated after delivery to a cell, and this translation provides a RNA-dependent RNA polymerase which then produces both antisense and sense transcripts from the delivered RNA. Thus the delivered RNA leads to the production of multiple daughter RNAs. These daughter RNAs, as well as collinear subgenomic transcripts, may be translated themselves to provide in situ expression of an encoded immunogen, or may be transcribed to provide further transcripts with the same sense as the delivered RNA which are translated to provide in situ expression of the immunogen. The overall result of this sequence of transcriptions is a huge amplification in the number of the introduced replicon RNAs and so the encoded immunogen becomes a major polypeptide product of the host cells.

One suitable system for achieving self-replication is to use an alphavirus-based RNA replicon. These (+) stranded replicons are translated after delivery to a cell to give of a replicase (or replicase-transcriptase). The replicase is translated as a polyprotein which auto cleaves to provide a replication complex which creates genomic (−) strand copies of the (+) strand delivered RNA. These (−) strand transcripts can themselves be transcribed to give further copies of the (+) stranded parent RNA and also to give a subgenomic transcript which encodes the immunogen. Translation of the subgenomic transcript thus leads to in situ expression of the immunogen by the infected cell. Suitable alphavirus replicons can use a replicase from a sindbis virus, a semliki forest virus, an eastern equine encephalitis virus, a Venezuelan equine encephalitis virus, etc. Mutant or wild-type viruses sequences can be used e.g. the attenuated TC83 mutant of VEEV has been used in replicons.

A preferred self-replicating RNA molecule thus encodes (i) a RNA-dependent RNA polymerase which can transcribe RNA from the self-replicating RNA molecule and (ii) an immunogen. The polymerase can be an alphavirus replicase e.g. comprising one or more of alphavirus proteins nsP1, nsP2, nsP3 and nsP4.

Whereas natural alphavirus genomes encode structural virion proteins in addition to the non structural replicase polyproteinin particular embodiments, a self-replicating RNA molecule of the invention does not encode alphavirus structural proteins. Thus a particular self replicating RNA can lead to the production of genomic RNA copies of itself in a cell, but not to the production of RNA-containing virions. The inability to produce these virions means that, unlike a wild-type alphavirus, the self-replicating RNA molecule cannot perpetuate itself in infectious form. The alphavirus structural proteins which are necessary for perpetuation in wild-type viruses are absent from self replicating RNAs of the invention and their place is taken by gene(s) encoding the immunogen of interest, such that the subgenomic transcript encodes the immunogen rather than the structural alphavirus virion proteins.

Thus a self-replicating RNA molecule useful with the invention may have two open reading frames. One open reading frame encodes a replicase e.g., the first, (5') open reading frame; the other open reading frame encodes an immunogen, e.g., the second, (3') open reading frame. In some embodiments the RNA may have additional (e.g. downstream) open reading frames e.g. to encode further immunogens (see below) or to encode accessory polypeptides.

A self-replicating RNA molecule can have a 5' sequence which is compatible with the encoded replicase.

Self-replicating RNA molecules can have various lengths but they are typically about 5000-25000 nucleotides long e.g. 8000-15000 nucleotides, or 9000-12000 nucleotides. Thus the RNA is longer than seen in siRNA or conventional mRNA delivery. In some embodiments, the self-replicating RNA is greater than about 2000 nucleotides, such as greater than about: 9000, 12000, 15000, 18000, 21000, 24000, or more nucleotides long.

A RNA molecule may have a 5' cap (e.g. a 7-methylguanosine). This cap can enhance in vivo translation of the RNA.

The 5' nucleotide of a RNA molecule useful with the invention may have a 5' triphosphate group. In a capped RNA this may be linked to a 7-methylguanosine via a 5'-to-5' bridge. A 5' triphosphate can enhance RIG-I binding and thus promote adjuvant effects.

A RNA molecule may have a 3' poly A tail. It may also include a poly A polymerase recognition sequence (e.g. AAUAAA) near its 3' end.

A RNA molecule useful with the invention for immunization purposes will typically be single-stranded. Single-stranded RNAs can generally initiate an adjuvant effect by binding to TLR7, TLR8, RNA helicases and/or PKR. RNA delivered in double-stranded form (dsRNA) can bind to TLR3, and this receptor can also be triggered by dsRNA which is formed either during replication of a single-stranded RNA or within the secondary structure of a single-stranded RNA.

RNA molecules for immunization purposes can conveniently be prepared by in vitro transcription (IVT). IVT can use a (cDNA) template created and propagated in plasmid form in bacteria, or created synthetically (for example by gene synthesis and/or polymerase chain-reaction (PCR) engineering methods). For instance, a DNA-dependent RNA polymerase (such as the bacteriophage T7, T3 or SP6 RNA polymerases) can be used to transcribe the RNA from a DNA template. Appropriate capping and poly A addition reactions can be used as required (although the replicon's poly-A is usually encoded within the DNA template). These RNA polymerases can have stringent requirements for the transcribed 5' nucleotide(s) and in some embodiments these requirements must be matched with the requirements of the encoded replicase, to ensure that the IVT transcribed RNA can function efficiently as a substrate for its self-encoded replicase.

As discussed in WO2011/005799, the self-replicating RNA can include (in addition to any 5' cap structure) one or more nucleotides having a modified nucleobase. For instance, a self-replicating RNA can include one or more modified pyrimidine nucleobases, such as pseudouridine and/or 5 methylcytosine residues. In some embodiments, however, the RNA includes no modified nucleobases, and may include no modified nucleotides i.e. all of the nucleotides in the RNA are standard A, C, G and U ribonucleotides (except for any 5' cap structure, which may include a 7' methylguanosine). In other embodiments, the RNA may include a 5' cap comprising a 7' methylguanosine, and the first 1, 2 or 3 5' ribonucleotides may be methylated at the 2' position of the ribose.

A RNA used with the invention for immunization purposes ideally includes only phosphodiester linkages between nucleosides, but in some embodiments it can contain phosphoramidate, phosphorothioate, and/or methylphosphonate linkages.

The invention includes embodiments where multiple species of RNAs are formulated with a lipid composition provided by the invention, such as 2, 3, 4, 5, 6, 7, 8, 9, 10, or more species of RNA, including different classes of RNA (such as mRNA, siRNA, self-replicating RNAs, and combinations thereof).

Immunogens

RNA molecules used with the invention for immunization purposes, in some embodiments, encode a polypeptide immunogen. In these embodiments, after administration, the RNA is translated in vivo and the immunogen can elicit an immune response in the recipient. The immunogen may elicit an immune response against a pathogen (e.g. a bacterium, a virus, a fungus or a parasite) but, in some embodiments, it elicits an immune response against an allergen or a tumor antigen. The immune response may comprise an antibody response (usually including IgG) and/or a cell mediated immune response. The polypeptide immunogen will typically elicit an immune response which recognises the corresponding pathogen (or allergen or tumor) polypeptide, but in some embodiments the polypeptide may act as a mimotope to elicit an immune response which recognises a saccharide. The immunogen will typically be a surface polypeptide e.g. an adhesin, a hemagglutinin, an envelope glycoprotein, a spike glycoprotein, etc.

The RNA molecule can encode a single polypeptide immunogen or multiple polypeptides. Multiple immunogens can be presented as a single polypeptide immunogen (fusion polypeptide) or as separate polypeptides. If immunogens are expressed as separate polypeptides from a replicon then one or more of these may be provided with an upstream IRES or an additional viral promoter element. Alternatively, multiple immunogens may be expressed from a polyprotein that encodes individual immunogens fused to a short autocatalytic protease (e.g. foot-and-mouth disease virus 2A protein), or as inteins.

In certain embodiments, polypeptide immunogens (e.g., 1, 2, 3, 4, 5, 6, 7, 8, 9, 10, or more immunogens) may be used, either alone or together with a RNA molecule, such as a self-replicating RNA, encoding one or more immunogens (either the same or different as the polypeptide immunogens).

In some embodiments the immunogen elicits an immune response against one of these bacteria:

*Neisseria meningitidis*: useful immunogens include, but are not limited to, membrane proteins such as adhesins, autotransporters, toxins, iron acquisition proteins, and factor H binding protein. A combination of three useful polypeptides is disclosed in Giuliani et al. (2006) *Proc Natl Acad Sci USA* 103(29):10834-9.

*Streptococcus pneumoniae*: useful polypeptide immunogens are disclosed in WO2009/016515. These include, but are not limited to, the RrgB pilus subunit, the beta-N-acetyl-hexosaminidase precursor (spr0057), spr0096, General stress protein GSP-781 (spr2021, SP2216), serine/threonine kinase StkP (SP1732), and pneumococcal surface adhesin PsaA.

*Streptococcus pyogenes*: useful immunogens include, but are not limited to, the polypeptides disclosed in WO02/34771 and WO2005/032582.

*Moraxella catarrhalis*.

*Bordetella pertussis*: Useful pertussis immunogens include, but are not limited to, pertussis toxin or toxoid (PT), filamentous haemagglutinin (FHA), pertactin, and agglutinogens 2 and 3.

*Staphylococcus aureus*: Useful immunogens include, but are not limited to, the polypeptides disclosed in WO2010/119343, such as a hemolysin, esxA, esxB, ferrichrome-binding protein (sta006) and/or the sta011 lipoprotein.

*Clostridium tetani*: the typical immunogen is tetanus toxoid.

*Corynebacterium diphtheriae*: the typical immunogen is diphtheria toxoid.

*Haemophilus influenzae*: Useful immunogens include, but are not limited to, the polypeptides disclosed in WO2006/110413 and WO2005/111066.

*Pseudomonas aeruginosa*

*Streptococcus agalactiae*: useful immunogens include, but are not limited to, the polypeptides disclosed in WO02/34771.

*Chlamydia trachomatis*: Useful immunogens include, but are not limited to, PepA, LcrE, ArtJ, DnaK, CT398, OmpH-like, L7/L12, OmcA, AtoS, CT547, Eno, HtrA and MurG (e.g. as disclosed in WO2005/002619). LcrE (WO2006/138004) and HtrA (WO2009/109860) are two preferred immunogens.

*Chlamydia pneumoniae*: Useful immunogens include, but are not limited to, the polypeptides disclosed in WO02/02606.

*Helicobacter pylori*: Useful immunogens include, but are not limited to, CagA, VacA, NAP, and/or urease (WO03/018054).

*Escherichia coli*: Useful immunogens include, but are not limited to, immunogens derived from enterotoxigenic *E. coli* (ETEC), enteroaggregative *E. coli* (EAggEC), diffusely adhering *E. coli* (DAEC), enteropathogenic *E. coli* (EPEC), extraintestinal pathogenic *E. coli* (ExPEC) and/or enterohemorrhagic *E. coli* (EHEC). ExPEC strains include uropathogenic *E. coli* (UPEC) and meningitis/sepsis-associated *E. coli* (MNEC). Useful UPEC immunogens are disclosed in WO2006/091517 and WO2008/020330. Useful MNEC immunogens are disclosed in WO2006/089264. A useful immunogen for several *E. coli* types is AcfD (WO2009/104092).

*Bacillus anthracis*

*Yersinia pestis*: Useful immunogens include, but are not limited to, those disclosed in WO2007/049155 and WO2009/031043.

*Staphylococcus epidermis*
*Clostridium perfringens* or *Clostridium botulinums*
*Legionella pneumophila*
*Coxiella burnetii*
*Brucella*, such as *B. abortus, B. canis, B. melitensis, B. neotomae, B. ovis, B. suis, B. pinnipediae*.
*Francisella*, such as *F. novicida, F. philomiragia, F. tularensis*.
*Neisseria gonorrhoeae*
*Treponema pallidum*
*Haemophilus ducreyi*
*Enterococcus faecalis* or *Enterococcus faecium*
*Staphylococcus saprophyticus*
*Yersinia enterocolitica*
*Mycobacterium tuberculosis*
*Rickettsia*
*Listeria monocytogenes*
*Vibrio cholerae*
*Salmonella typhi*
*Borrelia burgdorferi*
*Porphyromonas gingivalis*
*Klebsiella*

In some embodiments the immunogen elicits an immune response against one of these viruses:

Orthomyxovirus: Useful immunogens can be from an influenza A, B or C virus, such as the hemagglutinin, neuraminidase or matrix M2 proteins. Where the immunogen is an influenza A virus hemagglutinin it may be from any subtype e.g. H1, H2, H3, H4, H5, H6, H7, H8, H9, H10, H11, H12, H13, H14, H15 or H16.

Paramyxoviridae viruses: immunogens include, but are not limited to, those derived from Pneumoviruses (e.g. respiratory syncytial virus, RSV), Rubulaviruses (e.g. mumps virus), Paramyxoviruses (e.g. parainfluenza virus), Metapneumoviruses and Morbilliviruses (e.g. measles virus).

Poxviridae: immunogens include, but are not limited to, those derived from Orthopoxvirus such as Variola vera, including but not limited to, Variola major and Variola minor.

Picornavirus: immunogens include, but are not limited to, those derived from Picornaviruses, such as Enteroviruses, Rhinoviruses, Heparnavirus, Cardioviruses and Aphthoviruses. In one embodiment, the enterovirus is a poliovirus e.g. a type 1, type 2 and/or type 3 poliovirus. In another embodiment, the enterovirus is an EV71 enterovirus. In another embodiment, the enterovirus is a coxsackie A or B virus.

Bunyavirus: immunogens include, but are not limited to, those derived from an Orthobunyavirus, such as California encephalitis virus, a Phlebovirus, such as Rift Valley Fever virus, or a Nairovirus, such as Crimean-Congo hemorrhagic fever virus.

Heparnavirus: immunogens include, but are not limited to, those derived from a Heparnavirus, such as hepatitis A virus (HAV).

Filovirus: immunogens include, but are not limited to, those derived from a filovirus, such as an Ebola virus (including a Zaire, Ivory Coast, Reston or Sudan ebolavirus) or a Marburg virus.

Togavirus: immunogens include, but are not limited to, those derived from a Togavirus, such as a Rubivirus, an Alphavirus, or an Arterivirus. This includes rubella virus.

Flavivirus: immunogens include, but are not limited to, those derived from a Flavivirus, such as Tick-borne encephalitis (TBE) virus, Dengue (types 1, 2, 3 or 4) virus, Yellow Fever virus, Japanese encephalitis virus, Kyasanur Forest Virus, West Nile encephalitis virus, St. Louis encephalitis virus, Russian spring-summer encephalitis virus, Powassan encephalitis virus.

Pestivirus: immunogens include, but are not limited to, those derived from a Pestivirus, such as Bovine viral diarrhea (BVDV), Classical swine fever (CSFV) or Border disease (BDV).

Hepadnavirus: immunogens include, but are not limited to, those derived from a Hepadnavirus, such as Hepatitis B virus. A composition can include hepatitis B virus surface antigen (HBsAg).

Other hepatitis viruses: A composition can include an immunogen from a hepatitis C virus, delta hepatitis virus, hepatitis E virus, or hepatitis G virus.

Rhabdovirus: immunogens include, but are not limited to, those derived from a Rhabdovirus, such as a Lyssavirus (e.g. a Rabies virus) and Vesiculovirus (VSV).

Caliciviridae: immunogens include, but are not limited to, those derived from Calciviridae, such as Norwalk virus (Norovirus), and Norwalk-like Viruses, such as Hawaii Virus and Snow Mountain Virus.

Coronavirus: immunogens include, but are not limited to, those derived from a SARS coronavirus, avian infectious bronchitis (IBV), Mouse hepatitis virus (MHV), and Porcine transmissible gastroenteritis virus (TGEV). The coronavirus immunogen may be a spike polypeptide.

Retrovirus: immunogens include, but are not limited to, those derived from an Oncovirus, a Lentivirus (e.g. HIV-1 or HIV-2) or a Spumavirus.

Reovirus: immunogens include, but are not limited to, those derived from an Orthoreovirus, a Rotavirus, an Orbivirus, or a Coltivirus.

Parvovirus: immunogens include, but are not limited to, those derived from Parvovirus B19.

Herpesvirus: immunogens include, but are not limited to, those derived from a human herpesvirus, such as, by way of example only, Herpes Simplex Viruses (HSV) (e.g. HSV types 1 and 2), Varicella-zoster virus (VZV), Epstein-Barr virus (EBV), Cytomegalovirus (CMV), Human Herpesvirus 6 (HHV6), Human Herpesvirus 7 (HHV7), and Human Herpesvirus 8 (HHV8).

Papovaviruses: immunogens include, but are not limited to, those derived from Papillomaviruses and Polyomaviruses. The (human) papillomavirus may be of serotype 1, 2, 4, 5, 6, 8, 11, 13, 16, 18, 31, 33, 35, 39, 41, 42, 47, 51, 57, 58, 63 or 65 e.g. from one or more of serotypes 6, 11, 16 and/or 18.

Adenovirus: immunogens include those derived from serotype 36 (Ad-36).

In some embodiments, the immunogen elicits an immune response against a virus which infects fish, such as: infectious salmon anemia virus (ISAV), salmon pancreatic disease virus (SPDV), infectious pancreatic necrosis virus (IPNV), channel catfish virus (CCV), fish lymphocystis disease virus (FLDV), infectious hematopoietic necrosis virus (IHNV), koi herpesvirus, salmon picorna-like virus (also known as picorna-like virus of atlantic salmon), landlocked salmon virus (LSV), atlantic salmon rotavirus (ASR), trout strawberry disease virus (TSD), coho salmon tumor virus (CSTV), or viral hemorrhagic septicemia virus (VHSV).

Fungal immunogens may be derived from Dermatophytres, including: *Epidermophyton floccusum, Microsporum audouini, Microsporum canis, Microsporum distortum, Microsporum equinum, Microsporum gypsum, Microsporum nanum, Trichophyton concentricum, Trichophyton equinum, Trichophyton gallinae, Trichophyton gypseum, Trichophyton megnini, Trichophyton mentagrophytes, Trichophyton quinckeanum, Trichophyton rubrum, Trichophyton schoenleini, Trichophyton tonsurans, Trichophyton verrucosum, T. verrucosum* var. album, var. discoides, var. ochraceum, *Trichophyton violaceum*, and/or *Trichophyton faviforme*; or from *Aspergillus fumigatus, Aspergillus flavus, Aspergillus niger, Aspergillus nidulans, Aspergillus terreus, Aspergillus sydowii, Aspergillus flavatus, Aspergillus glaucus, Blastoschizomyces capitatus, Candida albicans, Candida enolase, Candida tropicalis, Candida glabrata, Candida krusei, Candida parapsilosis, Candida stellatoidea, Candida kusei, Candida parakwsei, Candida lusitaniae, Candida pseudotropicalis, Candida guilliermondi, Cladosporium carrionii, Coccidioides immitis, Blastomyces dermatidis, Cryptococcus neoformans, Geotrichum clavatum, Histoplasma capsulatum, Klebsiella pneumoniae, Microsporidia, Encephalitozoon* spp., *Septata intestinalis* and *Enterocytozoon bieneusi*; the less common are *Brachiola* spp, *Microsporidium* spp., *Nosema* spp., *Pleistophora* spp., *Trachipleistophora* spp., *Vittaforma* spp *Paracoccidioides brasiliensis, Pneumocystis carinii, Pythiumn insidiosum, Pityrosporum ovale, Sacharomyces cerevisae, Saccharomyces boulardii, Saccharomyces pombe, Scedosporium apiospermum, Sporothrix schenckii, Trichosporon beigelii, Toxoplasma gondii, Penicillium marneffei, Malassezia* spp., *Fonsecaea* spp., *Wangiella* spp., *Sporothrix* spp., *Basidiobolus* spp., *Conidiobolus* spp., *Rhizopus* spp, *Mucor* spp, *Absidia* spp, *Mortierella* spp, *Cunninghamella* spp, *Saksenaea* spp., *Alternaria* spp, *Curvularia* spp, *Helminthosporium* spp, *Fusarium* spp, *Aspergillus* spp, *Penicillium* spp, *Monolinia* spp, *Rhizoctonia* spp, *Paecilomyces* spp, *Pithomyces* spp, and *Cladosporium* spp.

In some embodiments the immunogen elicits an immune response against a parasite from the *Plasmodium* genus, such as *P. falciparum, P. vivax, P. malariae* or *P. ovale*. Thus the invention may be used for immunising against malaria. In some embodiments the immunogen elicits an immune response against a parasite from the Caligidae family, particularly those from the *Lepeophtheirus* and *Caligus* genera e.g. sea lice such as *Lepeophtheirus salmonis* or *Caligus rogercresseyi*.

In some embodiments the immunogen elicits an immune response against: pollen allergens (tree-, herb, weed-, and grass pollen allergens); insect or arachnid allergens (inhalant, saliva and venom allergens, e.g. mite allergens, cockroach and midges allergens, hymenopthera venom allergens); animal hair and dandruff allergens (from e.g. dog, cat, horse, rat, mouse, etc.); and food allergens (e.g. a gliadin). Important pollen allergens from trees, grasses and herbs are such originating from the taxonomic orders of Fagales, Oleales, Pinales and platanaceae including, but not limited to, birch (Betula), alder (Alnus), hazel (Corylus), hornbeam (Carpinus) and olive (Olea), cedar (Cryptomeria and Juniperus), plane tree (Platanus), the order of Poales including grasses of the genera *Lolium, Phleum, Poa, Cynodon, Dactylis, Holcus, Phalaris, Secale,* and *Sorghum*, the orders of Asterales and Urticales including herbs of the genera *Ambrosia, Artemisia,* and *Parietaria*. Other important inhalation allergens are those from house dust mites of the genus *Dermatophagoides* and *Euroglyphus*, storage mite e.g. *Lepidoglyphys, Glycyphagus* and *Tyrophagus*, those from cockroaches, midges and fleas e.g. *Blatella, Periplaneta, Chironomus* and *Ctenocepphalides*, and those from mammals such as cat, dog and horse, venom allergens including such originating from stinging or biting insects such as those from the taxonomic order of Hymenoptera including bees (Apidae), wasps (Vespidea), and ants (Formicoidae).

In some embodiments the immunogen is a tumor antigen selected from: (a) cancer-testis antigens such as NY-ESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors; (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT; (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolase A (associated with, e.g., lung cancer), PRAME (associated with, e.g., melanoma), HER-2/neu (associated with, e.g., breast, colon, lung and ovarian cancer), mammaglobin, alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer); (d) shared antigens, for example, melanoma-melanocyte differentiation antigens such as MART-1/Melan A, gp100, MC1R, melanocyte-stimulating hormone receptor, tyrosinase, tyrosinase related protein-1/TRP1 and tyrosinase related protein-2/TRP2 (associated with, e.g., melanoma); (e) prostate associated antigens such as PAP, PSA, PSMA, PSH-P1, PSM-P1, PSM-P2, associated with e.g., prostate cancer; (f) immunoglobulin idiotypes (associated with myeloma and B cell lymphomas, for example). In certain embodiments, tumor immunogens include, but are not limited to, p15, Hom/Mel-40, H-Ras, E2A-PRL, H4-RET, IGH-IGK, MYL-RAR, Epstein Barr virus antigens, EBNA, human papillomavirus (HPV) antigens, including E6 and E7, hepatitis B and C virus antigens, human T-cell lymphotropic virus antigens, TSP-180, p185erbB2, p180erbB-3, c-met, mn-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein/cyclophilin C-associated protein), TAAL6, TAG72, TLP, TPS, and the like.

Pharmaceutical Compositions

A pharmaceutical composition of the invention, particularly one useful for immunization, may include one or more small molecule immunopotentiators. For example, the composition may include a TLR2 agonist (e.g. Pam3CSK4), a TLR4 agonist (e.g. an aminoalkyl glucosaminide phosphate, such as E6020), a TLR7 agonist (e.g. imiquimod), a TLR8 agonist (e.g. resiquimod) and/or a TLR9 agonist (e.g. IC31). Any such agonist ideally has a molecular weight of <2000 Da. Such agonist(s) can, in some embodiments, be encapsulated with the RNA inside liposomes, or encapsulated or complexed with LNPs, but in other embodiments they are unencapsulated or uncomplexed.

Pharmaceutical compositions of the invention may have an osmolality of between 200 mOsm/kg and 400 mOsm/kg, e.g. between 240-360 mOsm/kg, or between 290-310 mOsm/kg.

Pharmaceutical compositions of the invention may include one or more preservatives, such as thiomersal or 2 phenoxyethanol. Mercury-free compositions can be made and preservative-free vaccines can be prepared.

Compositions comprise an immunologically effective amount of lipid compositions described herein (e.g., liposomes and LNPs), as well as any other components, as needed. Immunologically effective amount refers to the amount administered to an individual, either in a single dose or as part of a series, is effective for treatment (e.g., prophylactic immune response against a pathogen). This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctors assessment of the medical situation, and other relevant factors. It is expected that the amount will fall in a relatively broad range that can be determined through routine trials. The compositions of the invention will generally be expressed in terms of the amount of RNA per dose. A preferred dose has ≤100 μg RNA (e.g. from 10-100 μg, such as about 10 μg, 25 μg, 50 μg, 75 μg or 100 μg), but expression can be seen at much lower levels e.g. ≤1 μg/dose, ≤100 ng/dose, ≤10 ng/dose, ≤1 ng/dose, etc.

The invention also provides a delivery device (e.g. syringe, nebuliser, sprayer, inhaler, dermal patch, etc.) containing a pharmaceutical composition of the invention. This device can be used to administer the composition to a vertebrate subject.

Liposomes or LNPs of the invention do not comprise ribosomes.

Methods of Treatment and Medical Uses

The liposome-formulated or LNP-formulated RNA and pharmaceutical compositions described herein are for in vivo use for inducing an immune response against an immunogen of interest.

The invention provides a method for inducing an immune response in a vertebrate comprising administering an effective amount of the liposome-formulated or LNP-formulated RNA, or pharmaceutical composition, as described herein. The immune response is preferably protective and preferably involves antibodies and/or cell-mediated immunity. The compositions may be used for both priming and boosting purposes. Alternatively, a prime-boost immunization schedule can be a mix of RNA and the corresponding polypeptide immunogen (e.g., RNA prime, protein boost).

The invention also provides a liposome, LNP, or pharmaceutical composition for use in inducing an immune response in a vertebrate.

The invention also provides the use of a liposome, LNP, or pharmaceutical composition in the manufacture of a medicament for inducing an immune response in a vertebrate.

By inducing an immune response in the vertebrate by these uses and methods, the vertebrate can be protected against various diseases and/or infections e.g. against bacterial and/or viral diseases as discussed above. The liposomes, LNPs, and compositions are immunogenic, and are more preferably vaccine compositions. Vaccines according to the invention may either be prophylactic (i.e. to prevent infection) or therapeutic (i.e. to treat infection), but will typically be prophylactic.

The vertebrate is preferably a mammal, such as a human or a large veterinary mammal (e.g. horses, cattle, deer, goats, pigs). As used herein "large mammal" refers to mammals having a typical or average adult weight of at least 5 kg, preferably at least 7 kg. Such large mammals can include, for example, humans, non-human primates, dogs, pigs, cattle, deer, goats, and is meant to exclude small mammals, such as mice, rats, guinea pigs, and other rodents.

Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc.

Vaccines prepared according to the invention may be used to treat both children and adults. Thus a human patient may be less than 1 year old, less than 5 years old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population. Compositions of the invention will generally be administered directly to a patient. Direct delivery may be accomplished by parenteral injection (e.g. subcutaneously, intraperitoneally, intravenously, intramuscularly, intradermally, or to the interstitial space of a tissue; intraglossal injection is not typically used for immunization purposes. Alternative delivery routes include rectal, oral (e.g. tablet, spray), buccal, sublingual, vaginal, topical, transdermal or transcutaneous, intranasal, ocular, aural, pulmonary or other mucosal administration. Intradermal and intramuscular administration are two preferred routes. Injection may be via a needle (e.g. a hypodermic needle), but needle-free injection may alternatively be used. A typical intramuscular dose is 0.5 ml.

The invention may be used to induce systemic and/or mucosal immunity, preferably to elicit an enhanced systemic and/or mucosal immunity.

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.). In one embodiment, multiple doses may be administered approximately 6 weeks, 10 weeks and 14 weeks after birth, e.g. at an age of 6 weeks, 10 weeks and 14 weeks, as often used in the World Health Organisation's Expanded Program on Immunisation ("EPI"). In an alternative embodiment, two primary doses are administered about two months apart, e.g. about 7, 8 or 9 weeks apart, followed by one or more booster doses about 6 months to 1 year after the second primary dose, e.g. about 6, 8, 10 or 12 months after the second primary dose. In a further embodiment, three primary doses are administered about two months apart, e.g. about 7, 8 or 9 weeks apart, followed by one or more booster doses about 6 months to 1 year after the third primary dose, e.g. about 6, 8, 10, or 12 months after the third primary dose.

EXAMPLES

Cationic Lipids of Formula (I)

The following examples are intended to illustrate the invention and are not to be construed as being limitations thereon. Temperatures are given in degrees centigrade. If not mentioned otherwise, all evaporative concentrations are performed under reduced pressure, preferably between about 15 mm Hg and 100 mm Hg (=20-133 mbar). The structure of final products, intermediates and starting materials is confirmed by standard analytical methods, e.g., microanalysis or spectroscopic characteristics, e.g., MS, IR, or NMR. Abbreviations used are those conventional in the art, some of which are defined below.

Flash column purification is preferably carried out on silica gel using an appropriate eluent of isocratic or gradient composition.

HPLC analysis is performed on a Waters Atlantis dC18 column (4.6×150 mm, 3 mm), with gradient elution (0% to 95% acetonitrile in water modified with 0.1% v/v trifluoroacetic acid over 20 min and a flow rate of 1.4 mL/min), unless otherwise described.

1H NMR spectra were recorded on a Bruker Avance II 400 MHz spectrometer. All chemical shifts are reported in parts per million (δ) relative to tetramethylsilane. The following abbreviations are used to denote signal patterns: s=singlet, d=doublet, t=triplet, q=quartet, m=multiplet, br=broad. ES-MS data were recorded using a Waters LTC Premier mass spectrometer with a dual electrospray ionization source on an Agilent 1100 liquid chromatograph. Sulfadimethoxine [Sigma, m/z=311.0814 (M+1)] was used as a reference acquired through the LockSpray™ channel every third scan. The mass accuracy of the system has been found to be <5 ppm.

ABBREVIATIONS

AcOH acetic acid
Aq aqueous
Ar aryl
Atm atmosphere
BOC tert-Butyl-carbonate
br.s., bs broad singlet
° C. Celsius
$CD_2Cl_2$ deuterated dichloromethane
$CDCl_3$ deuterated chloroform
$CH_2Cl_2$, DCM dichloromethane
$CH_3CN$, MeCN acetonitrile
d doublet
dd doublet of doublets
ddd doublet of doublets of doublets
DIPEA N-ethyldiisopropylamine
DME 1,4-dimethoxyethane
DMF N,N-dimethylformamide
DMAP dimethyl aminopyridine
DMSO dimethylsulfoxide
dt doublet of triplets
EDC 1-ethyl-3-(3-dimethylaminopropyl)carbodiimide
EtOAc ethyl acetate
EtOH ethanol
FCC flash column chromatography
h hour
HBTU (2-(1H-benzotriazole-1-yl)-1,1,3,3-tetramethyluronium hexafluorophosphate
HCl hydrochloric acid
HMPA hexamethylphosphoramide
HPLC high pressure liquid chromatography
HT high throughput
IBX 2-Iodoxybenzoic acid
i-PrOH isopropyl alcohol
$H_2O$ water
K kelvin
KOH potassium hydroxide
LC liquid chromatography
M molar
m multiplet
MeOH methanol
$MgSO_4$ magnesium sulfate
MHz mega herz
mL milliliter
mm millimeter
mmol millimole
min. minute
mRNA messenger ribonucleic acid MS mass spectroscopy
mw microwave
NaH sodium hydride
NaHMDS sodium hexamethyldisilazane
NaOEt sodium ethoxide
NaOH sodium hydroxide
$Na_2SO_4$ sodium sulfate
$NEt_3$ triethylamine
ng nanogram
$NH_3$ ammonia
NMR nuclear magnetic resonance
quint. quintuplet
Pd/C palladium on carbon
Rf retardation factor
rt room temperature
Rt Retention time
s singlet
siRNA small interfering ribonucleic acid
SM starting material
t triplet
TFA trifluoroacetic acid
THF tetrahydrofuran
TLC thin layer chromatography
UPLC ultra performance liquid chromatography
wt weight
μg microgram
μL microliter
PMA phosphomolybdic acid
RBF round bottom flask
TBS tert-butyl silyl
All compounds are named using AutoNom.
LC Specificity:

LC method 1: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 60/40 to 0.1/99.9 was applied over 1.4 min., then held for 0.6 min. (1.0 mL/min. as solvent flow) at an oven temperature of 50° C.

LC method 2: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 60/40 to 0.1/99.9 was applied over 3.4 min., then held for 1.6 min. (1.0 mL/min. as solvent flow) at an oven temperature of 50° C.

LC method 3: The retention times (Rt) were obtained on an Agilent 110 system with an inertsil C8 column, 3.0 μm, 3.0×30 mm. A gradient of $H_2O$ (+0.1% formic acid)/$CH_3CN$ (+0.1% formic acid) 60/40 to 5/95 was applied over 1.0 min., then held for 1.0 min. (2.0 mL/min. as solvent flow) at an oven temperature of 18° C.

LC method 4: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 0/100 was applied over 2.0 min., then held for 3.0 min. (1.0 mL/min. as solvent flow) at an oven temperature of 50° C.

LC method 5: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 0/100 was applied over 1.0 min., then held for 1.0 min. (1.0 mL/min. as solvent flow) at an oven temperature of 50° C.

LC method 6: The retention times (Rt) were obtained on an Agilent 110 system with an inertsil C8 column, 3.0 μm, 3.0×30 mm. A gradient of $H_2O$ (+0.1% formic acid)/$CH_3CN$ (+0.1% formic acid) 60/40 to 5/95 was applied over 1.0 min., then held for 1.0 min. (2.0 mL/min. as solvent flow) at an oven temperature of 18° C.

LC method 7: The retention times (Rt) were obtained on an Agilent 110 system with an inertsil C8 column, 3.0 μm, 3.0×30 mm. A gradient of $H_2O$ (+0.1% formic acid)/$CH_3CN$ (+0.1% formic acid) 60/40 to 5/95 was applied over 1.0 min., then held for 1.0 min. (2.0 mL/min. as solvent flow) at an oven temperature of 18° C.

LC method 8: The retention times (Rt) were obtained on an Agilent 110 system with an inertsil C8 column, 3.0 μm, 3.0×30 mm. A gradient of $H_2O$ (+5 mM ammonium formate, 2% MeCN)/$CH_3CN$ (+0.1% formic acid) 60/40 to 5/95 was applied over 1.0 min., then held for 1.0 min. (2.0 mL/min. as solvent flow) at an oven temperature of 18° C.

LC method 9: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 60/40 to 2/98 was applied over 3.4 min., then held for 1.7 min. (1.0 mL/min. as solvent flow) at an oven temperature of 50° C.

LC method 10: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 45/55 to 1/99 was applied over 0.7 min., then held for 1.3 min. (1.0 mL/min. as solvent flow) at an oven temperature of 50° C.

LC method 11: The retention times (Rt) were obtained on a Waters Acquity SDS system with an Acquity BEH C18 1.7 μm 2.1×50 mm column. A gradient of $H_2O$ (+0.1% formic acid)/$CH_3CN$ (+0.1% formic acid) 60/40 to 1/99 was applied over 3.4 min., then held for 1.7 min. (1.0 mL/min. as solvent flow) at an oven temperature of 50° C.

LC method 12: The retention times (Rt) were obtained on a Waters Acquity SDS system with an Acquity BEH C18 1.7 μm 2.1×50 mm column. A gradient of $H_2O$ (+0.1% formic acid)/$CH_3CN$ (+0.1% formic acid) 45/55 to 1/99 was applied over 1.4 min., then a gradient of 1/99 to 0/100 was applied over 3.7 min. (1.0 mL/min. as solvent flow) at an oven temperature of 50° C.

LC Method 13: The retention times (Rt) were obtained on an Agilent 1100 system with an XBridge C18 Column, 3.5 μm, 2.1×50 mm. A gradient of $H_2O$ (+0.1% formic acid)/$CH_3CN$ 95/5 to 5/95 was applied over 1.7 min., then held for 0.2 min. (2.0 mL/min. as solvent flow), then changed to 95/5 over 0.1 min at an oven temperature of 40° C.

LC Method 14: The retention times (Rt) were obtained on a Waters Acquity SDS system with an Acquity BEH 1.7 μm 2.1×50 mm column. A gradient of $H_2O$ (+0.1% formic acid)/$CH_3CN$ (+0.1% formic acid) 60/40 to 0.1/99.9 was applied over 1.4 min., then held for 0.6 min. (1.0 mL/min. as solvent flow) at an oven temperature of 50° C.

LC Method 15: The retention times (Rt) were obtained on an Agilent 1100 system with an Atlantis C18 Column, 3.5 μm, 3.0×30 mm. A gradient of $H_2O$ (+0.05% trifluoroacetic acid)/$CH_3CN$ 60/40 to 2/98 was applied over 1.7 min., then held for 0.3 min. (2.0 mL/min. as solvent flow), then changed to 60/40 over 0.1 min at an oven temperature of 40° C.

Insofar as the production of the starting materials is not particularly described, the compounds are known or may be prepared analogously to methods known in the art or as described hereafter.

The following examples are illustrative of the invention without any limitation.

Synthesis of Example 1

Preparation of Intermediate 1a: (9Z,9'Z,12Z,12'Z)-2-(hydroxymethyl)propane-1,3-diyl bis(octadeca-9,12-dienoate)

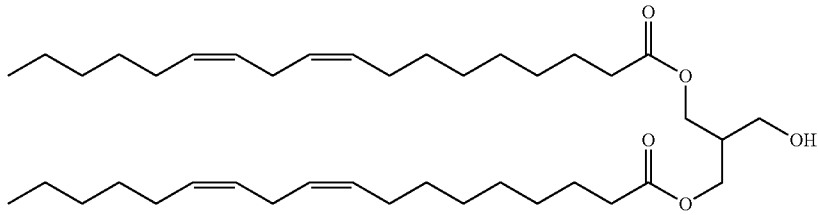 [SMILES: CCCCC/C=C\C/C=C\CCCCCCCC(=O)OCC(CO)COC(=O)CCCCCCC/C=C\C/C=C\CCCCC]

In a round bottom flask, linoleic acid (95.0 g, 339 mmol), DMAP (4.14 g, 33.90 mmol), DIPEA (74.1 ml, 424 mmol), and 2-(hydroxymethyl)propane-1,3-diol (18.0 g, 170 mmol) were taken into dichloromethane (435 mL). EDC (81.0 g, 424 mmol) was added in one portion, and the reaction was stirred at ambient temperature. After 24 h, the reaction is concentrated under reduced pressure with silica gel powder for dry loading and the residue was purified on silica gel (Biotage) using ethyl acetate/heptane (0% to 40%) as eluent, to provide 47 g of the desired product as a colorless oil.

$^1$H NMR (400 MHz, CDCl$_3$): δ=5.19-5.50 (m, 8H), 4.19 (tt, J=11.83, 5.87 Hz, 4H), 3.51-3.69 (m, 2H), 2.78 (t, J=6.53 Hz, 4H), 2.33 (t, J=7.53 Hz, 4H), 2.20 (quint, J=5.83 Hz, 2H), 2.06 (q, J=6.78 Hz, 8H), 1.49-1.72 (m, 5H), 1.20-1.46 (m, 26H), 0.79-0.98 (m, 6H) ppm.

Preparation of Final Compounds

Scheme 1

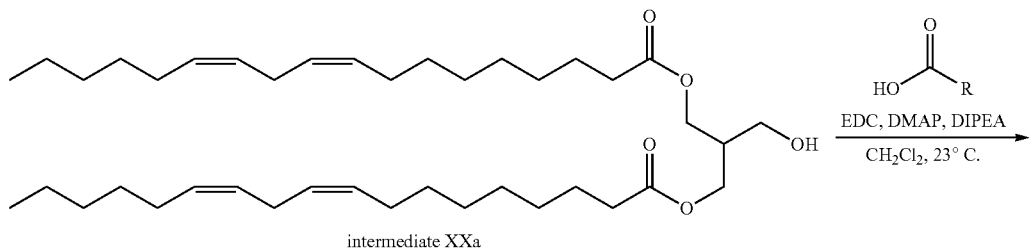

intermediate XXa

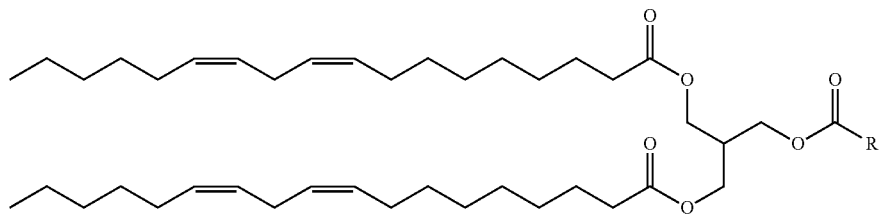

Example 1

(9Z,9'Z,12Z,12'Z)-2-(((1,3-dimethylpyrrolidine-3-carbonyl)oxy)methyl)propane-1,3-diyl bis(octadeca-9,12-dienoate)

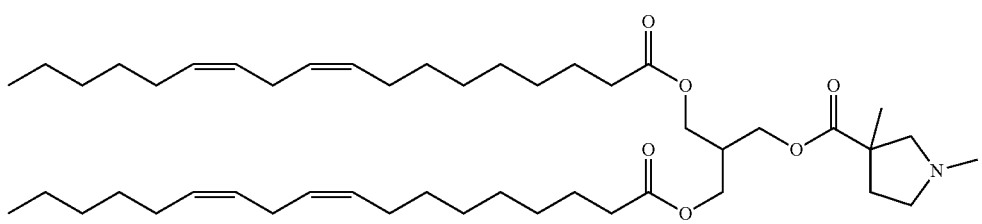 [SMILES: CCCCC/C=C\C/C=C\CCCCCCCC(=O)OCC(COC(=O)CCCCCCC/C=C\C/C=C\CCCCC)COC(=O)C1(C)CCN(C)C1]

In a round bottom flask, Intermediate 1a (15.0 g, 23.77 mmol), DMAP (0.581 g, 4.75 mmol), DIPEA (8.30 ml, 47.5 mmol) and 1,3-dimethylpyrrolidine-3-carboxylic acid (5.11 g, 35.7 mmol) were taken into dichloromethane (78 mL). EDC (9.11 mg, 47.5 mmol) was added in one portion, and the reaction was stirred at ambient temperature. After 24 h, the reaction was concentrated under reduced pressure with dry silica gel for dry loading and the residue was purified on silica gel (Biotage) using ethyl acetate/heptane (0% to 80%) as eluent to provide 15 g (82% yield) of the desired product as a colorless oil.

$^1$H NMR (400 MHz, CDCl$_3$): δ=5.26-5.47 (m, 8H), 4.08-4.21 (m, 6H), 2.97 (d, J=9.29 Hz, 1H), 2.78 (t, J=6.53 Hz, 4H), 2.56-2.69 (m, 2H), 2.24-2.49 (m, 10H), 2.05 (q, J=6.78 Hz, 8H), 1.54-1.76 (m, 5H), 1.22-1.42 (m, 31H), 0.89 (t, J=6.78 Hz, 6H) ppm. MS (M+1)=756.7, Rt=1.31 min (LC method 1).

The following examples can be prepared using similar methods to those employed for the synthesis of Example 1.

Example 2

(9Z,9'Z,12Z,12'Z)-2-(((3-(4-methylpiperazin-1-yl)propanoyl)oxy)methyl)propane-1,3-diyl bis(octadeca-9,12-dienoate)

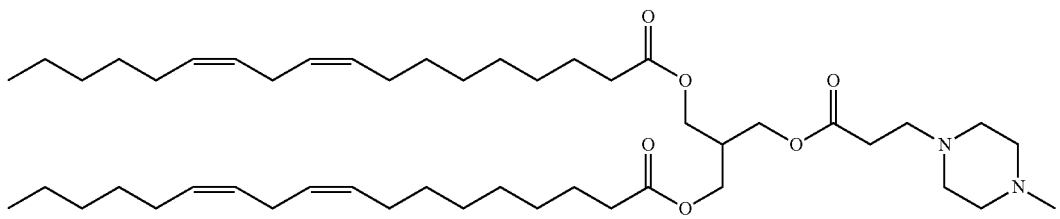 [SMILES: CCCCC/C=C\C/C=C\CCCCCCCC(=O)OCC(COC(=O)CCCCCCC/C=C\C/C=C\CCCCC)COC(=O)CCN1CCN(C)CC1]

$^1$H NMR (400 MHz, CD$_2$Cl$_2$): δ=5.42 (m, 8H), 4.12 (m, 6H), 2.82 (q, 4H), 2.68 (m, 2H), 2.60-2.22 (m, 13H), 2.25 (s, 3H), 2.05 (m, 8H), 1.62 (m, 6H), 1.40-1.22 (m, 28H), 0.92 (t, 6H) ppm.

MS (M+1)=786.0, Rt=2.65 min (LC method 2).

Example 3

(9Z,9'Z,12Z,12'Z)-2-(((4-(pyrrolidin-1-yl)butanoyl)oxy)methyl)propane-1,3-diyl bis(octadeca-9,12-dienoate)

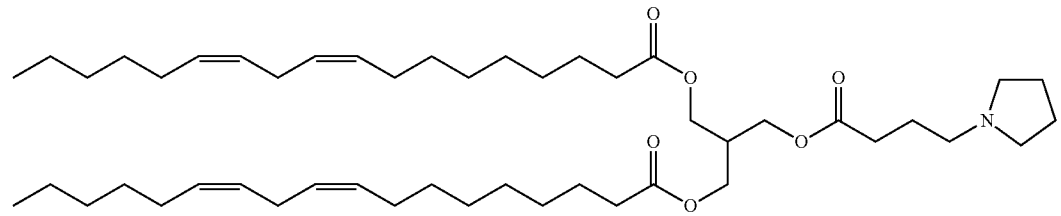 [SMILES: CCCCC/C=C\C/C=C\CCCCCCCC(=O)OCC(COC(=O)CCCCCCC/C=C\C/C=C\CCCCC)COC(=O)CCCN1CCCC1]

$^1$H NMR (400 MHz, CD$_2$Cl$_2$): δ=5.40 (m, 8H), 4.15 (d, 6H), 2.82 (q, 4H), 2.68-2.30 (m, 9H), 2.06 (m, 8H), 1.85 (m, 6H), 1.62 (m, 6H), 1.40-1.22 (m, 30H), 0.92 (t, 6H) ppm. MS (M+1)=771.0, Rt=2.72 min (LC method 2).

Example 4

(9Z,9'Z,12Z,12'Z)-2-(((4-(piperidin-1-yl)butanoyl)oxy)methyl)propane-1,3-diyl bis(octadeca-9,12-dienoate)

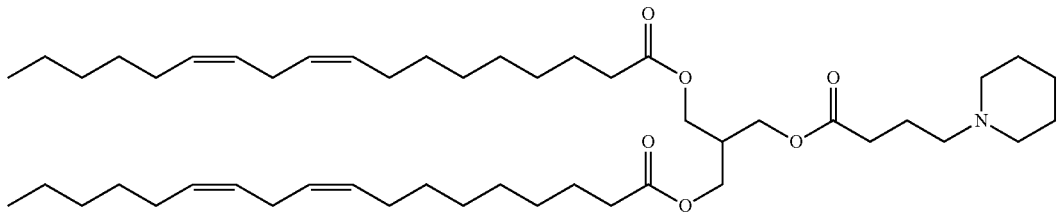 [SMILES: CCCCC/C=C\C/C=C\CCCCCCCC(=O)OCC(COC(=O)CCCCCCC/C=C\C/C=C\CCCCC)COC(=O)CCCN1CCCCC1]

¹H NMR (400 MHz, CD₂Cl₂): δ=5.42 (m, 8H), 4.17 (d, 6H), 2.86 (q, 4H), 2.48-2.22 (m, 13H), 2.02 (m, 8H), 1.82-1.42 (m, 10H), 1.35 (m, 30H), 0.90 (t, 6H) ppm. MS (M+1)=786.0, Rt=2.75 min (LC method 2).

Example 5

(9Z,9'Z,12Z,12'Z)-2-(((3-(dimethylamino)propanoyl)oxy) methyl)propane-1,3-diyl bis(octadeca-9,12-dienoate)

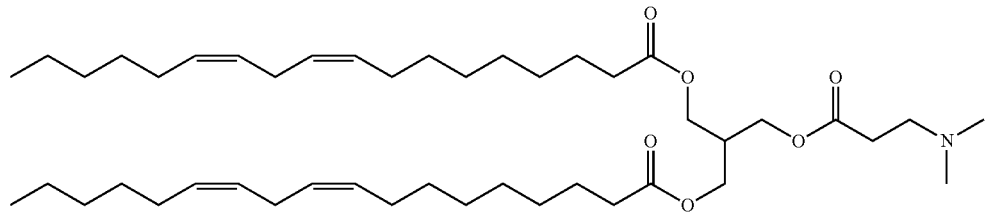 [SMILES: CCCCC/C=C\C/C=C\CCCCCCCC(=O)OCC(COC(=O)CCCCCCC/C=C\C/C=C\CCCCC)COC(=O)CCN(C)C]

¹H NMR (400 MHz, CDCl₃): δ=5.45-5.25 (m, 8H), 4.20-4.10 (m, 6H), 2.78 (t, J=8.0 Hz, 4H), 2.60 (t, J=8.0 Hz, 2H), 2.49 (t, J=8.0 Hz, 2H), 2.44-2.38 (m, 1H), 2.31 (t, J=8.0 Hz, 4H), 2.24 (s, 6H), 2.11-1.97 (m, 8H), 1.69-1.58 (m, 6H), 1.40-1.24 (m, 26H), 0.91-0.87 (m, 6H) ppm.
MS (M+1)=731.5, Rt=1.22 min (LC method 3).

Example 6

(9Z,9'Z,12Z,12'Z)-2-((2-(dimethylamino)acetoxy) methyl)propane-1,3-diyl bis(octadeca-9,12-dienoate)

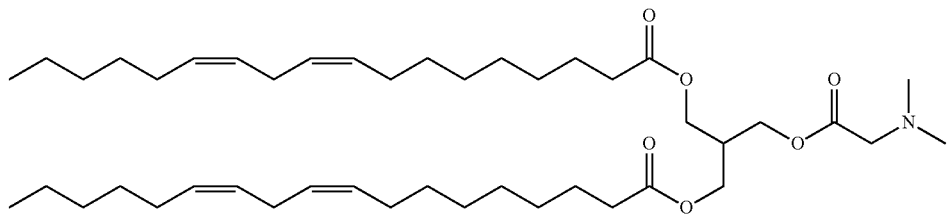 [SMILES: CCCCC/C=C\C/C=C\CCCCCCCC(=O)OCC(COC(=O)CCCCCCC/C=C\C/C=C\CCCCC)COC(=O)CN(C)C]

¹H NMR (400 MHz, CDCl₃): δ=5.44-5.29 (m, 8H), 4.20 (d, J=4.0 Hz, 2H), 4.14 (d, J=4.0 Hz, 4H), 3.19 (s, 2H), 2.77 (t, J=8.0 Hz, 4H), 2.45-2.39 (m, 1H), 2.36 (s, 6H), 2.31 (t, J=8.0 Hz, 4H), 2.11-1.99 (m, 8H), 1.68-1.56 (m, 6H), 1.40-1.24 (m, 26H), 0.91-0.87 (m, 6H) ppm. MS (M+1)= 717.4, Rt=1.95 min (LC method 3).

Example 7

(9Z,9'Z,12Z,12'Z)-2-(((3-(diethylamino)propanoyl)oxy)methyl)propane-1,3-diyl bis(octadeca-9,12-dienoate)

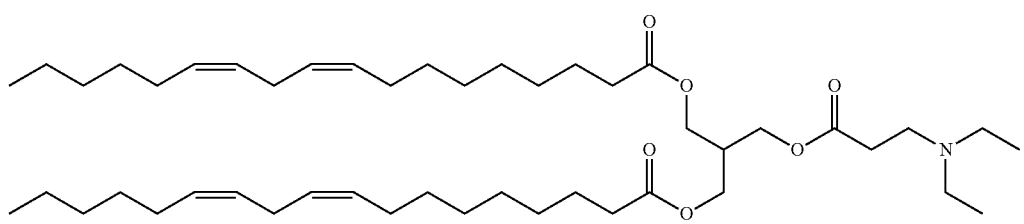 [SMILES: CCCCC/C=C\C/C=C\CCCCCCCC(=O)OCC(COC(=O)CCCCCCC/C=C\C/C=C\CCCCC)COC(=O)CCN(CC)CC]

¹H NMR (400 MHz, CDCl₃): δ=5.43-5.30 (m, 8H), 4.18-4.10 (m, 6H), 2.81-2.76 (m, 6H), 2.55-2.37 (m, 7H), 2.31 (t, J=8.0 Hz, 4H), 2.11-1.97 (m, 8H), 1.69-1.58 (m, 6H), 1.40-1.24 (m, 28H), 1.02 (t, J=8.0 Hz, 4H), 0.91-0.87 (m, 6H) ppm. MS (M+1)=759.6, Rt=1.35 min (LC method 3).

Example 8

(9Z,9'Z,12Z,12'Z)-2-(((1,4-dimethylpiperidine-4-carbonyl)oxy)methyl)propane-1,3-diyl bis(octadeca-9,12-dienoate)

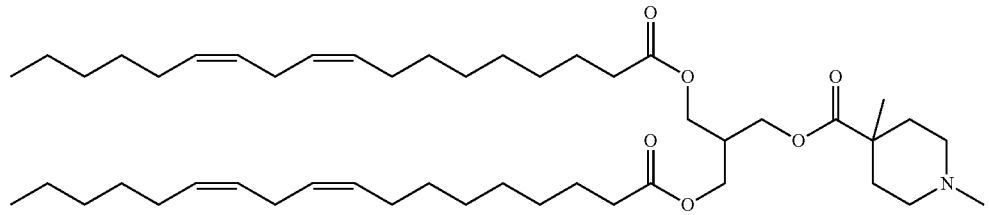 [SMILES: CCCCC/C=C\C/C=C\CCCCCCCC(=O)OCC(COC(=O)CCCCCCC/C=C\C/C=C\CCCCC)COC(=O)C1(C)CCN(C)CC1]

¹H NMR (400 MHz, CDCl₃): δ=5.28-5.45 (m, 8H), 4.10-4.19 (m, 6H), 2.77 (t, J=6.53 Hz, 4H), 2.62 (br. s., 2H), 2.42 (dt, J=12.05, 6.02 Hz, 1H), 2.23-2.36 (m, 8H), 1.99-2.17 (m, 12H), 1.47-1.68 (m, 6H), 1.25-1.42 (m, 27H), 1.20 (s, 3H), 0.89 (t, J=6.78 Hz, 6H) ppm. MS (M+1)=770.6, Rt=1.55 min (LC method 7).

Example 9

(9Z,9'Z,12Z,12'Z)-2-(((1-(cyclopropylmethyl)piperidine-4-carbonyl)oxy)methyl)propane-1,3-diyl bis(octadeca-9,12-dienoate)

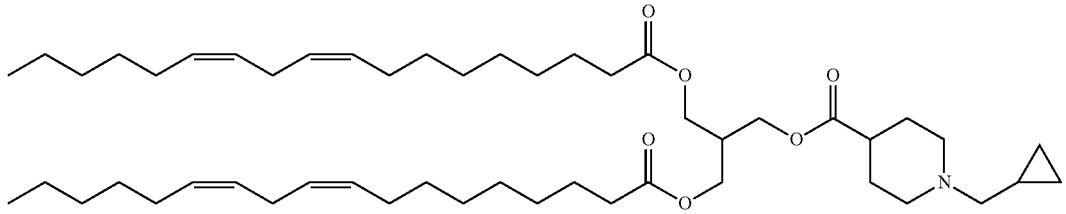 [SMILES: CCCCC/C=C\C/C=C\CCCCCCCC(=O)OCC(COC(=O)CCCCCCC/C=C\C/C=C\CCCCC)COC(=O)C1CCN(CC2CC2)CC1]

¹H NMR (400 MHz, CDCl₃): δ=5.27-5.46 (m, 8H), 4.08-4.19 (m, 6H), 3.03 (d, J=11.04 Hz, 2H), 2.77 (t, J=6.53 Hz, 4H), 2.40 (dt, J=12.05, 6.02 Hz, 1H), 2.31 (t, J=7.65 Hz, 5H), 2.25 (d, J=6.27 Hz, 2H), 2.05 (q, J=6.61 Hz, 10H), 1.93 (d, J=11.54 Hz, 2H), 1.74-1.86 (m, 2H), 1.61 (t, J=6.90 Hz, 5H), 1.23-1.42 (m, 27H), 0.89 (m, J=6.90 Hz, 7H), 0.48-0.57 (m, 2H), 0.10 (q, J=4.94 Hz, 2H) ppm. MS (M+1)=796.7, Rt=1.62 min (LC method 7).

Example 10

(9Z,9'Z,12Z,12'Z)-2-(((3-morpholinopropanoyl)oxy)methyl)propane-1,3-diyl bis(octadeca-9,12-dienoate)

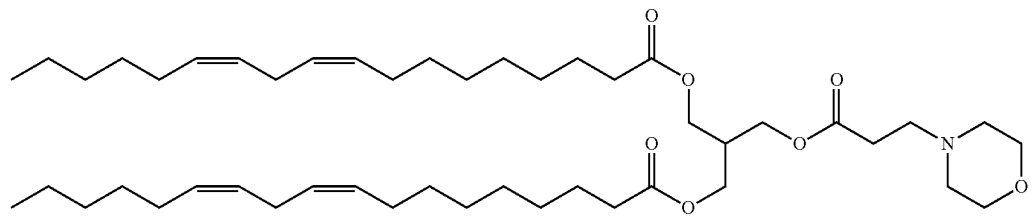 [SMILES: CCCCC/C=C\C/C=C\CCCCCCCC(=O)OCC(COC(=O)CCCCCCC/C=C\C/C=C\CCCCC)COC(=O)CCN1CCOCC1]

¹H NMR (400 MHz, CDCl₃): δ=5.40 (m, 8H), 4.18 (m, 8H), 3.62 (bs, 4H), 2.78 (t, 3H), 2.68 (m, 2H), 2.60-2.32 (m, 6H), 2.28 (m, 4H), 2.05 (m, 7H), 1.68-1.52 (m, 3H), 1.38-1.18 (m, 30H), 0.90 (t, 6H) ppm. MS (M+1)=773.0, Rt=2.89 min (LC method 2).

Example 11

(9Z,9'Z,12Z,12'Z)-2-(((4-(dimethylamino)butanoyl)oxy)methyl)propane-1,3-diyl bis(octadeca-9,12-dienoate)

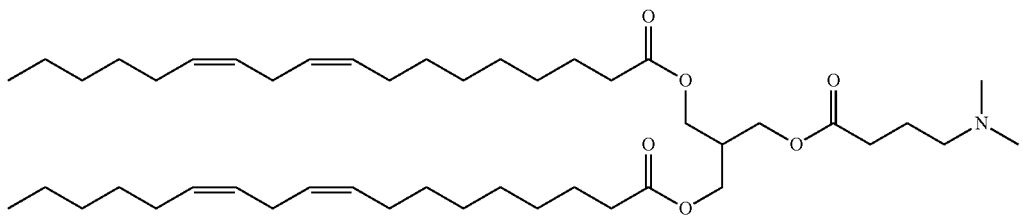 [SMILES: CCCCC/C=C\C/C=C\CCCCCCCC(=O)OCC(COC(=O)CCCCCCC/C=C\C/C=C\CCCCC)COC(=O)CCCN(C)C]

¹H NMR (400 MHz, CDCl₃): δ=5.40 (m, 8H), 4.16 (m, 6H), 2.82 (m, 3H), 2.48-2.20 (m, 13H), 2.01 (m, 7H), 1.82 (m, 3H), 168 (m, 5H), 1.42-1.22 (m, 30H), 0.91 (t, 6H) ppm. MS (M+1)=745.0, Rt=2.61 min (LC method 2).

Preparation of Example 12

Intermediate 12a: 8-(benzyloxy)octan-1-ol

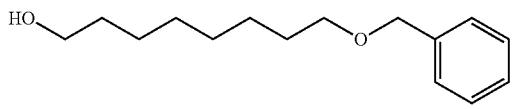 [SMILES: OCCCCCCCCOCc1ccccc1]

In a round bottom flask, 1,8-octanediol (10 g, 68.4 mmol) was dissolved in anhydrous DMF (300 ml) and anhydrous THF (100 mL). The solution was cooled in an ice-water bath, and NaH (60% dispersion in mineral oil) (2.462 g, 61.5 mmol) was added portion wise. Benzyl bromide (12.87 g, 75 mmol) was then added. The reaction was slowly warmed to ambient temperature. After 6 h, the reaction was diluted with 150 mL H₂O and then extracted with EtOAc. The combined organic layers were washed with saturated aqueous NaHCO₃ solution, dried over MgSO₄ and filtered. The filtrate was concentrated under reduced pressure. The residue was purified on silica gel using ethyl acetate/heptane as eluent to provide 5.9 g of the expected product.

¹H NMR (400 MHz, CDCl₃) δ=7.42-7.19 (m, 5H), 4.51 (s, 2H), 3.70-3.57 (m, 2H), 3.47 (t, J=6.7 Hz, 2H), 1.73-1.43 (m, 4H), 1.43-1.30 (m, 8H).

Intermediate 12b: 8-(benzyloxy)octanoic acid

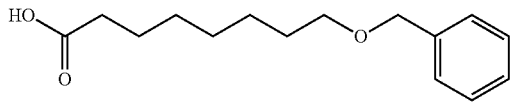 [SMILES: O=C(O)CCCCCCCOCc1ccccc1]

In a round bottom flask, Intermediate 12a (5.9 g, 24.96 mmol) was dissolved in acetone (200 ml), and cooled in an ice-water bath. Jones Reagent (2M, 14.98 mL, 30.0 mmol) was added dropwise. The reaction was stirred for 1 h and then 20 mLMeOH was added. The reaction was stirred for 30 min. The reaction was filtered and the filtrate was concentrated under reduced pressure. The concentrate was diluted with EtOAc and washed twice with saturated aqueous NaHCO₃. The organic layer was washed with brine, dried over MgSO₄, and filtered. The filtrate was concentrated under reduced pressure to provide 5.2 g of the expected product, which was used without further purification.

¹H NMR (400 MHz, CDCl₃) δ=7.44-7.20 (m, 5H), 4.51 (s, 2H), 3.58-3.36 (m, 2H), 2.47-2.26 (m, 2H), 1.77-1.54 (m, 4H), 1.48-1.28 (m, 6H).

Intermediate 12c: 2-(hydroxymethyl)propane-1,3-diyl bis(8-(benzyloxy)octanoate)

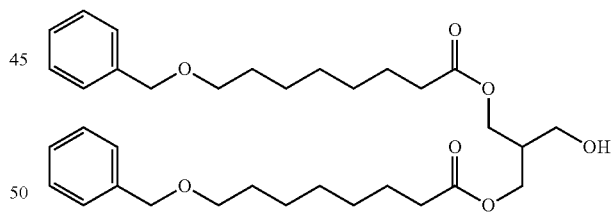

In a round bottom flask, 2-(hydroxymethyl)propane-1,3-diol (500 mg, 4.71 mmol), DTPS (N,N-dimethylpyridine-4-amine, 4-methylbenzenesulfonate salt) (1382 mg, 4.71 mmol), and Intermediate 12b (2595 mg, 10.37 mmol) were dissolved in anhydrous DCM (25 mL). DIPEA (3.29 ml, 18.85 mmol) and EDC (2077 mg, 10.84 mmol) were added and the reaction was stirred at ambient temperature for 72 h. The reaction mixture was on silica gel using ethyl acetate/heptane eluent to provide 790 mg of the expected product.

MS (M+NH₄⁺)=588.5, Rt=1.52 min (LC method 8).

Intermediate 12d: 2-(((1,3-dimethylpyrrolidine-3-carbonyl)oxy)methyl)propane-1,3-diyl bis(8-(benzyloxy)octanoate)

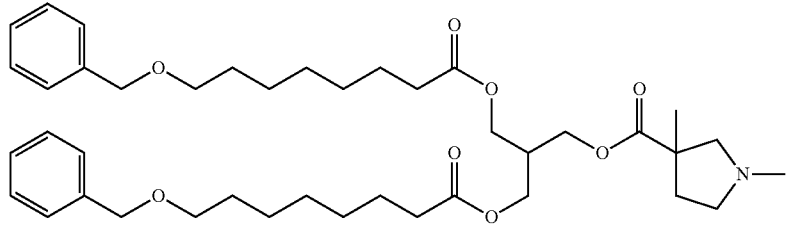 [SMILES: CN1CCC(C)(C(=O)OCC(COC(=O)CCCCCCCOCc2ccccc2)COC(=O)CCCCCCCOCc2ccccc2)C1]

In a high pressure microwave safe vial, Intermediate 12c (790 mg, 1.38 mmol), DTPS (406 mg, 1.38 mmol), 1,3-dimethylpyrrolidine-3-carboxylic acid (218 mg, 1.52 mmol), and EDC (318 mg, 1.66 mmol) were dissolved in 10 mL DCM. DIPEA (0.967 ml, 5.54 mmol) was added and the vial was sealed. The reaction mixture was heated under microwave irradiation at 80° C. for 40 min. An additional 200 mg of 1,3-dimethylpyrrolidine-3-carboxylic acid and 300 mg of EDC were added and the reaction was heated under microwave irradiation at 80° C. for an additional 40 min. The reaction mixture was on silica gel using ethyl acetate/heptane eluent to provide 560 mg of the expected product.

MS (M+1)=696.5, Rt=1.15 min (LC method 8).

Intermediate 12e: 2-(((1,3-dimethylpyrrolidine-3-carbonyl)oxy)methyl)propane-1,3-diyl bis(8-hydroxyoctanoate)

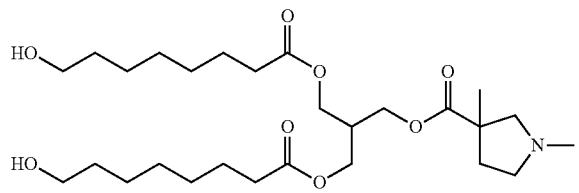 [SMILES: CN1CCC(C)(C(=O)OCC(COC(=O)CCCCCCCO)COC(=O)CCCCCCCO)C1]

In a round bottom flask, Intermediate 12d (460 mg, 0.759 mmol) was dissolved in anhydrous THF (10 ml). AcOH (0.022 ml, 0.380 mmol) and 10% Pd/C (wet, degussa type) (170 mg, 0.152 mmol) were added. The flask was evacuated and purged with nitrogen gas, then a hydrogen balloon was administered at 1 atm and the reaction was heated with stirring at 40° C. After 24 h, 10 drops of AcOH and another equivalent of 10% Pd/C was added. The reaction was evacuated and purged with nitrogen gas, and a hydrogen balloon (1 atm) was administered. The reaction was warmed to 45° C. After 5 h, the reaction was filtered over celite with MeOH, and the solvents were removed under reduced pressure to provide 450 mg of the expected product.

$^1$H NMR (400 MHz, CDCl$_3$): δ=4.26-4.05 (m, 6H), 3.64 (t, J=6.5 Hz, 4H), 3.41-3.23 (m, 2H), 3.12 (d, J=11.0 Hz, 1H), 2.96-2.76 (m, 1H), 2.71-2.56 (m, 3H), 2.55-2.39 (m, 2H), 2.32 (t, J=7.4 Hz, 4H), 1.96 (ddd, J=7.8, 9.2, 13.4 Hz, 1H), 1.70-1.50 (m, 8H), 1.43 (s, 3H), 1.41-1.30 (m, 12H) ppm.

Example 12

2-(((1,3-dimethylpyrrolidine-3-carbonyl)oxy)methyl)propane-1,3-diyl bis(8-(octanoyloxy)octanoate)

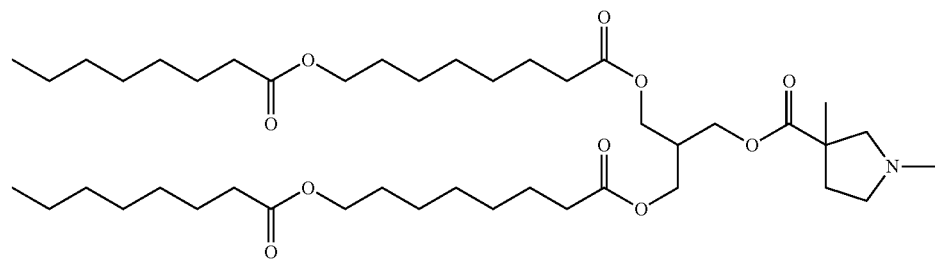 [SMILES: CCCCCCCC(=O)OCCCCCCCC(=O)OCC(COC(=O)CCCCCCCOC(=O)CCCCCCC)COC(=O)C1(C)CCN(C)C1]

In a round bottom flask, Intermediate 12e (450 mg, 0.873 mmol) and TEA (6.93 ml, 49.7 mmol) were dissolved in anhydrous DCM (15 ml) and cooled in an ice-water bath. Octanoyl chloride (0.374 ml, 2.182 mmol) was added. After 1 h, the reaction mixture was purified on silica gel using dichloromethane/methanol as eluent to provide impure product. The product was further purified by RP-HPLC utilizing water/acetonitrile/iPrOH (0.1% TFA modifier) as eluent to provide product as the TFA salt. The material was desalted through a BE-NH$_2$ column to provide 120 mg of the expected product.

$^1$H NMR (400 MHz, CDCl$_3$): δ=4.21-4.10 (m, 6H), 4.05 (t, J=6.7 Hz, 4H), 2.94 (d, J=9.3 Hz, 1H), 2.59 (t, J=6.9 Hz, 2H), 2.50-2.22 (m, 14H), 1.78-1.52 (m, 13H), 1.49-1.21 (m, 31H), 0.96-0.77 (m, 6H) ppm. MS (M+1)=769.7, Rt=1.28 min (LC method 4).

Preparation of Example 13

Intermediate 13a: 4,4-bis(octyloxy)butanenitrile

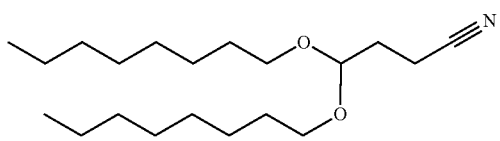 [SMILES: CCCCCCCCOC(CCC#N)OCCCCCCCC]

To a mixture of 4,4-diethoxybutanenitrile (15 g, 95 mmol) and octanol (37.3 g, 286 mmol) was added pyridinium p-toluenesulfonate (1.2 g, 4.77 mmol) and the mixture was heated to 105° C. After 72 h, the reaction mixture is cooled and purified on silica gel using ethyl acetate/heptane as eluent to provide 9.34 g of the expected product.

$^1$H NMR (400 MHz, CDCl$_3$): δ=4.56 (t, J=5.40 Hz, 1H), 3.61 (dt, J=9.16, 6.59 Hz, 2H), 3.44 (dt, J=9.22, 6.68 Hz, 2H), 2.43 (t, J=7.28 Hz, 2H), 1.95 (td, J=7.34, 5.40 Hz, 2H), 1.50-1.66 (m, 4H), 1.17-1.44 (m, 20H), 0.80-0.95 (m, 6H) ppm.

Intermediate 13b: 4,4-bis(octyloxy)butanoic acid

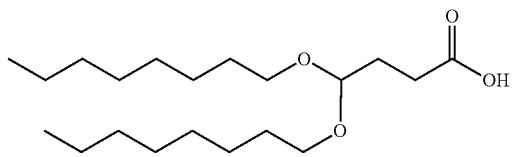 [SMILES: CCCCCCCCOC(CCC(=O)O)OCCCCCCCC]

In a high pressure reaction vessel, Intermediate 13a (9.34 g, 28.7 mmol) is dissolved in 30 mL EtOH. KOH (4.83 g) is dissolved in 30 mL water and the KOH solution was added to the EtOH solution. The tube was sealed and heated to 110° C. overnight. The mixture was cooled and diluted with EtOAc. 1N HCl was added to adjust pH to 5, and the aqueous phase was extracted with EtOAc twice. The combined organic extracts were dried over MgSO$_4$, filtered and concentrated under reduced pressure to provide 10.9 g of the expected product.

$^1$H NMR (400 MHz, CDCl$_3$): δ=4.46 (t, J=5.52 Hz, 1H), 3.46-3.59 (m, 2H), 3.08-3.46 (m, 3H), 2.18 (t, J=7.28 Hz, 2H), 1.72-1.89 (m, 2H), 1.46-1.63 (m, 4H), 1.28 (d, J=3.76 Hz, 20H), 0.79-0.96 (m, 6H) ppm.

Intermediate 13c:
(9Z,12Z)-3-hydroxy-2-(hydroxymethyl)propyl octadeca-9,12-dienoate

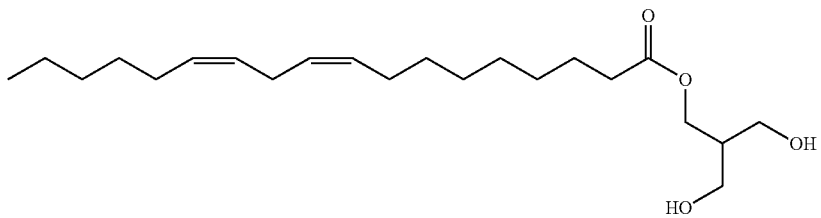 [SMILES: CCCCC/C=C\C/C=C\CCCCCCCC(=O)OCC(CO)CO]

In a round bottom flask, linoleic acid (23.78 g, 85 mmol), DMAP (2.072 g, 16.96 mmol), DIPEA (22.22 ml, 127 mmol), and 2-(hydroxymethyl)propane-1,3-diol (9 g, 85 mmol) were taken into dichloromethane (200 mL). EDC (24.39 g, 127 mmol) was added in one portion, and the reaction was stirred at ambient temperature. After 24 h, the reaction is concentrated under reduced pressure, and the concentrate is purified on silica gel with ethyl acetate/heptane as eluent to provide 12.4 g of the expected product. 9.5 g of Intermediate 1a was also isolated.

$^1$H NMR (400 MHz, CDCl$_3$): δ=4.27 (d, J=6.27 Hz, 2H), 3.77 (qd, J=11.25, 5.14 Hz, 4H), 2.78 (t, J=6.40 Hz, 2H), 2.23-2.48 (m, 4H), 1.90-2.15 (m, 6H), 1.53-1.76 (m, 3H), 1.15-1.45 (m, 14H), 0.77-0.98 (m, 3H) ppm.

Intermediate 13d: (9Z,12Z)-3-((4,4-bis(octyloxy)butanoyl)oxy)-2-(hydroxymethyl)propyl octadeca-9,12-dienoate

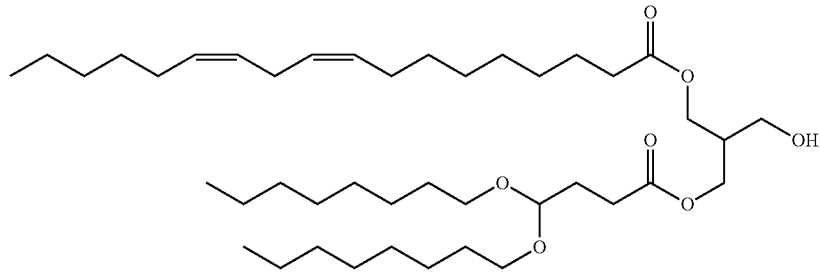 [SMILES: CCCCC/C=C\C/C=C\CCCCCCCC(=O)OCC(CO)COC(=O)CCC(OCCCCCCCC)OCCCCCCCC]

In a round bottom flask, Intermediate 13b (10.9 g, 31.6 mmol), DMAP (773 mg, 6.33 mmol), DIPEA (11.05 ml, 63.3 mmol), and Intermediate 13c (13.99 g, 38 mmol) were taken into dichloromethane (100 mL). EDC (12.13 g, 63.3 mmol) was added in one portion, and the reaction was stirred at ambient temperature. After 24 h, the reaction was concentrated under reduced pressure. The concentrate was purified on silica gel with 0-20% EtOAc/heptane as eluent to provide 11.2 g of the expected product.

$^1$H NMR (400 MHz, CDCl$_3$): δ=5.27-5.45 (m, 4H), 4.50 (t, J=5.52 Hz, 1H), 4.08-4.25 (m, 4H), 3.50-3.69 (m, 4H), 3.41 (dt, J=9.22, 6.68 Hz, 2H), 2.78 (t, J=6.53 Hz, 2H), 2.42 (t, J=7.53 Hz, 2H), 2.33 (t, J=7.53 Hz, 2H), 2.13-2.29 (m, 2H), 2.00-2.13 (m, 4H), 1.88-2.00 (m, 2H), 1.49-1.69 (m, 7H), 1.20-1.44 (m, 32H), 0.83-0.95 (m, 9H) ppm.

Preparation of Final Compounds

Scheme 2

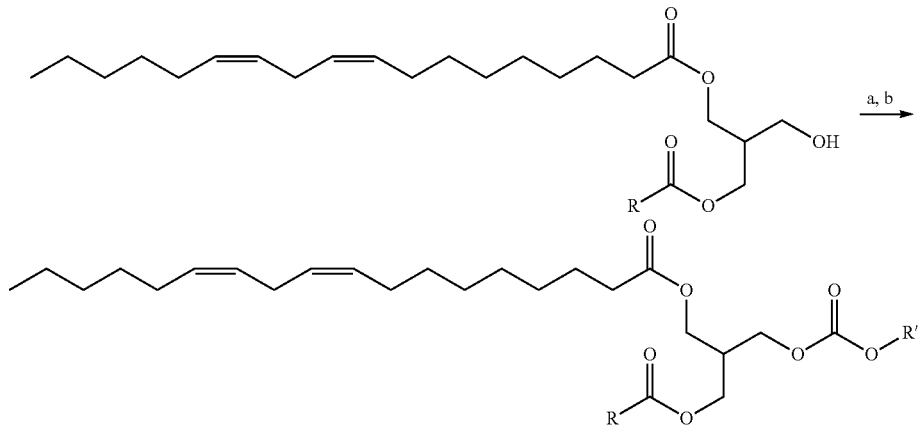

a) 4-nitrophenylchloroformate, pyridine, DMAP, CH$_2$Cl$_2$, 23° C. b) ROH, 23° C.

Example 13

(9Z,12Z)-3-((4,4-bis(octyloxy)butanoyl)oxy)-2-((((3-(diethylamino)propoxy)carbonyl)oxy)methyl)propyl octadeca-9,12-dienoate

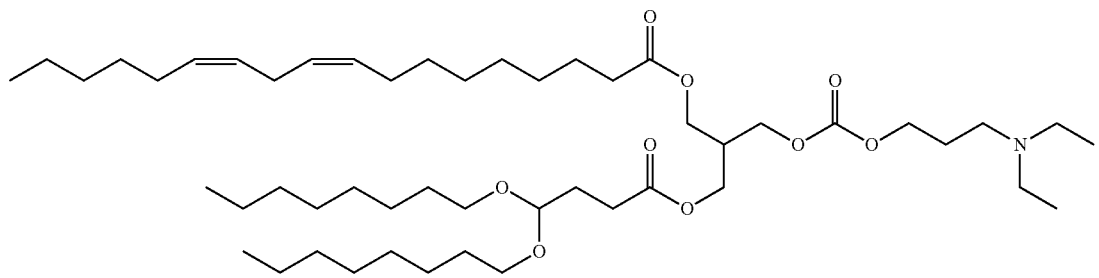 [SMILES: CCCCC/C=C\C/C=C\CCCCCCCC(=O)OCC(COC(=O)CCC(OCCCCCCCC)OCCCCCCCC)COC(=O)OCCCN(CC)CC]

In a round-bottom flask, 4-nitrophenylchloroformate (6.5 g, 32.2 mmol) was dissolved in DCM (100 mL). Pyridine (2.61 ml, 32.2 mmol) and DMAP (591 mg, 4.83 mmol) were added, followed by Intermediate 13d (11.2 g, 16.11 mmol), and mixture was stirred at ambient temperature for one hour. 3-diethylamino-1-propanol (12.69 g, 97 mmol) was added, and the reaction was continued overnight. The reaction was concentrated under reduced pressure, and the concentrate was purified on silica gel with ethyl acetate/heptane as eluent to provide 12.15 g of the expected compound.

$^1$H NMR (400 MHz, CDCl$_3$): δ=5.16-5.51 (m, 4H), 4.49 (t, J=5.52 Hz, 1H), 3.99-4.33 (m, 8H), 3.56 (dt, J=9.22, 6.68 Hz, 2H), 3.40 (dt, J=9.22, 6.68 Hz, 2H), 2.77 (t, J=6.65 Hz, 2H), 2.53 (q, J=6.94 Hz, 6H), 2.36-2.47 (m, 3H), 2.31 (t, J=7.53 Hz, 2H), 2.05 (q, J=6.61 Hz, 4H), 1.88-1.99 (m, 2H), 1.76-1.88 (m, 2H), 1.51-1.66 (m, 6H), 1.20-1.41 (m, 34H), 1.02 (t, J=7.15 Hz, 6H), 0.83-0.95 (m, 9H) ppm. MS (M+1)=852.8, Rt=2.64 min (LC method 4).

The following examples can be prepared using similar methods to those employed for the synthesis of Example 13:

Example 14

(9Z,12Z)-3-((4,4-bis(octyloxy)butanoyl)oxy)-2-((((3-(dimethylamino)propoxy)carbonyl)oxy)methyl) propyl octadeca-9,12-dienoate

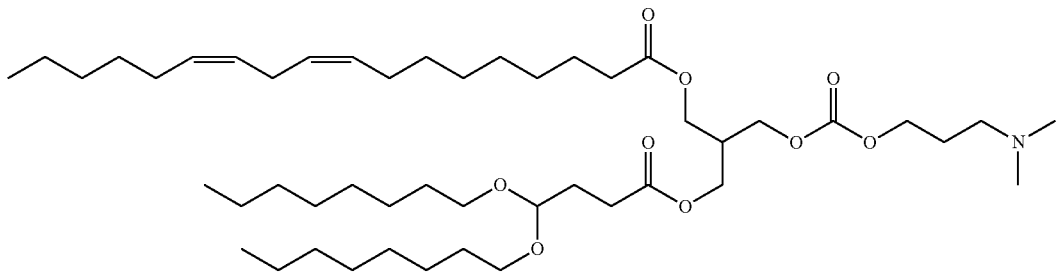 [SMILES: CCCCC/C=C\C/C=C\CCCCCCCC(=O)OCC(COC(=O)CCC(OCCCCCCCC)OCCCCCCCC)COC(=O)OCCCN(C)C]

$^1$H NMR (400 MHz, CDCl$_3$): δ=5.29-5.45 (m, 4H), 4.50 (t, J=5.65 Hz, 1H), 4.19-4.25 (m, 4H), 4.16 (dd, J=5.90, 1.38 Hz, 4H), 3.58 (dt, J=9.29, 6.78 Hz, 2H), 3.42 (dt, J=9.22, 6.68 Hz, 2H), 2.79 (t, J=6.53 Hz, 2H), 2.35-2.49 (m, 5H), 2.33 (t, J=7.65 Hz, 2H), 2.26 (s, 6H), 2.07 (q, J=6.78 Hz, 4H), 1.91-1.99 (m, 2H), 1.87 (quint., J=6.96 Hz, 2H), 1.52-1.68 (m, 6H), 1.22-1.43 (m, 34H), 0.85-0.96 (m, 9H) ppm. MS (M+1)=824.8, Rt=1.32 min (LC method 3).

Example 15

(9Z,12Z)-3-((4,4-bis(octyloxy)butanoyl)oxy)-2-(((((1-ethylpiperidin-3-yl)methoxy)carbonyl)oxy) methyl)propyl octadeca-9,12-dienoate

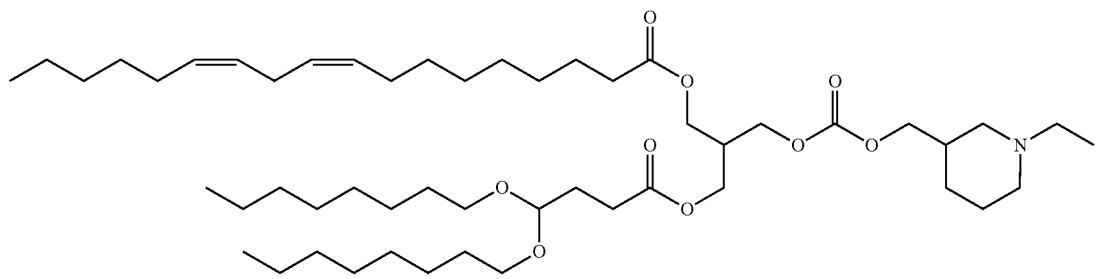 [SMILES: CCCCC/C=C\C/C=C\CCCCCCCC(=O)OCC(COC(=O)CCC(OCCCCCCCC)OCCCCCCCC)COC(=O)OCC1CCCN(CC)C1]

$^1$H NMR (400 MHz, CDCl$_3$): δ=5.25-5.46 (m, 4H), 4.49 (t, J=5.52 Hz, 1H), 4.17 (dd, J=19.32, 5.77 Hz, 6H), 4.02-4.09 (m, 1H), 3.91-4.00 (m, 1H), 3.57 (dt, J=9.22, 6.68 Hz, 2H), 3.40 (dt, J=9.22, 6.68 Hz, 2H), 2.82-2.99 (m, 2H), 2.77 (t, J=6.40 Hz, 2H), 2.36-2.48 (m, 5H), 2.31 (t, J=7.53 Hz, 2H), 2.05 (q, J=6.78 Hz, 5H), 1.84-1.97 (m, 3H), 1.50-1.81 (m, 12H), 1.21-1.41 (m, 31H), 0.94-1.14 (m, 5H), 0.80-0.94 (m, 9H) ppm. MS (M+1)=865.1, Rt=2.64 min (LC method 4).

Example 16

2-((((2-(diethylamino)ethoxy)carbonyl)oxy)methyl)
propane-1,3-diylbis(2-heptylundecanoate)

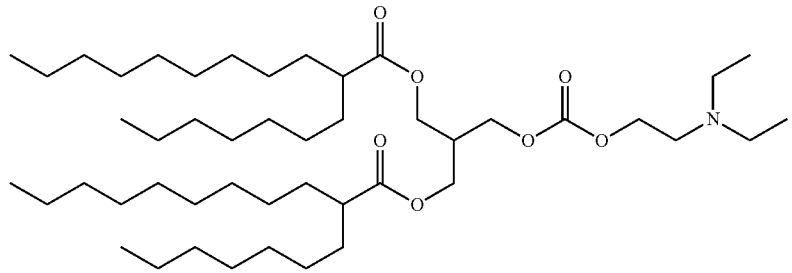 [SMILES: CCCCCCCCCC(CCCCCCC)C(=O)OCC(COC(=O)OCCN(CC)CC)COC(=O)C(CCCCCCC)CCCCCCCCC]

$^1$H NMR (400 MHz, CDCl$_3$) δ=4.24-4.11 (m, 8H), 2.73 (t, J=6.4 Hz, 2H), 2.58 (q, J=7.0 Hz, 4H), 2.49-2.39 (m, 1H), 2.39-2.27 (m, 2H), 1.67-1.51 (m, 5H), 1.51-1.37 (m, 5H), 1.36-1.16 (m, 46H), 1.03 (t, J=7.2 Hz, 6H), 0.93-0.84 (m, 12H) ppm. $^{13}$C NMR (100 MHz, CDCl$_3$) δ=176.18 (2C), 155.0, 66.26, 65.11, 61.13 (2C), 50.96, 47.63 (2C), 45.65 (2C), 37.54, 32.32 (2C), 31.88 (2C), 31.81 (2C), 27.44 (4C), 29.57 (2C), 29.56 (2C), 29.50 (2C), 29.46 (2C), 29.30 (2C), 29.12 (2C), 27.44 (2C), 22.67 (2C), 22.63 (2C), 14.12 (2C), 14.09 (2C), 11.82 (2C) ppm.

Example 17

(9Z,12Z)-3-(((2-(diethylamino)ethoxy)carbonyl)
oxy)-2-(((2-heptylundecanoyl)oxy)methyl)propyl
octadeca-9,12-dienoate

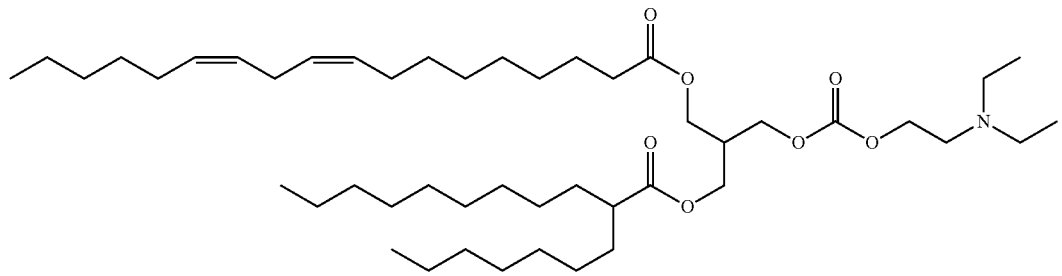 [SMILES: CCCCC/C=C\C/C=C\CCCCCCCC(=O)OCC(COC(=O)OCCN(CC)CC)COC(=O)C(CCCCCCC)CCCCCCCCC]

$^1$H NMR (400 MHz, CDCl$_3$): δ=5.45-5.28 (m, 4H), 4.25-4.10 (m, 8H), 2.78 (t, J=6.7 Hz, 2H), 2.73 (t, J=6.4 Hz, 2H), 2.58 (q, J=7.3 Hz, 4H), 2.48-2.39 (m, 1H), 2.38-2.27 (m, 3H), 2.05 (q, J=6.7 Hz, 4H), 1.68-1.52 (m, 6H), 1.50-1.18 (m, 38H), 1.03 (t, J=7.2 Hz, 6H), 0.93-0.84 (m, 9H) ppm. MS (M+1)=779.8, Rt=1.73 min (LC method 5).

Example 18

2-((((3-(dimethylamino)propoxy)carbonyl)oxy)
methyl)propane-1,3-diyl bis(2-heptylundecanoate)

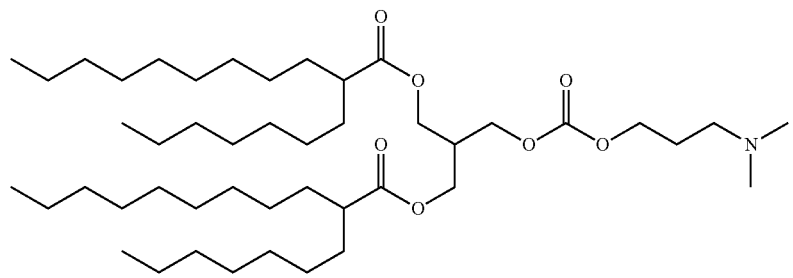 [SMILES: CCCCCCCCCC(CCCCCCC)C(=O)OCC(COC(=O)OCCCN(C)C)COC(=O)C(CCCCCCC)CCCCCCCCC]

¹H NMR (400 MHz, CDCl₃): δ=4.23-4.11 (m, 8H), 2.48-2.28 (m, 5H), 2.23 (s, 6H), 1.90-1.78 (m, 2H), 1.66-1.51 (m, 4H), 1.51-1.37 (m, 4H), 1.36-1.16 (m, 48H), 0.92-0.83 (m, 12H) ppm. MS (M+1)=769.7, Rt=1.82 min (LC method 5).

Example 19

(9Z,12Z)-3-(((3-(diethylamino)propoxy)carbonyl)oxy)-2-(((2-heptylundecanoyl)oxy)methyl)propyl octadeca-9,12-dienoate

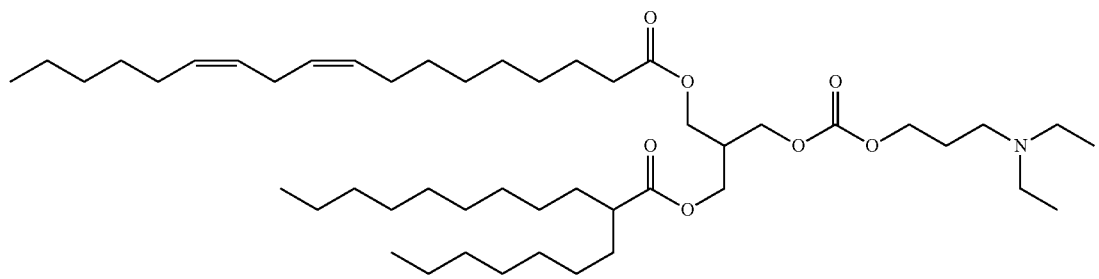 [SMILES: CCCCC/C=C\C/C=C\CCCCCCCC(=O)OCC(COC(=O)OCCCN(CC)CC)COC(=O)C(CCCCCCC)CCCCCCCCC]

¹H NMR (400 MHz, CDCl₃): δ=5.46-5.27 (m, 4H), 4.25-4.10 (m, 8H), 2.78 (t, J=6.7 Hz, 2H), 2.51 (q, J=7.1 Hz, 6H), 2.47-2.39 (m, 1H), 2.38-2.28 (m, 3H), 2.05 (q, J=6.8 Hz, 4H), 1.87-1.76 (m, 2H), 1.72-1.51 (m, 5H), 1.51-1.17 (m, 39H), 1.05-0.98 (m, 6H), 0.93-0.84 (m, 9H) ppm.

MS (M+1)=793.7, Rt=1.25 min (LC method 6).

Synthesis of Example 20

Intermediate 20a: ethyl 3-octylundec-2-enoate

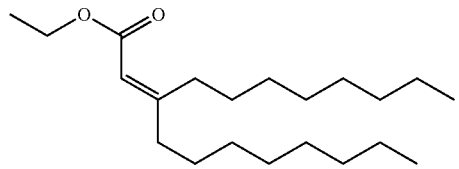 [SMILES: CCCCCCCCC(=CC(=O)OCC)CCCCCCCC]

A solution of 9-heptadecanone (15 g, 59 mmol) and triethylphosphonoacetate (13.2 g, 59 mmol) was stirred in THF (100 mL). To this reaction was added NaOEt (26.4 mL, 21% in EtOH, 70.7 mmol) and the resulting solution was heated to reflux for 48 h. The reaction was acidified with 1M HCl and then diluted with EtOAc. The organic layer was collected and washed with saturated aqueous sodium bicarbonate. The resulting organic material was dried over sodium sulfate and the volatiles removed under reduced pressure to yield a crude material that was purified by silica gel chromatography using heptanes/EtOAc as eluent, providing 11.7 g of the desired product.

¹H NMR (400 MHz, CDCl₃): δ=5.62 (s, 1H), 4.01-4.26 (m, 2H), 2.49-2.68 (m, 2H), 2.13 (m, 2H), 1.44 (dd, J=7.33, 4.80 Hz, 4H), 1.17-1.35 (m, 23H), 0.83-0.98 (m, 6H) ppm.

Intermediate 20b: ethyl 3-octylundecanoate

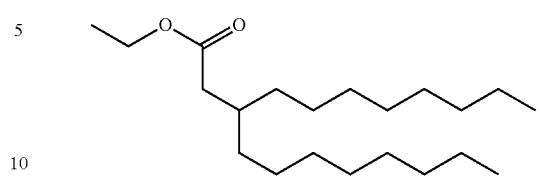

Intermediate 20a (11.75 g, 36.2 mmol) was stirred in DCM (16.5 mL) and MeOH (165 mL). Pd/C (3.85 g, 10% Pd/C) was added and the reaction flask was fitted with a balloon filled with hydrogen. The reaction was stirred at room temperature for 24 h. The reaction was degassed with nitrogen and filtered through celite with a wash of DCM and MeOH. The filtrate was collected and the volatiles removed under reduced pressure to provide 10.6 g of the desired product.

¹H NMR (400 MHz, CDCl₃) δ=(q, J=7.16 Hz, 2H), 2.39 (t, J=7.45 Hz, 2H), 2.22 (d, J=6.82 Hz, 2H), 1.84 (br. s., 1H), 1.56 (t, J=7.20 Hz, 2H), 1.19-1.36 (m, 27H), 0.81-0.95 (m, 6H) ppm.

Intermediate 20c: 3-octylundecanoic acid

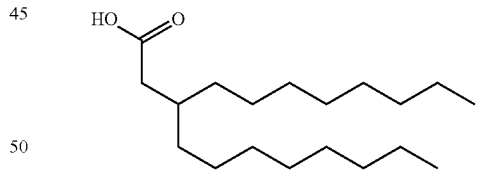

Intermediate 20b (10.6 g, 32.5 mmol) was stirred with NaOH (9.74 mL, 10M, 97.4 mmol) in MeOH (100 mL) and DCM (10 mL). The reaction was heated to reflux overnight. Aqueous HCl was added to neutralize the solution, the volatiles were removed under reduced pressure and the resulting material was taken back up in DCM. The organics were washed with aqueous saturated sodium bicarbonate and the resulting aqueous layer was extracted with DCM. The combined organics were dried over magnesium sulfate, filtered, and concentrated under reduced pressure. The material was purified by silica gel chromatography using heptanes/EtOAc as eluent. The resulting material was taken up in DCM and loaded onto an NH₂ functionalized column. The column was washed with DCM and then DCM/MeOH. The product was eluted with acidic methanol and the eluent concentrated under reduced pressure.

The residue was taken up in DCM and washed with saturated aqueous sodium bicarbonate, dried over magnesium sulfate, filtered, and concentrated under reduced pressure to provide 6.5 g of the desired product.

$^1$H NMR (400 MHz, CDCl$_3$) δ=2.28 (d, J=7.07 Hz, 2H) 1.86 (br. s., 1H) 1.15-1.44 (m, 28H) 0.82-0.97 (m, 6H) ppm.

Example 20

(9Z,12Z)-3-(((2-(dimethylamino)ethoxy)carbonyl)oxy)-2-(((3-octylundecanoyl)oxy)methyl)propyl octadeca-9,12-dienoate

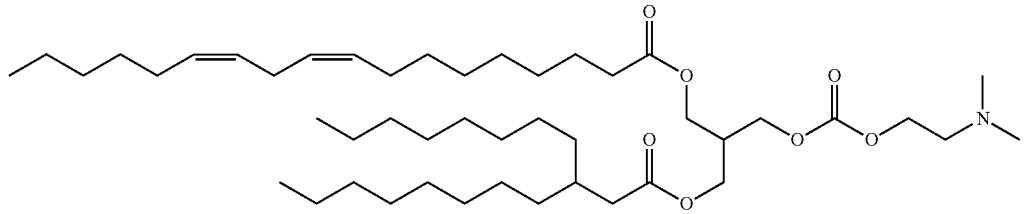 [SMILES: CCCCC/C=C\C/C=C\CCCCCCCC(=O)OCC(COC(=O)CC(CCCCCCCC)CCCCCCCC)COC(=O)OCCN(C)C]

Example 20 can be prepared using similar methods to those employed for the synthesis of Example 13.

$^1$H NMR (400 MHz, CDCl$_3$): δ=5.45-5.25 (m, 4H), 4.26-4.17 (m, 4H), 4.13 (dd, J=1.9, 5.9 Hz, 4H), 2.81-2.72 (m, 2H), 2.58 (t, J=5.8 Hz, 2H), 2.46-2.35 (m, 1H), 2.34-2.18 (m, 10H), 2.10-1.97 (m, 4H), 1.89-1.74 (m, 1H), 1.69-1.47 (m, 4H), 1.45-0.98 (m, 40H), 0.91-0.82 (m, 9H) ppm.

MS (M+1)=765.5, Rt=1.27 min (LC method 6).

The following examples can be prepared using similar methods to those employed for the synthesis of Example 20 and Example 13:

Example 21

2-((((3-(diethylamino)propoxy)carbonyl)oxy)methyl)propane-1,3-diyl bis(3-octylundecanoate)

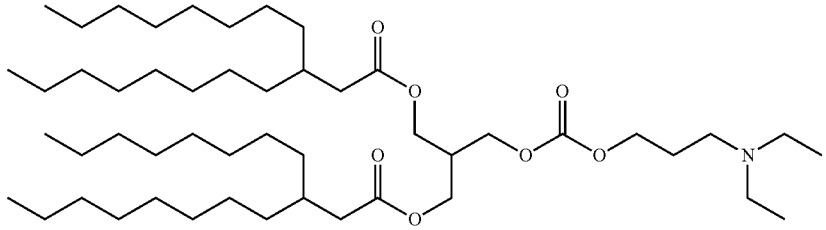 [SMILES: CCCCCCCCC(CCCCCCCC)CC(=O)OCC(COC(=O)CC(CCCCCCCC)CCCCCCCC)COC(=O)OCCCN(CC)CC]

$^1$H NMR (400 MHz, CDCl$_3$): δ=4.25-4.11 (m, 6H), 4.07 (t, J=6.8 Hz, 1H), 3.65 (t, J=6.5 Hz, 1H), 3.70-3.60 (m, 1H), 2.52 (q, J=7.0 Hz, 4H), 2.47-2.37 (m, 1H), 2.34-2.20 (m, 4H), 1.88-1.75 (m, 2H), 1.73-1.52 (m, 4H), 1.42-1.17 (m, 59H), 1.01 (t, J=7.0 Hz, 4H), 0.95 (t, J=7.4 Hz, 2H), 0.88 (t, J=6.8 Hz, 8H) ppm. MS (M+1)=825.7, Rt=1.33 min (LC method 6).

Example 22

(9Z,12Z)-3-(((3-(diethylamino)propoxy)carbonyl)oxy)-2-(((3-octylundecanoyl)oxy)methyl)propyl octadeca-9,12-dienoate

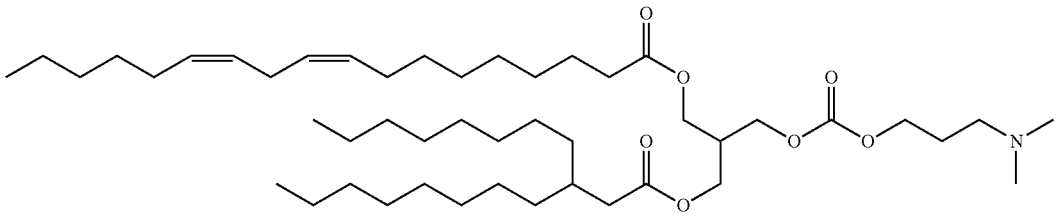 [SMILES: CCCCC/C=C\C/C=C\CCCCCCCC(=O)OCC(COC(=O)CC(CCCCCCCC)CCCCCCCC)COC(=O)OCCCN(C)C]

¹H NMR (400 MHz, CDCl₃): δ=5.45-5.27 (m, 4H), 4.24-4.10 (m, 8H), 2.78 (t, J=6.7 Hz, 2H), 2.51 (q, J=7.1 Hz, 6H), 2.47-2.37 (m, 1H), 2.31 (t, J=7.7 Hz, 2H), 2.25 (d, J=7.0 Hz, 2H), 2.05 (q, J=6.8 Hz, 4H), 1.89-1.75 (m, 3H), 1.72-1.53 (m, 3H), 1.42-1.17 (m, 41H), 1.01 (t, J=7.2 Hz, 6H), 0.95-0.83 (m, 9H) ppm. MS (M+1)=807.4, Rt=1.29 min (LC method 3).

Synthesis of Example 23

Intermediate 23a: methyl 3-hexylnon-2-enoate

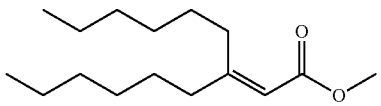 [SMILES: CCCCCCC(=CC(=O)OC)CCCCCC]

To a suspension of sodium hydride (60% in paraffin oil, 14.16 g, 335 mmol) in THF (500 mL), cooled in an ice-water bath, was slowly added trimethyl phosphonoacetate (50.74 g, 278.8 mmol). After 2 h, tridecan-7-one (6.5 g, 32.8 mmol) was slowly added, and the reaction was warmed to ambient temperature. After 1 h, the reaction was heated to reflux. After 4 days, the reaction was cooled, and 1N HCl (aq) was added to quench the reaction. The reaction was extracted with ethyl acetate (3×200 mL). The combined organic extracts were dried over sodium sulfate, filtered, and concentrated under reduced pressure. The concentrate was purified on silica gel, using ethyl acetate/hexanes as eluent to provide 8.0 g of the desired product.

TLC (silica gel, 10% ethyl acetate in hexanes): R_f=0.72.

Intermediate 23b: 3-hexylnon-2-en-1-ol

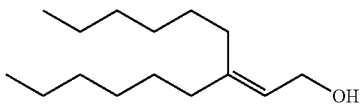 [SMILES: CCCCCCC(=CCO)CCCCCC]

To a solution of Intermediate 23a (8.1 g, 31.9 mmol) in THF (100 mL), cooled in an ice-water bath, was added diisobutylaluminum hydride (25% in toluene, 54.4 mL, 95.6 mmol). After 30 min. the reaction was brought to ambient temperature. After 6 h, the reaction was cooled in an ice-water bath and quenched with ice-cold water (50 mL) and 1N HCl (aq, 15 mL). The reaction was extracted with ethyl acetate (2×50 mL). The combined organic extracts were washed with water (2×60 mL) and brine (60 mL). The organic extract was dried over sodium sulfate, filtered, and concentrated under reduced pressure. The concentrate was purified on silica-gel, using ethyl acetate/hexanes as eluent to provide 6.8 g of the desired product.

TLC (silica gel, 20% ethyl acetate in hexanes): R_f=0.29.

Intermediate 23c: 3-hexylnon-2-enal

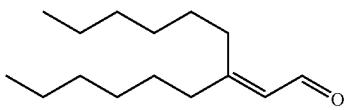 [SMILES: CCCCCCC(=CC=O)CCCCCC]

To a stirred suspension of IBX (21.0 g, 75.12 mmol) in DMSO (30 mL), warmed to 30° C., was added Intermediate 23b in THF (100 mL). The reaction was maintained at 25-30° C. for 2 h. The reaction was diluted with diethyl ether and filtered through celite with diethyl ether washes. The filtrate was washed with water (2×200 mL) and brine (200 mL). The organic extract was dried over sodium sulfate, filtered, and concentrated under reduced pressure to provide 6.0 g of the desired product, which was used without further purification.

TLC (silica gel, 10% ethyl acetate in hexanes): R_f=0.50.

Intermediate 23d: 7-hexyltrideca-4,6-dienoic acid

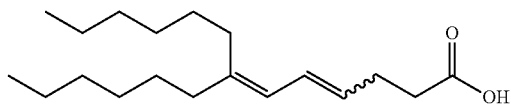 [SMILES: CCCCCCC(=CC=CCCC(=O)O)CCCCCC]

To a suspension of (3-carboxypropyl)triphenylphosphonium bromide (19.09 g, 44.6 mmol) in THF (80 mL) and HMPA (5 mL), cooled in an ice-water bath, was added NaHMDS (1.0M in THF, 111 mL, 111 mmol). Intermediate 23c (5.0 g, 22.3 mmol) in THF (20 mL), was slowly added, and the reaction was warmed to 30° C. After 16 h, the reaction was diluted with 200 mL water and acidified with 2N HCl (aq). The reaction was extracted with ethyl acetate (3×100 mL). The combined organic extracts were dried over sodium sulfate, filtered, and concentrated under reduced pressure. The concentrate was purified on silica gel with ethyl acetate/hexanes as eluent to provide 4.0 g of the desired product.

TLC (silica gel, 30% EtOAc in n-hexane): R_f=0.21.

Intermediate 23e: 7-hexyltridecanoic acid

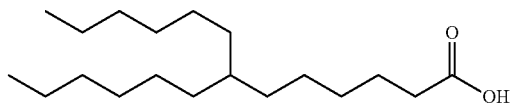 [SMILES: CCCCCCC(CCCCCC)CCCCCC(=O)O]

To a suspension of Intermediate 23d (4.0 g, 13.6 mmol) in methanol (100 mL) in a Paar-shaker vessel was added Pd/C (10% Pd/C, 2.0 g). The reaction was placed on the shaker apparatus and pressurized to 60 psi hydrogen gas. After 2 h, the reaction mixture was filtered through celite with methanol washings (2×50 mL). The filtrate was concentrated under reduced pressure, and the concentrate was purified on silica gel with ethyl acetate/n-hexane as eluent to provide 3.9 g of the desired product.

TLC (silica gel, 30% EtOAc in n-hexane): R_f=0.21.

Example 23

(9Z,12Z)-3-(((3-(diethylamino)propoxy)carbonyl)oxy)-2-(((7-hexyltridecanoyl)oxy)methyl)propyl octadeca-9,12-dienoate

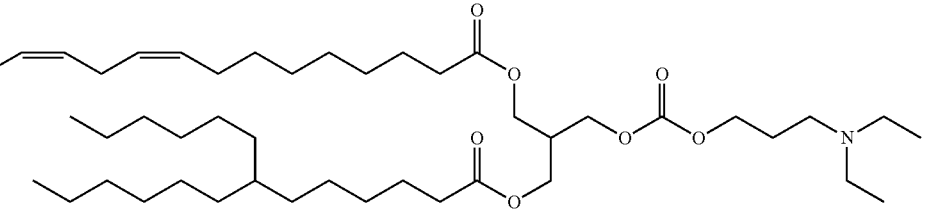

Example 23 can be prepared using similar methods to those employed for the synthesis of Example 13.

$^1$H NMR (400 MHz, CDCl$_3$): δ=5.27-5.46 (m, 4H), 4.08-4.26 (m, 8H), 2.78 (t, J=6.40 Hz, 2H), 2.52 (q, J=6.86 Hz, 6H), 2.43 (dt, J=11.98, 5.93 Hz, 1H), 2.31 (t, J=7.53 Hz, 4H), 2.05 (q, J=6.61 Hz, 4H), 1.77-1.89 (m, 2H), 1.55-1.70 (m, 6H), 1.14-1.47 (m, 39H), 1.02 (t, J=7.15 Hz, 6H), 0.83-0.95 (m, 9H) ppm. MS (M+1)=806.3, Rt=1.91 min (LC method 7).

Example 24

(9Z,12Z)-3-(((3-(diethylamino)propoxy)carbonyl)oxy)-2-(((9-pentyltetradecanoyl)oxy)methyl)propyl octadeca-9,12-dienoate

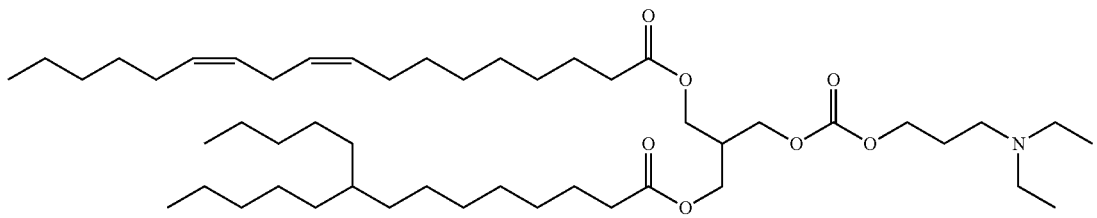 [SMILES: CCCCC/C=C\C/C=C\CCCCCCCC(=O)OCC(COC(=O)CCCCCCCC(CCCCC)CCCCC)COC(=O)OCCCN(CC)CC]

Example 24 can be prepared using similar methods to those employed for the synthesis of Example 13.

$^1$H NMR (400 MHz, CDCl$_3$): δ=5.28-5.45 (m, 4H), 4.11-4.24 (m, 8H), 2.78 (t, J=6.53 Hz, 2H), 2.53 (q, J=6.69 Hz, 6H), 2.43 (dt, J=11.86, 5.99 Hz, 1H), 2.31 (t, J=7.65 Hz, 4H), 2.05 (q, J=6.78 Hz, 4H), 1.83 (quint., J=6.84 Hz, 2H), 1.57-1.67 (m, 4H), 1.14-1.43 (m, 41H), 1.03 (t, J=7.15 Hz, 6H), 0.84-0.96 (m, 9H) ppm. MS (M+1)=806.6, Rt=1.67 min (LC method 6).

Synthesis of Example 25

Intermediate 25a: 3-heptyldec-2-enal

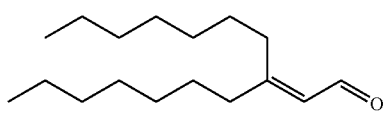 [SMILES: CCCCCCCC(=CC=O)CCCCCCC]

Intermediate 25a can be prepared using similar methods to those employed for the preparation of Intermediate 23c in the synthesis of Example 23.

TLC (silica gel, 10% EtOAc in hexanes): R$_f$=0.63.

Intermediate 25b: methyl 5-heptyldodeca-2,4-dienoate

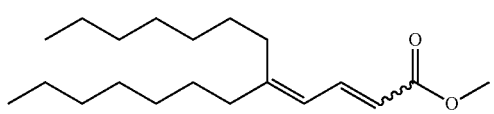 [SMILES: CCCCCCCC(=CC=CC(=O)OC)CCCCCCC]

To a suspension of sodium hydride (55% in paraffin oil, 3.5 g, 74.3 mmol) in THF (70 mL), cooled in an ice-water bath, was added trimethylphosphonoacetate (9.6 mL, 59.5 mmol). After 10 min, Intermediate 25a (7.5 g, 29.7 mmol) in THF (10 mL) was added, and the reaction was allowed to warm to ambient temperature. After 2 h, the reaction was quenched by slow addition of ice-cold water (20 mL). The reaction was extracted with ethyl acetate (2×100 mL). the organic extracts were washed with water and brine. The organics were dried over sodium sulfate, filtered, and concentrated under reduced pressure to provide 8.0 g of the desired product.

TLC (silica gel, 10% EtOAc in hexanes): R$_f$=0.75.

Intermediate 25c: methyl 5-heptyldodecanoate

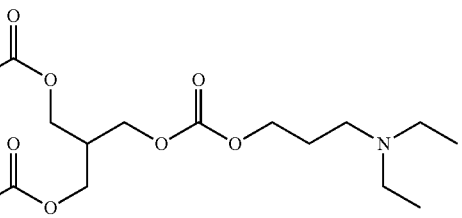

To a solution of Intermediate 25b (8.0 g, 25.95 mmol) in methanol (350 mL) was added palladium on carbon (10% Pd/C, 1.0 g). The reaction was carried out under 1 atm of hydrogen delivered by a balloon. After 14 h, the reaction was filtered through celite with methanol washes. The filtrate was concentrated under reduced pressure to provide 7.7 g of the desired product.

TLC (silica gel, 5% methanol in dichloromethane): R$_f$=0.63.

Intermediate 25d: 5-heptyldodecanoic acid

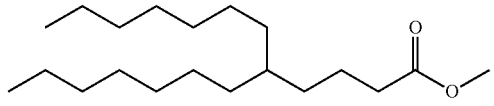 [SMILES: CCCCCCCC(CCCCCCC)CCCC(=O)OC]

To a mixture of 5N sodium hydroxide (aq, 125 mL) and methanol (350 mL) was added Intermediate 25c (7.7 g, 24.7 mmol), and the reaction was heated to reflux. After 16 h, the reaction was cooled in an ice-water bath and quenched by addition of concentrated aqueous HCl until acidic. The mixture was extracted with ethyl acetate (2×250 mL). The organic extracts were dried over sodium sulfate, filtered, and concentrated under reduced pressure. The concentrate was purified on silica gel with ethyl acetate/hexanes as eluent to provide 7.0 g of the desired product.

TLC (silica gel, 50% EtOAc/heptane): R$_f$=0.82.

Example 25

(9Z,12Z)-3-(((3-(diethylamino)propoxy)carbonyl)oxy)-2-(((5-heptyldodecanoyl)oxy)methyl)propyl octadeca-9,12-dienoate

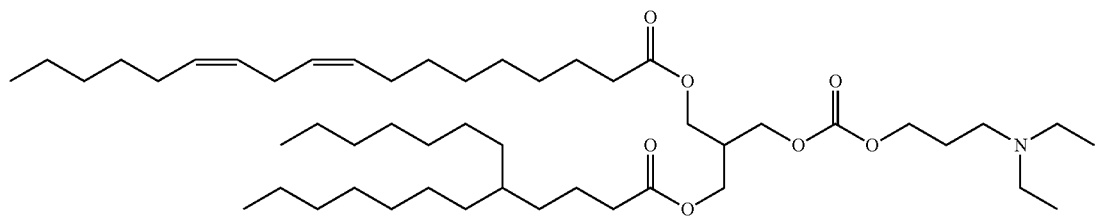 [SMILES: CCCCC/C=C\C/C=C\CCCCCCCC(=O)OCC(COC(=O)CCCC(CCCCCCC)CCCCCCC)COC(=O)OCCCN(CC)CC]

Example 25 can be prepared using similar methods to those employed for the synthesis of Example 13.

$^1$H NMR (400 MHz, CDCl$_3$): δ=5.30-5.45 (m, 4H), 4.14-4.25 (m, 8H), 2.79 (t, J=6.65 Hz, 2H), 2.55 (q, J=6.78 Hz, 6H), 2.45 (dt, J=11.98, 5.93 Hz, 1H), 2.32 (q, J=7.53 Hz, 4H), 2.07 (q, J=6.61 Hz, 4H), 1.84 (dt, J=13.93, 6.84 Hz, 2H), 1.55-1.68 (m, 4H), 1.22-1.41 (m, 41H), 1.04 (t, J=7.15 Hz, 6H), 0.86-0.97 (m, 9H) ppm. MS (M+1)=806.6, Rt=1.76 min (LC method 6).

Synthesis of Example 26

Intermediate 26a: heptyl 2,2-bis(heptyloxy)acetate

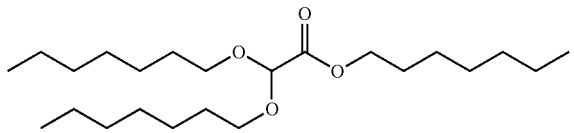 [SMILES: CCCCCCCOC(=O)C(OCCCCCCC)OCCCCCCC]

To a solution of methyl 2,2-dimethoxyacetate (5.0 g, 37.3 mmol) in heptanol (26.3 mL, 186 mmol) was added camphorsulfonic acid (0.43 g, 1.86 mmol), and the reaction was heated to 100° C., overnight. The reaction was cooled to ambient temperature and concentrated under reduced pressure. The concentrate was purified on silica gel with dichloromethane/heptane as eluent to provide 4.0 g of the desired compound.

$^1$H NMR (400 MHz, CDCl$_3$): δ=4.86 (s, 1H), 4.21 (t, J=6.78 Hz, 2H), 3.52-3.69 (m, 4H), 1.55-1.77 (m, 6H), 1.20-1.45 (m, 24H), 0.82-0.98 (m, 9H) ppm.

Intermediate 26b: 2,2-bis(heptyloxy)acetic acid

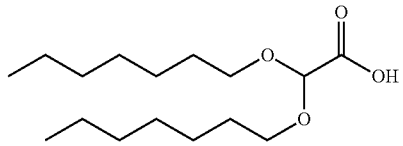 [SMILES: CCCCCCCOC(OCCCCCCC)C(=O)O]

To a solution of Intermediate 26a (4.06 g, 10.5 mmol) in methanol (50 mL) was added sodium hydroxide (2N aq, 7.88 mL, 15.8 mmol), and the mixture was stirred at ambient temperature overnight. The reaction was diluted with ethyl acetate and brine. The aqueous layer was titrated to neutral pH with 1N aq HCl, and was extracted with ethyl acetate. The combined organics were dried over sodium sulfate, filtered, and concentrated under reduced pressure. The concentrate was purified on silica gel (equilibrated with 0.4N ammonia and 2% methanol in dichloromethane) with methanol/dichloromethane as eluent to provide 2.3 g of the desired compound.

$^1$H NMR (400 MHz, CDCl$_3$): δ=4.88 (s, 1H), 3.53-3.71 (m, 4H), 1.63 (quin, J=6.84 Hz, 4H), 1.18-1.43 (m, 16H), 0.84-0.97 (m, 6H) ppm.

Example 26

(9Z,12Z)-3-(2,2-bis(heptyloxy)acetoxy)-2-((((2-(dimethylamino)ethoxy)carbonyl)oxy)methyl)propyl octadeca-9,12-dienoate

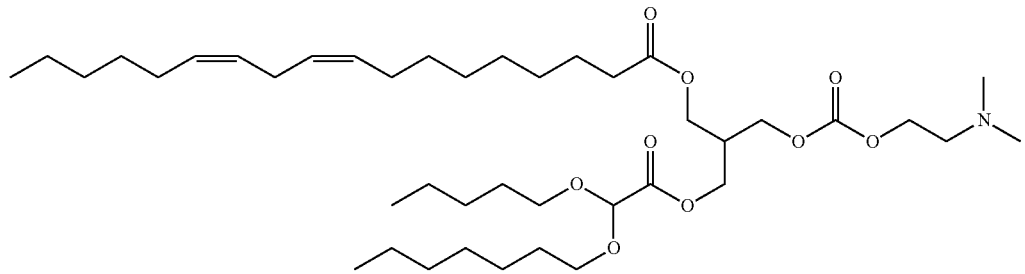 [SMILES: CCCCC/C=C\C/C=C\CCCCCCCC(=O)OCC(COC(=O)OCCN(C)C)COC(=O)C(OCCCCC)OCCCCCCC]

Example 26 can be prepared using similar methods to those employed for the synthesis of Example 13.

$^1$H NMR (CDCl$_3$): δ=5.21-5.51 (m, 4H), 4.89 (s, 1H), 4.20-4.34 (m, 6H), 4.16 (d, J=5.8 Hz, 2H), 3.49-3.67 (m, 4H), 2.78 (t, J=6.6 Hz, 2H), 2.59 (t, J=5.8 Hz, 2H), 2.41-2.55 (m, 1H), 2.24-2.37 (m, 8H), 2.06 (q, J=6.8 Hz, 4H), 1.62 (quin, J=6.9 Hz, 6H), 1.20-1.44 (m, 30H), 0.89 (dq, J=6.8, 3.5 Hz, 9H) ppm. MS (M+1)=754.5, Rt=1.17 min (LC method 6).

Synthesis of Example 27

Intermediate 27a: methyl 6,6-dimethoxyhexanoate

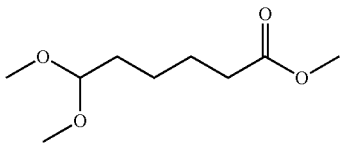

Methyl 6-oxohexanoate (11 g, 76 mmol) was taken into methanol (60 mL) and conc. sulfuric acid (244 uL, 4.58 mmol) was added. The reaction was heated to reflux overnight. The reaction was cooled to ambient temperature and diluted with water. The mixture was extracted with ethyl acetate. The combined organic extracts were dried over sodium sulfate, filtered, and concentrated under reduced pressure. The concentrate was purified on silica gel with ethyl acetate/heptane as eluent to afford 12.1 g of the desired compound.

$^1$H NMR (400 MHz, CDCl$_3$) δ=4.37 (t, J=5.77 Hz, 1H), 3.68 (s, 3H), 3.33 (s, 6H), 2.34 (t, J=7.53 Hz, 2H), 1.57-1.73 (m, 4H), 1.34-1.46 (m, 2H) ppm.

Example 27

(9Z,12Z)-3-((6,6-bis(octyloxy)hexanoyl)oxy)-2-((((3-(diethylamino)propoxy)carbonyl)oxy)methyl)propyl octadeca-9,12-dienoate

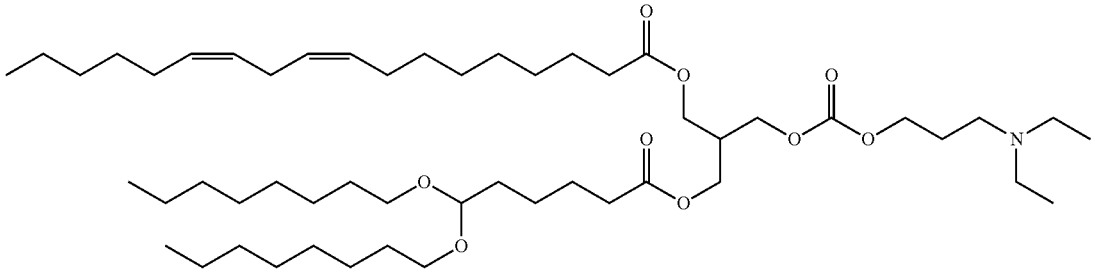 [SMILES: CCCCC/C=C\C/C=C\CCCCCCCC(=O)OCC(COC(=O)CCCCC(OCCCCCCCC)OCCCCCCCC)COC(=O)OCCCN(CC)CC]

Example 27 can be prepared using similar methods to those employed for the synthesis of Example 26 and Example 13.

$^1$H NMR (400 MHz, CDCl$_3$): δ=5.25-5.47 (m, 4H), 4.45 (t, J=5.65 Hz, 1H), 4.08-4.27 (m, 8H), 3.55 (dt, J=9.22, 6.68 Hz, 2H), 3.34-3.45 (m, 2H), 2.77 (t, J=6.27 Hz, 2H), 2.52 (q, J=7.03 Hz, 6H), 2.42 (dt, J=11.86, 5.99 Hz, 1H), 2.25-2.37 (m, 4H), 2.05 (q, J=6.78 Hz, 4H), 1.76-1.88 (m, 2H), 1.50-1.75 (m, 12H), 1.20-1.47 (m, 34H), 1.02 (t, J=7.15 Hz, 6H), 0.81-0.95 (m, 9H) ppm. MS (M+1)=881.1, Rt=2.73 min (LC method 4).

Synthesis of Example 28

Intermediate 28a: diethyl 2-(4-(benzyloxy)butyl)malonate

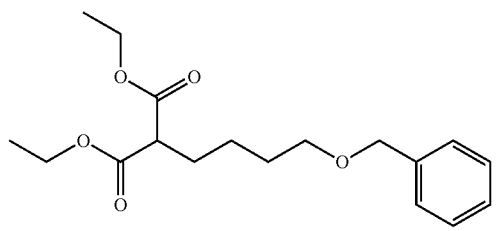 [SMILES: CCOC(=O)C(CCCCOCc1ccccc1)C(=O)OCC]

To a suspension of sodium hydride (60% dispersion in mineral oil, 4.93 g, 123 mmol) in THF (100 mL), was slowly added diethyl malonate (31.2 mL, 206 mmol). Once gas evolution had ceased, (4-bromobutoxy)methylbenzene (25 g, 103 mmol) was added and the reaction was heated to 90° C. After 6 h, the reaction was cooled to ambient temperature and diluted with diethyl ether (100 mL) and water (100 mL). The aqueous layer was further extracted with diethyl ether (2×100 mL). The combined organic extracts were dried over sodium sulfate, filtered, and concentrated under reduced pressure. The concentrate was purified on silica gel with ethyl acetate/heptane as eluent to provide the desired product contaminated with diethyl malonate. Fractional distillation at 60° C. and reduced pressure removed diethyl malonate to provide 24.3 g of the desired product.

$^1$H NMR (400 MHz, CDCl$_3$) δ=7.28-7.39 (m, 5H), 4.51 (s, 2H), 4.16-4.25 (m, 4H), 3.49 (t, J=6.53 Hz, 2H), 3.34 (t, J=7.53 Hz, 1H), 1.89-1.98 (m, 2H), 1.61-1.72 (m, 2H), 1.39-1.49 (m, 2H), 1.28 (t, J=7.00 Hz, 6H) ppm.

Intermediate 28b: 2-(4-(benzyloxy)butyl)propane-1,3-diol

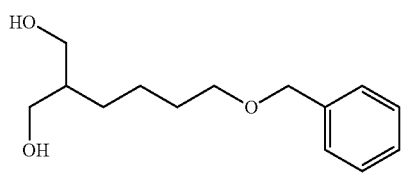 [SMILES: OCC(CO)CCCCOCc1ccccc1]

To a mixture of Intermediate 28a (20.0 g, 62.0 mmol) in THF (100 mL) was added lithium aluminum hydride (5.18 g, 136 mmol). After 48 h, the reaction was quenched with slow addition of ice-cold water. The mixture was extracted with ethyl acetate (2×100 mL), and the organic extracts were concentrated under reduced pressure. The concentrate was purified on silica gel with methanol/heptane as eluent to provide 6.6 g of the desired product.

$^1$H NMR (400 MHz, CDCl$_3$) δ=7.29-7.40 (m, 5H), 4.52 (s, 2H), 3.82 (dd, J=10.54, 3.51 Hz, 2H), 3.67 (dd, J=10.42, 7.65 Hz, 2H), 3.49 (t, J=6.53 Hz, 2H), 2.38 (br. s., 2H), 1.72-1.84 (m, 1H), 1.58-1.68 (m, 2H), 1.38-1.49 (m, 2H), 1.24-1.33 (m, 2H) ppm.

Intermediate 28c:
2-(4-(benzyloxy)butyl)propane-1,3-diyl dioctanoate

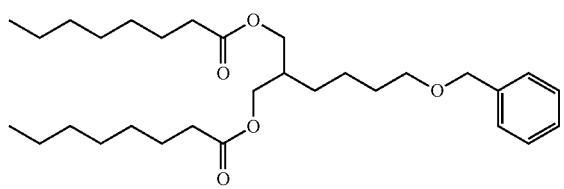 [SMILES: CCCCCCCC(=O)OCC(CCCCOCc1ccccc1)COC(=O)CCCCCCC]

Intermediate 28b (2.0 g, 8.39 mmol), pyridine (1.49 mL, 18.5 mmol), and DMAP (0.051 g, 0.42 mmol) were mixed in dichloromethane (30 mL). To this mixture was slowly added octanoyl chloride (3.18 mL, 18.5 mmol). After 1 h, the mixture was poured into 6M HCl (aq, 20 mL), and was extracted with diethyl ether (2×40 mL). The combined organic extracts were dried over sodium sulfate, filtered, and concentrated under reduced pressure. The concentrate was purified on silica gel with ethyl acetate/heptane eluent to provide 3.2 g of the desired product.

$^1$H NMR (400 MHz, CDCl$_3$) δ=7.30-7.40 (m, 5H), 4.52 (s, 2H), 4.07 (qd, J=11.04, 5.77 Hz, 4H), 3.49 (t, J=6.40 Hz, 2H), 2.31 (t, J=7.53 Hz, 4H), 2.01 (spt, J=6.00 Hz, 1H), 1.53-1.72 (m, 6H), 1.35-1.50 (m, 4H), 1.22-1.35 (m, 16H), 0.83-0.95 (m, 6H) ppm.

Intermediate 28d:
2-(4-hydroxybutyl)propane-1,3-diyl dioctanoate

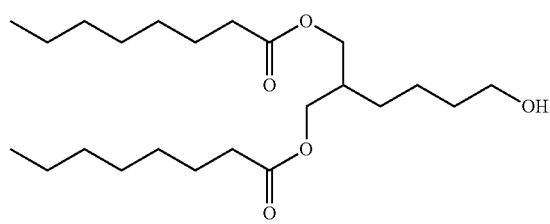 [SMILES: CCCCCCCC(=O)OCC(CCCCO)COC(=O)CCCCCCC]

Palladium on carbon (10% Pd/C, 20 mg) and Intermediate 28c (3.2 g, 6.52 mmol) were taken into methanol (10 mL) in a Paar shaker reaction vessel. The reaction was pressurized to 54 psi with hydrogen gas and shaken at ambient temperature overnight. The reaction was filtered through celite and the filtrate was concentrated under reduced pressure. The concentrate was purified on silica gel with ethyl acetate/heptane as eluent to provide 2.06 g of the desired compound.

$^1$H NMR (400 MHz, CDCl$_3$) δ=3.99-4.17 (m, 4H), 3.67 (t, J=6.40 Hz, 2H), 2.32 (t, J=7.53 Hz, 4H), 2.02 (spt, J=5.80 Hz, 1H), 1.54-1.71 (m, 7H), 1.37-1.52 (m, 4H), 1.20-1.37 (m, 16H), 0.83-0.95 (m, 6H) ppm.

Intermediate 28e:
6-(octanoyloxy)-5-((octanoyloxy)methyl)hexanoic acid

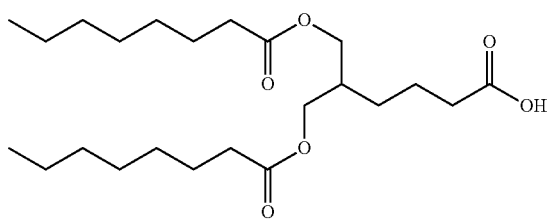 [SMILES: CCCCCCCC(=O)OCC(CCCC(=O)O)COC(=O)CCCCCCC]

To a solution of Intermediate 28d (3.35 g, 8.37 mmol) in acetone (30 mL), cooled in an ice-water bath, was added Jones' reagent (2M aq, 6.7 mL, 13.4 mmol). The reaction was allowed to warm to ambient temperature. After 2 h, methanol (1 mL) was added and allowed to react for 5 min. The reaction was concentrated under reduced pressure, and the concentrate was diluted with ethyl acetate (50 mL) and water (540 mL). The organic extract was dried over sodium sulfate, filtered, and concentrated under reduced pressure. The concentrate was purified on silica gel with ethyl acetate/heptane as eluent to provide 2.78 g of the desired compound.

MS (M+1)=415.4, Rt=1.32 min (LC method 3).

Example 28

2-(3-ethyl-11-(((9Z,12Z)-octadeca-9,12-dienoyloxy)methyl)-8,14-dioxo-7,9,13-trioxa-3-azaheptadecan-17-yl)propane-1,3-diyl dioctanoate

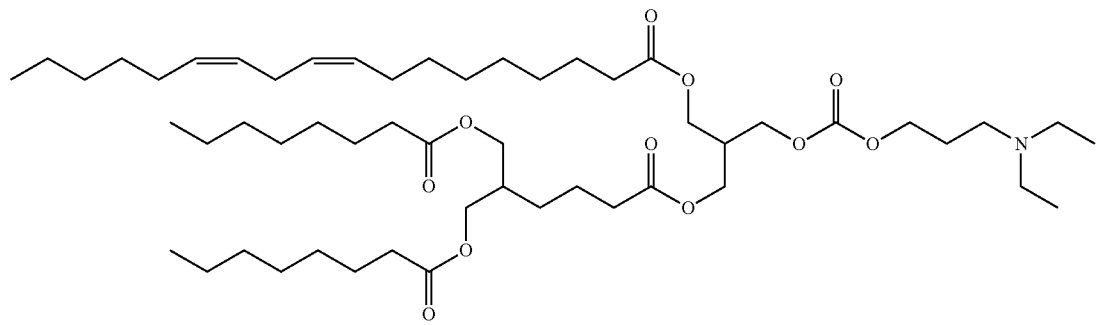 [SMILES: CCCCC/C=C\C/C=C\CCCCCCCC(=O)OCC(COC(=O)CCCC(COC(=O)CCCCCCC)COC(=O)CCCCCCC)COC(=O)OCCCN(CC)CC]

Example 28 can be prepared using similar methods to those employed for the synthesis of Example 13.

$^1$H NMR (400 MHz, CDCl$_3$): δ=5.27-5.45 (m, 4H), 4.17-4.24 (m, 4H), 4.15 (d, J=6.02 Hz, 4H), 4.06 (qd, J=11.00, 5.65 Hz, 4H), 2.77 (t, J=6.65 Hz, 2H), 2.37-2.71 (m, 7H), 2.26-2.37 (m, 8H), 1.95-2.10 (m, 5H), 1.85 (br. s., 2H), 1.54-1.74 (m, 8H), 1.20-1.45 (m, 32H), 1.04 (br. s., 6H), 0.83-0.95 (m, 9H) ppm. MS (M+1)=922.8, Rt=1.71 min (LC method 4).

The following examples can be prepared from Intermediate 1a using similar methods to those employed for the synthesis of Example 13:

Example 29

(9Z,9'Z,12Z,12'Z)-2-((((3-(dimethylamino)propoxy)carbonyl)oxy)methyl)propane-1,3-diyl bis(octadeca-9,12-dienoate)

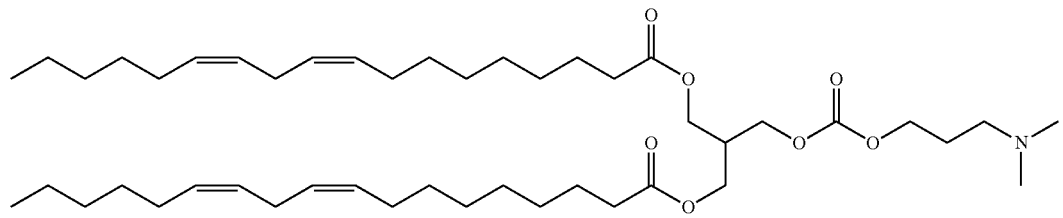 [SMILES: CCCCC/C=C\C/C=C\CCCCCCCC(=O)OCC(COC(=O)CCCCCCC/C=C\C/C=C\CCCCC)COC(=O)OCCCN(C)C]

$^1$H NMR (400 MHz, CDCl$_3$): δ=5.43-5.30 (m, 8H), 4.22-4.10 (m, 8H), 2.78 (t, J=8.0 Hz, 4H), 2.47-2.29 (m, 7H), 2.24 (s, 6H), 2.09-2.02 (m, 8H), 1.90-1.80 (m, 2H), 1.55-1.62 (m, 4H), 1.39-1.26 (m, 28H), 0.91-0.88 (m, 6H) ppm. MS (M+1)=761.7, Rt=1.21 min (LC method 4).

Example 30

(9Z,9'Z,12Z,12'Z)-2-((((3-(diethylamino)propoxy)carbonyl)oxy)methyl)propane-1,3-diyl bis(octadeca-9,12-dienoate)

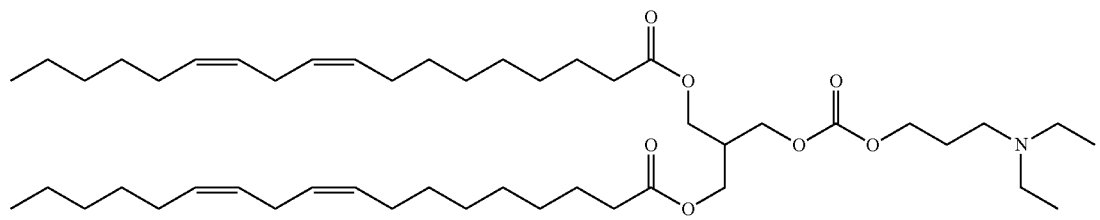 [SMILES: CCCCC/C=C\C/C=C\CCCCCCCC(=O)OCC(COC(=O)CCCCCCC/C=C\C/C=C\CCCCC)COC(=O)OCCCN(CC)CC]

$^1$H NMR (400 MHz, CDCl$_3$): δ=5.42-5.30 (m, 8H), 4.21-4.14 (m, 8H), 2.78 (m, 4H), 2.51 (q, J=7.1 Hz, 6H), 2.46-2.38 (m, 1H), 2.31 (t, J=7.7 Hz, 4H), 2.05 (q, J=6.7 Hz, 8H), 1.81 (quin, J=7.0 Hz, 2H), 1.65-1.58 (m, 4H), 1.39-1.24 (m, 28H), 1.01 (t, J=7.2 Hz, 6H), 0.91-0.88 (m, 6H) ppm. MS (M+1)=790.5, Rt=1.23 min (LC method 5).

Example 31

(9Z,9'Z,12Z,12'Z)-2-((((2-(dimethylamino)ethoxy)carbonyl)oxy)methyl)propane-1,3-diyl bis(octadeca-9,12-dienoate)

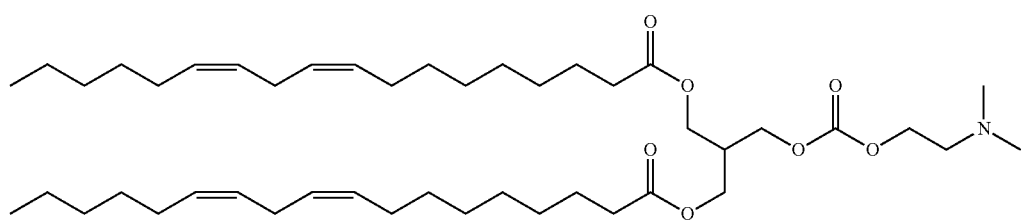

¹H NMR (400 MHz, CDCl₃): δ=5.45-5.27 (m, 8H), 4.27-4.18 (m, 4H), 4.14 (d, J=6.0 Hz, 4H), 2.81-2.73 (m, 4H), 2.59 (t, J=5.6 Hz, 2H), 2.48-2.36 (m, 1H), 2.36-2.24 (m, 10H), 2.05 (q, J=6.8 Hz, 8H), 1.70-1.53 (m, 5H), 1.43-1.19 (m, 27H), 0.96-0.83 (m, 6H) ppm. MS (M+1)= 748.5, Rt=1.23 min (LC method 5).

The following examples can be prepared from Intermediate 13d using similar methods to those employed for the synthesis of Example 1:

Example 32

(9Z,12Z)-3-((4,4-bis(octyloxy)butanoyl)oxy)-2-(((3-(dimethylamino)propanoyl)oxy)methyl)propyl octadeca-9,12-dienoate

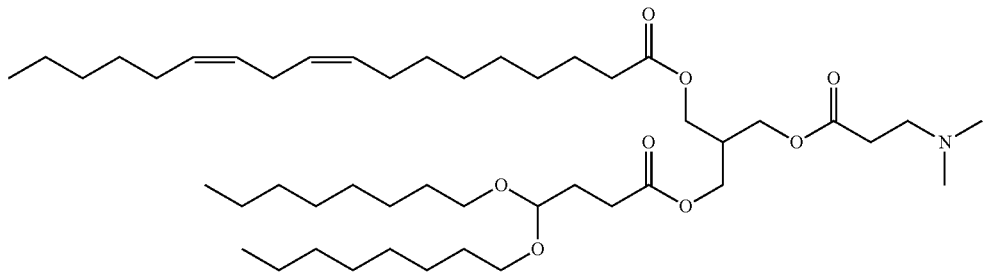 [SMILES: CCCCC/C=C\C/C=C\CCCCCCCC(=O)OCC(COC(=O)CCC(OCCCCCCCC)OCCCCCCCC)COC(=O)CCN(C)C]

¹H NMR (400 MHz, CDCl₃): δ=5.26-5.45 (m, 4H), 4.49 (t, J=5.52 Hz, 1H), 4.04-4.22 (m, 6H), 3.57 (dt, J=9.29, 6.78 Hz, 2H), 3.40 (dt, J=9.29, 6.78 Hz, 2H), 2.77 (t, J=6.40 Hz, 2H), 2.56-2.65 (m, 2H), 2.45-2.53 (m, 2H), 2.35-2.45 (m, 3H), 2.31 (t, J=7.65 Hz, 2H), 2.24 (s, 6H), 2.05 (q, J=6.78 Hz, 4H), 1.88-1.97 (m, 2H), 1.70 (br. s., 2H), 1.49-1.66 (m, 6H), 1.17-1.47 (m, 32H), 0.81-0.96 (m, 9H) ppm. MS (M+1)=795.0, Rt=2.61 min (LC method 4).

Example 33

3-((4,4-bis(octyloxy)butanoyl)oxy)-2-(((9Z,12Z)-octadeca-9,12-dienoyloxy)methyl)propyl 1-isopropylpiperidine-4-carboxylate

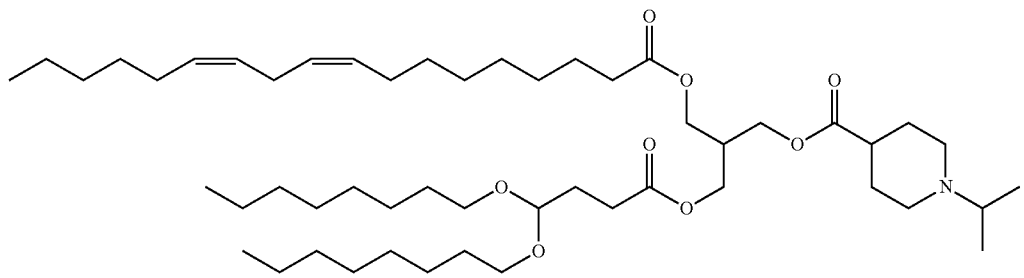 [SMILES: CCCCC/C=C\C/C=C\CCCCCCCC(=O)OCC(COC(=O)CCC(OCCCCCCCC)OCCCCCCCC)COC(=O)C1CCN(C(C)C)CC1]

¹H NMR (400 MHz, CDCl₃): δ=5.27-5.46 (m, 4H), 4.49 (t, J=5.65 Hz, 1H), 4.05-4.20 (m, 6H), 3.57 (dt, J=9.22, 6.68 Hz, 2H), 3.40 (dt, J=9.29, 6.78 Hz, 2H), 2.86 (d, J=11.54 Hz, 2H), 2.77 (t, J=6.40 Hz, 2H), 2.71 (dt, J=13.05, 6.53 Hz, 1H), 2.35-2.46 (m, 3H), 2.23-2.34 (m, 3H), 2.17 (t, J=10.79 Hz, 2H), 2.05 (q, J=6.78 Hz, 4H), 1.85-1.98 (m, 4H), 1.48-1.80 (m, 10H), 1.20-1.43 (m, 32H), 1.03 (d, J=6.53 Hz, 6H), 0.81-0.95 (m, 9H) ppm. MS (M+1)=849.1, Rt=2.62 min (LC method 4).

Example 34

3-((4,4-bis(octyloxy)butanoyl)oxy)-2-(((9Z,12Z)-octadeca-9,12-dienoyloxy)methyl)propyl 1-(cyclopropylmethyl)piperidine-4-carboxylate

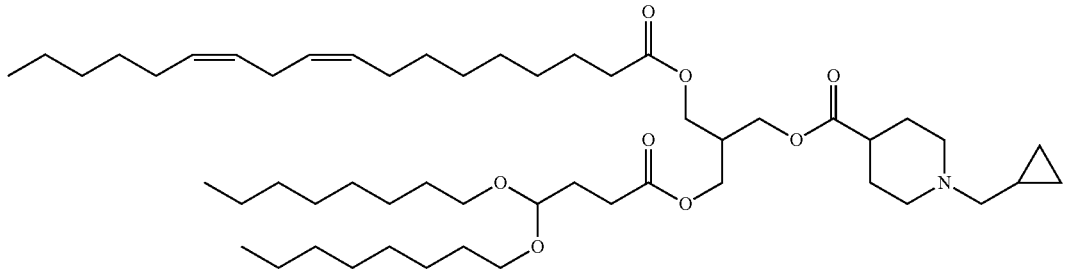 [SMILES: CCCCC/C=C\C/C=C\CCCCCCCC(=O)OCC(COC(=O)CCC(OCCCCCCCC)OCCCCCCCC)COC(=O)C1CCN(CC2CC2)CC1]

$^1$H NMR (400 MHz, CDCl$_3$) δ=5.27-5.45 (m, 4H), 4.49 (t, J=5.52 Hz, 1H), 4.07-4.18 (m, 6H), 3.57 (dt, J=9.29, 6.65 Hz, 2H), 3.40 (dt, J=9.22, 6.68 Hz, 2H), 3.02 (d, J=11.29 Hz, 2H), 2.77 (t, J=6.65 Hz, 2H), 2.35-2.45 (m, 3H), 2.27-2.35 (m, 3H), 2.24 (d, J=6.53 Hz, 2H), 1.97-2.11 (m, 6H), 1.86-1.97 (m, 4H), 1.72-1.85 (m, 2H), 1.49-1.72 (m, 8H), 1.20-1.42 (m, 32H), 0.80-0.95 (m, 10H), 0.47-0.56 (m, 2H), 0.10 (q, J=4.77 Hz, 2H) ppm. MS (M+1)=861.1, Rt=2.65 min (LC method 4).

Example 35

3-((4,4-bis(octyloxy)butanoyl)oxy)-2-(((9Z,12Z)-octadeca-9,12-dienoyloxy)methyl)propyl 1-methyl-pyrrolidine-3-carboxylate

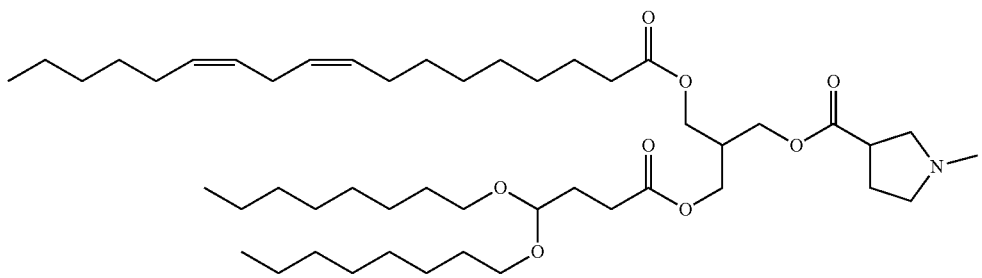 [SMILES: CCCCC/C=C\C/C=C\CCCCCCCC(=O)OCC(COC(=O)CCC(OCCCCCCCC)OCCCCCCCC)COC(=O)C1CCN(C)C1]

$^1$H NMR (400 MHz, CDCl$_3$): δ=5.25-5.47 (m, 4H), 4.49 (t, J=5.52 Hz, 1H), 4.06-4.20 (m, 6H), 3.57 (dt, J=9.03, 6.78 Hz, 2H), 3.40 (dt, J=9.16, 6.71 Hz, 2H), 2.98-3.11 (m, 1H), 2.73-2.86 (m, 3H), 2.48-2.71 (m, 3H), 2.34-2.47 (m, 6H), 2.31 (t, J=7.53 Hz, 2H), 2.00-2.16 (m, 6H), 1.87-1.98 (m, 2H), 1.70 (br. s., 2H), 1.50-1.66 (m, 6H), 1.18-1.42 (m, 32H), 0.82-0.95 (m, 9H) ppm. MS (M+1)=807.0, Rt=2.60 min (LC method 4).

Synthesis of Example 36

Intermediate 36a: (9Z,9'Z,12Z,12'Z)-2-(hydroxymethyl)-2-(((9Z,12Z)-octadeca-9,12-dienoyloxy)methyl)propane-1,3-diyl bis(octadeca-9,12-dienoate)

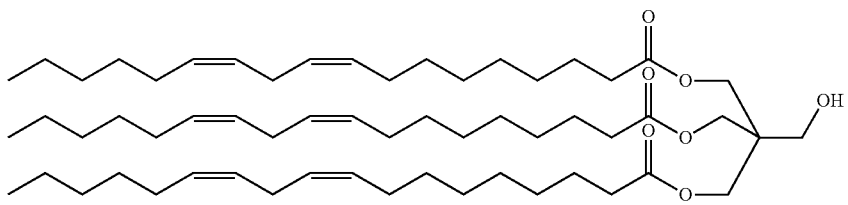 [SMILES: CCCCC/C=C\C/C=C\CCCCCCCC(=O)OCC(CO)(COC(=O)CCCCCCC/C=C\C/C=C\CCCCC)COC(=O)CCCCCCC/C=C\C/C=C\CCCCC]

To a mixture of linoleic Acid (6.18 g, 22.04 mmol) and EDC (4.51 g, 23.50 mmol) in DCM (100 ml) were added DIPEA (5.13 mL, 29.4 mmol) and DMAP (0.538 g, 4.41 mmol). After 1 h, pentaerythritol (1 g, 7.35 mmol) was added and the mixture was stirred at ambient temperature for 3 days. The reaction was concentrated under reduced pressure, and the concentrate was purified on silica gel with ethyl acetate/heptane as eluent to provide 770 mg of the desired product.

$^1$H NMR (400 MHz, CDCl$_3$): δ=5.26-5.48 (m, 12H), 4.13 (s, 6H), 3.50 (d, J=7.03 Hz, 2H), 2.79 (t, J=6.53 Hz, 6H), 2.35 (t, J=7.65 Hz, 6H), 1.99-2.14 (m, 12H), 1.57-1.71 (m, 7H) 1.20-1.44 (m, 42H), 0.90 (m, 9H) ppm.

Example 36

(9Z,9'Z,12Z,12'Z)-2-((((3-(diethylamino)propoxy)carbonyl)oxy)methyl)-2-(((9Z,12Z)-octadeca-9,12-dienoyloxy)methyl)propane-1,3-diylbis(octadeca-9,12-dienoate)

To a solution of Intermediate 13d (300 mg, 0.431 mmol) in DMF (15 mL) was added (S)-1-methylpyrrolidine-2-carboxylic acid (168 mg, 1.29 mmol), HATU (660 mg, 1.72 mmol), DIPEA (0.46 mL, 2.59 mmol) and DMAP (106 mg, 0.86 mmol) sequentially. The resulting mixture was stirred for 24 h at rt. The reaction mixture was diluted with water (100 mL) and extracted with EtOAc (2×100 mL). The combined organic layers were washed with brine (100 mL), dried over Na$_2$SO$_4$, and concentrated under reduced pressure to obtain brown liquid. The concentrate was purified on silica gel with 15% EtOAc/hexane as eluent to provide 190 mg of the desired compound.

$^1$H NMR (400 MHz, CDCl$_3$): δ=5.38 (m, 4H), 4.48 (t, J=8 Hz, 1H), 4.20 (d, J=8 Hz, 2H), 4.16 (d, J=8 Hz, 4H), 3.58 (q, J=8 Hz, 2H), 3.40 (q, J=8 Hz, 2H), 3.15 (m, 1H), 2.98 (m, 1H), 2.78 (t, J=6 Hz, 2H), 2.44-2.38 (m, 6H), 2.30 (m, 2H), 2.18-2.02 (m, 5H), 1.92 (m, 4H), 1.48 (m, 2H), 1.42 (m, 4H), 1.38-1.20 (m, 36H), 0.84 (m, 9H) ppm.

MS (M+1)=807.1, Rt=2.85 min (LC method 9).

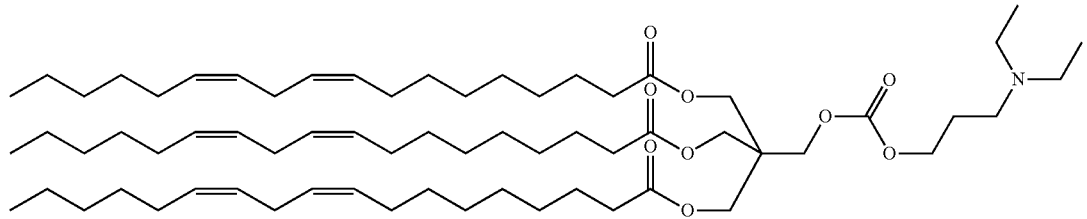 [SMILES: CCCCC/C=C\C/C=C\CCCCCCCC(=O)OCC(COC(=O)CCCCCCC/C=C\C/C=C\CCCCC)(COC(=O)CCCCCCC/C=C\C/C=C\CCCCC)COC(=O)OCCCN(CC)CC]

Example 36 can be prepared using similar methods to those employed for the synthesis of Example 13.

$^1$H NMR (CDCl$_3$): δ=5.25-5.51 (m, 12H), 4.16-4.26 (m, 4H), 4.13 (s, 6H), 2.78 (t, J=6.5 Hz, 6H), 2.46-2.58 (m, 6H), 2.32 (t, J=7.7 Hz, 6H), 2.06 (q, J=6.6 Hz, 12H), 1.76-1.88 (m, 2H), 1.61 (t, J=7.0 Hz, 6H), 1.23-1.44 (m, 42H), 1.02 (t, J=7.2 Hz, 6H), 0.85-0.96 (m, 9H) ppm.

MS (M+1)=1080.6, Rt=1.39 min (LC method 6).

The following examples can be prepared using similar methods to those employed for the synthesis of Example 1.

Example 37

(2S)-3-((4,4-bis(octyloxy)butanoyl)oxy)-2-(((9Z,12Z)-octadeca-9,12-dienoyloxy)methyl)propyl 1-methylpyrrolidine-2-carboxylate

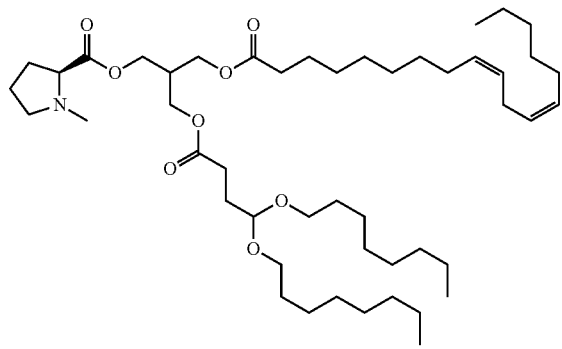 [SMILES: CCCCC/C=C\C/C=C\CCCCCCCC(=O)OCC(COC(=O)CCC(OCCCCCCCC)OCCCCCCCC)COC(=O)[C@@H]1CCCN1C]

Example 38

(2R)-3-((4,4-bis(octyloxy)butanoyl)oxy)-2-(((9Z,12Z)-octadeca-9,12-dienoyloxy)methyl)propyl 1-methylpyrrolidine-2-carboxylate

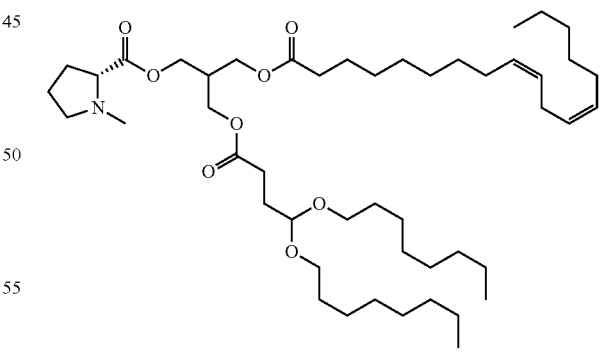

$^1$H NMR (400 MHz, CDCl$_3$): δ=5.38 (m, 4H), 4.48 (t, J=8 Hz, 1H), 4.20 (d, J=8 Hz, 2H), 4.16 (d, J=8 Hz, 4H), 3.58 (q, J=8 Hz, 2H), 3.40 (q, J=8 Hz, 2H), 3.15 (m, 1H), 2.98 (t, J=6 Hz, 1H), 2.78 (t, J=6 Hz, 2H), 2.44-2.38 (m, 6H), 2.30 (m, 2H), 2.18-2.02 (m, 5H), 1.92 (m, 4H), 1.48 (m, 2H), 1.42 (m, 4H), 1.38-1.20 (m, 36H), 0.84 (m, 9H) ppm.

MS (M+1)=807, Rt=2.77 min (LCmethod 9).

Example 39

3-((4,4-bis(octyloxy)butanoyl)oxy)-2-(((9Z,12Z)-octadeca-9,12-dienoyloxy)methyl)propyl 4-methyl-morpholine-2-carboxylate

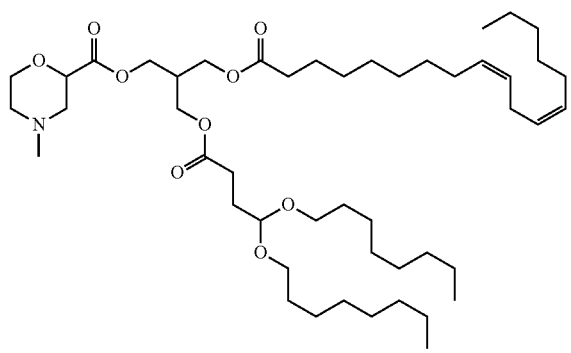

$^1$H NMR (400 MHz, CDCl$_3$): δ=5.38 (m, 4H), 4.44 (t, J=8 Hz, 1H), 4.25 (m, 3H), 4.18 (m, 4H), 4.0 (m, 1H), 3.70 (m, 1H), 3.48 (q, J=8 Hz, 2H), 3.40 (q, J=8 Hz, 2H), 2.86 (d, J=12 Hz, 1H), 2.68 (t, J=5.2 Hz, 2H), 2.52 (m, 1H), 2.40 (m, 3H), 2.30 (m, 7H), 2.02 (m, 4H), 1.92 (m, 2H), 1.62-1.52 (m, 6H), 1.40-1.22 (m, 34H), 0.82 (m, 9H) ppm.

MS (M+1)=823.1, Rt=1.28 min (LC method 10).

Example 40

3-((4,4-bis(octyloxy)butanoyl)oxy)-2-(((9Z,12Z)-octadeca-9,12-dienoyloxy)methyl)propyl 1,4-dimethylpiperidine-4-carboxylate

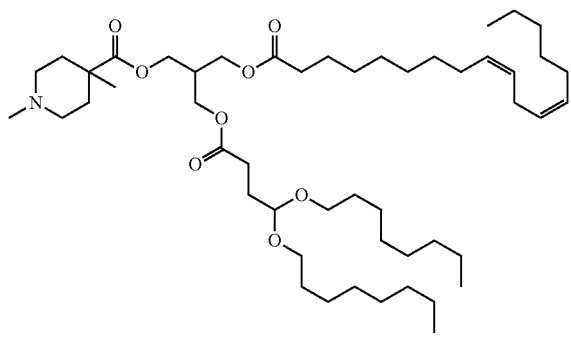 [SMILES: CCCCC/C=C\C/C=C\CCCCCCCC(=O)OCC(COC(=O)CCC(OCCCCCCCC)OCCCCCCCC)COC(=O)C1(C)CCN(C)CC1]

$^1$H NMR (400 MHz, CD$_2$Cl$_2$) δ=5.28-5.43 (m, 4H), 4.45 (t, J=5.50 Hz, 1H), 4.12 (dt, J=6.05, 1.31 Hz, 6H), 3.54 (dt, J=9.29, 6.72 Hz, 2H), 3.38 (dt, J=9.26, 6.62 Hz, 2H), 2.73-2.82 (m, 2H), 2.53 (br. s., 2H), 2.25-2.44 (m, 5H), 2.19 (s, 3H), 2.05 (q, J=6.89 Hz, 8H), 1.87 (td, J=7.58, 5.62 Hz, 2H), 1.42-1.64 (m, 8H), 1.22-1.38 (m, 34H), 1.17 (s, 3H), 0.83-0.93 (m, 9H) ppm.

MS (M+1)=835.5, Rt=2.69 min (LC method 9).

Example 41

3-((4,4-bis(octyloxy)butanoyl)oxy)-2-(((9Z,12Z)-octadeca-9,12-dienoyloxy)methyl)propyl 1-methyl-piperidine-4-carboxylate

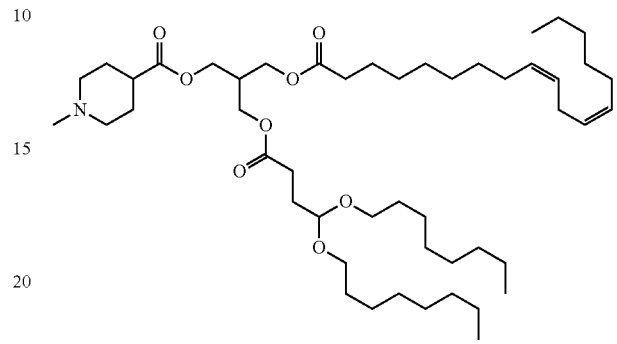

$^1$H NMR (400 MHz, CD$_2$Cl$_2$) δ=5.28-5.43 (m, 4H), 4.45 (t, J=5.50 Hz, 1H), 4.12 (dt, J=6.02, 1.45 Hz, 6H), 3.54 (dt, J=9.29, 6.66 Hz, 2H), 3.39 (dt, J=9.29, 6.66 Hz, 2H), 2.71-2.85 (m, 4H), 2.19-2.43 (m, 9H), 1.93-2.11 (m, 6H), 1.87 (m, 4H), 1.66-1.78 (m, 2H), 1.48-1.63 (m, 6H), 1.25-1.38 (m, 34H), 0.83-0.92 (m, 9H) ppm.

MS (M+1)=821.4, Rt=2.68 min (LC method 9).

Example 42

3-((4,4-bis(octyloxy)butanoyl)oxy)-2-(((9Z,12Z)-octadeca-9,12-dienoyloxy)methyl)propyl 1-methyl-piperidine-3-carboxylate

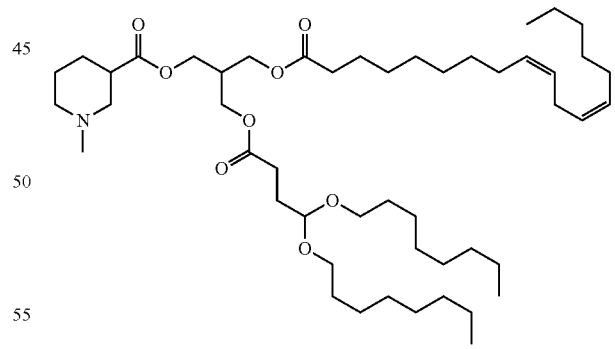

$^1$H NMR (400 MHz, ACETONITRILE-d$_3$) δ=5.43-5.28 (m, 4H), 4.45 (t, J=5.50 Hz, 1H), 4.10 (d, J=5.99 Hz, 5H), 3.54 (dt, J=9.38, 6.56 Hz, 2H), 3.38 (dt, J=9.41, 6.54 Hz, 2H), 2.74-2.82 (m, 3H), 2.50-2.60 (m, 2H), 2.25-2.39 (m, 5H), 2.19 (s, 5H), 2.06 (q, J=6.68 Hz, 5H), 1.86-1.75 (m, 3H), 1.72-1.62 (m, 1H), 1.62-1.45 (m, 7H), 1.39-1.21 (m, 35H), 0.94-0.83 (m, 9H) ppm.

MS (M+1)=821, Rt=2.72 min (LC method 9).

Example 43
3-((4,4-bis(octyloxy)butanoyl)oxy)-2-(((9Z,12Z)-octadeca-9,12-dienoyloxy)methyl)propyl 3-((dimethylamino)methyl)benzoate
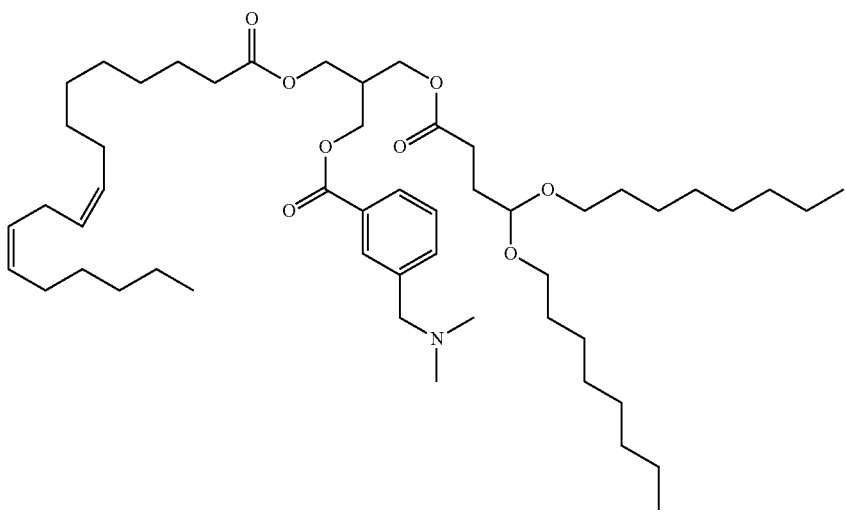 [SMILES: CCCCC/C=C\C/C=C\CCCCCCCC(=O)OCC(COC(=O)CCC(OCCCCCCCC)OCCCCCCCC)COC(=O)c1cccc(CN(C)C)c1]
$^1$H NMR (400 MHz, CDCl$_3$) δ=7.96-7.89 (m, 2H), 7.56 (d, J=7.8 Hz, 1H), 7.41 (t, J=7.7 Hz, 1H), 5.43-5.29 (m, 4H), 4.49 (t, J=5.5 Hz, 1H), 4.40 (d, J=6.0 Hz, 2H), 4.24 (dd, J=6.0, 1.7 Hz, 4H), 3.57 (dt, J=9.2, 6.7 Hz, 2H), 3.47 (s, 2H), 3.40 (dt, J=9.3, 6.7 Hz, 2H), 2.78 (t, J=6.6 Hz, 2H), 2.61-2.51 (m, 1H), 2.42 (t, J=7.6 Hz, 2H), 2.32 (t, J=7.6 Hz, 2H), 2.25 (s, 6H), 2.10-2.00 (m, 4H), 1.98-1.88 (m, 2H), 1.67-1.50 (m, 6H), 1.41-1.20 (m, 34H), 0.93-0.84 (m, 9H) ppm.
MS (M+1)=856.1, Rt=2.65 min (LC method 11).
Example 44
3-((4,4-bis(octyloxy)butanoyl)oxy)-2-(((9Z,12Z)-octadeca-9,12-dienoyloxy)methyl)propyl 4-((diethylamino)methyl)benzoate
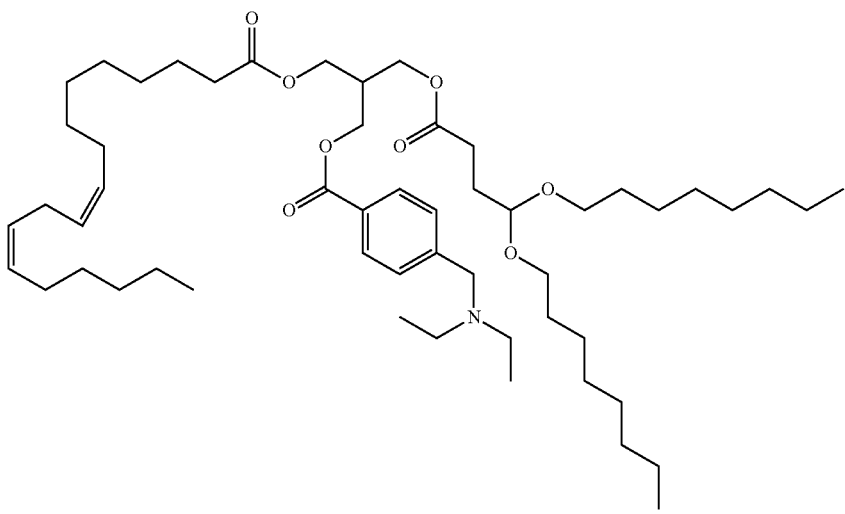 [SMILES: CCCCC/C=C\C/C=C\CCCCCCCC(=O)OCC(COC(=O)CCC(OCCCCCCCC)OCCCCCCCC)COC(=O)c1ccc(CN(CC)CC)cc1]

¹H NMR (400 MHz, CD₂Cl₂) δ=7.95 (d, J=7.9 Hz, 2H), 7.44 (d, J=7.6 Hz, 2H), 5.43-5.26 (m, 4H), 4.44 (t, J=5.6 Hz, 1H), 4.37 (d, J=5.9 Hz, 2H), 4.21 (dd, J=6.0, 1.7 Hz, 4H), 3.60 (s, 2H), 3.54 (dt, J=9.3, 6.7 Hz, 2H), 3.38 (dt, J=9.3, 6.7 Hz, 2H), 2.81-2.73 (m, 2H), 2.59-2.43 (m, 5H), 2.38 (t, J=7.5 Hz, 2H), 2.30 (t, J=7.5 Hz, 2H), 2.05 (q, J=6.9 Hz, 4H), 1.92-1.82 (m, 2H), 1.65-1.47 (m, 6H), 1.41-1.19 (m, 34H), 1.02 (t, J=6.8 Hz, 6H), 0.92-0.81 (m, 9H) ppm.

MS (M+2)=885.2, Rt=2.74 min (LC method 9).

The following examples can be prepared using similar methods to those employed for the synthesis of Example 13:

Example 45

(9Z,12Z)-3-((4,4-bis(octyloxy)butanoyl)oxy)-2-((((3-(pyrrolidin-1-yl)propoxy)carbonyl)oxy)methyl)propyl octadeca-9,12-dienoate

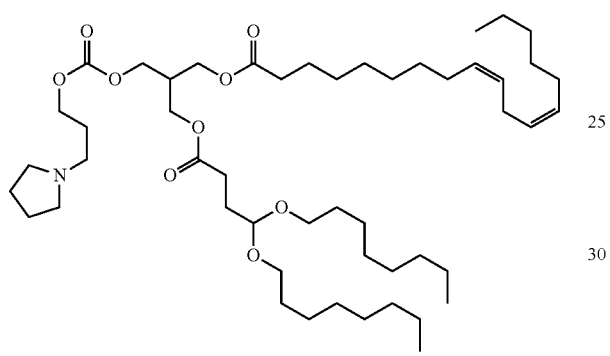

¹H NMR (400 MHz, CDCl₃): δ=5.38 (m, 4H), 4.44 (t, J=6 Hz, 1H), 4.18 (m, 8H), 3.58 (q, J=6 Hz, 2H), 3.38 (q, J=6 Hz, 2H), 2.78 (t, J=6 Hz, 2H), 2.58 (m, 6H), 2.40 (m, 3H), 2.30 (t, J=8 Hz, 2H), 2.18 (m, 4H), 1.90 (m, 4H), 1.78 (m, 4H), 1.70-1.50 (m, 9H), 1.40-1.22 (m, 31H), 0.82 (m, 9H) ppm.

MS (M+1)=851.1, Rt=1.14 min (LC method 10).

Example 46

(9Z,12Z)-3-((4,4-bis(octyloxy)butanoyl)oxy)-2-((((3-(4-methylpiperazin-1-yl)propoxy)carbonyl)oxy)methyl)propyl octadeca-9,12-dienoate

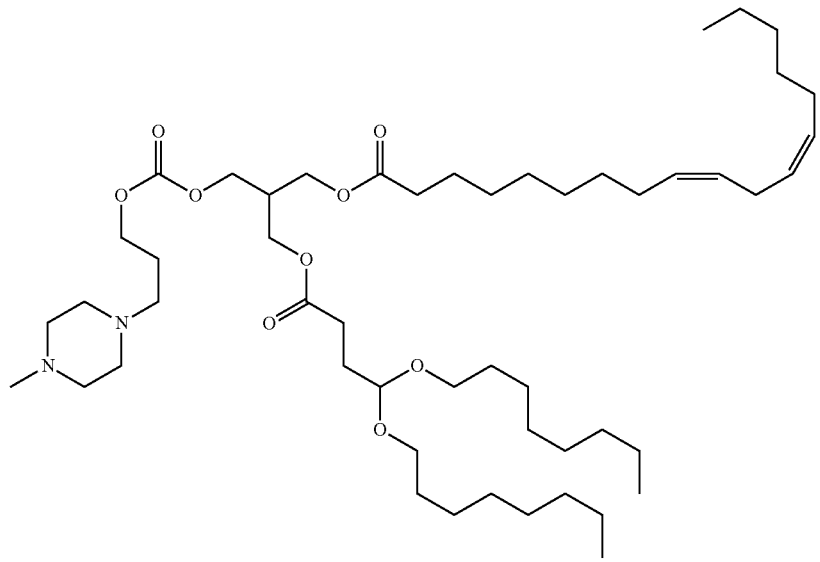 [SMILES: CCCCC/C=C\C/C=C\CCCCCCCC(=O)OCC(COC(=O)CCC(OCCCCCCCC)OCCCCCCCC)COC(=O)OCCCN1CCN(C)CC1]

¹H NMR (400 MHz, CDCl₃) δ=5.44-5.28 (m, 4H), 4.49 (t, J=5.5 Hz, 1H), 4.23-4.10 (m, 8H), 3.57 (dt, J=9.3, 6.7 Hz, 2H), 3.41 (dt, J=9.3, 6.7 Hz, 2H), 2.78 (t, J=6.6 Hz, 2H), 2.62-2.35 (m, 12H), 2.34-2.26 (m, 3H), 2.29 (s, 3H), 2.06 (q, J=6.6 Hz, 4H), 1.97-1.81 (m, 4H), 1.69-1.50 (m, 6H), 1.42-1.20 (m, 34H), 0.95-0.83 (m, 9H) ppm.

MS (M+1)=880.0, Rt=1.12 min (LC method 12).

Example 47

(9Z,12Z)-3-((4,4-bis(octyloxy)butanoyl)oxy)-2-(((((1-methylpyrrolidin-3-yl)oxy)carbonyl)oxy)methyl)propyl octadeca-9,12-dienoate

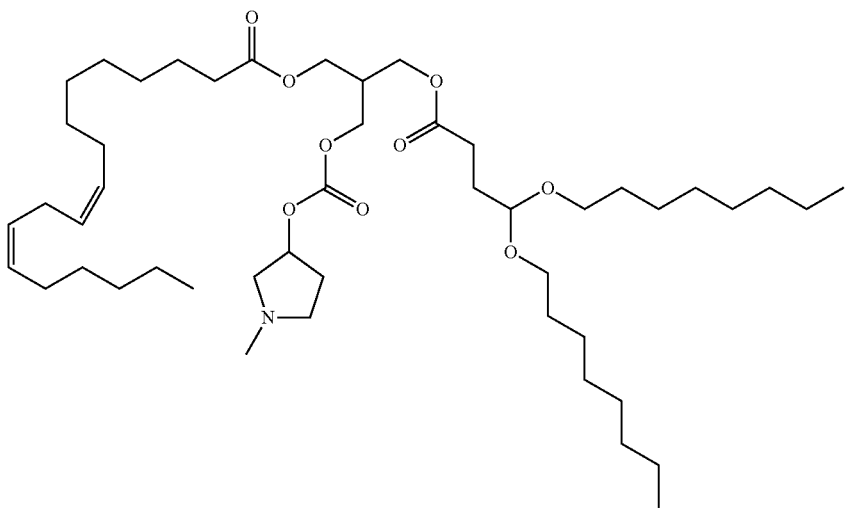 [SMILES: CCCCC/C=C\C/C=C\CCCCCCCC(=O)OCC(COC(=O)CCC(OCCCCCCCC)OCCCCCCCC)COC(=O)OC1CCN(C)C1]

$^1$H NMR (400 MHz, CD$_2$Cl$_2$) δ=5.26-5.44 (m, 4H), 5.04-5.13 (m, 1H), 4.45 (t, J=5.56 Hz, 1H), 4.08-4.21 (m, 6H), 3.54 (dt, J=9.26, 6.68 Hz, 2H), 3.38 (dt, J=9.29, 6.66 Hz, 2H), 2.78 (m, J=6.40, 6.40 Hz, 4H), 2.22-2.48 (m, 9H), 2.05 (q, J=6.85 Hz, 4H), 1.87 (m, J=7.60, 7.60, 5.50 Hz, 3H), 1.48-1.65 (m, 8H), 1.21-1.42 (m, 34H), 0.82-0.93 (m, 9H) ppm.

MS (M+1)=823.2, Rt=2.65 min (LC method 9).

Example 48

(9Z,12Z)-3-((4,4-bis(octyloxy)butanoyl)oxy)-2-(((((1-methylpiperidin-4-yl)oxy)carbonyl)oxy)methyl)propyl octadeca-9,12-dienoate

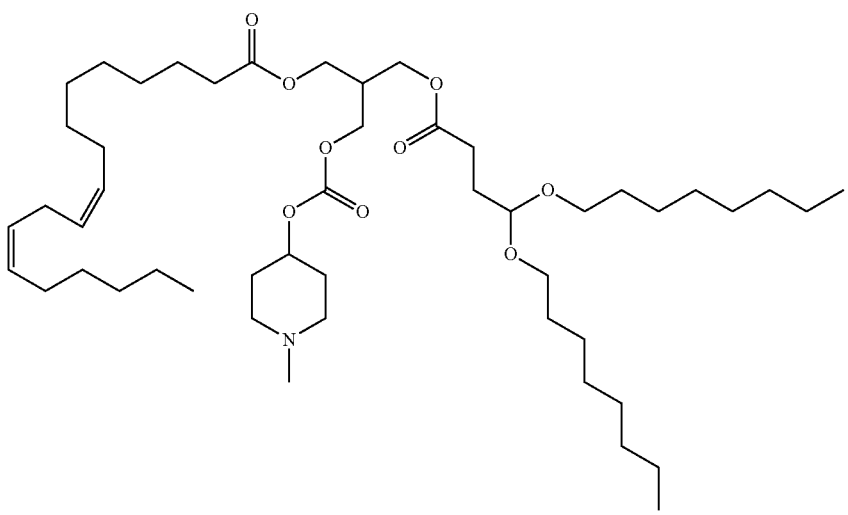 [SMILES: CCCCC/C=C\C/C=C\CCCCCCCC(=O)OCC(COC(=O)CCC(OCCCCCCCC)OCCCCCCCC)COC(=O)OC1CCN(C)CC1]

$^1$H NMR (400 MHz, CD$_2$Cl$_2$) δ=5.26-5.43 (m, 4H), 4.52-4.76 (m, 1H), 4.45 (t, J=5.50 Hz, 1H), 4.17 (d, J=5.99 Hz, 2H), 4.12 (dd, J=5.93, 1.65 Hz, 4H), 3.54 (dt, J=9.29, 6.66 Hz, 2H), 3.38 (dt, J=9.29, 6.66 Hz, 2H), 2.77 (br. s, 4H), 2.14-2.44 (m, 9H), 2.05 (q, J=6.85 Hz, 4H), 1.67-2.00 (m, 5H), 1.44-1.64 (m, 8H), 1.23-1.40 (m, 34H), 0.83-0.93 (m, 9H) ppm.

MS (M+1)=837.3, Rt=2.75 min (LC method 9).

Example 49

(9Z,12Z)-3-((4,4-bis(octyloxy)butanoyl)oxy)-2-
(((((1-methylazetidin-3-yl)oxy)carbonyl)oxy)methyl)
propyl octadeca-9,12-dienoate

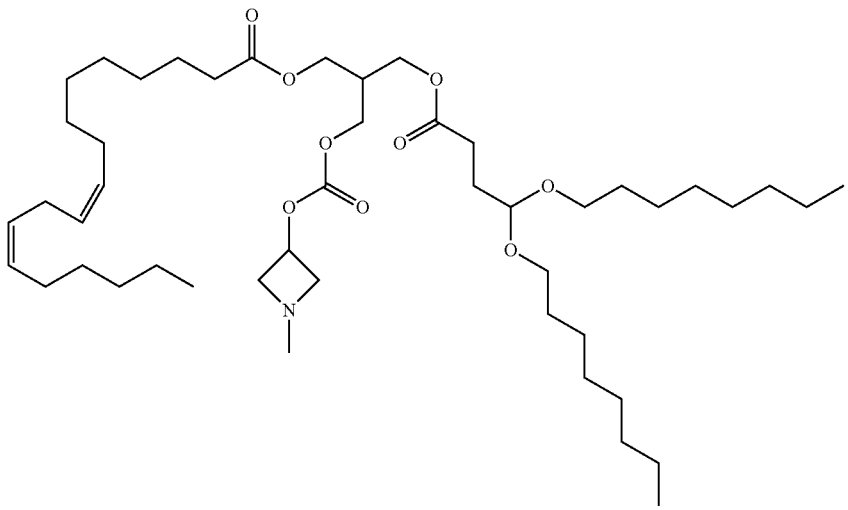 [SMILES: CCCCC/C=C\C/C=C\CCCCCCCC(=O)OCC(COC(=O)CCC(OCCCCCCCC)OCCCCCCCC)COC(=O)OC1CN(C)C1]

$^1$H NMR (400 MHz, $CD_2Cl_2$) δ=5.28-5.44 (m, 4H), 4.95-5.03 (m, 1H), 4.45 (t, J=5.50 Hz, 1H), 4.07-4.23 (m, 6H), 3.76-3.92 (m, 2H), 3.55 (dt, J=9.29, 6.72 Hz, 2H), 3.39 (dt, J=9.26, 6.68 Hz, 2H), 3.15-3.30 (m, 2H), 2.78 (t, J=6.36 Hz, 2H), 2.25-2.50 (m, 8H), 2.06 (q, J=6.85 Hz, 4H), 1.87 (td, J=7.55, 5.56 Hz, 2H), 1.46-1.64 (m, 6H), 1.20-1.41 (m, 34H), 0.84-0.94 (m, 9H), ppm.

MS (M+1)=809.2, Rt=2.72 min (LC method 9).

Example 50

(9Z,12Z)-3-((4,4-bis(octyloxy)butanoyl)oxy)-2-
(((((1-ethylpiperidin-4-yl)oxy)carbonyl)oxy)methyl)
propyl octadeca-9,12-dienoate

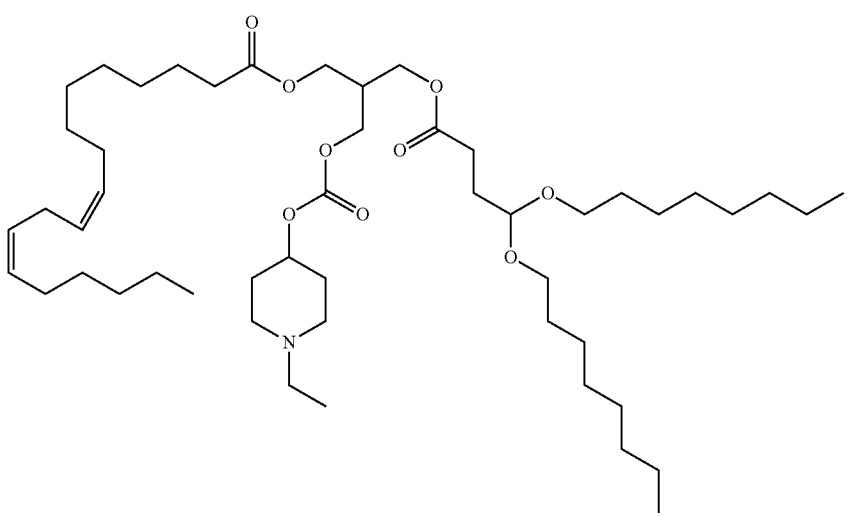 [SMILES: CCCCC/C=C\C/C=C\CCCCCCCC(=O)OCC(COC(=O)CCC(OCCCCCCCC)OCCCCCCCC)COC(=O)OC1CCN(CC)CC1]

$^1$H NMR (400 MHz, $CD_2Cl_2$) δ=5.43-5.28 (m, 4H), 4.66-4.54 (m, 1H), 4.45 (t, J=5.5 Hz, 1H), 4.17 (d, J=6.1 Hz, 2H), 4.12 (dd, J=6.0, 1.7 Hz, 4H), 3.54 (dt, J=9.3, 6.7 Hz, 2H), 3.38 (dt, J=9.3, 6.7 Hz, 2H), 2.81-2.75 (m, 2H), 2.75-2.64 (m, 2H), 2.45-2.33 (m, 5H), 2.30 (t, J=7.6 Hz, 2H), 2.25-2.11 (m, 2H), 2.05 (q, J=6.8 Hz, 4H), 1.99-1.82 (m, 4H), 1.78-1.64 (m, 2H), 1.64-1.47 (m, 6H), 1.41-1.19 (m, 34H), 1.04 (t, J=7.1 Hz, 3H), 0.93-0.82 (m, 9H) ppm.

MS (M+1)=850.8, Rt=2.65 min (LC method 9).

Example 51

(9Z,12Z)-3-((4,4-bis(octyloxy)butanoyl)oxy)-2-
(((((1-methylpiperidin-4-yl)methoxy)carbonyl)oxy)
methyl)propyl octadeca-9,12-dienoate

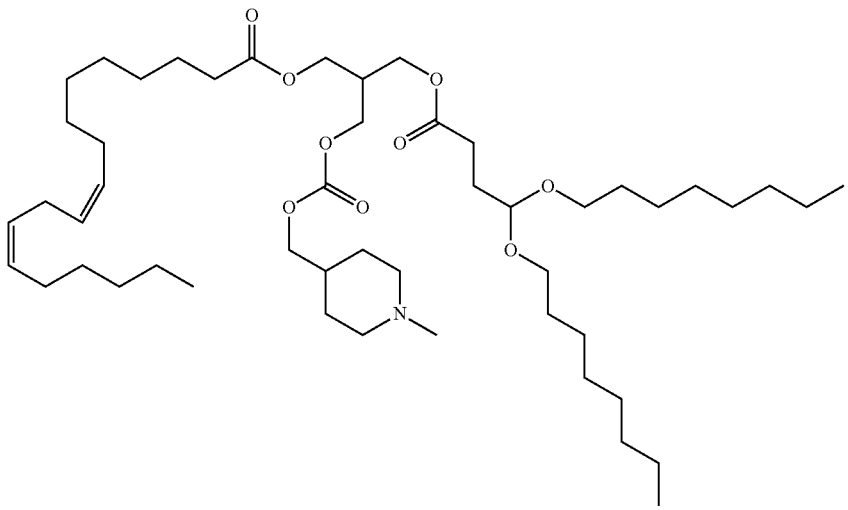 [SMILES: CCCCC/C=C\C/C=C\CCCCCCCC(=O)OCC(COC(=O)CCC(OCCCCCCCC)OCCCCCCCC)COC(=O)OCC1CCN(C)CC1]

¹H NMR (400 MHz, CD₂Cl₂) δ: 5.43-5.26 (m, 4H), 4.45 (t, J=5.6 Hz, 1H), 4.18 (d, J=6.0 Hz, 2H), 4.12 (dd, J=6.1, 1.4 Hz, 4H), 3.97 (d, J=6.5 Hz, 2H), 3.56 (dt, J=9.3, 6.7 Hz, 2H), 3.38 (dt, J=9.2, 6.6 Hz, 2H), 2.88-2.74 (m, 4H), 2.46-2.33 (m, 3H), 2.30 (t, J=7.6 Hz, 2H), 2.22 (s, 3H), 2.05 (q, J=6.8 Hz, 4H), 1.97-1.82 (m, 4H), 1.74-1.47 (m, 9H), 1.41-1.20 (m, 36H), 0.93-0.83 (m, 9H) ppm.

MS (M+1)=851.1, Rt=2.67 min (LC method 9).

Example 52

(9Z,12Z)-3-((4,4-bis(octyloxy)butanoyl)oxy)-2-
(((((1,2,2,6,6-pentamethylpiperidin-4-yl)oxy)carbo-
nyl)oxy)methyl)propyl octadeca-9,12-dienoate

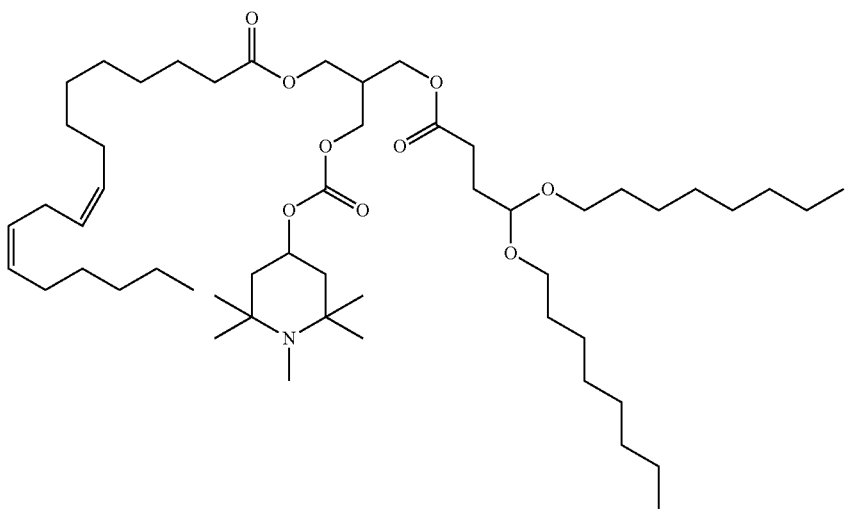 [SMILES: CCCCC/C=C\C/C=C\CCCCCCCC(=O)OCC(COC(=O)CCC(OCCCCCCCC)OCCCCCCCC)COC(=O)OC1CC(C)(C)N(C)C(C)(C)C1]

¹H NMR (400 MHz, CDCl₃) δ=5.36 (m, J=7.50, 1.80 Hz, 4H), 4.83-4.94 (m, 1H), 4.49 (t, J=5.50 Hz, 1H), 4.18 (dd, J=16.02, 5.87 Hz, 6H), 3.57 (m, J=9.30, 6.70, 6.70 Hz, 2H), 3.41 (m, J=9.29 Hz, 2H), 2.78 (t, J=6.48 Hz, 2H), 2.41 (m, J=7.70, 7.70 Hz, 3H), 2.31 (t, J=7.58 Hz, 2H), 2.25 (s, 3H), 2.06 (q, J=6.77 Hz, 4H), 1.89-1.97 (m, 4H), 1.48-1.67 (m, 8H), 1.21-1.42 (m, 34H), 1.18 (s, 6H), 1.08 (s, 6H), 0.85-0.93 (m, 9H) ppm.

MS (M+1)=893.3, Rt=2.74 min (LC method 9).

Example 53

(9Z,12Z)-3-((4,4-bis(octyloxy)butanoyl)oxy)-2-((((3-(dimethylamino)propyl)carbamoyl)oxy)methyl) propyl octadeca-9,12-dienoate

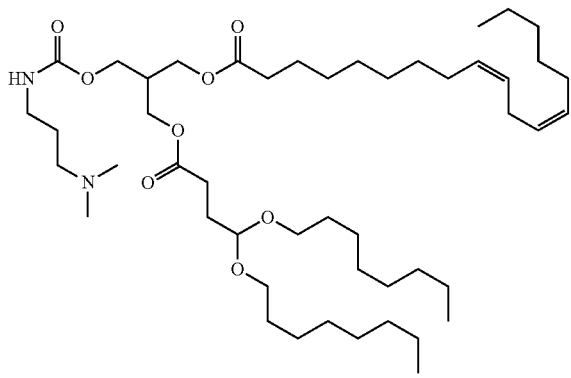 [SMILES: CCCCC/C=C\C/C=C\CCCCCCCC(=O)OCC(COC(=O)CCC(OCCCCCCCC)OCCCCCCCC)COC(=O)NCCCN(C)C]

$^1$H NMR (400 MHz, CDCl$_3$): δ=5.64 (bs, 1H), 5.40-5.24 (m, 4H), 4.44 (t, J=6 Hz, 1H), 4.10 (bs, 5H), 3.58 (q, J=6 Hz, 2H), 3.40 (q, J=6 Hz, 2H), 3.20 (m, 2H), 2.78 (t, J=6 Hz, 2H), 2.41-2.24 (m, 5H), 2.20 (s, 6H), 2.08 (q, J=6 Hz, 4H), 1.92 (q, J=8 Hz, 2H), 1.70-1.44 (m, 17H), 1.38-1.20 (m, 28H), 0.82 (m, 9H) ppm.
MS (M+1)=824, Rt=2.63 min (LC method 9).

Synthesis of Example 54

Intermediate 54a:
4,4-bis((2-propylpentyl)oxy)butanenitrile

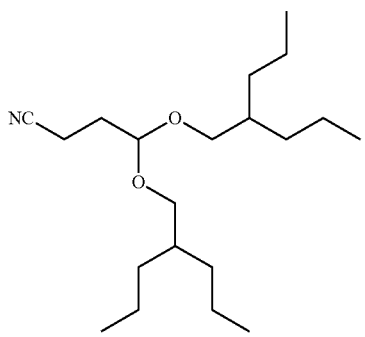 [SMILES: CCCC(CCC)COC(CCC#N)OCC(CCC)CCC]

To a mixture of 3-cyanopropionaldehydedimethylacetal (2.0 g, 15.48 mmol) and propylpentan-1-ol (8.0 g, 61.94 mmol) was added pyridinium p-toluenesulfonate (194 mg, 0.774 mmol) and the reaction was heated to 105° C. for 20 h. Reaction mixture was directly purified by flash column chromatography, eluting with 10% EtOAc/hexane to afford a 4.0 g of the desired compound as a pale yellow liquid.

TLC: Rf=0.9 (EtOAc: Hexane, 1:9); PMA active.

Intermediate 54b:
4,4-bis((2-propylpentyl)oxy)butanoic acid

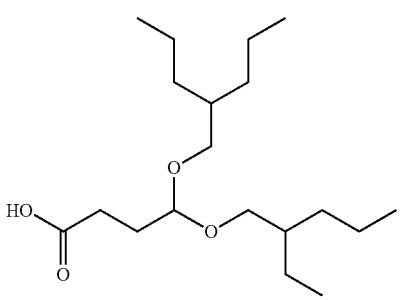 [SMILES: CCCC(CC)COC(CCC(=O)O)OCC(CCC)CCC]

A solution of intermediate 54a (4 g, 12.26 mmol) in 30 mL of ethanol and 30 mL of water was added KOH (2.5 g, 36.88 mmol). The reaction mixture was sealed and heated to stir at 110° C. for 20 h. Reaction mixture was cooled to 0° C. and acidified with 1N HCl and extracted with EtOAc (3×50 mL). The combined organic layers were dried over sodium sulfate and evaporated to dryness to afford brown color viscous liquid, Intermediate 2b, in 4 g.

TLC: Rf=0.1 (EtOAc: Hexane, 1:9), PMA active.

Intermediate 54c: (9Z,12Z)-3-((4,4-bis((2-propylpentyl)oxy)butanoyl)oxy)-2-(hydroxymethyl)propyl octadeca-9,12-dienoate

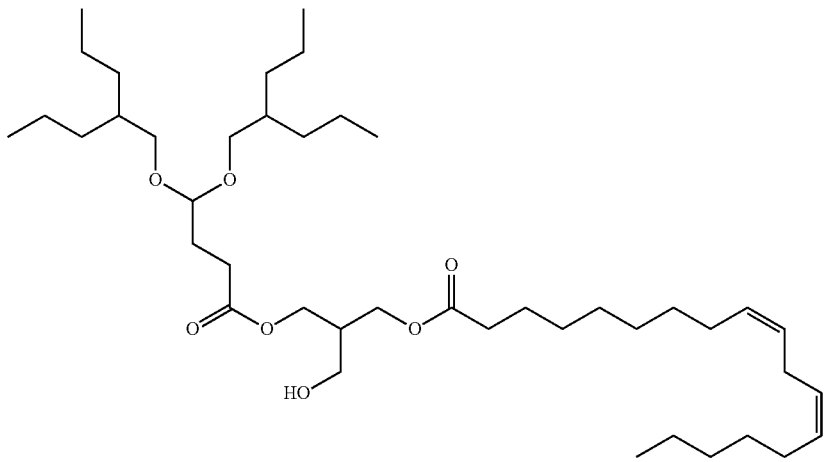 [SMILES: CCCCC/C=C\C/C=C\CCCCCCCC(=O)OCC(CO)COC(=O)CCC(OCC(CCC)CCC)OCC(CCC)CCC]

In a round bottom flask, intermediate 13c (1.1 g, 2.98 mmol), DMAP (73 mg, 0.596 mmol), DIPEA (1.0 mL, 5.96 mmol), and intermediate 54b (1.02 g, 2.98 mmol) were taken into DMF (10 mL). HATU (1.36 g, 3.58 mmol) was added in one portion, and the reaction was stirred at ambient temperature overnight. After completion, the reaction was quenched with 50 mL of water and extracted with (3×50 mL) of EtOAc. The combined organic layers were washed with brine solution, dried over sodium sulfate and evaporated to dryness to afford pale yellow color liquid crude. The product was purified by flash-chromatography (Silica gel 230-400 mesh) eluting with 20% EtOAc/hexane to provide 700 mg of the desired product as a yellow oil.

TLC: Rf=0.8 (EtOAc: Hexane, 3:7), PMA active.

Example 54

3-((4,4-bis((2-propylpentyl)oxy)butanoyl)oxy)-2-(((9Z,12Z)-octadeca-9,12-dienoyloxy)methyl)propyl 1,4-dimethylpiperidine-4-carboxylate

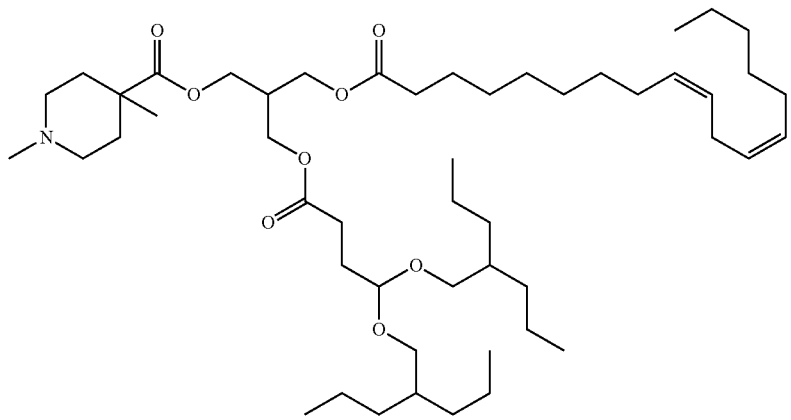 [SMILES: CCCCC/C=C\C/C=C\CCCCCCCC(=O)OCC(COC(=O)CCC(OCC(CCC)CCC)OCC(CCC)CCC)COC(=O)C1(C)CCN(C)CC1]

Example 54 can be prepared using similar methods to those employed for the synthesis of example 1.

$^1$H NMR (400 MHz, CDCl$_3$) δ=5.43-5.29 (m, 4H), 4.45 (t, J=5.4 Hz, 1H), 4.15 (dt, J=6.0, 2.9 Hz, 6H), 3.47 (dd, J=9.2, 5.7 Hz, 2H), 3.28 (dd, J=9.2, 5.7 Hz, 2H), 2.78 (t, J=6.5 Hz, 2H), 2.67-2.52 (m, 2H), 2.47-2.37 (m, 3H), 2.32 (t, J=7.6 Hz, 2H), 2.25 (s, 3H), 2.17-1.99 (m, 8H), 1.97-1.87 (m, 2H), 1.67-1.47 (m, 6H), 1.41-1.21 (m, 30H), 1.20 (s, 3H), 0.90 (t, J=6.9 Hz, 15H) ppm.

MS (M+1)=834.9, Rt=1.11 min (LC method 12).

Synthesis of Example 55

Intermediate 55a: methyl 6,6-bis((2-propylpentyl)oxy)hexanoate

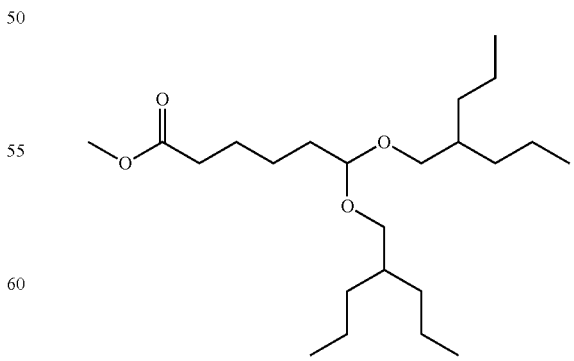

Intermediate 55a can be prepared using similar methods to those employed for the preparation of Intermediate 54a in the synthesis of Example 54.

TLC: Rf=0.6 (EtOAc: Hexane, 1:9), PMA active.

Intermediate 55b:
6,6-bis((2-propylpentyl)oxy)hexanoic acid

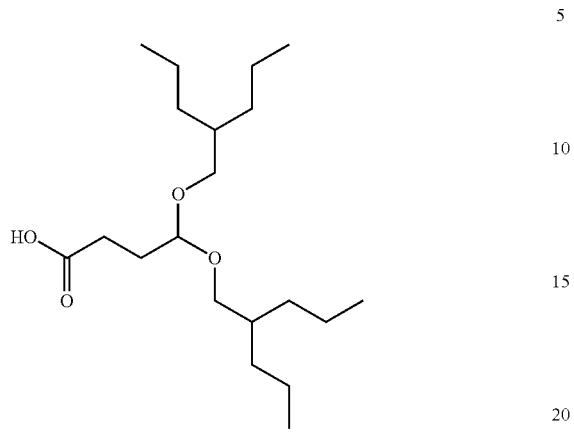

Intermediate 55b can be prepared using similar methods to those employed for the preparation of Intermediate 54b in the synthesis of Example 54.

TLC (silica gel, 20% EtOAc in hexanes): Rf=0.2, PMA active.

Intermediate 55c: (9Z,12Z)-3-((6,6-bis((2-propylpentyl)oxy)hexanoyl)oxy)-2-(hydroxymethyl)propyl octadeca-9,12-dienoate

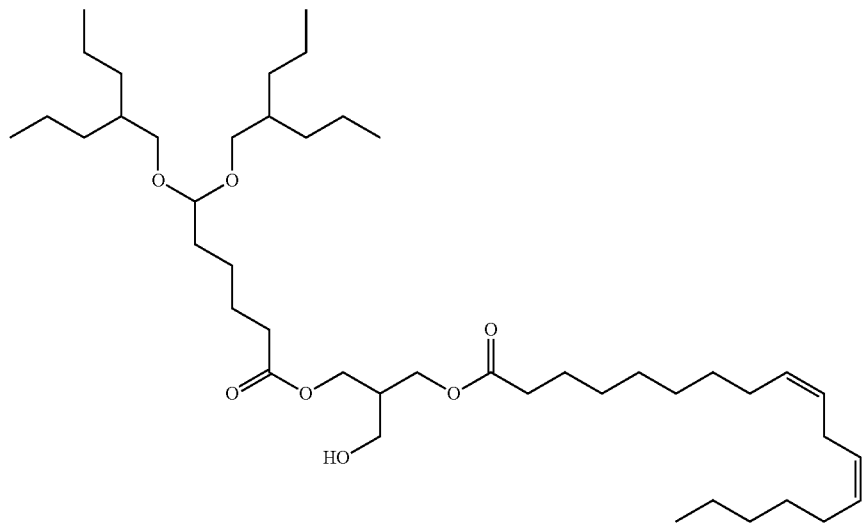 [SMILES: CCCCC/C=C\C/C=C\CCCCCCCC(=O)OCC(CO)COC(=O)CCCCC(OCC(CCC)CCC)OCC(CCC)CCC]

Intermediate 55c can be prepared using similar methods to those employed for the preparation of Intermediate 54c in the synthesis of Example 54.

TLC (silica gel, 30% EtOAc in hexanes): Rf=0.8, PMA active.

Example 55

3-((6,6-bis((2-propylpentyl)oxy)hexanoyl)oxy)-2-(((9Z,12Z)-octadeca-9,12-dienoyloxy)methyl)propyl 1,4-dimethylpiperidine-4-carboxylate

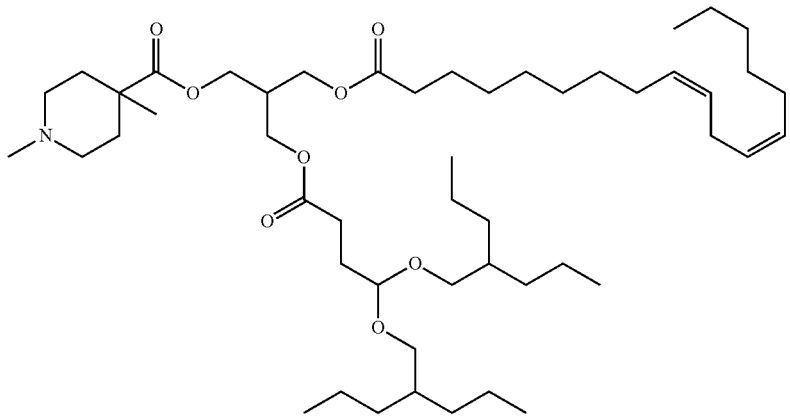 [SMILES: CCCCC/C=C\C/C=C\CCCCCCCC(=O)OCC(COC(=O)CCC(OCC(CCC)CCC)OCC(CCC)CCC)COC(=O)C1(C)CCN(C)CC1]

Example 55 can be prepared using similar methods to those employed for the synthesis of example 1.

$^1$H NMR (400 MHz, CDCl$_3$) δ=5.43-5.29 (m, 4H), 4.41 (t, J=5.6 Hz, 1H), 4.18-4.09 (m, 6H), 3.46 (dd, J=9.2, 5.7 Hz, 2H), 3.27 (dd, J=9.2, 5.8 Hz, 2H), 2.78 (t, J=6.5 Hz, 2H), 2.67-2.54 (m, 2H), 2.47-2.37 (m, 1H), 2.36-2.28 (m, 4H), 2.25 (s, 3H), 2.17-1.99 (m, 8H), 1.71-1.46 (m, 10H), 1.41-1.21 (m, 32H), 1.20 (s, 3H), 0.90 (t, J=6.9 Hz, 15H) ppm. MS (M+1)=862.9, Rt=1.16 min (LC method 12).

Synthesis of Example 56

Intermediate 56a: 10-(octyloxy)-10-oxodecanoic acid

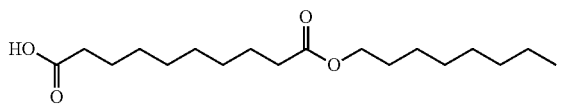 [SMILES: CCCCCCCCOC(=O)CCCCCCCCC(=O)O]

To a solution of sebacic acid (20 g, 98.88 mmol) in 200 mL of DMF was added HATU (49 g, 128.55 mmol) and DIPEA (35 mL, 197.77 mmol). Then 1-octanol (15.6 mL, 98.88 mmol) was added, followed by DMAP (6 g, 49.44 mmol) and the reaction mixture was stirred at room temperature for 2 h. The reaction mixture was quenched with 200 mL of water and extracted with (3×100 mL) of EtOAc. The combined organic layers were washed with (2×200 mL) of brine solution, dried over sodium sulfate and evaporated to dryness to afford colorless viscous liquid in crude form. The product was purified by flash-chromatography (Silica gel 230-400 mesh) eluting with 2% MeOH in DCM to provide 12 g of the expected Intermediate 3a as a low melting white solid.

TLC: Rf=0.6 (MeOH: DCM, 1:9), PMA active.

Intermediate 56b: 1-(3-hydroxy-2-(hydroxymethyl)propyl) 10-octyl decanedioate

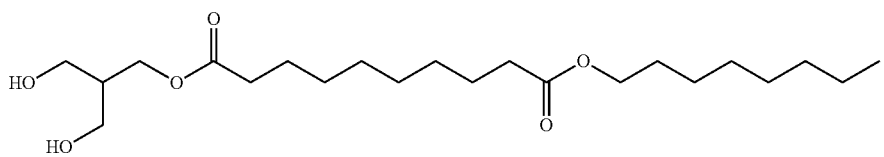 [SMILES: CCCCCCCCOC(=O)CCCCCCCCC(=O)OCC(CO)CO]

To a solution of 2-(hydroxymethyl)propane-1,3-diol (2.0 g, 18.84 mmol) and intermediate 56a (5.9 g, 18.84 mmol) in 50 mL of DMF was added HATU (7.1 g, 18.84 mmol) and DIPEA (6.5 mL, 37.69 mmol), followed by DMAP (230 mg, 1.88 mmol). The reaction was stirred at 30° C. for 16 h under a nitrogen atmosphere. The reaction mixture was quenched with 50 mL of water and extracted with (3×50 mL) of EtOAc. The combined organic layers were washed with brine solution, dried over sodium sulfate and evaporated to dryness to afford liquid crude. The product was purified by flash-chromatography (Silica gel: 230-400 mesh) eluting with 60% EtOAc/hexane to afford 1.6 g of the desired product as colorless viscous liquid.

TLC: Rf=0.3 (EtOAc: Hexane, 1:1), PMA active.

Intermediate 56c: 1-(3-hydroxy-2-(((9Z,12Z)-octadeca-9,12-dienoyloxy)methyl)propyl) 10-octyl decanedioate

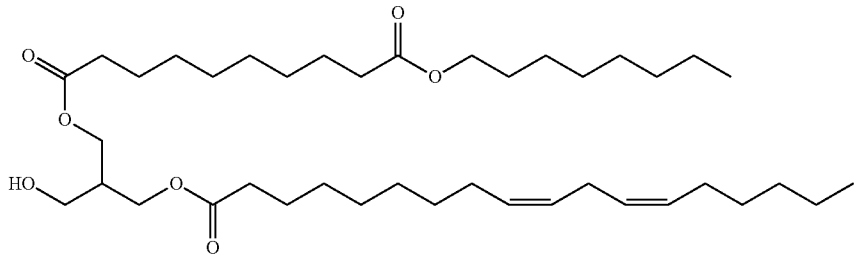 [SMILES: CCCCC/C=C\C/C=C\CCCCCCCC(=O)OCC(CO)COC(=O)CCCCCCCCC(=O)OCCCCCCCC]

To a solution of intermediate 56b (800 mg, 1.99 mmol) and linoleic acid (560 mg, 1.99 mmol) in 10 mL of DCM was added EDC.HCl (570 mg, 2.98 mmol), DIPEA (0.7 mL, 3.96 mmol), then DMAP (24 mg, 0.19 mmol). The reaction mixture was stirred at room temperature for 8 h under nitrogen. The reaction mixture was quenched with 50 mL of water and extracted with (3×50 mL) of EtOAc. The combined organic layers were washed with brine solution, dried over sodium sulfate and evaporated to dryness to afford liquid crude. The product was purified by flash chromatography (Silica gel: 230-400 mesh) eluting with 30% EtOAc/hexane to afford 500 mg of the desired compound, as a colorless viscous liquid.

TLC: Rf=0.5 (EtOAc: Hexane, 3:7), PMA active.

Example 56

1-(3-((1,3-dimethylpyrrolidine-3-carbonyl)oxy)-2-(((9Z,12Z)-octadeca-9,12-dienoyloxy)methyl)propyl) 10-octyl decanedioate

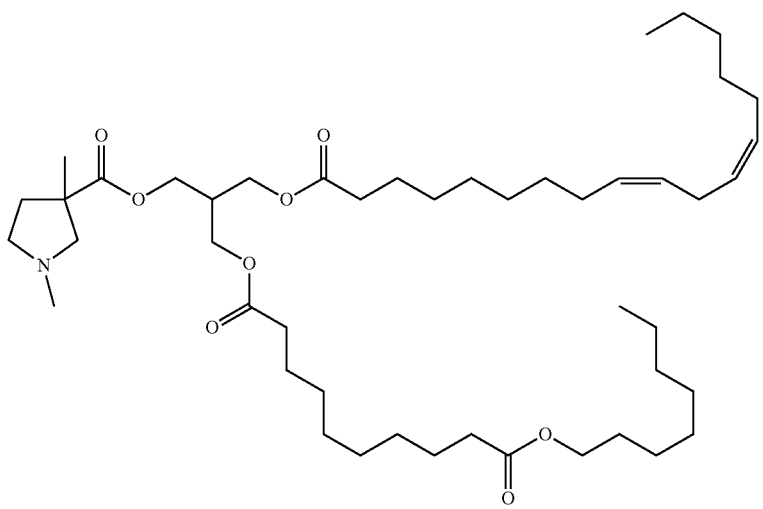 [SMILES: CCCCC/C=C\C/C=C\CCCCCCCC(=O)OCC(COC(=O)CCCCCCCCC(=O)OCCCCCCCC)COC(=O)C1(C)CCN(C)C1]

Example 56 can be prepared using similar methods to those employed for the synthesis of example 1.

$^1$H NMR (400 MHz, CDCl$_3$): δ=5.44-5.28 (m, 4H), 4.18-4.11 (m, 6H), 4.06 (t, J=6.8 Hz, 2H), 2.94 (d, J=9.3 Hz, 1H), 2.78 (t, J=6.5 Hz, 2H), 2.63-2.54 (m, 2H), 2.50-2.35 (m, 3H), 2.35-2.25 (m, 9H), 2.06 (q, J=6.7 Hz, 4H), 1.72-1.54 (m, 9H), 1.42-1.22 (m, 35H), 0.94-0.84 (m, 6H) ppm.

MS (M+1)=790.7, Rt=0.99 min (LC method 12).

Synthesis of Example 57

Intermediate 57a:
2-(hydroxymethyl)propane-1,3-diyl bis(4,4-bis(octyloxy)butanoate)

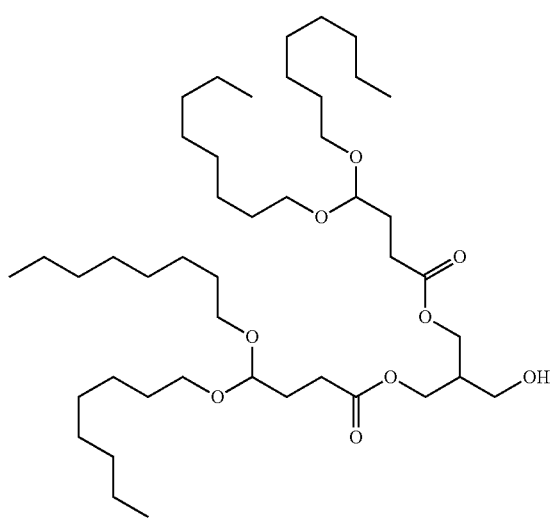 [SMILES: CCCCCCCCOC(CCC(=O)OCC(CO)COC(=O)CCC(OCCCCCCCC)OCCCCCCCC)OCCCCCCCC]

To a solution of 2(hydroxymethyl)propane-1,3,diol (0.20 g, 1.88 mmol) and Intermediate 13b (1.30 g, 3.76 mmol) in 10 mL of DMF was added HATU (1.45 g, 3.76 mmol) and DIPEA (1.30 mL, 7.54 mmol), followed by DMAP (0.046 g, 0.37 mmol), and the mixture was stirred at 30° C. for 16 h under nitrogen. The reaction mixture was quenched with 50 mL of water and extracted with 3×50 mL of EtOAc. The combined organic layers were washed with brine solution, dried over sodium sulfate and evaporated to dryness to afford a crude oil. The mixture was purified on silica gel, eluting with 30% EtOAc/heptane to provide 0.50 g of the desired product.

TLC (silica gel, 30% EtOAc/heptane, PMA stain): $R_f$=0.46.

Example 57

2-(((1-methylpyrrolidine-3-carbonyl)oxy)methyl)propane-1,3-diyl bis(4,4-bis(octyloxy)butanoate)

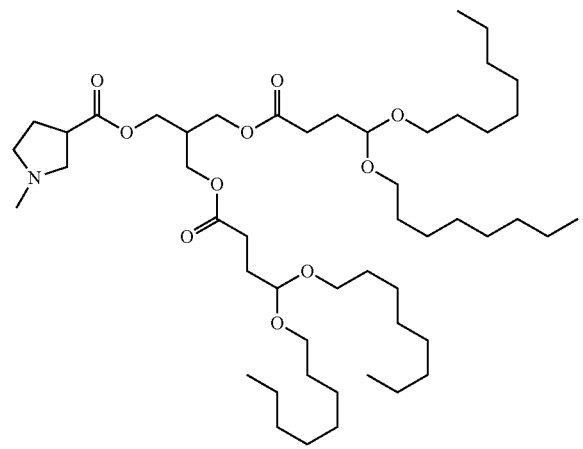 [SMILES: CCCCCCCCOC(CCC(=O)OCC(COC(=O)CCC(OCCCCCCCC)OCCCCCCCC)COC(=O)C1CCN(C)C1)OCCCCCCCC]

The following examples can be prepared using similar methods to those employed for the synthesis of example 1, with intermediate 57a.

$^1$H NMR (CDCl$_3$): δ=4.48 (t, J=6 Hz, 2H), 4.16 (m, 6H), 3.46 (q, J=6 Hz, 4H), 3.38 (q, J=6 Hz, 4H), 3.05 (m, 1H), 2.80 (t, J=8 Hz, 1H), 2.68-2.42 (m, 4H), 2.38 (t, J=8 Hz, 5H), 2.32 (s, 3H), 2.10 (q, J=8 Hz, 2H), 1.90 (q, J=8 Hz, 4H), 1.48 (m, 7H), 1.30 (m, 40H), 0.82 (m, 12H) ppm.

MS (M+1)=871.1, Rt=1.19 min (LC method 12).

Example 58

2-(((1,3-dimethylpyrrolidine-3-carbonyl)oxy)methyl)propane-1,3-diyl bis(4,4-bis(octyloxy)butanoate)

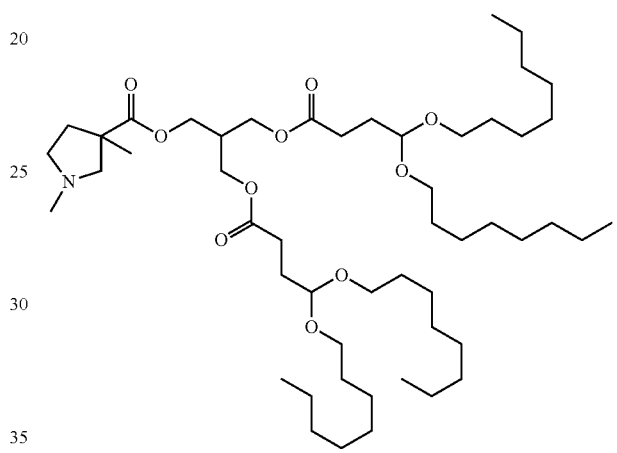

$^1$H NMR (CDCl$_3$): δ=4.50 (t, J=6 Hz, 2H), 4.18 (m, 6H), 3.58 (q, J=6 Hz, 4H), 3.40 (q, J=6 Hz, 4H), 2.90 (bm, 1H), 2.58 (bm, 3H), 2.42-2.28 (m, 10H), 1.90 (m, 4H), 1.68 (bm, 2H), 1.58 (m, 6H), 1.38 (s, 3H), 1.22 (m, 40H), 0.82 (m, 12H) ppm.

MS (M+1)=885.2, Rt=1.24 min (LC method 12).

Example 59

2-(((3-(dimethylamino)propanoyl)oxy)methyl)propane-1,3-diyl bis(4,4-bis(octyloxy)butanoate)

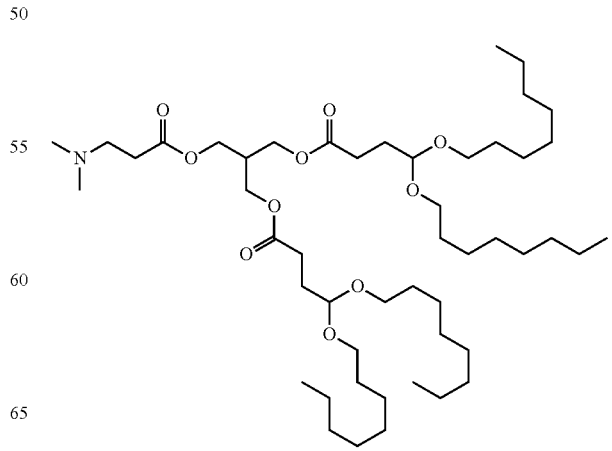

¹H NMR (CDCl₃): δ=4.50 (t, J=6 Hz, 2H), 4.18 (m, 6H), 3.58 (q, J=6 Hz, 4H), 3.38 (q, J=6 Hz, 4H), 2.60 (t, J=6 Hz, 2H), 2.50 (t, J=6 Hz, 2H), 2.38 (m, 5H), 2.02 (s, 6H), 1.90 (m, 4H), 1.78 (m, 8H), 1.40-1.20 (m, 40H), 0.82 (m, 12H) ppm.

MS (M+1)=859.1, Rt=1.22 min (LC method 12).

Example 60

2-(((1-methylpyrrolidine-3-carbonyl)oxy)methyl) propane-1,3-diyl bis(6,6-bis(octyloxy)hexanoate)

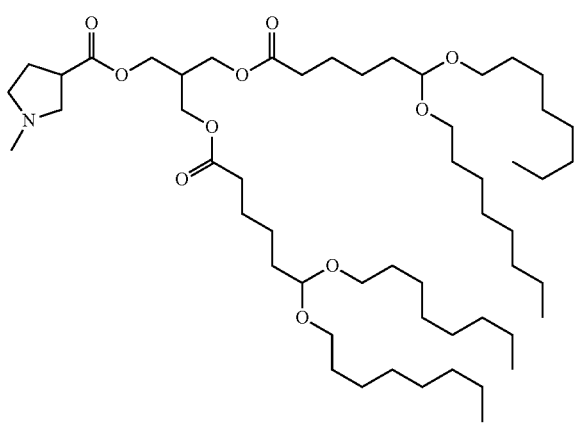 [SMILES: CCCCCCCCOC(CCCCC(=O)OCC(COC(=O)CCCCC(OCCCCCCCC)OCCCCCCCC)COC(=O)C1CCN(C)C1)OCCCCCCCC]

Example 60 can be prepared using similar methods to those employed for the synthesis of Example 57 starting from intermediate 27a.

¹H NMR (400 MHz, ACETONITRILE-d₃): δ=4.41 (t, J=5.62 Hz, 2H), 4.15-4.06 (m, 6H), 3.52 (dt, J=9.35, 6.57 Hz, 4H), 3.37 (dt, J=9.38, 6.50 Hz, 4H), 3.07-2.98 (m, 1H), 2.76-2.65 (m, 2H), 2.52 (td, J=6.94, 3.48 Hz, 2H), 2.39-2.26 (m, 7H), 2.08-1.99 (m, 3H), 1.64-1.44 (m, 16H), 1.39-1.21 (m, 44H), 0.94-0.83 (m, 12H) ppm.

MS (M+1)=927 Rt=2.97 min (LC method 9).

Synthesis of Example 61

Intermediate 61a: methyl 6,6-bis((2-propylpentyl)oxy)hexanoate

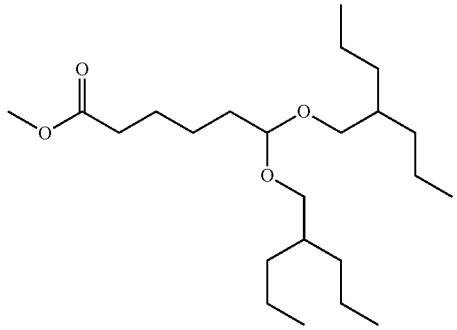 [SMILES: CCCC(CCC)COC(CCCCC(=O)OC)OCC(CCC)CCC]

A neat mixture of intermediate 27a (2.50 g, 13.14 mmol), 2-propyl pentanol (8.24 mL, 52.57 mmol), and KHSO₄ (0.050 g) was heated to 70° C. for 3 h. The mixture was then cooled to room temperature and diluted with 80 mL of water, then extracted with EtOAc (2×100 mL). The organic layers were combined, washed with 100 mL of brine, then dried over sodium sulfate and concentrated to obtain a colorless oil. The crude mixture was purified by flash column chromotography over silica gel, eluting with 3% EtOAc/heptane to provide 2.20 g of the desired product.

TLC (silica gel, 10% EtOAc/heptane, PMA stain): R_f=0.88.

Intermediate 61 b: 6,6-bis((2-propylpentyl)oxy)hexanoic acid

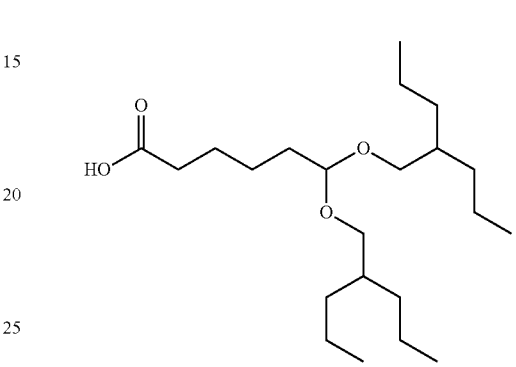

A solution of intermediate 61a (2.20 g, 5.69 mmol) in 100 mL of water/methanol/THF (1:1:1) was treated with solid NaOH (1.13 g, 28.42 mmol). The mixture was heated to reflux for 3 h. The mixture was then cooled to room temperature and neutralized with 1N HCl. The aqueous mixture was extracted with EtOAc (2×100 mL) and the organic layers were combined, washed with brine (200 mL), dried over sodium sulfate, and concentrated to give a colorless liquid (2.0 g). The crude product was used in the next step without purification.

TLC (silica gel, 10% EtOAc/heptane, PMA stain): R_f=0.14.

Intermediate 61c: 2-(hydroxymethyl)propane-1,3-diyl bis(6,6-bis((2-propylpentyl)oxy)hexanoate)

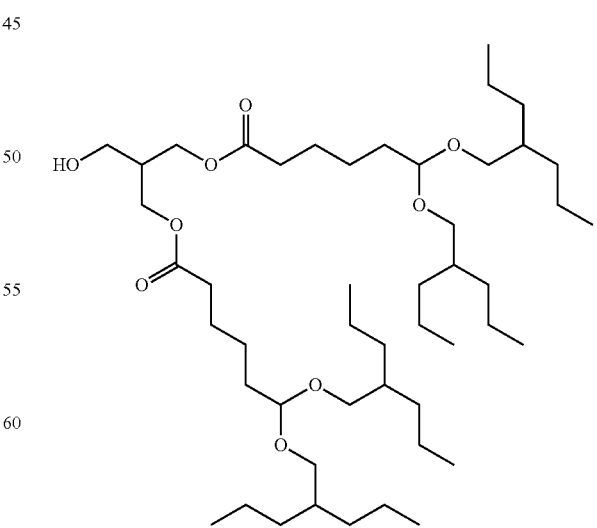

To a solution of 2(hydroxymethyl)propane-1,3,diol (0.40 g, 3.77 mmol) and Intermediate 61 b (1.41 g, 3.77 mmol) in DCM (40 mL) was added EDC.HCl (1.08 g, 5.65 mmol) and TEA (1.60 mL, 11.30 mmol), followed by DMAP (0.46 g, 3.77 mmol). The mixture was stirred for 24 h at room temperature. The mixture was then diluted with water (100 mL), and extracted with DCM (2×150 mL). The organic layers were combined, washed with water (100 mL), dried over sodium sulfate, and concentrated to obtain a pale green liquid. The crude mixture was purified by flash column chromatography over silica gel, eluting with 20-30% EtOAc/heptane to provide 0.51 g of the desired product.

TLC (silica gel, 30% EtOAc/heptane, PMA stain): $R_f$=0.83.

Example 61

2-(((1-methylpyrrolidine-3-carbonyl)oxy)methyl) propane-1,3-diyl bis(6,6-bis((2-propylpentyl)oxy) hexanoate)

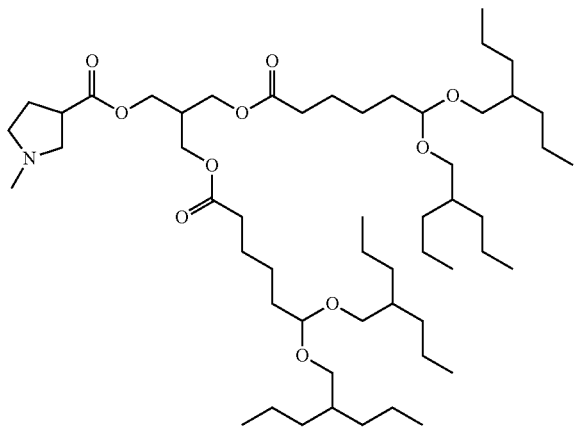 [SMILES: CCCC(CCC)COC(CCCCC(=O)OCC(COC(=O)CCCCC(OCC(CCC)CCC)OCC(CCC)CCC)COC(=O)C1CCN(C)C1)OCC(CCC)CCC]

Example 61 can be prepared using similar methods to those employed for the synthesis of example 1.

$^1$H NMR (400 MHz, CDCl$_3$) δ=4.41 (t, J=5.7 Hz, 2H), 4.19-4.09 (m, 6H), 3.46 (dd, J=9.2, 5.7 Hz, 4H), 3.27 (dd, J=9.3, 5.9 Hz, 4H), 3.10-2.99 (m, 1H), 2.85-2.77 (m, 1H), 2.71-2.48 (m, 3H), 2.45-2.38 (m, 1H), 2.36 (s, 3H), 2.33 (t, J=7.7 Hz, 4H), 2.15-2.06 (m, 2H), 1.71-1.50 (m, 12H), 1.45-1.16 (m, 36H), 0.93-0.85 (m, 24H).

MS (M+1)=927.1, Rt=1.18 min (LC method 12).

Synthesis of Example 62

Intermediate 62a: 5-(benzyloxy)pentyl methanesulfonate

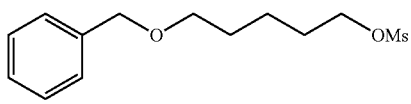 [SMILES: CS(=O)(=O)OCCCCCOCc1ccccc1]

Et$_3$N (10.79 mL, 78 mmol) was added in one portion via syringe to a solution of 5-Benzyloxy-1-pentanol (10.08 g, 51.9 mmol) in DCM (75 mL) in a round bottom flask charged with a magnetic stir bar at 0° C. under N$_2$. Next, MsCl (4.85 mL, 62.3 mmol) was added dropwise via syringe in 4 separate portions at a rate such that the internal temperature did not exceed 15° C. The reaction was allowed to continue to stir for 1 hour, after which it was diluted with H$_2$O (200 mL) and DCM (150 mL). The organic layer was separated, and the aqueous layer was washed with DCM (225 mL). The combined organic layers were washed with brine (200 mL), dried with Na$_2$SO$_4$, filtered, and concentrated under reduced pressure to provide the title compound as a crude orange oil (14.46 g).

MS (M+1)=272.9, Rt=1.33 min (LC method 13).

Intermediate 62b: diethyl 2-(5-(benzyloxy)pentyl)malonate

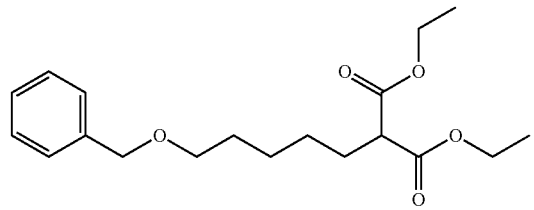 [SMILES: CCOC(=O)C(CCCCCOCc1ccccc1)C(=O)OCC]

To a cold, 0° C., solution of diethyl malonate (7.5 g, 46.8 mmol) in dry DMF (100 mL) under N$_2$ atmosphere was added 60% NaH (2.23 g, 56.2 mmol) portionwise over 10 min. The evolution of gas was observed. The mixture was stirred at 0° C. for 30 min then Intermediate 62a (14.46 g, 51.5 mmol) in dry DMF (41 mL) was added dropwise over 10 min followed by tetrabutylammonium iodide (1.73 g, 4.68 mmol). The mixture was then heated at 100° C. for 1.5 h. The mixture was cooled to rt and left overnight. The mixture was then quenched with sat. NH$_4$Cl (50 mL) and diluted with H$_2$O (100 mL). The mixture was extracted with EtOAc (2×200 mL). The combined organic layers were washed with H$_2$O (100 mL) and brine (100 mL), dried over MgSO$_4$, filtered, and concentrated on vacuo. The residue was purified by silica gel column chromatography eluting with 0-30% EtOAc/heptane to afford the title compound as an oil (11.7 g).

MS (M+1)=336.6, Rt=1.64 min (LC method 13).

Intermediate 62c: 2-(5-(benzyloxy)pentyl)propane-1,3-diol

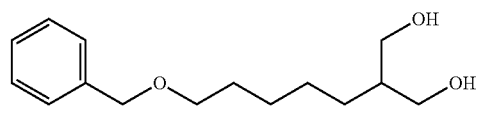 [SMILES: OCC(CO)CCCCCOCc1ccccc1]

To a cold solution, 0° C., of Intermediate 62b (5.5 g, 16.35 mmol) in dry THF (20 mL) under N$_2$ was added 2.0M LiAlH$_4$ in THF (24.52 mL, 49.0 mmol) dropwise, over 15 min. The mixture was allowed to warm to rt and stirred overnight. The mixture was cooled to 0° C., treated again with 2.0M LiAlH$_4$ in THF (16.35 mL, 32.7 mmol), allowed to warm to rt, and stirred over the weekend. The reaction was cooled to 0° C. and quenched with EtOAc (9.30 mL) dropwise over 10 min. The mixture was then treated with H$_2$O (3.10 mL) dropwise, a 15% NaOH solution (3.10 mL) dropwise, and then additional H$_2$O (9.30 mL) dropwise. The mixture was stirred for 30 min at rt. The mixture was filtered through a pad of Celite. The Celite was washed with EtOAc. The filtrate was concentrated under reduced pressure to afford the title compound as a semi-wax solid (1.52 g).

MS (M+1)=253.0, Rt=1.37 min (LC method 13).

Intermediate 62d:
2-(5-(benzyloxy)pentyl)propane-1,3-diyl dioctanoate

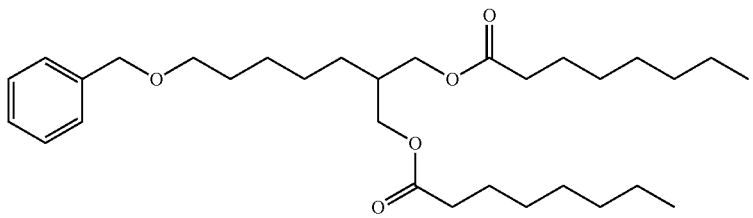 [SMILES: CCCCCCCC(=O)OCC(CCCCCOCc1ccccc1)COC(=O)CCCCCCC]

Pyridine (1.21 mL, 14.96 mmol) was added dropwise via syringe over ~30 seconds to a solution of Intermediate 62c (1.51 g, 5.98 mmol) in DCM (20 mL) in a round bottom flask charged with a magnetic stir bar at 0° C. under $N_2$. Next, octanoyl chloride (2.145 mL, 12.57 mmol) was added dropwise via syringe over several minutes, and the reaction was allowed to warm to rt and stirred overnight. The mixture was diluted with sat. $NH_4Cl$ (100 mL) and $CH_2Cl_2$ (100 mL). The organic layer was separated. The aqueous layer was extracted with $CH_2Cl_2$ (100 mL), and the combined organics were dried over $MgSO_4$, filtered, and concentrated under reduced pressure. The crude material was purified by silica gel column chromatography eluting with 0-10% EtOAc/heptane to afford the title compound as a colorless oil (2.88 g).

MS (M+1)=505.6, Rt=1.77 min (LC method 14).

Intermediate 62e:
2-(5-hydroxypentyl)propane-1,3-diyl dioctanoate

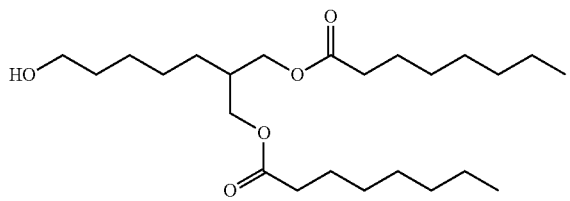 [SMILES: CCCCCCCC(=O)OCC(CCCCCO)COC(=O)CCCCCCC]

To a solution of Intermediate 62d (2.5 g, 4.95 mmol) in MeOH (25 mL) at rt was added 10% Pd/C, wet degussa type (264 mg). The mixture was stirred under a $H_2$ balloon overnight. The crude reaction mixture was filtered through a pad of celite and filtrate was concentrated under reduced pressure to afford the title compound as a colorless oil (2.0 g).

$^1$H NMR (400 MHz, $CD_2Cl_2$) δ=4.11-3.96 (m, 4H), 3.59 (t, J=6.5 Hz, 2H), 2.28 (t, J=7.5 Hz, 4H), 2.04-1.91 (m, 1H), 1.66-1.48 (m, 7H), 1.41-1.34 (m, 6H), 1.34-1.20 (m, 16H), 0.88 (t, J=6.8 Hz, 6H).

Intermediate 62f:
7-(octanoyloxy)-6-((octanoyloxy)methyl)heptanoic acid

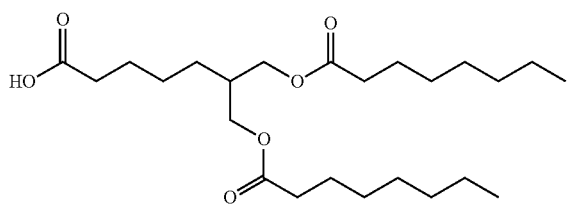 [SMILES: CCCCCCCC(=O)OCC(CCCCC(=O)O)COC(=O)CCCCCCC]

TEMPO (0.151 g, 0.965 mmol) was added in one portion to Intermediate 62e (2.0 g, 4.82 mmol) in MeCN:$H_2O$ (46.84 mL, 1:1 ratio) in a vial charged with a magnetic stir bar at rt. Next, iodobenzene diacetate (3.42 g, 10.61 mmol) was added in one portion, and the reaction was allowed to continue to stir at rt overnight, after which the reaction was quenched with 15% aqueous sodium thiosulfate (50 mL). The reaction was diluted with $H_2O$ and extracted with EtOAc (3×100 mL). The combined organic layers were dried with $Na_2SO_4$, filtered, and concentrated under reduced pressure to provide a pale yellow oil. The oil was dissolved in toluene (15 mL) and concentrated under reduced pressure (×6) to provide a pale yellow oil, which was dissolved in DCM and concentrated under reduced pressure (×3) to provide the title compound (plus minor aromatic impurities which could correspond to either residual toluene or iodobenzene) as a pale yellow oil (2.0 g).

MS (M−1)=427.2, Rt=1.73 min (LC method 15).

Intermediate 62 g: 2-(5-(3-hydroxy-2-(hydroxymethyl)propoxy)-5-oxopentyl)propane-1,3-diyl dioctanoate

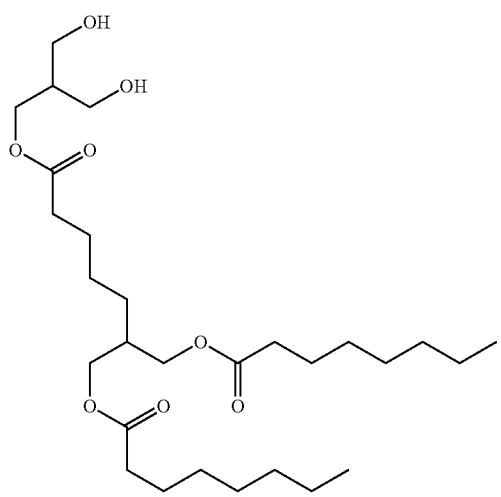 [SMILES: CCCCCCCC(=O)OCC(CCCCC(=O)OCC(CO)CO)COC(=O)CCCCCCC]

In a 250 mL round bottom flask, intermediate 62f (5.0 g, 11.67 mmol), DMAP (0.285 g, 2.333 mmol), DIPEA (3.06 mL, 17.50 mmol), and 2-(hydroxymethyl)propane-1,3-diol (1.238 g, 11.67 mmol) were taken into dichloromethane (35 mL) and DMF (17.5 mL). EDC.HCl (3.35 g, 17.50 mmol) was added in one portion, and the reaction was stirred at ambient temperature overnight. The reaction was concentrated under reduced pressure at 40° C. heating to remove DMF. The crude mixture was purified by flash column chromatography, eluting with 0-50% EtOAc/heptane to afford 2.35 g of the desired product as a colorless oil.

MS (M+1)=517.6, Rt=0.72 min (LC method 10).

Intermediate 62 h: 2-(5-(3-(dodecanoyloxy)-2-(hydroxymethyl)propoxy)-5-oxopentyl)propane-1,3-diyl dioctanoate

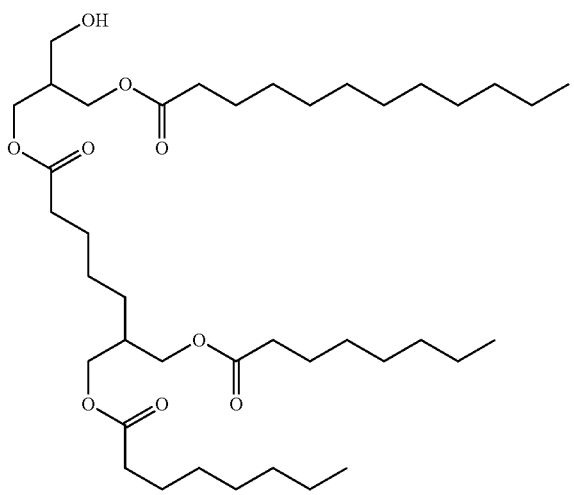 [SMILES: CCCCCCCCCCCC(=O)OCC(CO)COC(=O)CCCCC(COC(=O)CCCCCCC)COC(=O)CCCCCCC]

In a round bottom flask, intermediate 62 g (326 mg, 0.631 mmol), DMAP (14.03 mg, 0.115 mmol), DIPEA (0.150 mL, 0.861 mmol), and dodecanoic acid (115 mg, 0.617 mmol) were taken into dichloromethane (3 mL). EDC.HCl (165 mg, 0.861 mmol) was added in one portion, and the reaction was stirred at ambient temperature overnight. After 18 h, the reaction mixture was purified by flash column chromatography, eluting with 0-50% EtOAc/heptane to afford 201 mg of the desired product.

MS (M+Na)=721.8, Rt=1.14 min (LC method 10).

Example 62

2-(5-(3-(dodecanoyloxy)-2-(((1-methylpyrrolidine-3-carbonyl)oxy)methyl)propoxy)-5-oxopentyl)propane-1,3-diyl dioctanoate

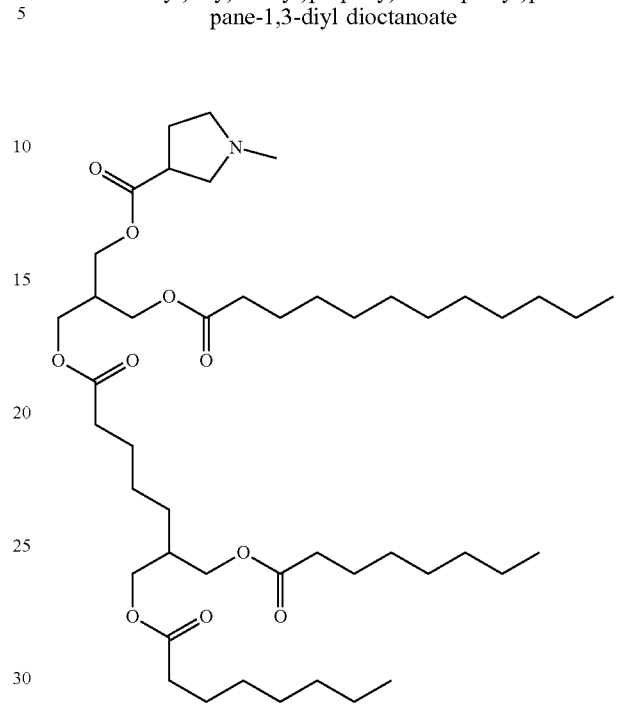

Example 62 can be prepared using similar methods to those employed for the synthesis of example 1.

$^1$H NMR (400 MHz, CDCl$_3$): δ=4.19-4.02 (m, 10H), 3.38 (m, 2H), 3.16 (m, 1H), 2.69 (m, 4H), 2.44-2.30 (m, 10H), 2.0 (m, 1H), 1.63 (m, 8H), 1.40-1.28 (m, 38H), 0.9 (m, 9H) ppm.

MS (M+1)=810.9, Rt=0.93 min (LC method 10).

Synthesis of Example 63

Intermediate 63a: 2-(5-(3-hydroxy-2-((palmitoyloxy)methyl)propoxy)-5-oxopentyl)propane-1,3-diyl dioctanoate

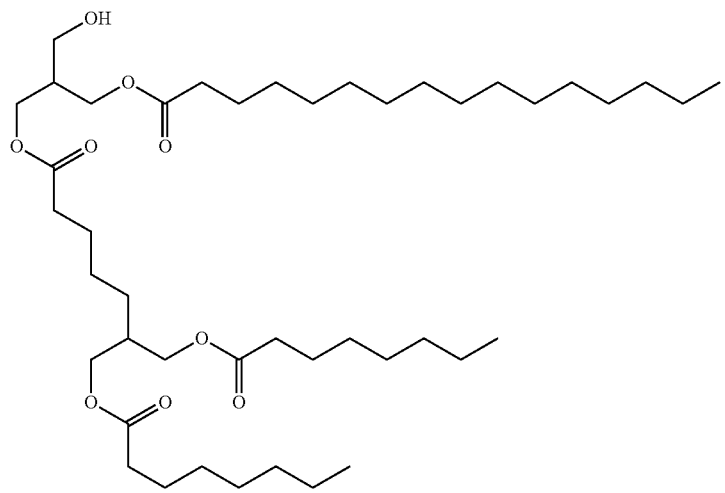 [SMILES: CCCCCCCCCCCCCCCC(=O)OCC(CO)COC(=O)CCCCC(COC(=O)CCCCCCC)COC(=O)CCCCCCC]

In a round bottom flask, intermediate 62 g (363 mg, 0.702 mmol), DMAP (14.29 mg, 0.117 mmol), DIPEA (0.153 mL, 0.877 mmol), and palmitic acid (150 mg, 0.585 mmol) were taken into dichloromethane (3 mL). EDC.HCl (168 mg, 0.877 mmol) was added in one portion, and the reaction was stirred at ambient temperature overnight. The reaction mixture was directly purified by flash column chromatography, eluting with 0-50% EtOAc/heptane to afford 265 mg of the desired product as a colorless oil.

MS (M+Na)=777.9, Rt=1.44 min (LC method 10).

Example 63

2-(5-(3-((1-methylpyrrolidine-3-carbonyl)oxy)-2-((palmitoyloxy)methyl)propoxy)-5-oxopentyl)propane-1,3-diyl dioctanoate

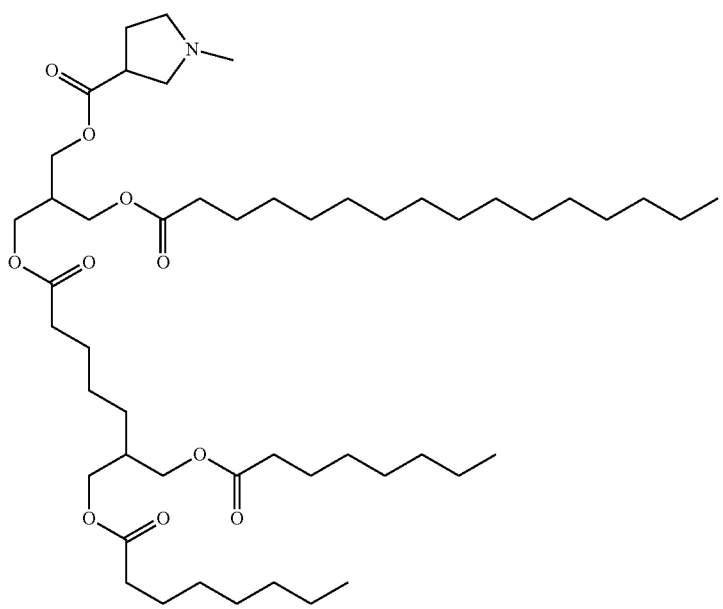 [SMILES: CCCCCCCCCCCCCCCC(=O)OCC(COC(=O)CCCCC(COC(=O)CCCCCCC)COC(=O)CCCCCCC)COC(=O)C1CCN(C)C1]

Example 63 can be prepared using similar methods to those employed for the synthesis of example 1.

$^1$H NMR (400 MHz, CDCl$_3$): δ 4.20-4.02 (m, 10H), 3.81 (m, 1H), 3.51 (m, 1H), 3.25 (m, 1H), 2.95 (m, 4H), 2.65 (m, 1H), 2.36-2.30 (m, 12H), 1.40-1.28 (m, 52H), 0.90 (m, 9H) ppm.

MS (M+1)=867, Rt=0.80 min (LC method 10).

Synthesis of Example 64

Intermediate 64a: 2-(5-(3-hydroxy-2-((tetradecanoyloxy)methyl)propoxy)-5-oxopentyl)propane-1,3-diyl dioctanoate

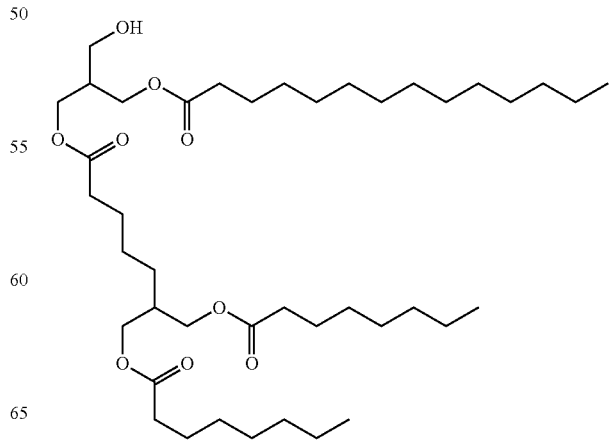

In a round bottom flask, Intermediate 62 g (311 mg, 0.602 mmol), DMAP (13.37 mg, 0.109 mmol), DIPEA (0.143 mL, 0.821 mmol), and tetradecanoic acid (125 mg, 0.547 mmol) were taken into dichloromethane (3 mL). EDC.HCl (157 mg, 0.821 mmol) was added in one portion, and the reaction was stirred at ambient temperature overnight. The reaction mixture was directly purified by flash column chromatography, eluting with 0-50% EtOAc/heptane to afford 200 mg of the desired product.

MS (M+Na)=749.8, Rt=1.28 min (LC method 10).

Example 64

2-(5-(3-((1-methylpyrrolidine-3-carbonyl)oxy)-2-((tetradecanoyloxy)methyl)propoxy)-5-oxopentyl) propane-1,3-diyl dioctanoate

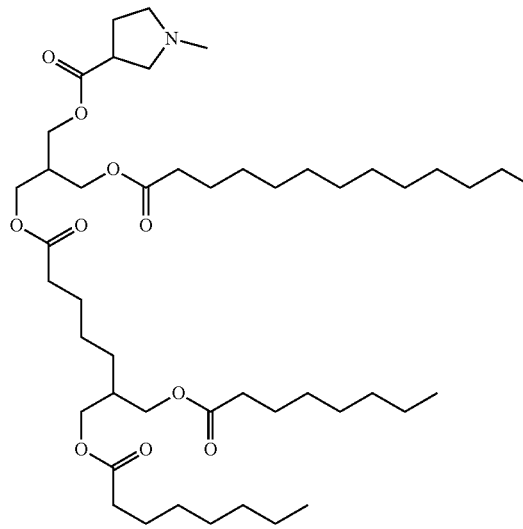

Example 64 can be prepared using similar methods to those employed for the synthesis of example 1

$^1$H NMR (400 MHz, CDCl$_3$): δ=4.16 (m, 6H), 4.06 (m, 4H), 3.38 (m, 1H), 3.16 (m, 1H), 2.79 (m, 3H), 2.36 (m, 11H), 2.0 (m, 1H), 1.62 (m, 9H), 1.40-1.28 (m, 42H), 0.9 (m, 9H) ppm. MS (M+1)=838.9, Rt=0.75 min (LC method 10).

Synthesis of Example 65

Intermediate 65a:
3-hydroxy-2-(hydroxymethyl)propyl 4,4-bis(octyloxy)butanoate

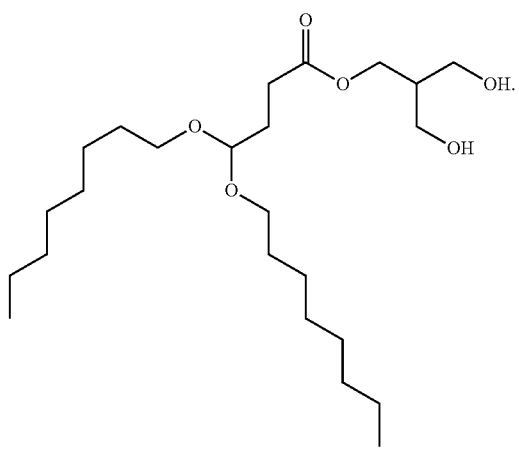 [SMILES: CCCCCCCCOC(CCC(=O)OCC(CO)CO)OCCCCCCCC]

Intermediate 13b, (7.6 g, 22.06 mmol), DMAP (0.539 g, 4.41 mmol), DIPEA (7.71 mL, 44.1 mmol), and 2-(hydroxymethyl)propane-1,3-diol (4.68 g, 44.1 mmol) were taken into dichloromethane (100 mL) and DMF (50 mL) in a round bottom flask. EDC.HCl (8.46 g, 44.1 mmol) was added in one portion, and the reaction was stirred at ambient temperature overnight. The reaction was concentrated in vacuo to remove DMF. The crude was diluted and purified by flash column chromatography, eluting with 0-50% EtOAc/heptane to afford 3.72 g of the desired product as a colorless oil.

MS (M+Na)=455.5, Rt=0.81 min (LC method 10).

Intermediate 65b: 3-((4,4-bis(octyloxy)butanoyl) oxy)-2-(hydroxymethyl)propyl dodecanoate

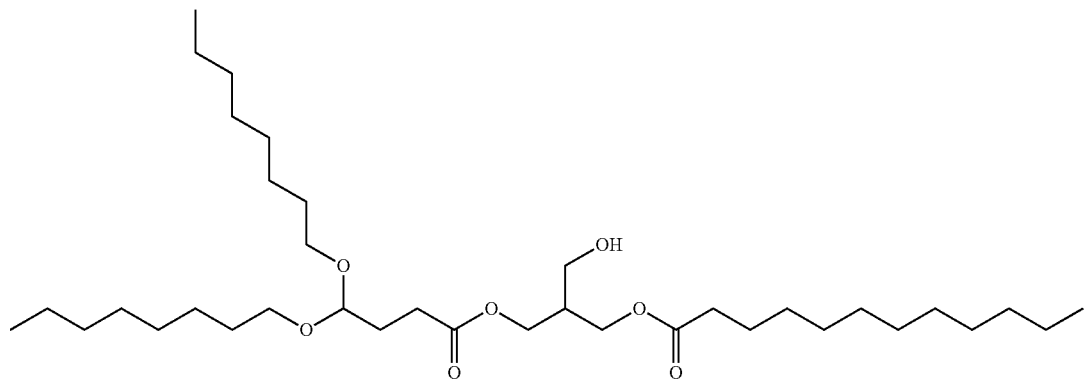 [SMILES: CCCCCCCCCCCC(=O)OCC(CO)COC(=O)CCC(OCCCCCCCC)OCCCCCCCC]

Intermediate 65a (321 mg, 0.741 mmol), DMAP (16.47 mg, 0.135 mmol), DIPEA (0.177 mL, 1.011 mmol), and dodecanoic acid (135 mg, 0.674 mmol) were taken into dichloromethane (3 mL) in a round bottom flask. EDC.HCl (194 mg, 1.011 mmol) was added in one portion, and the reaction was stirred at ambient temperature overnight. The crude mixture was directly purified by flash column chromatography, eluting with 0-50% EtOAc/heptane to afford 195 mg of the desired product as a colorless oil.

MS (M+Na)=637.7, Rt=1.35 min (LC method 10).

Example 65

3-((4,4-bis(octyloxy)butanoyl)oxy)-2-((dodecanoyloxy)methyl)propyl 1-methylpyrrolidine-3-carboxylate

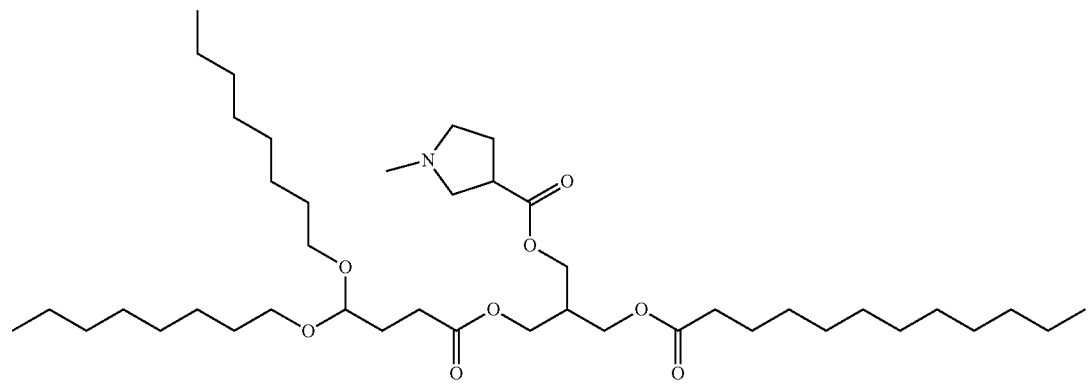 [SMILES: CCCCCCCCCCCC(=O)OCC(COC(=O)CCC(OCCCCCCCC)OCCCCCCCC)COC(=O)C1CCN(C)C1]

Example 65 can be prepared using similar methods to those employed for the synthesis of example 1.

$^1$H NMR (400 MHz, CDCl$_3$): δ=4.50 (t, J=5.5 Hz, 1H), 4.16 (m, 6H), 3.57 (dt, J=9.3, 6.7 Hz, 2H), 3.42 (dt, J=9.3, 6.7 Hz, 2H), 2.95 (bm, 1H), 2.71 (bm, 2H), 2.42 (m, 4H), 2.33 (m, J=7.6 Hz, 3H),1.93 (td, J=7.5, 5.6 Hz, 2H), 1.57 (m, 7H), 1.28 (m, 40H), 0.92 (m, 9H) ppm.

MS (M+1)=726.8, Rt=0.99 min (LC method 10).

Synthesis of Example 66

Intermediate 66a: 3-((4,4-bis(octyloxy)butanoyl)oxy)-2-(hydroxymethyl)propyl tetradecanoate

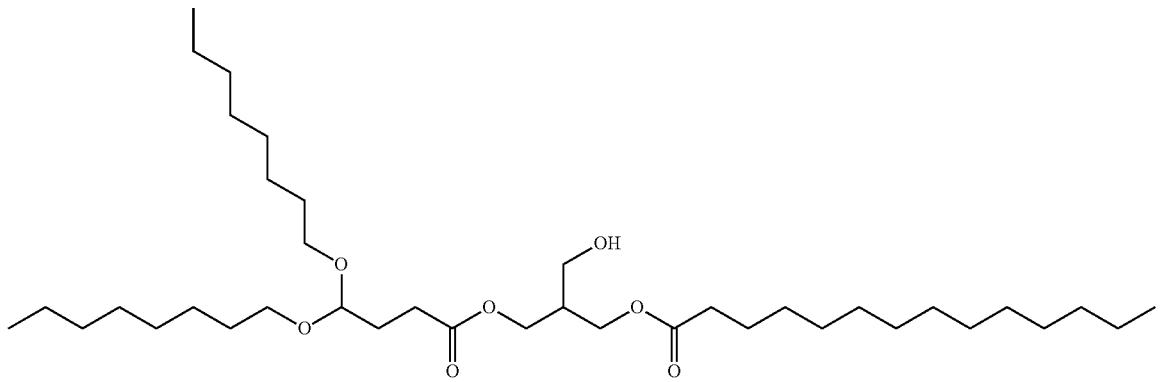 [SMILES: CCCCCCCCCCCCCC(=O)OCC(CO)COC(=O)CCC(OCCCCCCCC)OCCCCCCCC]

Intermediate 65a (313 mg, 0.723 mmol), DMAP (16.05 mg, 0.131 mmol), DIPEA (0.172 mL, 0.985 mmol), and tetradecanoic acid (150 mg, 0.657 mmol) were taken into dichloromethane (30 mL) in a round bottom flask. EDC.HCl (189 mg, 0.985 mmol) was added in one portion, and the reaction was stirred at ambient temperature overnight. The crude was directly purified by flash column chromatography, eluting with 0-50% EtOAc/heptane to afford 200 mg of the desired product a colorless oil.

MS (M+23)=665.8, Rt=1.51 min (LC method 10).

Example 66

3-((4,4-bis(octyloxy)butanoyl)oxy)-2-((tetradecanoyloxy)methyl)propyl 1-methylpyrrolidine-3-carboxylate

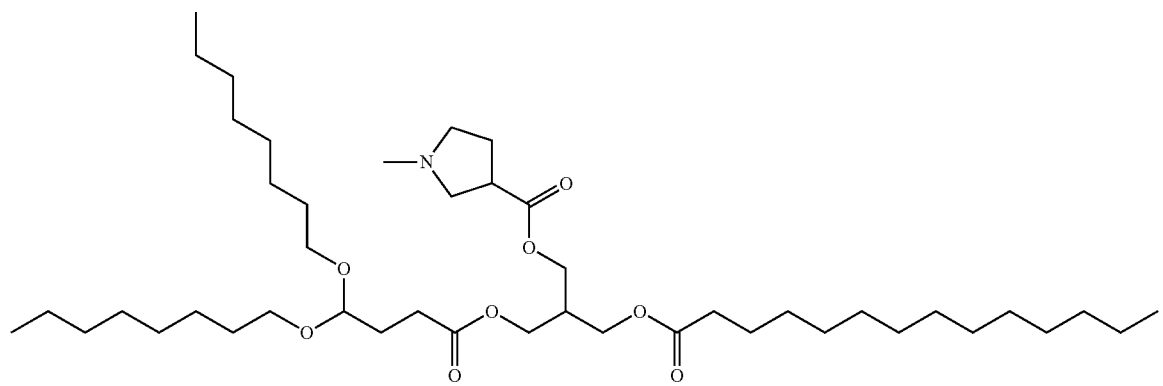 [SMILES: CCCCCCCCCCCCCC(=O)OCC(COC(=O)CCC(OCCCCCCCC)OCCCCCCCC)COC(=O)C1CCN(C)C1]

Example 66 can be prepared using similar methods to those employed for the synthesis of example 1

$^1$H NMR (400 MHz, CDCl$_3$): δ=4.52 (t, J=5.4 Hz, 1H), 4.16 (m, 6H), 3.58 (dt, J=9.2, 6.7 Hz, 2H), 3.42 (m, 1H), 2.92 (bm, 4H), 2.56 (bm, 1H), 2.52 (bm, 1H), 2.42 (m, 4H), 2.33 (m, 2H), 1.93 (m, 2H), 1.57 (m, 7H), 1.30 (m, 43H), 0.92 (m, 9H) ppm.

MS (M+1)=754.9, Rt=0.79 min (LC method 10).

Synthesis of Example 67

Intermediate 67a: 3-((4,4-bis(octyloxy)butanoyl)oxy)-2-(hydroxymethyl)propyl palmitate

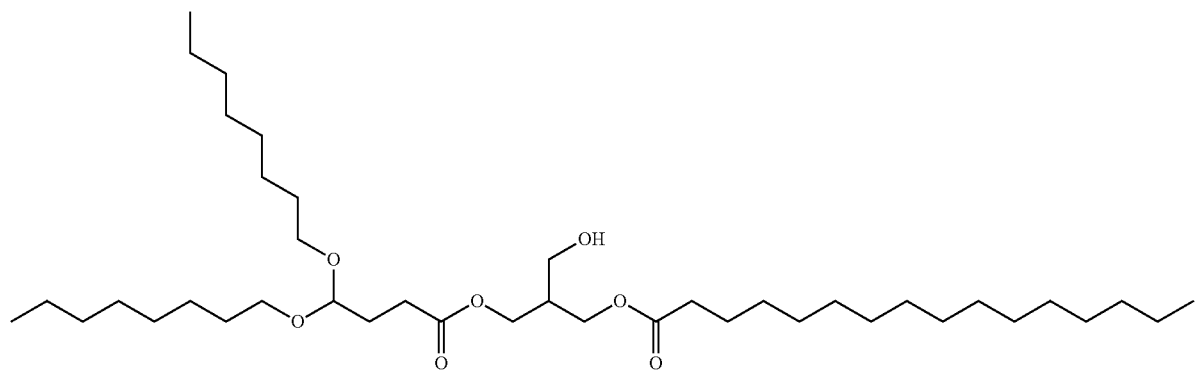 [SMILES: CCCCCCCCCCCCCCCC(=O)OCC(CO)COC(=O)CCC(OCCCCCCCC)OCCCCCCCC]

Intermediate 65a (306 mg, 0.708 mmol), DMAP (15.72 mg, 0.129 mmol), DIPEA (0.169 mL, 0.965 mmol), and palmitic acid (165 mg, 0.643 mmol) were taken into dichloromethane (30 mL) in a round bottom flask. EDC.HCl (185 mg, 0.965 mmol) was added in one portion, and the reaction was stirred at ambient temperature overnight. The crude was directly purified by flash column chromatography, eluting with 0-50% EtOAc/heptane to afford 194 mg of the desired product as a colorless oil.

MS (M+Na)=693.8, Rt=2.32 min (LC method 12).

Example 67

3-((4,4-bis(octyloxy)butanoyl)oxy)-2-((palmitoyloxy)methyl)propyl 1-methylpyrrolidine-3-carboxylate

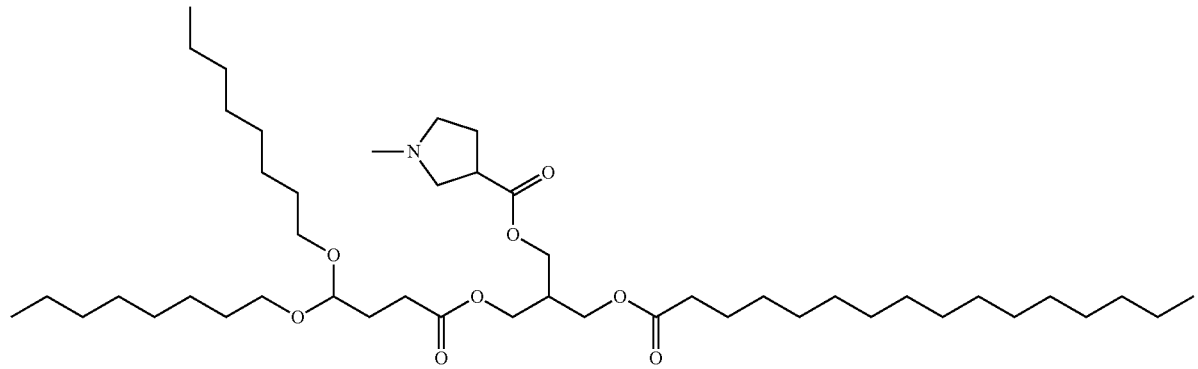 [SMILES: CCCCCCCCCCCCCCCC(=O)OCC(COC(=O)CCC(OCCCCCCCC)OCCCCCCCC)COC(=O)C1CCN(C)C1]

Example 67 can be prepared using similar methods to those employed for the synthesis of example 1.

$^1$H NMR (400 MHz, CD$_2$Cl$_2$): δ=4.48 (t, J=8 Hz, 1H), 4.16 (m, 6H), 3.57 (m, 2H), 3.42 (m, 2H), 3.20 (bm, 1H), 2.56 (bm, 1H), 2.52 (bm, 1H), 2.39 (m, 8H), 2.22 (bm, 2H), 1.91 (m, 2H), 1.57 (m, 7H), 1.30 (m, 45H), 0.92 (m, 9H) ppm.

MS (M+1)=782.9, Rt=0.83 min (LC method 10).

Synthesis of Example 68

Intermediate 68a:
1-(3-hydroxy-2-(hydroxymethyl)propyl) 8-methyl octanedioate

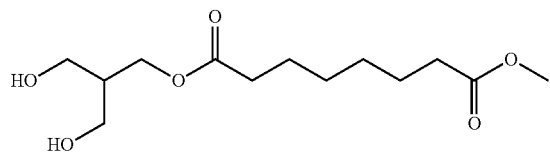 [SMILES: COC(=O)CCCCCCC(=O)OCC(CO)CO]

To a solution of 2-(hydroxymethyl)propane-1,3-diol (1.0 g, 9.423 mmol) and suberic acid monomethyl ester (1.77 g, 9.423 mmol) in DMF (20 mL) in a 50 mL RBF charged with a magnetic stir bar was added HATU (3.9 g, 10.365 mmol) then DIPEA (3.3 mL, 18.846 mmol), followed by DMAP (115 mg, 0.942 mmol). The reaction was stirred at 30° C. under N$_2$ for 16 hours, after which it was quenched with H$_2$O (50 mL). The organic layer was extracted with EtOAc (3×50 mL). The combined organic layers were washed with brine, dried over Na$_2$SO$_4$, and evaporated to dryness to afford a crude liquid. Crude product was purified by silica gel chromatography eluting with MeOH:DCM (product eluted at 4% MeOH:DCM) to afford desired product as a colorless viscous liquid (1.0 g).

TLC: Rf=0.1 (EtOAc: Hexane, 1:1), PMA active.

Intermediate 68b: 1-(3-((4,4-bis(octyloxy)butanoyl)oxy)-2-(hydroxymethyl)propyl) 8-methyl octanedioate

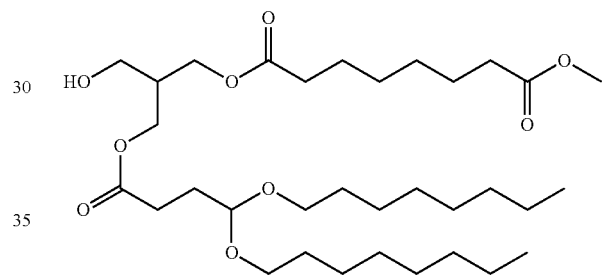

To a solution of Intermediate 68a (1.0 g, 3.623 mmol) and intermediate 13b in DMF (30 mL) in a 50 mL RBF charged with a magnetic stir bar was added HATU (1.4 g, 3.623 mmol) then DIPEA (1.3 mL, 7.246 mmol), followed by DMAP (44 mg, 0.362 mmol). The reaction was stirred at 30° C. for 16 hours under N$_2$, after which it was quenched with H$_2$O (50 mL) and extracted with EtOAc (3×50 mL). The combined organic layers were washed with brine, dried over Na$_2$SO$_4$, and evaporated to dryness to afford a crude liquid. The crude product was purified by silica gel chromatography eluting with EtOAc:hexane (product eluted at 30% EtOAc: hexane) to afford desired product as a pale yellow liquid (550 mg).

TLC: Rf=0.8 (EtOAc: Hexane, 1:1), PMA active.

Example 68

1-(3-((4,4-bis(octyloxy)butanoyl)oxy)-2-(((1-methylpyrrolidine-3-carbonyl)oxy)methyl)propyl) 8-methyl octanedioate

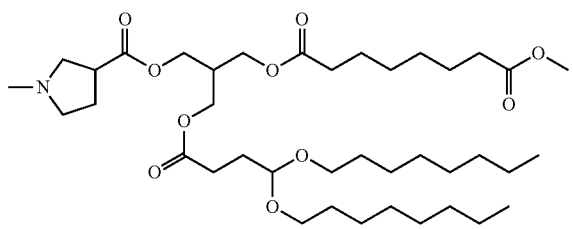

Example 68 can be prepared using similar methods to those employed for the synthesis of example 1.

1H NMR (400 MHz, CDCl$_3$): δ=4.48 (t, J=4 Hz, 1H), 4.12 (m, 6H), 3.65 (s, 3H), 3.48 (m, 2H), 3.28 (m, 2H), 3.10 (m, 1H), 2.82 (m, 1H), 2.70-2.52 (m, 3H), 2.40 (m, 6H), 2.30 (t, J=7.2 Hz, 4H), 2.10 (m, 2H), 1.90 (m, 2H), 1.60 (m, 6H), 1.30 (m, 26H), 0.82 (m, 6H) ppm.

MS (M+1)=714.7, Rt=0.65 min (LC method 10).

Synthesis of Example 69

Intermediate 69a: 1-(3-((4,4-bis(octyloxy)butanoyl)oxy)-2-(hydroxymethyl)propyl) 10-octyl decanedioate

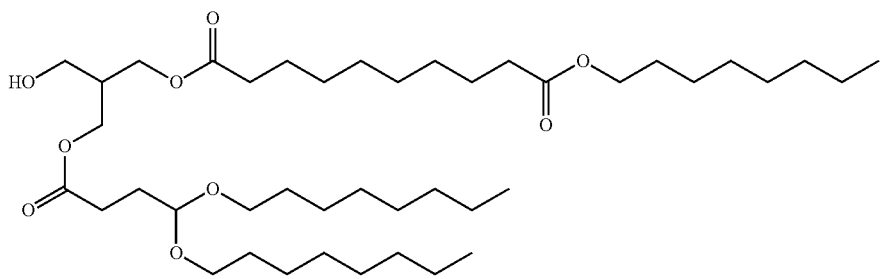 [SMILES: CCCCCCCCOC(=O)CCCCCCCCC(=O)OCC(CO)COC(=O)CCC(OCCCCCCCC)OCCCCCCCC]

To a solution of intermediate 56a (1.0 g, 2.485 mmol) and intermediate 13b (855 mg, 2.485 mmol) in DMF (30 mL) in a RBF charged with a magnetic stir bar was added HATU (944 mg, 2.485 mmol) and DIPEA (0.9 mL, 4.970 mmol), followed by DMAP (60 mg, 0.497 mmol). The reaction was stirred at 30° C. under N$_2$ for 16 hours, after which it was quenched with H$_2$O (50 mL). The organic layer was extracted with EtOAc (3×50 mL). The combined organic layers were washed with brine, dried over Na$_2$SO$_4$, and evaporated to dryness to afford a crude liquid. Crude product was purified by silica gel chromatography eluting with EtOAc:hexane (product eluted at 30% EtOAc:hexane) to afford desired product as a colorless viscous liquid (500 mg).

TLC: Rf=0.5 (EtOAc: Hexane, 3:7), PMA active.

Example 69

1-(3-((4,4-bis(octyloxy)butanoyl)oxy)-2-(((1-methylpyrrolidine-3-carbonyl)oxy)methyl)propyl) 10-octyl decanedioate

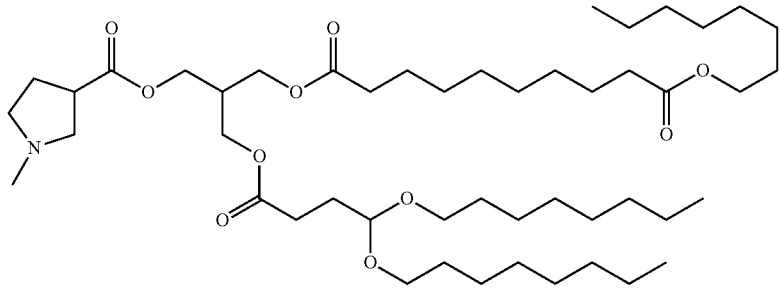 [SMILES: CCCCCCCCOC(=O)CCCCCCCCC(=O)OCC(COC(=O)CCC(OCCCCCCCC)OCCCCCCCC)COC(=O)C1CCN(C)C1]

Example 69 can be prepared using similar methods to those employed for the synthesis of example 1.

$^1$H NMR (400 MHz, CDCl$_3$): δ=4.48 (m, 1H), 4.18-4.02 (m, 8H), 3.48 (m, 2H), 3.40 (m, 2H), 3.02 (m, 1H), 2.80 (t, J=8.4 Hz, 1H), 2.64-2.44 (m, 3H), 2.38 (m, 3H), 2.32 (s, 3H), 2.24 (m, 4H), 2.08 (m, 2H), 1.86 (m, 2H), 1.60 (m, 10H), 1.25 (m, 38H), 0.82 (m, 9H) ppm.

MS (M+1)=840.8 Rt=0.77 min (LC method 10).

Example 70

1-(16-(((4,4-bis(octyloxy)butanoyl)oxy)methyl)-9-dodecyl-2-methyl-7,13-dioxo-6,8,12,14-tetraoxa-2-azaheptadecan-17-yl) 8-methyl octanedioate

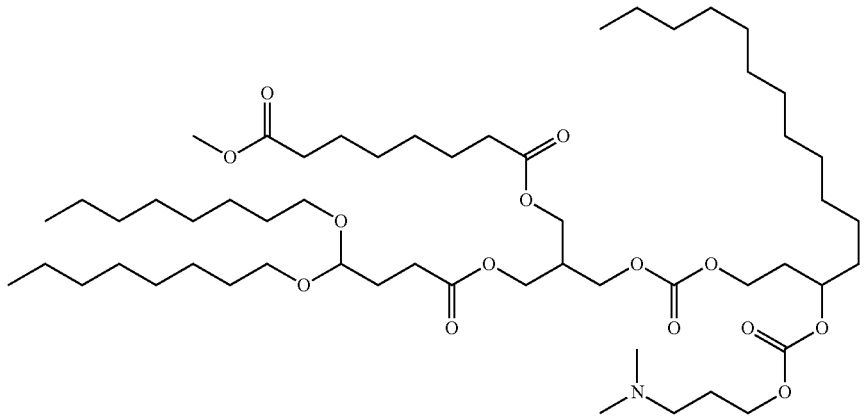 [SMILES: CCCCCCCCCCCCC(CCOC(=O)OCC(COC(=O)CCCCCCC(=O)OC)COC(=O)CCC(OCCCCCCCC)OCCCCCCCC)OC(=O)OCCCN(C)C]
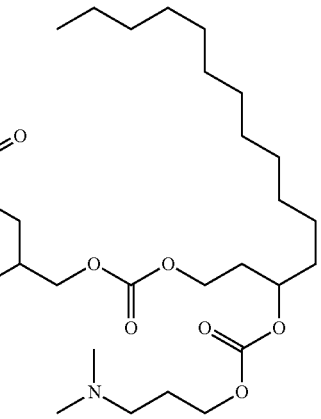

To a solution of intermediate 74e (described later, 372 mg, 0.995 mmol) in DCM (10 mL) in a RBF charged with a magnetic stir bar was added Et$_3$N (0.42 mL, 2.985 mmol) followed by slow addition of 4-nitrophenyl chloroformate (346 mg, 1.716 mmol) and DMAP (243 mg, 1.990 mmol). The resulting red solution was stirred for 1 hour, after which intermediate 68b (600 mg, 0.995 mmol) was added as a solution in DCM (5 mL). The reaction was stirred for 17 hours, after which it was quenched with H$_2$O (50 mL) and extracted with DCM (3×50 mL). The combined organic layers were dried over Na$_2$SO$_4$ and evaporated to dryness to afford a crude material. Crude product was purified by silica gel flash chromatography eluting with MeOH:DCM (product eluted at 4% MeOH:DCM) to afford desired product as a colorless viscous liquid (400 mg).

$^1$H NMR (400 MHz, CDCl$_3$): δ=4.80 (m, 1H), 4.44 (m, 1H), 4.20-4.10 (m, 10H), 3.66 (s, 3H), 3.58 (m, 2H), 3.38 (m, 2H), 2.42-2.18 (m, 9H), 2.22 (s, 6H), 1.98-180 (m, 6H), 1.60 (m, 12H), 1.38-1.20 (m, 42H), 0.82 (m, 9H) ppm.

MS (M+1)=1003.3, Rt=0.83 min (LC method 10).

Synthesis of Example 71

Intermediate 71a: 1-(3-((6,6-bis((2-propylpentyl)oxy)hexanoyl)oxy)-2-(hydroxymethyl)propyl) 10-octyl decanedioate

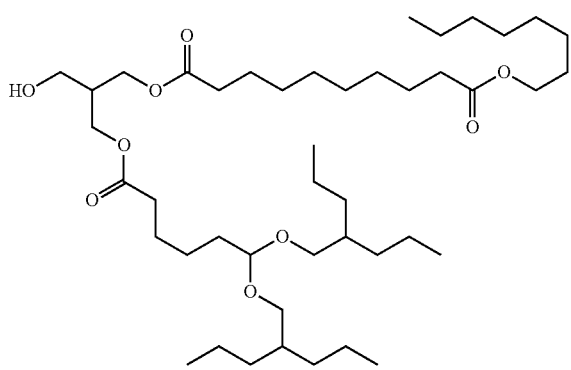 [SMILES: CCCCCCCCOC(=O)CCCCCCCCC(=O)OCC(CO)COC(=O)CCCCC(OCC(CCC)CCC)OCC(CCC)CCC]

To a solution of intermediate 56b (700 mg, 1.739 mmol) and intermediate 61b (650 mg, 1.739 mmol) in DMF (15 mL) in a RBF charged with a magnetic stir bar was added HATU (794 mg, 2.086 mmol) and DMAP (43 mg, 0.347 mmol), followed by DIPEA (0.4 mL, 2.086 mmol). The reaction was stirred at 30° C. under N$_2$ for 16 hours, after which it was quenched with H$_2$O (50 mL) and extracted with EtOAc (3×50 mL). The combined organic layers were washed with brine, dried over Na$_2$SO$_4$, and evaporated to dryness to afford a pale yellow crude liquid. Crude product was purified by silica gel chromatography eluting with EtOAc:hexane (product eluted at 20% EtOAc:hexane) to afford the desired product as a colorless liquid (700 mg).

TLC: Rf=0.6 (EtOAc: Hexane, 3:7), PMA active.

Example 71

1-(3-((6,6-bis((2-propylpentyl)oxy)hexanoyl)oxy)-2-(((1,4-dimethylpiperidine-4-carbonyl)oxy)methyl)propyl) 10-octyl decanedioate

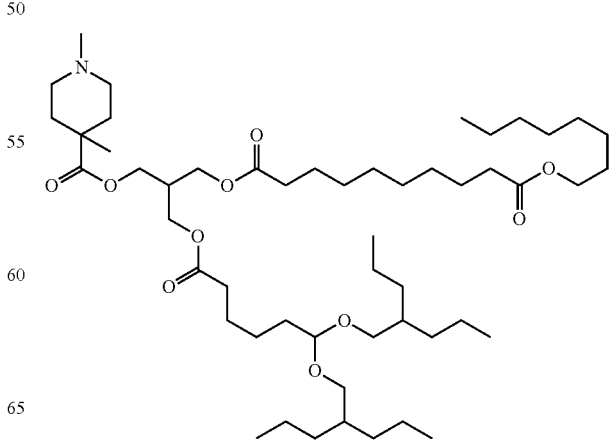

To a solution of 1,4-dimethylpiperidine-4-carboxylic acid (218 mg, 1.387 mmol) and Et₃N (0.52 mL, 3.7 mmol) in DCM (10 mL) in a RBF charged with a magnetic stir bar was added 2,4,6-trichlorobenzoyl chloride (340 mg, 1.387 mmol) slowly dropwise at 30° C. The reaction was stirred under N₂ for 4 hours, after which intermediate 71a (700 mg, 0.925 mmol) was added as a solution in DCM (5 mL). Next, DMAP (226 mg, 1.850 mmol) was added and the reaction was stirred for 20 hours, after which it was quenched with H₂O (20 mL) and extracted with DCM (3×50 mL). The combined organic layers were dried over Na₂SO₄ and evaporated to dryness to afford a crude solid. Crude product was purified by silica gel flash chromatography eluting with MeOH:DCM (product eluted at 4% MeOH:DCM) to afford the desired product as a pale yellow viscous liquid (650 mg).

¹H NMR (400 MHz, CDCl₃) δ=4.41 (t, J=5.6 Hz, 1H), 4.18-4.11 (m, 6H), 4.06 (t, J=6.8 Hz, 2H), 3.45 (dd, J=9.2, 5.7 Hz, 2H), 3.26 (dd, J=9.2, 5.8 Hz, 2H), 2.69-2.51 (br s, 2H), 2.47-2.37 (m, 1H), 2.36-2.20 (m, 9H), 2.18-1.99 (m, 4H), 1.71-1.45 (m, 14H), 1.44-1.17 (m, 36H), 1.20 (s, 3H), 0.95-0.83 (m, 15H) ppm.

MS (M+1)=896.7, Rt=2.61 min (LC method 9).

Synthesis of Example 72

Intermediate 72a: 1-(3-((6,6-bis((2-propylpentyl) oxy)hexanoyl)oxy)-2-(hydroxymethyl)propyl) 8-methyl octanedioate

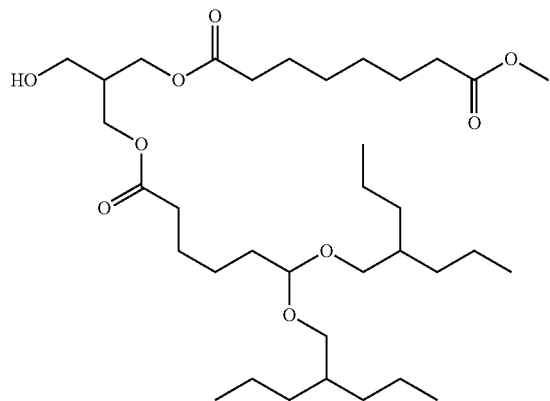 [SMILES: CCCC(CCC)COC(CCCCC(=O)OCC(CO)COC(=O)CCCCCCC(=O)OC)OCC(CCC)CCC]

To a solution of intermediate 68a (1.0 g, 3.623 mmol) and intermediate 61b (1.34 g, 3.623 mmol) in DMF (15 mL) in a RBF charged with a magnetic stir bar was added HATU (1.65 mg, 4.347 mmol) and DIPEA (1.3 mL, 7.246 mmol), followed by DMAP (44 mg, 0.362 mmol). The reaction was stirred at 30° C. under N₂ for 16 hours, after which it was quenched with H₂O (50 mL) and extracted with EtOAc (3×50 mL). The combined organic layers were washed with brine, dried over Na₂SO₄, and evaporated to dryness to afford a crude liquid. Crude product was purified by silica gel chromatography eluting with EtOAc:hexane (product eluted at 30% EtOAc:hexane) to afford desired product as a colorless liquid (830 mg).

TLC: Rf=0.4 (EtOAc: Hexane, 3:7), PMA active.

Example 72

1-(3-((6,6-bis((2-propylpentyl)oxy)hexanoyl)oxy)-2-(((1,4-dimethylpiperidine-4-carbonyl)oxy)methyl)propyl) 8-methyl octanedioate

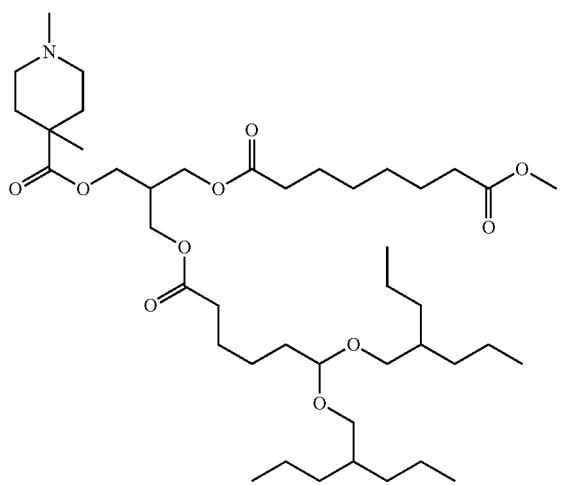 [SMILES: CCCC(CCC)COC(CCCCC(=O)OCC(COC(=O)CCCCCCC(=O)OC)COC(=O)C1(C)CCN(C)CC1)OCC(CCC)CCC]

To a solution of 1,4-dimethylpiperidine-4-carboxylic acid (310 mg, 1.974 mmol) and Et₃N (0.75 mL, 5.264 mmol) in DCM (10 mL) in a RBF charged with a magnetic stir bar was added 2,4,6-trichlorobenzoyl chloride (480 mg, 1.974 mmol) slowly dropwise at 30° C. The reaction was stirred under N₂ for 4 hours, after which intermediate 72a (830 mg, 1.316 mmol) was added as a solution in DCM (5 mL). Next, DMAP (320 mg, 2.632 mmol) was added and the reaction was stirred for 20 hours, after which it was quenched with H₂O (20 mL) and extracted with DCM (3×50 mL). The combined organic layers were dried over Na₂SO₄ and evaporated to dryness to afford a crude solid. Crude product was purified by silica gel flash chromatography eluting with MeOH:DCM (product eluted at 4% MeOH:DCM) to afford desired product as a pale yellow viscous liquid (670 mg).

¹H NMR (400 MHz, CDCl₃) δ=4.41 (t, J=5.6 Hz, 1H), 4.19-4.08 (m, 6H), 3.67 (s, 3H), 3.46 (dd, J=9.3, 5.7 Hz, 2H), 3.27 (dd, J=9.2, 5.8 Hz, 2H), 2.70-2.51 (br s, 2H), 2.47-2.37 (m, 1H), 2.37-2.19 (m, 9H), 2.18-1.98 (m, 4H), 1.72-1.45 (m, 12H), 1.44-1.174 (m, 22H), 1.20 (s, 3H), 0.93-0.86 (m, 12H) ppm.

MS (M+1)=770.4, Rt=1.82 min (LC method 9).

Synthesis of Example 73

Intermediate 73a: O'1,O1-(2-(hydroxymethyl)propane-1,3-diyl) 8-dimethyl dioctanedioate

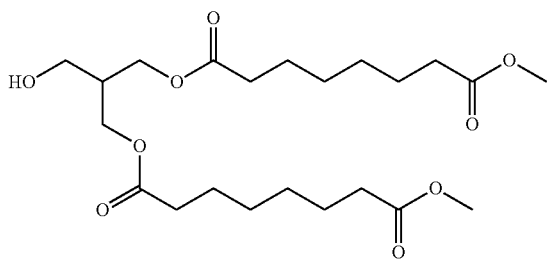 [SMILES: COC(=O)CCCCCCC(=O)OCC(CO)COC(=O)CCCCCCC(=O)OC]

To a solution of octanedioic acid, 1-methyl ester (2.0 g, 18.18 mmol) and 2(hydroxymethyl)propane-1,3-diol (3.50 g, 18.18 mmol) in DMF (20 mL) was added HATU (7.6 g, 20.00 mmol) and DIPEA (6.30 mL, 36.37 mmol), followed by DMAP (0.22 g, 1.81 mmol), and the mixture was stirred at 30° C. for 16 h under nitrogen. The reaction mixture was quenched with 50 mL of water and extracted with 3×50 mL of EtOAc. The combined organic layers were washed with brine solution, dried over sodium sulfate and evaporated to dryness to afford a crude oil. The mixture was purified on silica gel, eluting with 0-5% MeOH/DCM to provide 1.80 g of the desired product.

TLC (silica gel, 10% MeOH/DCM, PMA stain): $R_f$=0.46.

Example 73

8-dimethyl O'1,O1-(2-(((1-methylpyrrolidine-3-carbonyl)oxy)methyl)propane-1,3-diyl)dioctanedioate

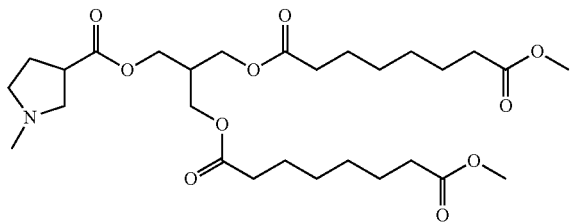 [SMILES: COC(=O)CCCCCCC(=O)OCC(COC(=O)CCCCCCC(=O)OC)COC(=O)C1CCN(C)C1]

Example 73 can be prepared using similar methods to those employed for the synthesis of example 1.

$^1$H NMR (CDCl$_3$): δ=4.18 (m, 6H), 3.62 (s, 6H), 3.40-3.02 (m, 4H), 2.80 (m, 1H), 2.62 (s, 3H), 2.30 (m, 11H), 1.62 (m, 8H), 1.30 (m, 8H) ppm.

MS (M+1)=558.2, Rt=0.17 min (LC method 10).

Synthesis of Example Example 74

Intermediate 74a:
3-((tert-butyldimethylsilyl)oxy)propanal

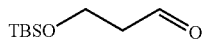

In a round-bottom flask equipped with a stir bar, Tertbutyldimethylsilyloxypropanol (20 g, 105 mmol) was dissolved in DCM (500 mL). Et$_3$N (43.9 mL, 315 mmol) was added. In a second flask equipped with a stirbar, SO$_3$.Py (25.1 g, 158 mmol) was dissolved in DMSO (100 mL, 1409 mmol). The resulting solution was added dropwise to the alcohol solution at 0° C. (in an ice-water bath). The reaction was stirred while warming to rt over the weekend. Water and DCM were added to the mixture in a separatory funnel. The organics were then washed with water, extracted in DCM, dried over MgSO$_4$, filtered and concentrated (cold) under reduced pressure to give crude product mixture. Purification by silica gel column chromatography (100% DCM) provided the title compound (17.7 g).

$^1$H NMR (400 MHz, CDCl$_3$) δ=9.81 (t, J=2.1 Hz, 1H), 3.99 (t, J=6.0 Hz, 2H), 2.61 (td, J=6.0, 2.3 Hz, 2H), 0.88 (s, 9H), 0.07 (s, 6H) ppm.

Intermediate 74b:
1-((tert-butyldimethylsilyl)oxy)pentadecan-3-ol

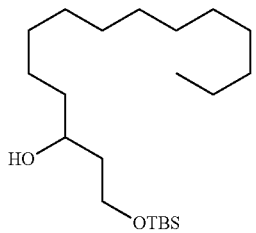 [SMILES: CCCCCCCCCCCCC(O)CCO[Si](C)(C)C(C)(C)C]

In a round-bottom flask, Intermediate 74a (17.7 g, 94 mmol) was dissolved in THF (100 mL), and cooled to 0° C. in an ice-water bath. Dodecylmagnesiumbromide, 1M in diethyl ether (132 mL, 132 mmol) was then added to the aldehyde dropwise over 10 min via pipette, the ice-bath was removed, and reaction was stirred at rt for 30 min. The reaction flask was cooled again to 0° C. in an ice-bath. Sat. NH$_4$Cl solution was added slowly to adjust to pH~7 (600 mL), and the mixture was poured into a 1 L separatory funnel. The organics were then washed with sat. ammonium chloride solution, extracted in EtOAc, dried over MgSO$_4$, filtered and concentrated under reduced pressure to give the crude product mixture. Purification by silica gel column chromatography (100% Heptanes for 2 column volumes, 0% to 2% EtOAc/Heptane for 1 column volume, 2% EtOAc/Heptane for 3 column volumes, 2% to 5% EtOAc/Heptane for 1 column volume, then 5% EtOAc/Heptane for 10 column volumes) provided the title compound (24.9 g).

$^1$H NMR (400 MHz, CDCl$_3$) δ=3.97-3.87 (m, 1H), 3.87-3.77 (m, 2H), 1.69-1.60 (m, 2H), 1.57-1.36 (m, 3H), 1.36-1.19 (br, 19H), 0.93-0.84 (m, 12H), 0.09 (s, 6H) ppm.

Intermediate 74c: 1-((tert-butyldimethylsilyl)oxy)pentadecan-3-yl (4-nitrophenyl)carbonate

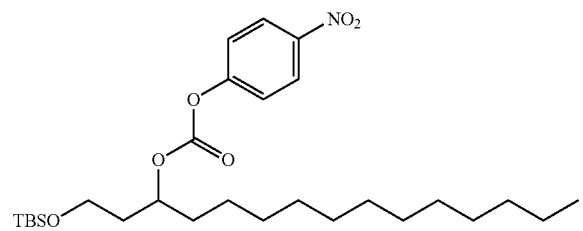 [SMILES: CCCCCCCCCCCCC(CCO[Si](C)(C)C(C)(C)C)OC(=O)Oc1ccc([N+](=O)[O-])cc1]

4-nitrophenyl carbonochloridate (2.08 g, 9.92 mmol) was added in one portion to a solution of Intermediate 74b (2.96 g, 8.27 mmol) in DCM (28 mL) in a round bottom flask charged with a magnetic stir bar at rt. The reaction was fitted with a septum and placed under N$_2$, after which pyridine (1.00 mL, 12.4 mmol) was added dropwise via syringe over several minutes. The reaction was allowed to stir at rt overnight. After 24 hours of reaction time, the reaction was diluted with H$_2$O (100 mL) and DCM (125 mL). The organic layer was separated, and the aqueous layer was washed with DCM (125 mL). The combined organic layers were washed with brine (100 mL), dried with Na$_2$SO$_4$, filtered, and concentrated under reduced pressure to provide an off white residue. The crude residue was purified by silica gel column chromatography (80 g column, liquid loading, 0-2.5%

EtOAc:heptane) to provide 3.14 g of the title compound (plus minor unidentified impurity peaks) as a colorless oil.

$^1$H NMR (400 MHz, CD$_2$Cl$_2$) δ=8.29-8.24 (m, 2H), 7.41-7.35 (m, 2H), 5.03-4.95 (m, 1H), 3.73 (dd, J=6.6, 5.7 Hz, 2H), 1.95-1.80 (m, 2H), 1.80-1.63 (m, 2H), 1.45-1.19 (m, 20H), 0.92-0.83 (m, 12H), 0.06 (s, 6H) ppm.

Intermediate 74d: 1-((tert-butyldimethylsilyl)oxy)pentadecan-3-yl (3-(diethylamino)propyl)carbonate

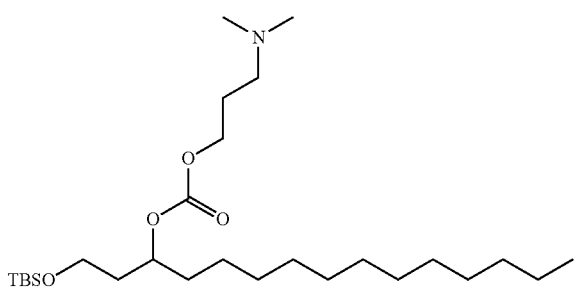 [SMILES: CCCCCCCCCCCCC(CCO[Si](C)(C)C(C)(C)C)OC(=O)OCCCN(C)C]

To a stirred solution of intermediate 74c (8.00 g, 15.3 mmol) in 50 mL of DCM was added 2(dimethylamino)propanol (7.1 mL, 61.1 mmol) and pyridine (7.5 mL, 91.7 mmol). Then DMAP (3.70 g, 30.5 mmol) was added and the clear yellow color solution was stirred at room temperature for 24 h under nitrogen atmosphere. The mixture was then quenched with 100 mL of water, extracted with DCM (2×200 mL), and the organic layers were combined, dried over sodium sulfate, and concentrated to afford a yellow oil. The crude mixture was purified by flash column chromatography (eluting with 4% MeOH/DCM) to provide 4.6 g of the desired product as a yellow oil.

TLC: Rf=0.36 (MeOH/DCM, 5:95), PMA active.

Intermediate 74e: 3-(diethylamino)propyl (1-hydroxypentadecan-3-yl)carbonate

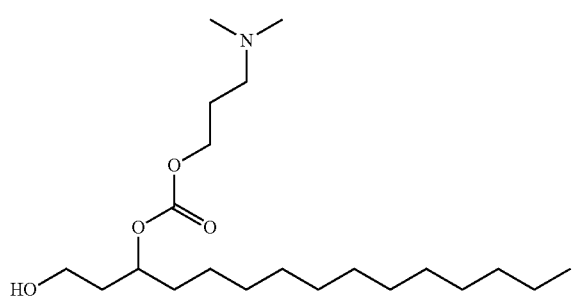 [SMILES: CCCCCCCCCCCCC(CCO)OC(=O)OCCCN(C)C]

To a solution of Intermediate 74d (450 mg, 0.923 mmol) in THF (10 mL) at 0° C. was added HF pyridine (70%, 1.6 mL, 55.4 mmol) dropwise. The mixture was stirred for 1 h then was slowly quenched with 50 mL of saturated sodium bicarbonate solution. The crude mixture was extracted with 50 mL of EtOAc, and the organic layer was dried over sodium sulfate and evaporated under reduced pressure to afford a pale green oil. This mixture was used in the next step without further purification.

TLC: Rf=0.17 (MeOH/DCM, 5:95), PMA active.

Example 74

O'1,O1-(2-(7-dodecyl-14-methyl-3,9-dioxo-2,4,8,10-tetraoxa-14-azapentadecyl)propane-1,3-diyl) 8-dimethyl dioctanedioate

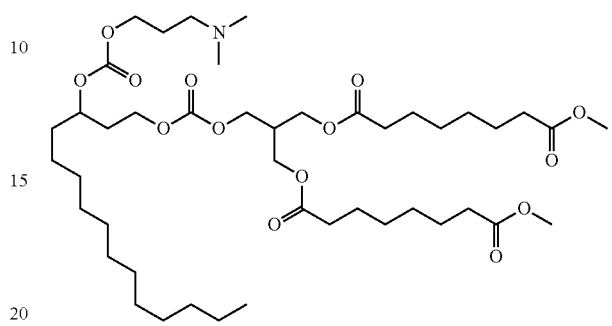

Example 74 can be prepared using similar methods to those employed for the synthesis of example 13.

$^1$H NMR (CDCl$_3$): δ=4.80 (m, 1H), 4.18 (m, 10H), 3.62 (s, 6H), 2.42-2.15 (m, 11H), 2.20 (s, 6H), 1.98 (m, 2H), 1.82 (m, 2H), 1.60 (m, 8H), 1.38-1.20 (m, 30H), 0.82 (t, J=8 Hz, 3H) ppm.

MS (M+1)=847.1, Rt=0.52 min (LC method 10).

Synthesis of Example 75

Intermediate 75a: O'1,O1-(2-(hydroxymethyl)propane-1,3-diyl) 10-dioctyl bis(decanedioate)

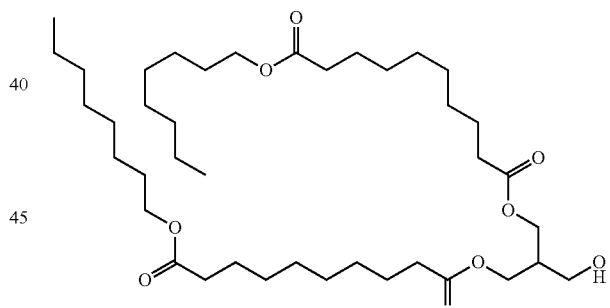

Intermediate 56a (5.9 g, 18.85 mmol) and 2(hydroxymethyl)propane-1,3,diol (1.0 g, 9.42 mmol) were dissolved in DMF (50 mL). HATU (7.1 g, 18.85 mmol) was added, followed by DIPEA (3.3 mL, 18.85 mmol), and finally DMAP (0.23 g, 1.88 mmol), and the mixture was stirred for 16 h at room temperature. The reaction mixture was quenched with 50 mL of water and extracted with 3×50 mL of EtOAc. The combined organic layers were washed with brine solution (2×50 mL), dried over sodium sulfate and evaporated to dryness to afford a crude oil. The mixture was purified on silica gel, eluting with 30% EtOAc/heptane to provide 1.40 g of the desired product.

TLC (silica gel, 30% EtOAc/heptane, PMA stain): R$_f$=0.51.

The following examples can be prepared using similar methods to those employed for the synthesis of example 13, with intermediates similar to 74e.

Example 75

O'1,O1-(2-(7-dodecyl-14-methyl-3,9-dioxo-2,4,8,10-tetraoxa-14-azapentadecyl)propane-1,3-diyl) 10-di-octyl bis(decanedioate)

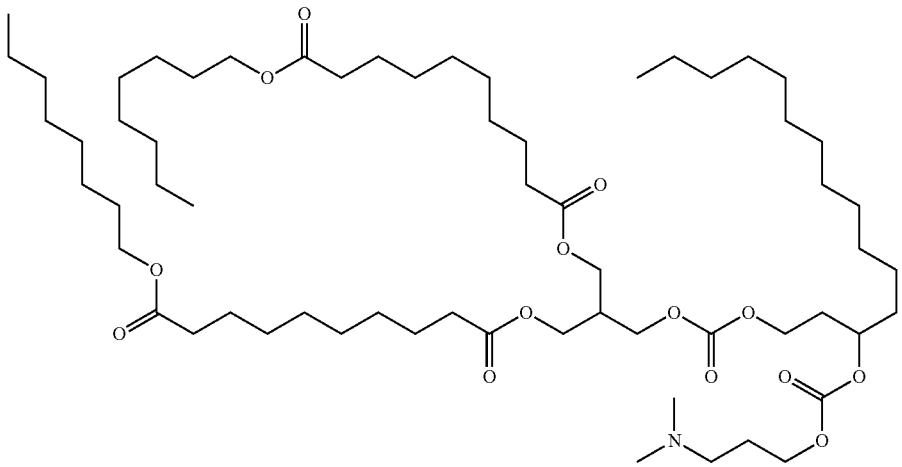 [SMILES: CCCCCCCCCCCCC(CCOC(=O)OCC(COC(=O)CCCCCCCCC(=O)OCCCCCCCC)COC(=O)CCCCCCCCC(=O)OCCCCCCCC)OC(=O)OCCCN(C)C]

$^1$H NMR (400 MHz, CDCl$_3$) δ=4.87-4.76 (m, 1H), 4.25-4.11 (m, 10H), 4.06 (t, J=6.8 Hz, 4H), 2.48-2.40 (m, 1H), 2.37 (t, J=7.3 Hz, 2H), 2.30 (q, J=7.4 Hz, 8H), 2.24 (s, 6H), 2.01-1.92 (m, 2H), 1.90-1.80 (m, 2H), 1.70-1.52 (m, 14H), 1.40-1.20 (m, 56H), 0.93-0.83 (m, 9H) ppm.
MS (M+1)=1099.2, Rt=1.29 min (LC method 12).

Example 76

O'1,O1-(2-(14-methyl-7-octyl-3,9-dioxo-2,4,8,10-tetraoxa-14-azapentadecyl)propane-1,3-diyl) 10-di-octyl bis(decanedioate)

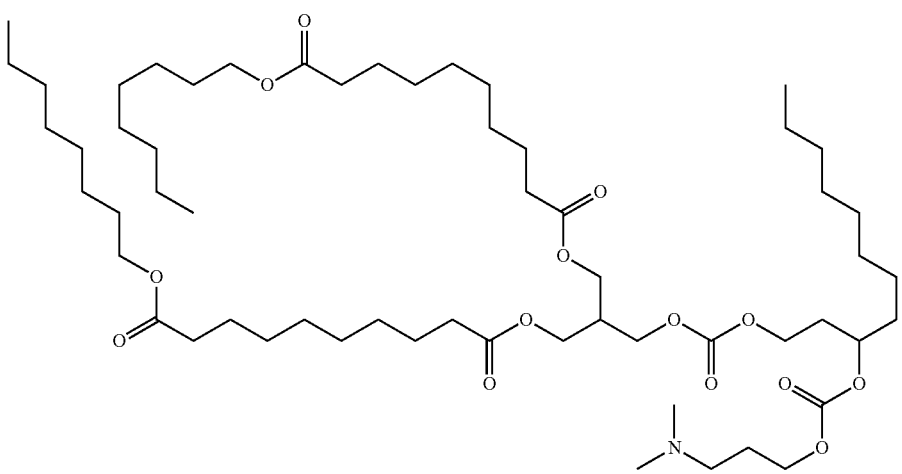 [SMILES: CCCCCCCCOC(=O)CCCCCCCCC(=O)OCC(COC(=O)CCCCCCCCC(=O)OCCCCCCCC)COC(=O)OCCC(CCCCCCCC)OC(=O)OCCCN(C)C]

$^1$H NMR (400 MHz, CDCl$_3$) δ=4.86-4.77 (m, 1H), 4.27-4.10 (m, 10H), 4.06 (t, J=6.7 Hz, 4H), 2.48-2.39 (m, 1H), 2.39-2.25 (m, 10H), 2.23 (s, 6H), 2.01-1.93 (m, 2H), 1.89-1.79 (m, 2H), 1.71-1.52 (m, 14H), 1.42-1.17 (m, 48H), 0.95-0.82 (m, 9H) ppm.
MS (M+1)=1043.3, Rt=2.69 min (LC method 9).

The following example can be prepared using similar methods to those employed for the synthesis of example 1.

Example 77

O'1,O1-(2-(((1,3-dimethylpyrrolidine-3-carbonyl)oxy)methyl)propane-1,3-diyl) 10-dioctyl bis(decanedioate)

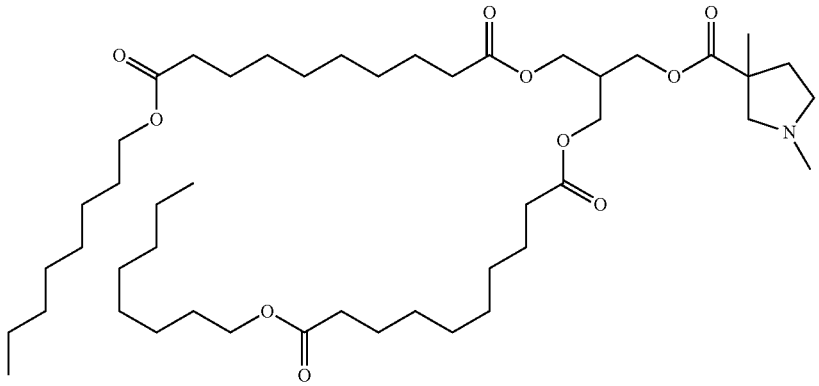 [SMILES: CCCCCCCCOC(=O)CCCCCCCCC(=O)OCC(COC(=O)CCCCCCCCC(=O)OCCCCCCCC)COC(=O)C1(C)CCN(C)C1]

$^1$H NMR (400 MHz, ACETONITRILE-d$_3$): δ=4.10 (d, J=5.87 Hz, 6H), 4.01 (t, J=6.60 Hz, 4H), 2.86 (d, J=9.17 Hz, 1H), 2.54-2.47 (m, 2H), 2.40-2.32 (m, 2H), 2.32-2.21 (m, 12H), 1.63-1.51 (m, 12H), 1.37-1.25 (m, 40H), 0.92-0.85 (m, 6H) ppm.

MS (M+1)=825, Rt=2.32 min (LC method 9).

siRNA Lipid Formulations

The lipid nanoparticles (LNPs) were formed by mixing equal volumes of lipids dissolved in alcohol with siRNA dissolved in a citrate buffer by an impinging jet process. The lipid solution contains a cationic lipid compound of the invention, a helper lipid (cholesterol), an optional neutral lipid (DSPC) and a PEG (PEG) lipid at a concentration of 8-16 mg/mL with a target of 12 mg/mL in an alcohol. The siRNA to total lipid ratio is approximately 0.05 (wt/wt). Where a LNP formulation contains four lipid components, the molar ratios of the lipids ranges from 20 to 70 mole percent for the cationic lipid with a target of 40-60, the mole percent of helper lipid ranges from 20 to 70 with a target of 30 to 50, the mole percent of neutral lipid ranges from 0-30, the mole percent of PEG lipid has a range from 1 to 6 with a target of 2 to 5. The concentration of siRNA solution ranges from 0.7 to 1.0 mg/mL with a target of 0.8 to 0.9 mg/mL in a sodium citrate: sodium chloride buffer pH 4-6, with a target of 4.5-5.5. The LNPs are formed by mixing equal volumes of lipid solution in ethanol with siRNA dissolved in a citrate buffer by an impinging jet process through a mixing device with ID ranging from 0.25 to 2.0 mm at a flow rate from 10 to 640 mL/min. The mixed LNP solution is held at room temperature for 0-24 hrs prior to a dilution step. The solution is then concentrated and diafiltered with suitable buffer by ultrafiltration or dialysis process using membranes with a MW cutoff from 30 to 500 KD. The final product is sterile filtered and stored at 4° C.

siRNA's

The siRNA used in the lipid nanoparticles described was made up of double stranded siRNA sequences specific to a target mRNA sequence.

1. FVII siRNA duplex sequence

```
                                   (SEQ ID NO: 1)
     5' UUu AAU UGA AAC cAA GAc Auu 3'

(SEQ ID NO: 2)
     5' uGu cuu GGu uuc AAu uAA Auu 3'
```

2. PLK1-424 siRNA duplex sequence

```
                                   (SEQ ID NO: 3)
     5' UAU UUA AgG AGG GUG AuC Uuu 3'

(SEQ ID NO: 4)
     5' AGA Uca cCC Ucc uuA AAU auu 3'
```

The following abbreviations are used in these sequences:
A=adenosine
U=uridine
G=guanosine
C=cytosine
a=2'-O-methyl-adenosine
u=2'-O-methyl-uridine
g=2'-O-methyl-guanosine
c=2'-O-methyl-cytosine Plasmid's

```
pcDNA3.1(-)Neo from LifeTechnologies Cat# V795-20
                                   (SEQ ID NO: 5)
GACGGATCGGGAGATCTCCCGATCCCCTATGGTGCACTCTCAGTACAATC

TGCTCTGATGCCGCATAGTTAAGCCAGTATCTGCTCCCTGCTTGTGTGTT

GGAGGTCGCTGAGTAGTGCGCGAGCAAAATTTAAGCTACAACAAGGCAAG

GCTTGACCGACAATTGCATGAAGAATCTGCTTAGGGTTAGGCGTTTTGCG

CTGCTTCGCGATGTACGGGCCAGATATACGCGTTGACATTGATTATTGAC

TAGTTATTAATAGTAATCAATTACGGGGTCATTAGTTCATAGCCCATATA

TGGAGTTCCGCGTTACATAACTTACGGTAAATGGCCCGCCTGGCTGACCG

CCCAACGACCCCCGCCCATTGACGTCAATAATGACGTATGTTCCCATAGT

AACGCCAATAGGGACTTTCCATTGACGTCAATGGGTGGAGTATTTACGGT

AAACTGCCCACTTGGCAGTACATCAAGTGTATCATATGCCAAGTACGCCC

CCTATTGACGTCAATGACGGTAAATGGCCCGCCTGGCATTATGCCCAGTA

CATGACCTTATGGGACTTTCCTACTTGGCAGTACATCTACGTATTAGTCA

TCGCTATTACCATGGTGATGCGGTTTTGGCAGTACATCAATGGGCGTGGA
```

```
TAGCGGTTTGACTCACGGGGATTTCCAAGTCTCCACCCCATTGACGTCAA
TGGGAGTTTGTTTTGGCACCAAAATCAACGGGACTTTCCAAAATGTCGTA
ACAACTCCGCCCCATTGACGCAAATGGGCGGTAGGCGTGTACGGTGGGAG
GTCTATATAAGCAGAGCTCTCTGGCTAACTAGAGAACCCACTGCTTACTG
GCTTATCGAAATTAATACGACTCACTATAGGGAGACCCAAGCTGGCTAGC
GTTTAAACGGGCCCTCTAGACTCGAGCGGCCGCCACTGTGCTGGATATCT
GCAGAATTCCACCACACTGGACTAGTGGATCCGAGCTCGGTACCAAGCTT
AAGTTTAAACCGCTGATCAGCCTCGACTGTGCCTTCTAGTTGCCAGCCAT
CTGTTGTTTGCCCCTCCCCCGTGCCTTCCTTGACCCTGGAAGGTGCCACT
CCCACTGTCCTTTCCTAATAAAATGAGGAAATTGCATCGCATTGTCTGAG
TAGGTGTCATTCTATTCTGGGGGGTGGGGTGGGGCAGGACAGCAAGGGGG
AGGATTGGGAAGACAATAGCAGGCATGCTGGGGATGCGGTGGGCTCTATG
GCTTCTGAGGCGGAAAGAACCAGCTGGGGCTCTAGGGGGTATCCCCACGC
GCCCTGTAGCGGCGCATTAAGCGCGGCGGGTGTGGTGGTTACGCGCAGCG
TGACCGCTACACTTGCCAGCGCCCAGCGCCCGCTCCTTTCGCTTTCTTC
CCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCA
AAAAACTTGATTAGGGTGATGGTTCACGTAGTGGGCCATCGCCCTGATAG
ACGGTTTTTCGCCCTTTGACGTTGGAGTCCACGTTCTTTAATAGTGGACT
CTTGTTCCAAACTGGAACAACACTCAACCCTATCTCGGTCTATTCTTTTG
ATTTATAAGGGATTTTGCCGATTTCGGCCTATTGGTTAAAAAATGAGCTG
ATTTAACAAAAATTTAACGCGAATTAATTCTGTGGAATGTGTGTCAGTTA
GGGTGTGGAAAGTCCCCAGGCTCCCCAGCAGGCAGAAGTATGCAAAGCAT
GCATCTCAATTAGTCAGCAACCAGGTGTGGAAAGTCCCCAGGCTCCCCAG
CAGGCAGAAGTATGCAAAGCATGCATCTCAATTAGTCAGCAACCATAGTC
CCGCCCCTAACTCCGCCCATCCCGCCCCTAACTCCGCCCAGTTCCGCCCA
TTCTCCGCCCCATGGCTGACTAATTTTTTTTATTTATGCAGAGGCCGAGG
CCGCCTCTGCCTCTGAGCTATTCCAGAAGTAGTGAGGAGGCTTTTTTGGA
GGCCTAGGCTTTTGCAAAAAGCTCCCGGGAGCTTGTATATCCATTTTCGG
ATCTGATCAAGAGACAGGATGAGGATCGTTTCGCATGATTGAACAAGATG
GATTGCACGCAGGTTCTCCGGCCGCTTGGGTGGAGAGGCTATTCGGCTAT
GACTGGGCACAACAGACAATCGGCTGCTCTGATGCCGCCGTGTTCCGGCT
GTCAGCGCAGGGGCGCCCGGTTCTTTTTGTCAAGACCGACCTGTCCGGTG
CCCTGAATGAACTGCAGGACGAGGCAGCGCGGCTATCGTGGCTGGCCACG
ACGGGCGTTCCTTGCGCAGCTGTGCTCGACGTTGTCACTGAAGCGGGAAG
GGACTGGCTGCTATTGGGCGAAGTGCCGGGGCAGGATCTCCTGTCATCTC
ACCTTGCTCCTGCCGAGAAAGTATCCATCATGGCTGATGCAATGCGGCGG
CTGCATACGCTTGATCCGGCTACCTGCCCATTCGACCACCAAGCGAAACA
TCGCATCGAGCGAGCACGTACTCGGATGGAAGCCGGTCTTGTCGATCAGG
ATGATCTGGACGAAGAGCATCAGGGGCTCGCGCCAGCCGAACTGTTCGCC
AGGCTCAAGGCGCGCATGCCCGACGGCGAGGATCTCGTCGTGACCCATGG

CGATGCCTGCTTGCCGAATATCATGGTGGAAAATGGCCGCTTTTCTGGAT
TCATCGACTGTGGCCGGCTGGGTGTGGCGGACCGCTATCAGGACATAGCG
TTGGCTACCCGTGATATTGCTGAAGAGCTTGGCGGCGAATGGGCTGACCG
CTTCCTCGTGCTTTACGGTATCGCCGCTCCCGATTCGCAGCGCATCGCCT
TCTATCGCCTTCTTGACGAGTTCTTCTGAGCGGGACTCTGGGGTTCGAAA
TGACCGACCAAGCGACGCCCAACCTGCCATCACGAGATTTCGATTCCACC
GCCGCCTTCTATGAAAGGTTGGGCTTCGGAATCGTTTTCCGGGACGCCGG
CTGGATGATCCTCCAGCGCGGGGATCTCATGCTGGAGTTCTTCGCCCACC
CCAACTTGTTTATTGCAGCTTATAATGGTTACAAATAAAGCAATAGCATC
ACAAATTTCACAAATAAAGCATTTTTTTCACTGCATTCTAGTTGTGGTTT
GTCCAAACTCATCAATGTATCTTATCATGTCTGTATACCGTCGACCTCTA
GCTAGAGCTTGGCGTAATCATGGTCATAGCTGTTTCCTGTGTGAAATTGT
TATCCGCTCACAATTCCACACAACATACGAGCCGGAAGCATAAAGTGTAA
AGCCTGGGGTGCCTAATGAGTGAGCTAACTCACATTAATTGCGTTGCGCT
CACTGCCCGCTTTCCAGTCGGGAAACCTGTCGTGCCAGCTGCATTAATGA
ATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGG
TATCAGCTCACTCAAAGGCGGTAATACGGTTATCCACAGAATCAGGGGAT
AACGCAGGAAAGAACATGTGAGCAAAAGGCCAGCAAAAGGCCAGGAACCG
TAAAAAGGCCGCGTTGCTGGCGTTTTTCCATAGGCTCCGCCCCCCTGACG
AGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCC
TGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTG
TAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAA
GACACGACTTATCGCCACTGGCAGCAGCCACTGGTAACAGGATTAGCAGA
GCGAGGTATGTAGGCGGTGCTACAGAGTTCTTGAAGTGGTGGCCTAACTA
CGGCTACACTAGAAGAACAGTATTTGGTATCTGCGCTCTGCTGAAGCCAG
TTACCTTCGGAAAAAGAGTTGGTAGCTCTTGATCCGGCAAACAAACCACC
GCTGGTAGCGGTTTTTTTGTTTGCAAGCAGCAGATTACGCGCAGAAAAAA
AGGATCTCAAGAAGATCCTTTGATCTTTTCTACGGGGTCTGACGCTCAGT
GGAACGAAAACTCACGTTAAGGGATTTTGGTCATGAGATTATCAAAAAGG
ATCTTCACCTAGATCCTTTTAAATTAAAAATGAAGTTTTAAATCAATCTA
AAGTATATATGAGTAAACTTGGTCTGACAGTTACCAATGCTTAATCAGTG
AGGCACCTATCTCAGCGATCTGTCTATTTCGTTCATCCATAGTTGCCTGA
CTCCCCGTCGTGTAGATAACTACGATACGGGAGGGCTTACCATCTGGCCC
CAGTGCTGCAATGATACCGCGAGACCCACGCTCACCGGCTCCAGATTTAT
CAGCAATAAACCAGCCAGCCGGAAGGGCCGAGCGCAGAAGTGGTCCTGCA
ACTTTATCCGCCTCCATCCAGTCTATTAATTGTTGCCGGGAAGCTAGAGT
AAGTAGTTCGCCAGTTAATAGTTTGCGCAACGTTGTTGCCATTGCTACAG
```

-continued

GCATCGTGGTGTCACGCTCGTCGTTTGGTATGGCTTCATTCAGCTCCGGT

TCCCAACGATCAAGGCGAGTTACATGATCCCCATGTTGTGCAAAAAAGC

GGTTAGCTCCTTCGGTCCTCCGATCGTTGTCAGAAGTAAGTTGGCCGCAG

TGTTATCACTCATGGTTATGGCAGCACTGCATAATTCTCTTACTGTCATG

CCATCCGTAAGATGCTTTTCTGTGACTGGTGAGTACTCAACCAAGTCATT

CTGAGAATAGTGTATGCGGCGACCGAGTTGCTCTTGCCCGGCGTCAATAC

GGGATAATACCGCGCCACATAGCAGAACTTTAAAAGTGCTCATCATTGGA

AAACGTTCTTCGGGGCGAAAACTCTCAAGGATCTTACCGCTGTTGAGATC

CAGTTCGATGTAACCCACTCGTGCACCCAACTGATCTTCAGCATCTTTTA

CTTTCACCAGCGTTTCTGGGTGAGCAAAAACAGGAAGGCAAAATGCCGCA

AAAAAGGGAATAAGGGCGACACGGAAATGTTGAATACTCATACTCTTCCT

TTTTCAATATTATTGAAGCATTTATCAGGGTTATTGTCTCATGAGCGGAT

ACATATTTGAATGTATTTAGAAAAATAAACAAATAGGGGTTCCGCGCACA

TTTCCCCGAAAAGTGCCACCTGACGTC pGEM-T7o-TEV-hLeptin-GAopt-2xhBG-120A sequence
(SEQ ID NO: 6)

GATCCGGAGGCCGGAGAATTGTAATACGACTCACTATAGGGAGACGCGTG

TTAAATAACAAATCTCAACACAACATATACAAAACAAACGAATCTCAAGC

AATCAAGCATTCTACTTCTATTGCAGCAATTTAAATCATTTCTTTTAAAG

CAAAAGCAATTTTCTGAAAATTTTCACCATTTACGAACGATAGCCGCCAC

CATGCACTGGGGAACCCTGTGCGGATTCCTGTGGCTGTGGCCCTACCTGT

TCTATGTGCAAGCCGTGCCCATCCAGAAGGTGCAGGACGACACCAAGACC

CTGATCAAGACCATCGTGACCCGGATCAACGACATCAGCCACACCCAGAG

CGTGTCCAGCAAGCAGAAAGTGACCGGCCTGGACTTCATCCCCGGCCTGC

ACCCTATCCTGACCCTGTCCAAGATGGACCAGACCCTGGCCGTGTACCAG

CAGATCCTGACCAGCATGCCCAGCCGGAACGTGATCCAGATCAGCAACGA

CCTGGAAAACCTGCGGGACCTGCTGCACGTGCTGGCCTTCAGCAAGAGCT

GCCATCTGCCTTGGGCCAGCGGCCTGGAAACCCTGGATTCTCTGGGCGGA

GTGCTGGAAGCCAGCGGCTACTCTACAGAGGTGGTGGCCCTGAGCAGACT

GCAGGGCAGCCTGCAGGATATGCTGTGGCAGCTGGATCTGAGCCCCGGCT

GCTAATAGCGGACCGGCGATAGATGAAGCTCGCTTTCTTGCTGTCCAATT

TCTATTAAAGGTTCCTTTGTTCCCTAAGTCCAACTACTAAACTGGGGGAT

ATTATGAAGGGCCTTGAGCATCTGGATTCTGCCTAATAAAAAACATTTAT

TTTCATTGCAGCTCGCTTTCTTGCTGTCCAATTTCTATTAAAGGTTCCTT

TGTTCCCTAAGTCCAACTACTAAACTGGGGGATATTATGAAGGGCCTTGA

GCATCTGGATTCTGCCTAATAAAAAACATTTATTTTCATTGCGGCCGCAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAGAAGAGCAAGCTTTCGA

TAGCGCTGTTCGTAGAAAAAAAAGAAGTAAATAATTACTACTTGCCATAT

AGACTAAATAGCTGCGCNTAATACATCTACACTTTCTANNATTGACAAGT

-continued

GATACGTTGCAAAAGGAGCAACACCCCACAGACTCGATGACTGCGCAGTC

ATACAGTGAAATTGCCCTAATGTCTTACCTCTGAAAGGGCTAAACGAAAG

TAGAGCACTATTCCGCGTAGCTATTTAGTGCGATCTTTTAGAAATATCAG

CCCAGAGAGCTGGGCTGATAAATATTTTATCCGACAAGACGAATTTTGCT

CAAATGAGTTAAAACGATGCTACCACTATCTGCTGCTTTTACGAGATCAG

CCCACCATTGCATCATCGGACGACGTTGCTCAAGATAATCACTGCGGTTA

TAAGCGCGACGCACCTCATTTTTGTCTACATGAGCAAGCGCTGCTTCAAT

GACATCAGGTGGAAATCCTTCCTCATTGAGTGCCGTACTGGCGATAGAAC

GCAAGCCGTGTGAAACAAGTACACCTCCTAAGCCAGCACGCTTGAGTGCT

GCATTCACTGTTTGGCTATTCATTGGTTGGTTGGGCTTGATACGGCTAGG

AAAGATAAATTCTCGGCCACCACTGAGAGGCTTCATCATTTCCAGAATAG

CAAGAGCCCCATCAGATAGTGGAACCGTATGGTCCCGGTTCATCTTCATT

CGAGCTGCAGGAATTTTCCATTCGCTAGCATTGAAATCGATCTCATCCCA

TCGAGCCTCAGCAGCTTCGGCAGGGCGGGTGATGGTTAGAAGTTGCCACA

TGAACAGGCATCTTGTGGACATGCTGATACTTGCCGTACGCATGGTGTGC

ATTAGCTGCGGAAGTTGATCCGGCCGGATGCTTGGCATGTTTTTCTTTTG

CGGTTTCTCGAAAGCTTGAGTATTCTATAGTGTCACCTAAATAGCTTGGC

GTAATCATGGTCATAGCTGTTTCCTGTGTGAAATTGTTATCCGCTCACAA

TTCCACACAACATACGAGCCGGAAGCATAAAGTGTAAAGCCTGGGGTGCC

TAATGAGTGAGCTAACTCACATTAATTGCGTTGCGCTCACTGCCCGCTTT

CCAGTCGGGAAACCTGTCGTGCCAGCTGCATTAATGAATCGGCCAACGCG

CGGGGAGAGGCGGTTTGCGTATTGGGCGCTATTCCGCTTCCTCGCTCACT

GACTCGCTGCGCTCGGTCGTTCGGCTGCGGCGAGCGGTATCAGCTCACTC

AAAGGCGGTAATACGGTTATCCACAGAATCAGGGGATAACGCAGGAAAGA

ACATGTGAGCAAAAGGCCAGCAAAAGGCCAGGAACCGTAAAAAGGCCGCG

TTGCTGGCGTTTTTCGATAGGCTCCGCCCCCCTGACGAGCATCACAAAAA

TCGACGCTCAAGTCAGAGGTGGCGAAACCCGACAGGACTATAAAGATACC

AGGCGTTTCCCCCTGGAAGCTCCCTCGTGCGCTCTCCTGTTCCGACCCTG

CCGCTTACCGGATACCTGTCCGCCTTTCTCCCTTCGGGAAGCGTGGCGCT

TTCTCATAGCTCACGCTGTAGGTATCTCAGTTCGGTGTAGGTCGTTCGCT

CCAAGCTGGGCTGTGTGCACGAACCCCCCGTTCAGCCCGACCGCTGCGCC

TTATCCGGTAACTATCGTCTTGAGTCCAACCCGGTAAGACACGACTTATC

GCCACTGGCAGCAGCCACTGGTAACAGGATTAGCAGAGCGAGGTATGTAG

GCGGTGCTACAGAGTTCTTGAAGTGGTGGCCTAACTACGGCTACACTAGA

AGGACAGTATTTGGTATCTGCGCTCTGCTGAAGCCAGTTACCTTCGGAAA

AAGAGTTGGTAGCTCTTGATCCGGCAAACAAACCACCGCTGGTAGCGGTG

GTTTTTTTGTTTGCAAGCAGCAGATTACGCGCAGAAAAAAAGGATCTCAA

GAAGATCCTTTGATCTTTTCTACGGGGTCTGACGCTCAGTGGAACGAAAA

CTCACGTTAAGGGATTTTGGTCATGAGATTATCAAAAGGATCTTCACCT

AGATCCTTTTAAATTAAAAATGAAGTTTTAAATCAATCTAAAGTATATAT

GAGTAAACTTGGTCTGACAGTTACCAATGCTTAATCAGTGAGGCACCTAT

```
CTCAGCGATCTGTCTATTTCGTTCATCCATAGTTGCCTGACTCCCCGTCG

TGTAGATAACTACGATACGGGAGGGCTTACCATCTGGCCCCAGTGCTGCA

ATGATACCGCGAGACCCACGCTCACCGGCTCCAGATTTATCAGCAATAAA

CCAGCCAGCCGGAAGGGCCGAGCGCAGAAGTGGTCCTGCAACTTTATCCG

CCTCCATCCAGTCTATTAATTGTTGCCGGGAAGCTAGAGTAAGTAGTTCG

CCAGTTAATAGTTTGCGCAACGTTGTTGGCATTGCTACAGGCATCGTGGT

GTCACGCTCGTCGTTTGGTATGGCTTCATTCAGCTCCGGTTCCCAACGAT

CAAGGCGAGTTACATGATCCCCCATGTTGTGCAAAAAAGCGGTTAGCTCC

TTCGGTCCTCCGATCGTTGTCAGAAGTAAGTTGGCCGCAGTGTTATCACT

CATGGTTATGGCAGCACTGCATAATTCTCTTACTGTCATGCCATCCGTAA

GATGCTTTTCTGTGACTGGTGAGTACTCAACCAAGTCATTCTGAGAATAG

TGTATGCGGCGACCGAGTTGCTCTTGCCCGGCGTCAATACGGGATAATAC

CGCGCCACATAGCAGAACTTTAAAAGTGCTCATCATTGGAAAACGTTCTT

CGGGGCGAAAACTCTCAAGGATCTTACCGCTGTTGAGATCCAGTTCGATG

TAACCCACTCGTGCACCCAACTGATCTTCAGCATCTTTTACTTTCACCAG

CGTTTCTGGGTGAGCAAAAACAGGAAGGCAAAATGCCGCAAAAAAGGGAA

TAAGGGCGACACGGAAATGTTGAATACTCATACTCTTCCTTTTTCAATAT

TATTGAAGCATTTATCAGGGTTATTGTCTCATGAGCGGATACATATTTGA

ATGTATTTAGAAAAATAAACAAATAGGGGTTCCGCGCACATTTCCCCGAA

AAGTGCCACCTGACGTCTAAGAAACCATTATTATCATGACATTAACCTAT

AAAAATAGGCGTATCACGAGGCCCTTTCGTCTCGCGCGTTTCGGTGATGA

CGGTGAAAACCTCTGACACATGCAGCTCCCGGAGACGGTCACAGCTTGTC

TGTAAGCGGATGCCGGGAGCAGACAAGCCCGTCAGGGCGCGTCAGCGGGT

GTTGGCGGGTGTCGGGGCTGGCTTAACTATGCGGCATCAGAGCAGATTGT

ACTGAGAGTGCACCATAAATTCGAGCTCGGTACCCGGG
``` mRNA's

Brief Description of mRNA Transcription Protocol

A circular plasmid DNA template is constructed that contains a mRNA transcription cassette consisting of the following features: a consensus T7 bacteriophage DNA-dependent RNA polymerase promoter, a 5' untranslated region (UTR), a Kozak sequence, and open reading frame, a 3' UTR, and a 120 nucleotide long polyadenosine (polyA120) tail (SEQ ID NO: 13). The plasmid DNA template is propagated in E. coli, isolated, and linearized by restriction enzyme digest immediately 3' of the poly120 tail. The plasmid DNA is combined with T7 RNA polymerase, ribonucleotide triphosphates, RNase inhibitor, pyrophosphatase enzyme, dithiothreitol, spermidine, and enzyme reaction buffer and is incubated for 1 hour at 37° C. DNase I enzyme is added to digest the plasmid DNA template and is incubated for 0.5 hours at 37° C. mRNA is isolated by sequential precipitation with lithium chloride, washing of the pellet in 70% ethanol, resuspension of the mRNA pellet in water, re-precipitation with isopropanol and sodium acetate, and washing of the pellet again in 70% ethanol. The final mRNA pellet is resuspended in water.

| Reagent | Concentration | Notes |
|---|---|---|
| Nuclease-free water | Remaining volume | |
| Tris-HCl pH 8.0 (mM) | 40 | |
| MgCl$_2$ (mM) | 20 | |
| ATP, CTP, GTP, UTP (mM) | 4 | |
| Pseudouridine (mM) | 4 | To make 100% PsU mRNA, do not include UTP in reaction. To make 100% unmodified mRNA, do not include PsU in reaction |
| DTT (mM) | 10 | |
| Spermidine (mM) | 2 | |
| Linearized plasmid DNA (ug/ul) | 0.05 | |
| Pyrophosphatase (U/ul) | 0.004 | |
| RNase inhibitor (U/ul) | 1 | |
| T7 RNA polymerase (U/ul) | 5 | |
| DNase I (U/ul) | 0.04 | |

TEV-hLeptin-GAopt-2×hBG-120A (SEQ ID NO:7)
Sequence Features:
Tobacco Etch Virus (TEV) 5' UTR: 14-154
Optimal Kozak sequence: 155-163
Human leptin encoding amino acids 1-167 of Protein Accession # NP_000221, sequence codon optimized by GeneArt: 164-664
2 stop codons: 665-670
2 copies of human beta-globin 3'UTR: 689-954
120 nucleotide polyA tail: 961-1080

```
GGGAGACGCGUGUUAAAUAACAAAUCUCAACACAACAUAUACAAAACAAA

CGAAUCUCAAGCAAUCAAGCAUUCUACUUCUAUUGCAGCAAUUUAAAUCA

UUUCUUUUAAAGCAAAAGCAAUUUUCUGAAAAUUUUCACCAUUUACGAAC

GAUAGCCGCCACCAUGCACUGGGGAACCCUGUGCGGAUUCCUGUGGCUGU

GGCCCUACCUGUUCUAUGUGCAAGCCGUGCCCAUCCAGAAGGUGCAGGAC

GACACCAAGACCCUGAUCAAGACCAUCGUGACCCGGAUCAACGACAUCAG

CCACACCCAGAGCGUGUCCAGCAAGCAGAAAGUGACCGGCCUGGACUUCA

UCCCCGGCCUGCACCCUAUCCUGACCCUGUCCAAGAUGGACCAGACCCUG

GCCGUGUACCAGCAGAUCCUGACCAGCAUGCCCAGCCGGAACGUGAUCCA

GAUCAGCAACGACCUGGAAAACCUGCGGGACCUGCUGCACGUGCUGGCCU

UCAGCAAGAGCUGCCAUCUGCCUUGGGCCAGCGGCCUGGAAACCCUGGAU

UCUCUGGGCGGAGUGCUGGAAGCCAGCGGCUACUCUACAGAGGUGGUGGC

CCUGAGCAGACUGCAGGGCAGCCUGCAGGAUAUGCUGUGGCAGCUGGAUC

UGAGCCCCGGCUGCUAAUAGCGGACCGGCGAUAGAUGAAGCUCGCUUUCU

UGCUGUCCAAUUUCUAUUAAAGGUUCCUUUGUUCCCUAAGUCCAACUACU

AAACUGGGGGAUAUUAUGAAGGGCCUUGAGCAUCUGGAUUCUGCCUAAUA

AAAAACAUUUAUUUUCAUUGCAGCUCGCUUUCUUGCUGUCCAAUUUCUAU

UAAAGGUUCCUUUGUUCCCUAAGUCCAACUACUAAACUGGGGGAUAUUAU

GAAGGGCCUUGAGCAUCUGGAUUCUGCCUAAUAAAAAACAUUUAUUUUCA

UUGCGGCCGCAAAAAAAAAAAAAAAAAAAAAAAAAAAAAAAAAAAAAAAA
```

-continued

AAAAAAAAAAAAAAAAAAAAAAAAAAAAAAAAAAAAAAAAAAAAAAAA

AAAAAAAAAAAAAAAAAAAAAAAAAAAAA

TEV-mEpo(NcoI)-2×hBG-120A (SEQ ID NO:8)
Sequence Features:
Tobacco Etch Virus (TEV) 5' UTR: 14-154
Optimal Kozak sequence: 155-163
Mouse erythropoietin encoding amino acids 1-191 of Protein Accession # NP_031968, sequence codon optimized by GeneArt: 164-739
Stop codons: 740-742
2 copies of human beta-globin 3'UTR: 743-1008
120 nucleotide polyA tail: 1009-1128

GGGAGACGCGUGUUAAAUAACAAAUCUCAACACAACAUAUACAAAACAAA

CGAAUCUCAAGCAAUCAAGCAUUCUACUUCUAUUGCAGCAAUUUAAAUCA

UUUCUUUUAAAGCAAAAGCAAUUUUCUGAAAAUUUUCACCAUUUACGAAC

GAUAGCCGCCACCAUGGGCGUGCCCGAAAGACCUACACUCCUGCUGCUGC

UGUCACUGCUGCUGAUCCCUCUGGGCCUGCCUGUGCUGUGUGCCCCCCCU

AGACUGAUCUGCGACAGCGAGAGUGCUGGAACGGUACAUCCUGGAAGCAA

AGAGGCCGAGAACGUGACGAUGGGAUGUGCCGAGGGCCCCAGACUGAGCG

AGAACAUCACCGUGCCCGACACCAAAGUGAACUUCUACGCCUGGAAGCGG

AUGGAAGUGGAAGAACAGGCCAUCGAAGUGUGGCAGGGCCUGAGCCUGCU

GAGCGAGGCUAUUCUGCAGGCACAGGCUCUGCUGGCCAACAGCAGCCAGC

CUCCUGAGACACUGCAGCUGCACAUCGACAAGGCCAUCAGCGGCCUGAGA

AGCCUGACCUCCCUGCUGAGGGUGCUGGGAGCCCAGAAAGAACUGAUGAG

CCCCCCUGACACCACCCCCCCUGCUCCUCUGAGAACUCUGACCGUGGACA

CCUUCUGCAAGCUGUUCCGGGUGUACGCCAACUUCCUGCGGGGCAAGCUG

AAGCUGUACACCGGCGAAGUGUGCAGACGGGGCGACAGAUGAAGCUCGCU

UUCUUGCUGUCCAAUUUCUAUUAAAGGUUCCUUUGUUCCCUAAGUCCAAC

UACUAAACUGGGGGAUAUUAUGAAGGGCCUUGAGCAUCUGGAUUCUGCCU

AAUAAAAAACAUUUAUUUUCAUUGCAGCUCGCUUUCUUGCUGUCCAAUUU

CUAUUAAAGGUUCCUUUGUUCCCUAAGUCCAACUACUAAACUGGGGGAUA

UUAUGAAGGGCCUUGAGCAUCUGGAUUCUGCCUAAUAAAAAACAUUUAUU

UUCAUUGCAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAAA

TEV-hFIX-GAopt-2×hBG-120A (SEQ ID NO:9)
Sequence Features:
Tobacco Etch Virus (TEV) 5' UTR: 14-154
Optimal Kozak sequence: 155-163
Human factor IX encoding amino acids 1-461 of Protein Accession # NP_000124, sequence codon optimized by GeneArt: 164-1962
2 stop codons: 1547-1552
2 copies of human beta-globin 3'UTR: 1571-1836
120 nucleotide polyA tail: 1843-1962

GGGAGACGCGUGUUAAAUAACAAAUCUCAACACAACAUAUACAAAACAAA

CGAAUCUCAAGCAAUCAAGCAUUCUACUUCUAUUGCAGCAAUUUAAAUCA

-continued

UUUCUUUUAAAGCAAAAGCAAUUUUCUGAAAAUUUUCACCAUUUACGAAC

GAUAGCCGCCACCAUGCAGCGCGUGAACAUGAUUAUGGCCGAGAGCCCUG

GCCUGAUCACCAUCUGCCUGCUGGGCUACCUGCUGAGCGCCGAGUGCACC

GUGUUUCUGGACCACGAGAACGCCAACAAGAUCCUGAACCGGCCCAAGCG

GUACAACAGCGGCAAGCUGGAAGAGUUCGUGCAGGGCAACCUGGAACGCG

AGUGCAUGGAAGAAGUGCAGCUUCGAAGAGGCCAGAGAGGUGUUCGAG

AACACCGAGCGGACCACCGAGUUCUGGAAGCAGUACGUGGACGGCGACCA

GUGCGAGAGCAACCCCUGUCUGAAUGGCGGCAGCUGCAAGGACGACAUCA

ACAGCUACGAGUGCUGGUGCCCCUUCGGCUUCGAGGGCAAGAACUGCGAG

CUGGACGUGACCUGCAACAUCAAGAACGGCAGAUGCGAGCAGUUCUGCAA

GAACAGCGCCGACAACAAGGUCGUGUGCUCCUGCACCGAGGGCUACAGAC

UGGCCGAGAACCAGAAGUCCUGCGAGCCCGCCGUGCCUUUCCCAUGUGGA

AGAGUGUCCGUGUCCCAGACCAGCAAGCUGACCAGAGCCGAGACAGUGUU

CCCCGACGUGGACUACGUGAACAGCACCGAGGCCGAGACAAUCCUGGACA

ACAUCACCCAGAGCACCCAGUCCUUCAACGACUUCACCAGAGUCGUGGGC

GGCGAGGAUGCCAAGCCUGGACAGUUCCCGUGGCAGGUGGUGCUGAACGG

AAAGGUGGACGCCUUUUGCGGCGGCAGCAUCGUGAACGAGAAGUGGAUCG

UGACAGCCGCCCACUGCGUGGAAACCGGCGUGAAGAUUACAGUGGUGGCC

GGCGAGCACAACAUCGAGGAAACCGAGCACACAGAGCAGAAACGGAACGU

GAUCAGAAUCAUCCCCCACCACAACUACAACGCCGCCAUCAACAAGUACA

ACCACGAUAUCGCCCUGCUGGAACUGGACGAGCCCCUGGUGCUGAAUAGC

UACGUGACCCCCAUCUGUAUCGCCGACAAAGAGUACACCAACAUCUUUCU

GAAGUUCGGCAGCGGCUACGUGUCCGGCUGGGGCAGAGUGUUUCACAAGG

GCAGAUCCGCUCUGGUGCUGCAGUACCUGAGAGUGCCUCUGGUGGACCGG

GCCACCUGUCUGAGAAGCACCAAGUUCACCAUCUACAACAACAUGUUCUG

CGCCGGCUUUCACGAGGGCGGCAGAGAUAGCUGUCAGGGCGAUUCGGCG

GCCCUCACGUGACAGAGGUGGAAGGCACCAGCUUUCUGACCGGCAUCAUC

AGCUGGGGCGAGGAAUGCGCCAUGAAGGGGAAGUACGGCAUCUACACCAA

GGUGUCCAGAUACGUGAACUGGAUCAAAGAAAAGACCAAGCUGACAUAAU

GACGGACCGGCGAUAGAUGAAGCUCGCUUUCUUGCUGUCCAAUUUCUAUU

AAAGGUUCCUUUGUUCCCUAAGUCCAACUACUAAACUGGGGGAUAUUAUG

AAGGGCCUUGAGCAUCUGGAUUCUGCCUAAUAAAAAACAUUUAUUUUCAU

UGCAGCUCGCUUUCUUGCUGUCCAAUUUCUAUUAAAGGUUCCUUUGUUCC

CUAAGUCCAACUACUAAACUGGGGGAUAUUAUGAAGGGCCUUGAGCAUCU

GGAUUCUGCCUAAUAAAAAACAUUUAUUUUCAUUGCGGCCGCAAAAAAAA

AAAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAAAAAA

TEV-Fluc(sapI)-2×hBG-120A (SEQ ID NO: 10)
Sequence Features:
Tobacco Etch Virus (TEV) 5' UTR: 14-154
Optimal Kozak sequence: 155-163

Sequence encoding polypeptide 99% identical (545/550 aa) to Firefly (Photinus pyralis) luciferase of Protein Accession # P08659: 164-1813

1 stop codon: 1814-1816

2 copies of human beta-globin 3'UTR: 1835-2100

120 nucleotide polyA tail: 2107-2226

GGGAGACGCGUGUUAAAUAACAAAUCUCAACACAACAUAUACAAAACAAA
CGAAUCUCAAGCAAUCAAGCAUUCUACUUCUAUUGCAGCAAUUUAAAUCA
UUUCUUUUAAAGCAAAAGCAAUUUUCUGAAAAUUUUCACCAUUUACGAAC
GAUAGCCGCCACCAUGGAAGACGCCAAAAACAUAAAGAAAGGCCCGGCGC
CAUUCUAUCCGCUGGAAGAUGGAACCGCUGGAGAGCAACUGCAUAAGGCU
AUGAAGAGAUACGCCCUGGUUCCUGGAACAAUUGCUUUUACAGAUGCACA
UAUCGAGGUGGACAUCACUUACGCUGAGUACUUCGAAAUGUCCGUUCGGU
UGGCAGAAGCUAUGAAACGAUAUGGGCUGAAUACAAAUCACAGAAUCGUC
GUAUGCAGUGAAAACUCUCUUCAAUUCUUUAUGCCGGUGUUGGGCGCGUU
AUUUAUCGGAGUUGCAGUUGCGCCCGCGAACGACAUUUAUAAUGAACGUG
AAUUGCUCAACAGUAUGGGCAUUUCGCAGCCUACCGUGGUGUUCGUUCC
AAAAAGGGGUUGCAAAAAAUUUUGAACGUGCAAAAAAAGCUCCCAAUCAU
CCAAAAAAUUAUUAUCAUGGAUUCUAAAACGGAUUACCAGGGAUUUCAGU
CGAUGUACACGUUCGUCACAUCUCAUCUACCUCCCGGUUUUAAUGAAUAC
GAUUUUGUGCCAGAGUCCUUCGAUAGGGACAAGACAAUUGCACUGAUCAU
GAACUCCUCUGGAUCUACUGGUCUGCCUAAAGGUGUCGCUCUGCCUCAUA
GAACUGCCUGCGUGAGAUUCUCGCAUGCCAGAGAUCCUAUUUUUGGCAAU
CAAAUCAUUCCGGAUACUGCGAUUUUAAGUGUUGUUCCAUUCCAUCACGG
UUUUGGAAUGUUUACUACACUCGGAUAUUUGAUAUGUGGAUUUCGAGUCG
UCUUAAUGUAUAGAUUUGAAGAGGAGCUGUUUCUGAGGAGCCUUCAGGAU
UACAAGAUUCAAAGUGCGCUGCUGGUGCCAACCCUAUUCUCCUUCUUCGC
CAAAAGCACUCUGAUUGACAAAUACGAUUUAUCUAAUUUACACGAAAUUG
CUUCUGGUGGCGCUCCCCUCUCUAAGGAAGUCGGGGAAGCGGUUGCCAAG
AGGUUCCAUCUGCCAGGUAUCAGGCAAGGAUAUGGGCUCACUGAGACUAC
AUCAGCUAUUCUGAUUACACCCGAGGGGGAUGAUAAACCGGGCGCGGUCG
GUAAAGUUGUUCCAUUUUUUGAAGCGAAGGUUGUGGAUCUGGAUACCGGG
AAAACGCUGGGCGUUAAUCAAAGAGGCGAACUGUGUGUGAGAGGUCCUAU
GAUUAUGUCCGGUUAUGUAAACAAUCCGGAAGCGACCAACGCCUUGAUUG
ACAAGGAUGGAUGGCUACAUUCUGGAGACAUAGCUUACUGGGACGAAGAC
GAACACUUCUUCAUCGUUGACCGCCUGAAGUCUCUGAUUAAGUACAAAGG
CUAUCAGGUGGCUCCCGCUGAAUUGGAAUCCAUCUUGCUCCAACACCCCA
ACAUCUUCGACGCAGGUGUCGCAGGUCUUCCCGACGAUGACGCCGGUGAA
CUUCCCGCCGCCGUUGUUGUUUUGGAGCACGGAAAGACGAUGACGGAAA
AGAGAUCGUGGAUUACGUCGCCAGUCAAGUAACAACCGCGAAAAAGUUGC
GCGGAGGAGUUGUGUUUGUGGACGAAGUACCGAAAGGUCUUACCGGAAAA
CUCGACGCAAGAAAAAUCAGAGAGAUCCUCAUAAAGGCCAAGAAGGGCGG
AAAGAUCGCCGUGUGACGGACCGGCGAUAGAUGAAGCUCGCUUUCUUGCU
GUCCAAUUUCUAUUAAAGGUUCCUUUGUUCCCUAAGUCCAACUACUAAAC
UGGGGGAUAUUAUGAAGGGCCUUGAGCAUCUGGAUUCUGCCUAAUAAAAA
ACAUUUAUUUUCAUUGCAGCUCGCUUUCUUGCUGUCCAAUUUCUAUUAAA
GGUUCCUUUGUUCCCUAAGUCCAACUACUAAACUGGGGGAUAUUAUGAAG
GGCCUUGAGCAUCUGGAUUCUGCCUAAUAAAAAACAUUUAUUUUCAUUGC
GGCCGCAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAA

Gtx7-Gluc-2×SinV-120A (SEQ ID NO:11)

Sequence Features:

5' UTR: 14-127

Kozak sequence: 128-133

Sequence encoding polypeptide identical to *Gaussia princeps* luciferase of Protein Accession # AAG54095: 134-688

1 stop codon: 689-691

2 copies of Sindbis Virus 3'UTR: 699-882

120 nucleotide polyA tail: 891-1010

GGGAGACGCGUGUUUCUGACAUCCGGCGGAAUUCUGACAUCCGGCGGAAU
UCUGACAUCCGGCGGAAUUCUGACAUCCGGCGGAAUUCUGACAUCCGGCG
GAAGACUCACAACCCCAGAAACAGACAGCCACCAUGGGAGUCAAAGUUCU
GUUUGCCCUGAUCUGCAUCGCUGUGGCCGAGGCCAAGCCCACCGAGAACA
ACGAAGACUUCAACAUCGUGGCCGUGGCCAGCAACUUCGCGACCACGGAU
CUCGAUGCUGACCGCGGGAAGUUGCCCGGCAAGAAGCUGCCGCUGGAGGU
GCUCAAAGAGAUGGAAGCCAAUGCCCGGAAAGCUGGCUGCACCAGGGGCU
GUCUGAUCUGCCUGUCCCACAUCAAGUGCACGCCCAAGAUGAAGAAGUUC
AUCCCAGGACGCUGCCACACCUACGAAGGCGACAAAGAGUCCGCACAGGG
CGGCAUAGGCGAGGCGAUCGUCGACAUUCCUGAGAUUCCUGGGUUCAAGG
ACUUGGAGCCAAUGGAGCAGUUCAUCGCACAGGUCGAUCUGUGUGUGGAC
UGCACAACUGGCUGCCUCAAAGGGCUUGCCAACGUGCAGUGUUCUGACCU
GCUCAAGAAGUGGCUGCCGCAACGCUGUGCGACCUUUGCCAGCAAGAUCC
AGGGCCAGGUGGACAAGAUCAAGGGGGCCGGUGGUGACUAACGGACCGAA
AACUCAAUGUAUUUCUGAGGAAGCGUGGUGCAUAAUGCCACGCAGUGUCU
ACAUAAUCAAUUUAUUAUUUCUUUUAUUUUAUUCACAUAAAACUCAAU
GUAUUUCUGAGGAAGCGUGGUGCAUAAUGCCACGCAGUGUCUACAUAAUC
AAUUUAUUAUUUCUUUUAUUUUAUUCACAUAGCGGCCGCAAAAAAAAAA
AAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAA
AA

Biological Evaluation

Packaging of mRNA

All equipment and disposable supplies are certified free of RNase activity by the manufacturer or rendered RNase free by use of the RNaseZap reagent (LifeTechnologies). mRNA is encapsulated at a cationic lipid amine to mRNA phosphate (N:P) molar ratio of 4:1. Lipids (cationic lipid, DSPC, cholesterol and lipidated PEG or stealth lipid) are dissolved in ethanol. The molar ratios are 40:10:38:2, respectively. The mixture is sonicated briefly, then gently agitated for 5 minutes and then maintained at 37° C. until use. mRNA is exchanged into citrate buffer pH 5.8-6.0 by use of Amicon Ultra-15 centrifugal concentrators, and the final concentration is adjusted to 0.5 mg/ml and held at 37° C. until use. An equal volume of lipids in ethanol, mRNA in citrate buffer, and citrate buffer alone are drawn into disposable syringes.

Tubing leading from syringes containing lipids and mRNA are attached to the T junction, and tubing leading from the syringe containing citrate buffer alone is paired with the tubing exiting the T-junction over a collection vessel containing a stir bar on an active stir plate. Syringes are placed in a syringe pump set to expel contents at a flow rate of 1 ml per minute. The pump is activated, and the collected mRNA in lipid nanoparticles is transferred to SnakeSkin dialysis tubing (10,000 MWCO, Thermo Scientific). Material is dialyzed against RNAse- and pyrogen-free 1× phosphate buffered saline overnight at 4° C.

Packaging of siRNA

The lipid nanoparticles (LNPs) were formed by mixing equal volumes of lipids dissolved in alcohol with siRNA dissolved in a citrate buffer by an impinging jet process. The lipid solution contains a cationic lipid compound of the invention, a helper lipid (cholesterol), an optional neutral lipid (DSPC) and a stealth lipid (S010, S024, S027, or S031) at a concentration of 8-16 mg/mL with a target of 12 mg/mL in an alcohol. The siRNA to total lipid ratio is approximately 0.05 (wt/wt). Where a LNP formulation contains four lipid components, the molar ratios of the lipids ranges from 20 to 70 mole percent for the cationic lipid with a target of 40-60, the mole percent of helper lipid ranges from 20 to 70 with a target of 30 to 50, the mole percent of neutral lipid ranges from 0-30, the mole percent of PEG lipid has a range from 1 to 6 with a target of 2 to 5. The concentration of siRNA solution ranges from 0.7 to 1.0 mg/mL with a target of 0.8 to 0.9 mg/mL in a sodium citrate: sodium chloride buffer pH 4-6, with a target of 4.5-5.5. The LNPs are formed by mixing equal volumes of lipid solution in ethanol with siRNA dissolved in a citrate buffer by an impinging jet process through a mixing device with ID ranging from 0.25 to 2.0 mm at a flow rate from 10 to 640 mL/min. The mixed LNP solution is held at room temperature for 0-24 hrs prior to a dilution step. The solution is then concentrated and diafiltered with suitable buffer by ultrafiltration process using membranes with a MW cutoff from 30 to 500 KD. The final product is sterile filtered and stored at 4° C.

Measurement of mRNA Encapsulation

Percent encapsulation of mRNA in lipid nanoparticles is determined using the Quant-iT Ribogreen RNA Assay kit (Life Technologies). The LNP-mRNA suspension is assayed in buffer (mRNA outside the particle), and buffer plus Triton X-100 detergent (total mRNA). The difference calculated is the mRNA inside the particle. Prepare a 1000 ng/mL stock from the RNA provided in the kit and use this to generate a standard curve (0 ng/ml, 15.63-1000 ng/ml) in TE and TE+0.75% Triton X-100. Prepare LNP-mRNA samples in TE buffer and TE buffer+0.75% Triton X-100 with appropriate dilution so that reading is in the range of standard curve (400-2,000 fold). In a 384-well plate (Costar non-treated #3573) add 0.04 ml of standard (in duplicate) or sample (in triplicate) per well. Dilute Ribogreen reagent 240-fold in TE buffer and add 0.06 ml per well. Mix contents of wells and measure fluorescence (excitation=480 nm, emission=520 nm). Subtract background values (no RNA) from standard and test sample values and determine the concentrations of RNA in the samples using the standard curves. Determine the percent encapsulation of the sample by dividing the difference in concentrations between sample+triton and sample in buffer alone by the sample+triton concentration.

Measurement of siRNA Encapsulation

SYBR Gold flourescence reagent is used for the determination of siRNA encapsulation in the DLP's. DLP's with and without triton x-100 are used to determine the free siRNA and total siRNA amounts. DLP's samples with and without triton X-100 were excited at 485 nm and flourescence emission is measured at 530 nm. Encapsulation efficiency is calculated based on the following formula:

Encapsulation efficiency: [(free siRNA concentration−total siRNA concentration)/(total siRNA concentration)]×100%

Encapsulation Data

TABLE 2

In-vitro encapsulation data for mRNA and siRNA

| | % encapsulation | |
| --- | --- | --- |
| Example | mRNA Leptin | siRNA FVII |
| 1 | 96.7 | 85.1 |
| 2 | 70.5 | NA |
| 3 | 32.5 | NA |
| 4 | 83.7 | NA |
| 7 | NA | 88.9 |
| 9 | NA | 86.7 |
| 10 | 1.9 | NA |
| 11 | 45.4 | NA |
| 12 | 27.3 | NA |
| 13 | 90.7 | 88.1 |
| 15 | 97.3 | NA |
| 18 | 84.8 | NA |
| 19 | 98.1 | NA |
| 22 | NA | 86.1 |
| 23 | 82.0 | NA |
| 24 | 86.6 | 89.1 |
| 25 | 95.3 | 88.7 |
| 26 | 96.9 | 80.0 |
| 27 | 80.8 | NA |
| 32 | 97.1 | NA |
| 33 | 97.4 | NA |
| 34 | 97.1 | NA |
| 35 | 97.3 | NA |
| 36 | 36.4 | 79.8 |
| 37 | 14.3 | NA |
| 38 | 9.6 | NA |
| 39 | 10.0 | NA |
| 40 | 97.2 | NA |
| 41 | 97.5 | NA |
| 42 | 90.3 | NA |
| 43 | 24.2 | NA |
| 44 | 22.4 | NA |
| 45 | 84.4 | NA |
| 46 | 63.5 | NA |
| 47 | 90.4 | NA |
| 48 | 92.8 | NA |
| 49 | 82.8 | NA |
| 50 | 83.9 | NA |
| 51 | 82.3 | NA |
| 52 | 32.2 | NA |
| 53 | 93.5 | NA |
| 56 | 83.3 | NA |
| 57 | 95.2 | NA |
| 58 | 86.0 | NA |
| 59 | 76.6 | NA |
| 60 | 89.1 | NA |
| 63 | 18.8 | NA |
| 64 | 87.9 | NA |
| 66 | 70.5 | NA |
| 67 | 62.8 | NA |

TABLE 2-continued

In-vitro encapsulation data for mRNA and siRNA

| | % encapsulation | |
|---|---|---|
| Example | mRNA Leptin | siRNA FVII |
| 68 | 5.9 | NA |
| 69 | 79.3 | NA |
| 70 | 92.1 | NA |
| 71 | 96.5 | NA |
| 72 | 31.2 | NA |
| 73 | 9.3 | NA |
| 74 | 23.0 | NA |

Packaging of Plasmid DNA

All equipment and disposable supplies are certified free of RNase activity by the manufacturer or rendered RNase free by use of the RNaseZap reagent (LifeTechnologies). Plasmid is encapsulated at a cationic lipid amine to DNA phosphate (N:P) molar ratio of 4:1. Lipids (cationic lipid, DSPC, cholesterol and lipidated PEG) are dissolved in ethanol. The molar ratios are 40:10:38:2, respectively. The mixture is sonicated briefly, then gently agitated for 5 minutes and then maintained at 37° C. until use. Plasmid is exchanged into citrate buffer pH 6.0 by use of Amicon Ultra-15 centrifugal concentrators, and the final concentration is adjusted to 0.053 mg/ml and held at 37° C. until use. An equal volume of lipids in ethanol, plasmid in citrate buffer, and citrate buffer alone are drawn into disposable syringes. Tubing leading from syringes containing lipids and DNA are attached to the T junction, and tubing leading from the syringe containing citrate buffer alone is paired with the tubing exiting the T-junction over a collection vessel containing a stir bar on an active stir plate. Syringes are placed in a syringe pump set to expel contents at a flow rate of 1 ml per minute. The pump is activated, and the collected DNA in lipid nanoparticles is transferred to SnakeSkin dialysis tubing (10,000 MWCO, Thermo Scientific). Material is dialyzed against RNAse- and pyrogen-free 1× phosphate buffered saline overnight at 4° C.

Measurement of Plasmid DNA Encapsulation

Percent encapsulation of plasmid DNA in lipid nanoparticles is determined using the Quant-iT Ribogreen RNA Assay kit (Life Technologies). The LNP-DNA suspension is assayed in buffer (DNA outside the particle), and buffer plus Triton X-100 detergent (total DNA). The difference calculated is the DNA inside the particle. Prepare a 1000 ng/mL stock using unpackaged plasmid and use this to generate a standard curve (0 ng/ml, 15.63-1000 ng/ml) in TE and TE+0.75% Triton X-100. Prepare LNP-plasmid samples in TE buffer and TE buffer+0.75% Triton X-100 with appropriate dilution so that reading is in the range of standard curve (25 fold). In a 384-well plate (Costar non-treated #3573) add 0.04 ml of standard (in duplicate) or sample (in triplicate) per well. Dilute Ribogreen reagent 240-fold in TE buffer and add 0.06 ml per well. Mix contents of wells and measure fluorescence (excitation=480 nm, emission=520 nm). Subtract background values (no DNA) from standard and test sample values and determine the concentrations of DNA in the samples using the standard curves. Determine the percent encapsulation of the sample by dividing the difference in concentrations between sample+triton and sample in buffer alone by the sample+triton concentration.

Polydispersity Index (PDI) Measurements

Unless indicated otherwise, all PDIs referred to herein are the PDI of the fully formed nanoparticle, as measured by dynamic light scattering on a Malvern Zetasizer. The nanoparticle sample was diluted in phosphate buffered saline (PBS) so that the count rate was approximately 200-400 kcts. The data is presented in Table 3 as a weighted average of the intensity measure.

The Particle Size of the Lipid Nanoparticle

Unless indicated otherwise, all particle size measurements referred to in Table 3 are the Z-average particle size of the fully formed nanoparticle, as measured by dynamic light scattering on a Malvern Zetasizer. The nanoparticle sample was diluted in phosphate buffered saline (PBS) so that the count rate is approximately 200-400 kcts.

Lipid Nanoparticle Characterization Data

TABLE 3 in vitro data on selected examples

| | Example 1 | | | Example 15 | | | Example 13 | | |
|---|---|---|---|---|---|---|---|---|---|
| Nucleic acid | % Encap. | Size (nM) | PDI | % Encap. | Size (nM) | PDI | % Encap. | Size (nM) | PDI |
| hLeptin mRNA | 96.7 | 100.0 | 0.105 | 97.3 | 119.8 | 0.125 | 95.4 | 127.6 | 0.093 |
| hFIX mRNA | 89.5 | 126.9 | 0.090 | 98.4 | 96.8 | 0.182 | 96.4 | 122.4 | 0.154 |
| FLuc mRNA | 86.8 | 119.0 | 0.152 | 98.1 | 100.7 | 0.132 | 98.3 | 121.9 | 0.140 |
| Gluc mRNA | 92.3 | 95.7 | 0.136 | 98.1 | 84.7 | 0.133 | 97.2 | 90.8 | 0.099 |
| mEPO mRNA | 94.7 | 107.2 | 0.145 | 98.3 | 90.1 | 0.125 | 98.5 | 113.7 | 0.129 |
| hLep plasmid | 93.0 | 105.1 | 0.182 | 93.6 | 94.5 | 0.149 | 95.9 | 121.5 | 0.158 |
| pDNA | 94.7 | 100.7 | 0.100 | 93.2 | 86.9 | 0.110 | 98.2 | 95.12 | 0.160 |
| FVII siRNA | 85.1 | 102.3 | 0.049 | | | | 88.1 | 101.5 | 0.037 |

In Vivo Data

Mouse Factor VII Dosing

Female CD-1 mice were received from Harlan Labs and maintained on standard lab chow and water ad libitum. The animals weighed approximately 25 gr at time of dosing. Formulated Factor VII siRNA was administered as a single dose intravenously via the lateral tail vein. Approximately 48 hours after injection, the mice were euthanized by $CO_2$ inhalation followed by exsanguination through the vena cava. The blood was collected in tubes containing 0.105M sodium citrate anticoagulant for plasma Factor VII activity analysis.

Factor VII Activity Assay

Plasma collected from injected mice was assayed for Factor VII enzyme activity using the Biophen FVII kit from Hyphen Biomedical (catalog number 221304). An assay standard curve was prepared using pooled plasma aliquots from the vehicle control animals. All samples were diluted to fall within the linear range of the standard curve and Factor VII activity relative to control plasma was reported.

Lipid nanoparticles comprising lipid compounds of formula (I) and the FVII siRNA duplex sequence listed above were tested in the Factor VII Activity Assay. The results of this assay are given in Table 3 4 below as a percent knock down of plasma Factor VII enzyme activity at a dose of 0.3 mg/kg and 0.03 mg/kg.

Mouse EPO ELISA

A rat anti-mouse Erythropoietin antibody is coated on 384-well white microtiter plates overnight, then blocked for assay. Then, plasma samples are diluted in a casein-based sample diluent and incubated on the plate with buffer controls and mouse EPO standards. The plate is then washed to remove unbound material. A biotinylated rat anti-mouse Erythropoietin antibody is then added to the plate to detect mouse EPO bound by the capture antibody. The plate is washed again and a streptavidin-conjugated horseradish peroxidase reagent is incubated on the plate. A third wash step is performed and a chemiluminescent reagent is added to the plate and immediately read by a capable plate reader using all wavelengths and a 50 millisecond integration time. Unknown samples are interpolated off the mouse EPO standard curve.

Human Factor IX ELISA

An sheep anti-human Factor IX antibody (Cat# FIX-EIA-C) from Enzyme Research Laboratories is coated on 384-well white microtiter plates overnight at a concentration of 5 ug/ml, then blocked for assay using KPL blocker (Cat#50-82-00). Then, plasma samples are diluted in a casein-based sample diluent and incubated on the plate with biological controls and a standard curve created from recombinant protein (Cat#HCIX-0040). The plate is then washed to remove unbound material. A biotinylated sheep anti-human Factor IX antibody (Cat# FIX-EIA-D) from Enzyme Research Laboratories is then added to the plate at 0.6 ug/ml to detect human Factor IX protein bound by the capture antibody. The plate is washed again and a streptavidin-conjugated horseradish peroxidase reagent (Cat#21140) diluted 1:1250, is incubated on the plate. A third wash step is performed and chemiluminescent reagents (Cat#1859678 & Cat#18596789) are combined and added to the plate and immediately read by a capable plate reader using all wavelengths and a 50 millisecond integration time. Unknown samples are interpolated off the human recombinant Factor IX standard curve.

Casein Sample Diluent, pH 7.20

The Sample Diluent contains 0.7% Casein, 1.7 mM Sodium Phosphate Monobasic, 8.1 mM Sodium Phosphate Dibasic Heptahydrate, 0.15M Sodium Chloride, 0.7% Triton X-100, and 0.1% Sodium Azide Biotinylated Antibody Casein Diluent, pH 7.15

The diluent contains 0.4% Casein, 1.7 mM Sodium Phosphate Monobasic, 8.1 mM Sodium Phosphate Dibasic Heptahydrate, 0.15M Sodium Chloride, and 0.1% Sodium Azide HRP Casein Diluent, pH 7.15

The diluent contains 0.4% Casein, 1.7 mM Sodium Phosphate Monobasic, 8.1 mM Sodium Phosphate Dibasic Heptahydrate, 0.15M Sodium Chloride, and 0.1% Chloroacetamide.Leptin hLEPTIN Human leptin in mouse plasma was measured by ELISA. Antibodies purchased from the R&D Systems duoset (Cat# DY398E, part#840279 for capture antibody and part#840280 for detection antibody) were reconstituted using PBS and titered, again using PBS. The capture antibody was coated at 4 ug/ml in 30 ul/well on a white Nunc® Maxisorp 384 well plate (Cat#460372). After an overnight incubation at room temperature the capture antibody was aspirated and the plate blocked for 2 hours at room temperature with 90 ul/well of KPL milk blocker (Cat#50-82-00). Once the incubation was completed the plate was aspirated and recombinant standards and samples were added to the plate at 30 ul/well for 2 hours at 37° C. while shaking at 600 rpm. Sample/standard dilutions were made using casein sample diluent. Washing/aspiration 3 times with 100 ul/well followed, using Teknova plate wash solution (Cat# P1192). Next, detection antibody was diluted using casein detection antibody diluent to 12.5 ng/ml and added at 30 ul/well for 2 hours room temperature. After this incubation, the plate was washed again and a solution of poly-streptavidin-HRP (Cat#21140) at a 1:1250 dilution in HRP dilution buffer was added to each well (30 ul/well) and incubated for 30 minutes room temperature. A final wash/aspiration removed the HRP solution and a chemiluminescent substrate was added at 30 ul/well (Cat#1859678 & 1859679). The plate was quickly read using a SpectramaxM5 plate reader with a 50 ms integration time. The dynamic range of the ELISA is from 100-2,000 pg/ml (6.25-125 pM) of human leptin. The assay is applicable to plasma from mice, rats and cynomolgus monkeys.

Mouse Intravenous Tail Vein Injection of Modified Synthetic Leptin mRNA

Before the tail vein injection, mouse body weights were recorded and diet weighted, with mice grouped according to their body weights. Mice were prepared by warming them under a heating lamp for ~2 minutes, with the mice about 12 inches from heat lamp.

For the tail vein injection procedure, the mice were placed in a restrainer and their tails cleaned with 70% alcohol. A 27 gauge needle (Becton Dickinson, Catalogue #305109) connected with a 1 ml syringe (Becton Dickinson, Catalogue #309659) was inserted into the tail vein, with bevel facing up, and the syringe plunger was pulled backwards to ensure blood is drawn into the syringe. The desired volume of modified synthetic leptin mRNA was injected by hand with moderate pressure and speed. The needle was then withdrawn and bleeding stopped by adding pressure to injection site with gauze.

Single housed, 8-9 week old, male C57BL/6 mice were used for the in vivo study. FPLC purified modified synthetic leptin mRNA (SEQ ID NO:6) in which the uridines were substituted with pseudouridine was packaged in a cationic lipid (N:P molar ratio=8:1) and then were diluted in injectable saline at a dose of 10 μg per average group body weight.

On day 0, animals were weighed and sorted according to average body weight. Mice were dosed, and food intake (FI) was recorded, on each of days 1-7 and days 9, 11, and 16.

Mouse Subcutaneous Injection of Modified Synthetic Leptin mRNA

Prior to subcutaneous injection, mouse body weights were recorded and diet weighted, with mice grouped according to their body weights. The mice were manually restrained and placed on a work surface. Their scruffs were pinched and lifted away from the underlying muscle, the space into which was inserted a 25 gauge needle connected with a 1 ml syringe. The syringe plunger was pulled backwards in such a way as to ensure no fluid was drawn into the syringe, and then the desired volume of leptin mRNA was hand injected with moderate pressure and speed. The needle was then withdrawn and the mice returned to their cages.

8-9 week old, male C57BL/6 mice were used for the in vivo study. FPLC purified modified synthetic leptin mRNA (SEQ ID NO: 6) in which the uridines were substituted with pseudouridine (N:P molar ratio=8:1) packaged in multiple cationic lipid were diluted in injectable saline at a dose of 10 µg per average group body weight.

On day 0, animals were weighed and sorted according to average body weight. ice were dosed at 9 AM and blood was taken at 9 AM on day 0. Blood was also taken at 9 AM on each of days 1 and 2 and assessed for leptin protein levels. Body weight and food intake were also recorded.

TABLE 4

In vivo data

| Nucleic acid | Example 1 | Example 15 | Example 13 |
|---|---|---|---|
| | Expression of protein (ng/ml) following IV injection of encapsulated mRNA in C57B6 mice (@ 24 h) | | |
| hLeptin | 12.3 ng/mL (0.4 mpk, C57) | | 3.8 ng/mL (0.4 mpk, C57) |
| mEPO | 22.5 ng/mL (0.2 mpk, ob/ob) | | |
| hFIX | 147.7 ng/mL (0.12 mpk, C57) | | 292.7 ng/mL (0.12 mpk, C57) |
| | Expression of protein (ng/ml) following SC injection of encapsulated mRNA in C57B6 mice | | |
| hLeptin | 2.5 ng/mL (0.4 mpk, C57) | 6.2 ng/mL (0.6 mpk, C57) | |
| | FVII knock-down (%) following IV injection of encapsulated siRNA in CD-1 mice | | |
| FVII | 69%/0.03 mpk | | 97%/0.03 mpk |

Immunogenicity Studies

Plasmid DNA encoding alphavirus replicons encoding the F protein of RSV as a transgene served as a template for synthesis of RNA in vitro. The replicons contain the alphavirus genetic elements required for RNA replication but lack those encoding gene products necessary for particle assembly; the structural proteins are instead replaced by a protein of interest (e.g. an immunogen, such as full-length RSV F protein) and so the replicons are incapable of inducing the generation of infectious particles. A T7bacteriophage promoter upstream of the alphavirus cDNA facilitates the synthesis of the replicon RNA in vitro. Other promoters, such as SP6 could be used as alternatives.

Transcriptions were performed for 2 hours at 37° C. in the presence of 7.5 mM (T7 RNA polymerase) or 5 mM (SP6 RNA polymerase) of each of the nucleoside triphosphates (ATP, CTP, GTP and UTP) following the instructions provided by the manufacturer (Ambion). Following transcription the template DNA was digested with TURBO DNase (Ambion). The replicon RNA was precipitated with LiCl and reconstituted in nuclease-free water. Uncapped RNA was capped post-transcriptionally with Vaccinia Capping Enzyme (VCE) using the ScriptCap m7G Capping System (Epicentre Biotechnologies) as outlined in the user manual; replicons capped in this way are given the "v" prefix e.g. vA317 is the A317 replicon capped by VCE. Post-transcriptionally capped RNA was precipitated with LiCl and reconstituted in nuclease-free water. The concentration of RNA samples was determined by measuring $OD_{260\ nm}$. Integrity of the in vitro transcripts was confirmed by denaturing agarose gel electrophoresis.

Encapsulation in DlinDMA-Based Liposomes

RNA was encapsulated in liposomes made essentially by the method of Geall et al. (2012) PNAS vol. 109 (36): 14604-14609, Jeffs et al. (2005) *Pharmaceutical Research* 22 (3):362-372, and Maurer et al. (2001) *Biophysical Journal*, 80: 2310-2326 The liposomes were made of 10% DSPC (zwitterionic), 40% cationic lipid, 48% cholesterol and 2% PEG-conjugated DMG (2 kDa PEG). These proportions refer to the % moles in the total liposome.

DSPC (1,2-Diastearoyl-sn-glycero-3-phosphocholine) was purchased from Genzyme. Cholesterol was obtained from Sigma-Aldrich. PEG-conjugated DMG (1,2-dimyristoyl-sn-glycero-3-phosphoethanolamine-N-[methoxy(polyethylene glycol), ammonium salt), DOTAP (1,2-dioleoyl-3-trimethylammonium-propane, chloride salt) and DC-chol (3β-[N—(N',N'-dimethylaminoethane)-carbamoyl]cholesterol hydrochloride) were from Avanti Polar Lipids.

Briefly, lipids were dissolved in ethanol (2 ml), a RNA replicon was dissolved in buffer (2 ml, 100 mM sodium citrate, pH 6) and these were mixed with 2 ml of buffer followed by 1 hour of equilibration. The mixture was then dialized overnight against 1×PBS. The resulting product contained liposomes, with ~70-95% encapsulation efficiency. For in vitro and in vivo experiments formulations were diluted to the required RNA concentration with 1×PBS.

The percentage of encapsulated RNA and RNA concentration were determined by Quant-iT RiboGreen RNA reagent kit (Invitrogen), following manufacturer's instructions. The ribosomal RNA standard provided in the kit was used to generate a standard curve. Liposomes were diluted 10× or 100× in 1×TE buffer (from kit) before addition of the dye. Separately, liposomes were diluted 10× or 100× in 1×TE buffer containing 0.5% Triton X before addition of the dye (to disrupt the liposomes and thus to assay total RNA). Thereafter an equal amount of dye was added to each solution and then ~180 µL of each solution after dye addition was loaded in duplicate into a 96 well tissue culture plate. The fluorescence (Ex 485 nm, Em 528 nm) was read on a microplate reader. All liposome formulations were dosed in vivo based on the encapsulated amount of RNA.

RSV Immunogenicity

A self-replicating replicon encoding RSV F protein was administered to BALB/c mice, 8 animals per group, by bilateral intramuscular vaccinations (50 µL per leg) on days 0 and 21 with the replicon (0.1 and 1 ng) formulated as liposomes with the lipids described below. All liposomes tested were composed of 40% cationic lipid, 10% DSPC, 48% cholesterol and 2% PEG-DMG with similar amounts of RNA. The liposomes were all prepared using the same technique as described above.

The liposome formulations tested generated immune responses with as little as 0.1 ng of self-replicating RNA, as determined by increased F-specific IgG titers.

% entrapment (% E), Concentration of RNA (Conc), particle size measured by DLS, and polydispersity reported by DLS of LNPs prepared with different cationic lipids

| | %E | | Conc (ug/mL) | | Size (nm) | | PDI | |
|---|---|---|---|---|---|---|---|---|
| Example | 1st IM | 2nd IM | 1st IM | 2nd IM | 1st IM | 2nd IM | 1st IM | 2nd IM |
| 1 | 96.21 | 91.99 | 10.352 | 11.279 | 139.1 | 133.5 | 0.122 | 0.11 |
| 15 | 94.26 | 96.64 | 10.203 | 10.091 | 144.7 | 139.4 | 0.121 | 0.097 |
| 35 | 93.46 | 93.9 | 10.059 | 9.937 | 135.2 | 137.5 | 0.119 | 0.108 |

-continued

| Example | %E 1st IM | %E 2nd IM | Conc (ug/mL) 1st IM | Conc (ug/mL) 2nd IM | Size (nm) 1st IM | Size (nm) 2nd IM | PDI 1st IM | PDI 2nd IM |
|---|---|---|---|---|---|---|---|---|
| 40 | 71.1 | 78.05 | 9.461 | 9.65 | 141 | 137.3 | 0.122 | 0.118 |
| 34 | 75.5 | 79.19 | 9.24 | 11.495 | 136.2 | 135.4 | 0.116 | 0.11 |
| 32 | 92.6 | 94.72 | 8.81 | 9.653 | 136.2 | 135 | 0.147 | 0.088 |
| 48 | 86.169 | 85.6 | 9.841 | 9.665 | 137.9 | 134.2 | 0.091 | 0.075 |

Immunogenicity data was two weeks after two immunizations of RNA expressing RSV-F of LNPs prepared with different cationic lipids. LNPs were prepared fresh for each immunization.

| Example | Immunogenicity (2wp2; log10 IgG titers) 1 ng | Immunogenicity (2wp2; log10 IgG titers) 0.1 ng |
|---|---|---|
| 1 | 4.08 | 3.99 |
| 15 | 4.63 | 4.45 |
| 35 | 4.86 | 4.53 |
| 40 | 4.74 | 4.31 |
| 34 | 4.36 | 3.73 |
| 32 | 4.92 | 4.77 |
| 48 | 5.02 | 4.58 |

It should be understood that for all numerical bounds describing some parameter in this application, such as "about," "at least," "less than," and "more than," the description also necessarily encompasses any range bounded by the recited values. Accordingly, for example, the description "at least 1, 2, 3, 4, or 5" also describes, inter alia, the ranges 1-2, 1-3, 1-4, 1-5, 2-3, 2-4, 2-5, 3-4, 3-5, and 4-5, et cetera.

For all patents, applications, or other reference cited herein, such as non-patent literature and reference sequence information, it should be understood that they are incorporated by reference in their entirety for all purposes as well as for the proposition that is recited. Where any conflict exists between a document incorporated by reference and the present application, this application will control. All information associated with reference gene sequences disclosed in this application, such as GeneIDs or accession numbers (typically referencing NCBI accession numbers), including, for example, genomic loci, genomic sequences, functional annotations, allelic variants, and reference mRNA (including, e.g., exon boundaries or response elements) and protein sequences (such as conserved domain structures), as well as chemical references (e.g., PubChem compound, PubChem substance, or PubChem Bioassay entries, including the annotations therein, such as structures and assays, et cetera), are hereby incorporated by reference in their entirety.

Headings used in this application are for convenience only and do not affect the interpretation of this application.

Preferred features of each of the aspects provided by the invention are applicable to all of the other aspects of the invention mutatis mutandis and, without limitation, are exemplified by the dependent claims and also encompass combinations and permutations of individual features (e.g., elements, including numerical ranges and exemplary embodiments) of particular embodiments and aspects of the invention, including the working examples. For example, particular experimental parameters exemplified in the working examples can be adapted for use in the claimed invention piecemeal without departing from the invention. For example, for materials that are disclosed, while specific reference of each of the various individual and collective combinations and permutations of these compounds may not be explicitly disclosed, each is specifically contemplated and described herein. Thus, if a class of elements A, B, and C are disclosed as well as a class of elements D, E, and F and an example of a combination of elements A-D is disclosed, then, even if each is not individually recited, each is individually and collectively contemplated. Thus, in this example, each of the combinations A-E, A-F, B-D, B-E, B—F, C-D, C-E, and C—F are specifically contemplated and should be considered disclosed from disclosure of A, B, and C; D, E, and F; and the example combination A-D. Likewise, any subset or combination of these is also specifically contemplated and disclosed. Thus, for example, the sub-groups of A-E, B-F, and C-E are specifically contemplated and should be considered disclosed from disclosure of A, B, and C; D, E, and F; and the example combination A-D. This concept applies to all aspects of this application, including elements of a composition of matter and steps of method of making or using the compositions.

The forgoing aspects of the invention, as recognized by the person having ordinary skill in the art following the teachings of the specification, can be claimed in any combination or permutation to the extent that they are novel and non-obvious over the prior art—thus, to the extent an element is described in one or more references known to the person having ordinary skill in the art, they may be excluded from the claimed invention by, inter alia, a negative proviso or disclaimer of the feature or combination of features.

What is claimed is:

1. A compound of formula (II) or a pharmaceutically acceptable salt thereof, wherein:

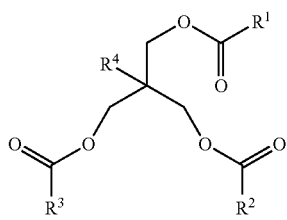

R¹ is selected from the group consisting of:

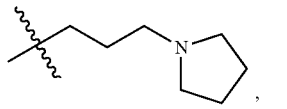

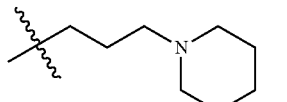

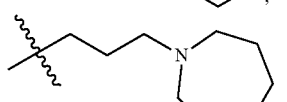

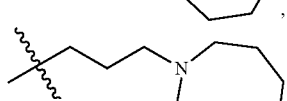

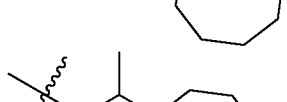

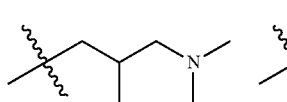

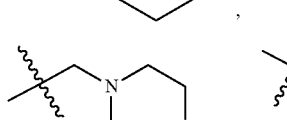

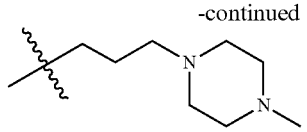

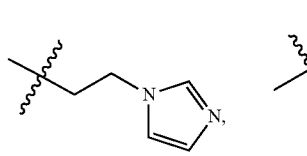

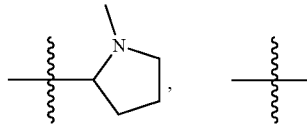

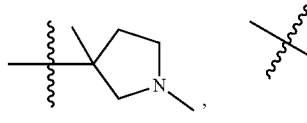

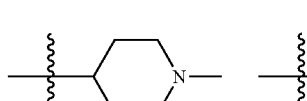

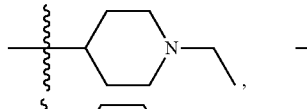

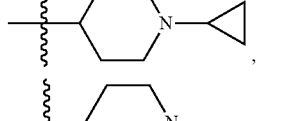

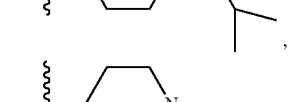

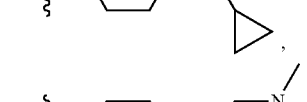

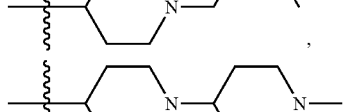

-continued

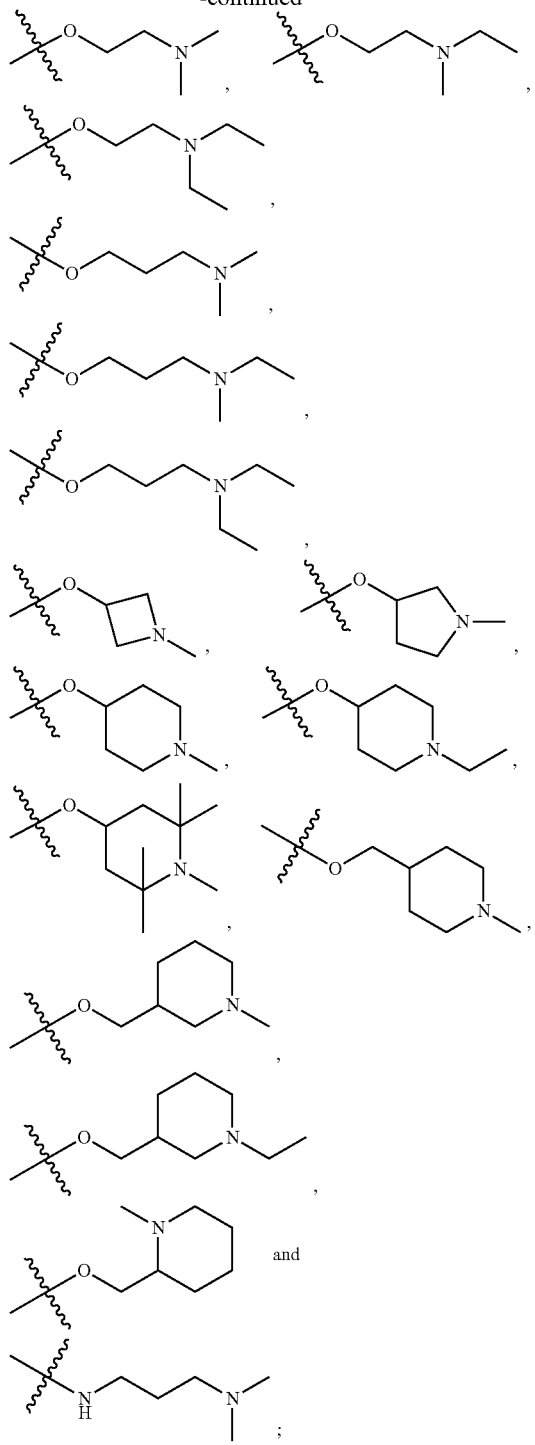

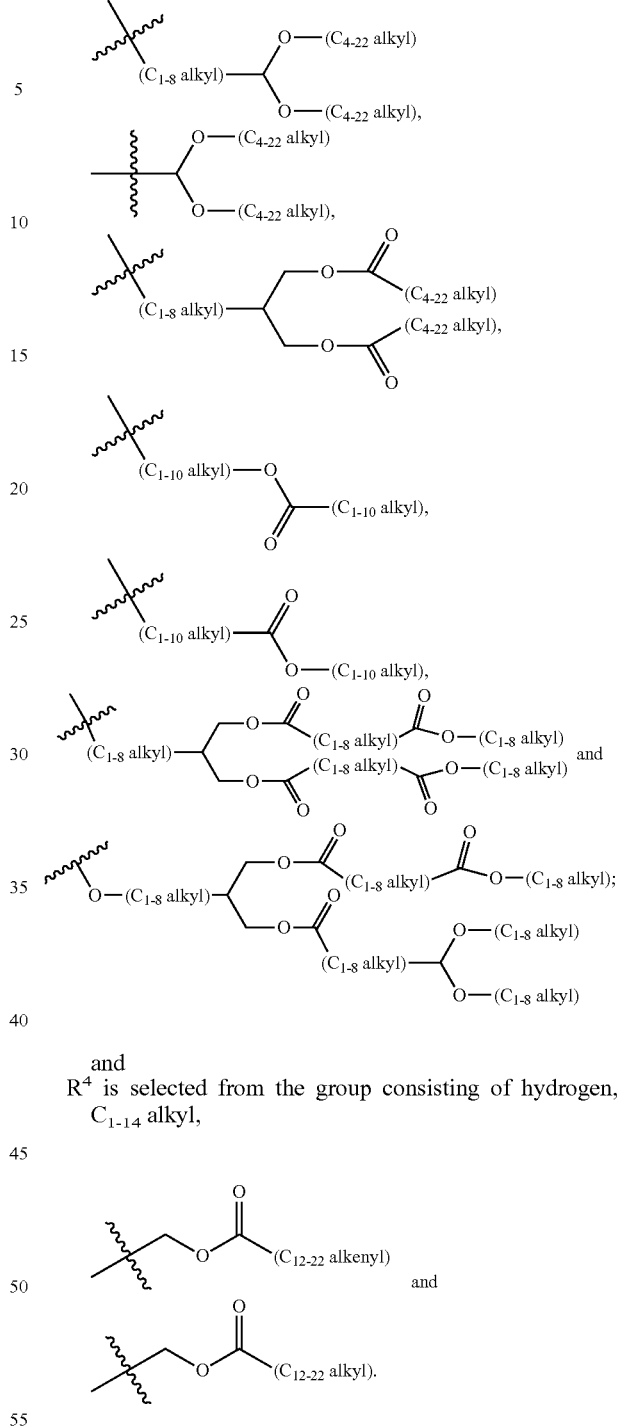

$R^2$ and $R^3$ are each independently selected from the group consisting of $C_{7-22}$ alkyl, $C_{12-22}$ alkenyl, $C_{3-8}$ cycloalkyl, each optionally substituted with 1, 2, or 3 $C_{1-8}$ alkyl groups;

and
$R^4$ is selected from the group consisting of hydrogen, $C_{1-14}$ alkyl,

2. The compound according to claim 1 or a pharmaceutically acceptable salt thereof, wherein $R^4$ is hydrogen.

3. The compound according to claim 1 or a pharmaceutically acceptable salt thereof, wherein $R^2$ is selected from the group consisting of:

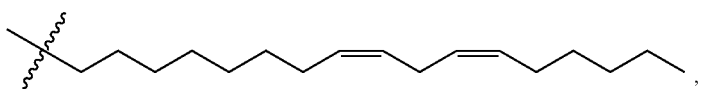

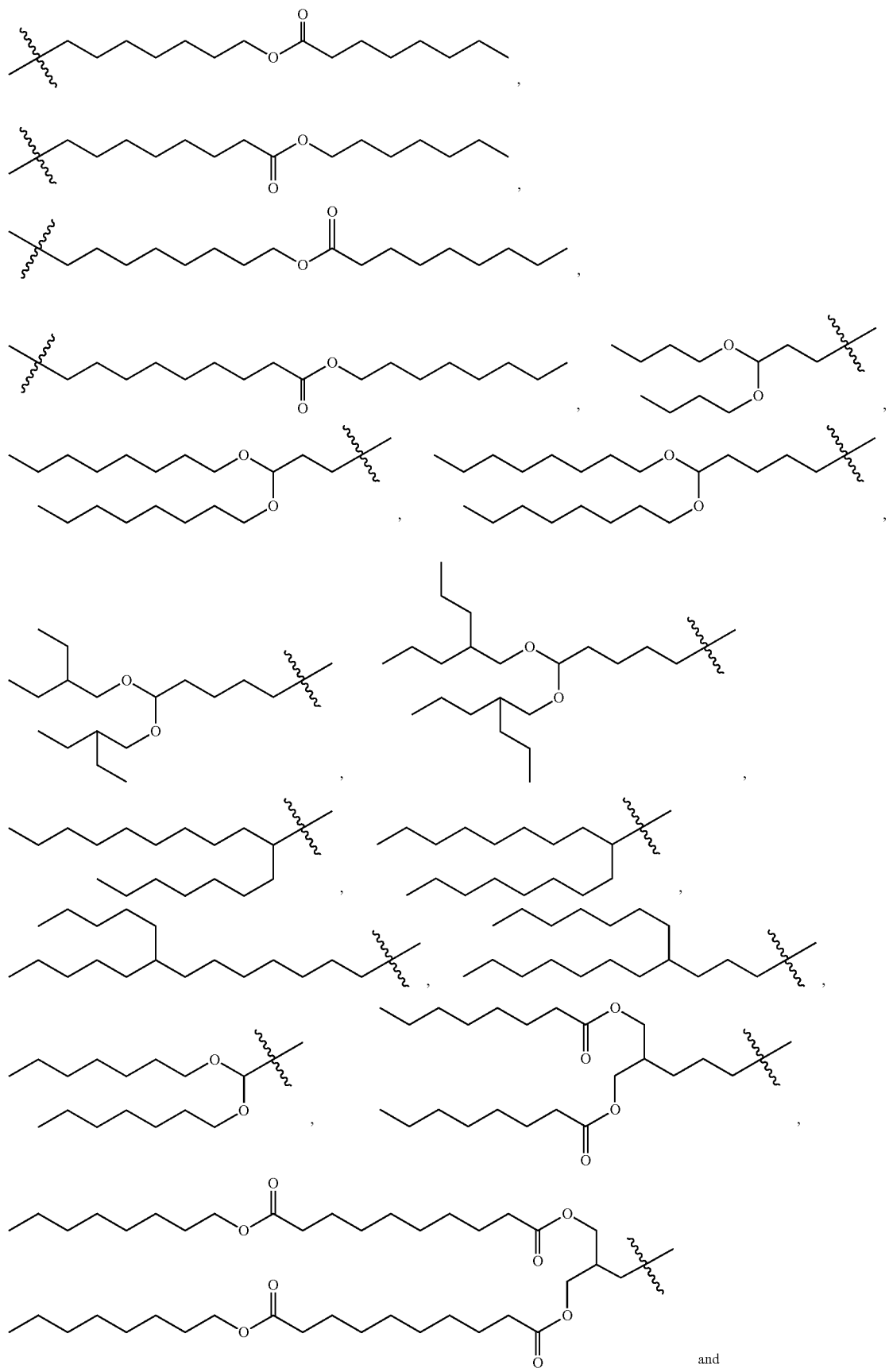

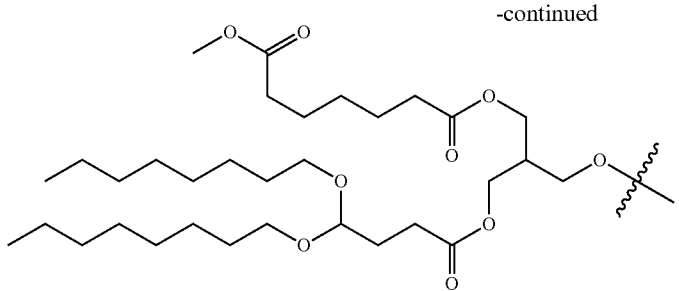

4. The compound according to claim 1 or a pharmaceutically acceptable salt thereof, wherein R³ is selected from the group consisting of

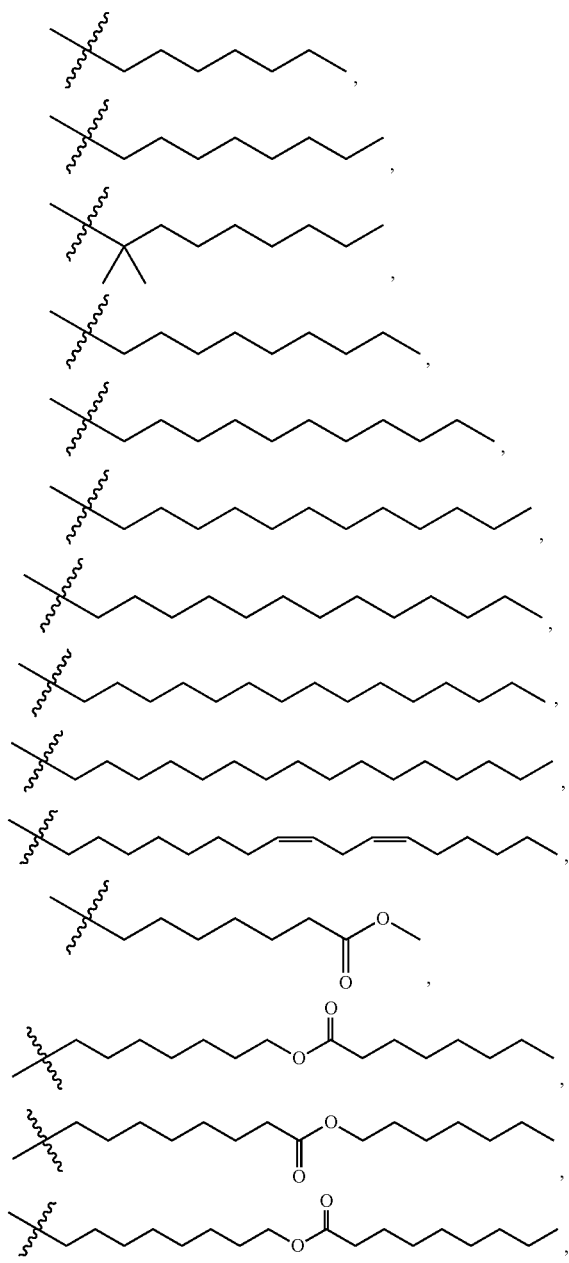

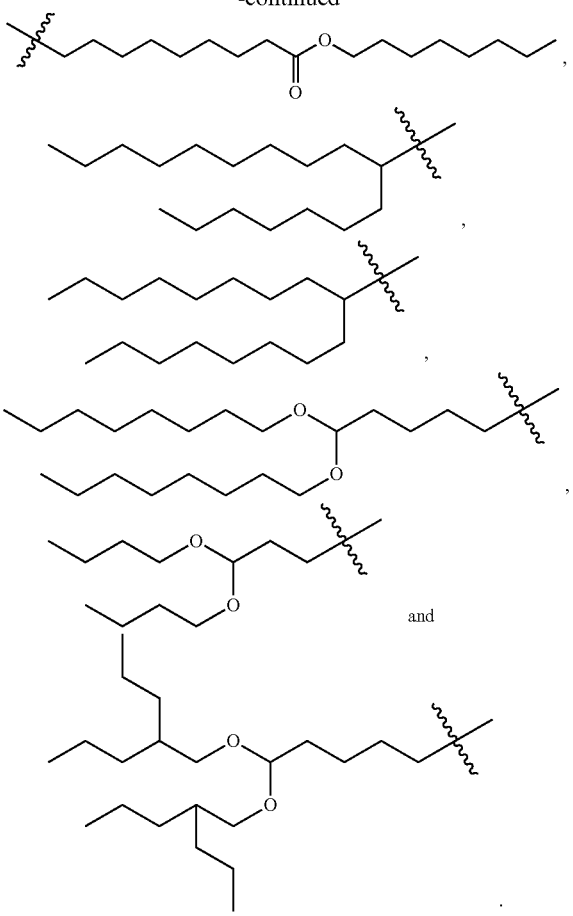

and

5. A compound or a pharmaceutically acceptable salt thereof, wherein the compound is selected from the group consisting of:

(9Z,9'Z,12Z,12'Z)-2-(((3-(4-methylpiperazin-1-yl)propanoyl)oxy)methyl)propane-1,3-diyl bis(octadeca-9,12-dienoate);

(9Z,9'Z,12Z,12'Z)-2-(((4-(pyrrolidin-1-yl)butanoyl)oxy)methyl)propane-1,3-diyl bis(octadeca-9,12-dienoate);

(9Z,9'Z,12Z,12'Z)-2-(((4-(piperidin-1-yl)butanoyl)oxy)methyl)propane-1,3-diyl bis(octadeca-9,12-dienoate);

(9Z,9Z,12Z,2'Z)-2-(((1,4-dimethylpiperidine-4-carbonyl)oxy)methyl)propane-1,3-diyl bis(octadeca-9,12-dienoate);

(9Z,9'Z,12Z,12'Z)-2-(((1-(cyclopropylmethyl)piperidine-4-carbonyl)oxy)methyl)propane-1,3-diyl bis(octadeca-9,12-dienoate);

(9Z,12Z)-3-((4,4-bis(octyloxy)butanoyl)oxy)-2-((((3-(diethylamino)propoxy)carbonyl)oxy)methyl)propyl octadeca-9,12-dienoate;

(9Z,12Z)-3-((4,4-bis(octyloxy)butanoyl)oxy)-2-((((3-(dimethylamino)propoxy)carbonyl)oxy)methyl)propyl octadeca-9,12-dienoate;

(9Z,12Z)-3-((4,4-bis(octyloxy)butanoyl)oxy)-2-(((((1-ethylpiperidin-3-yl)methoxy)carbonyl)oxy)methyl) propyl octadeca-9,12-dienoate;

2-((((2-(diethylamino)ethoxy)carbonyl)oxy)methyl)propane-1,3-diyl bis(2-heptylundecanoate);

(9Z,12Z)-3-(((2-(diethylamino)ethoxy)carbonyl)oxy)-2-(((2-heptylundecanoyl)oxy)methyl)propyl octadeca-9,12-dienoate;

2-((((3-(dimethylamino)propoxy)carbonyl)oxy)methyl) propane-1,3-diyl bis(2-heptylundecanoate);

(9Z,12Z)-3-(((3-(diethylamino)propoxy)carbonyl)oxy)-2-(((2-heptylundecanoyl)oxy)methyl)propyl octadeca-9,12-dienoate;

(9Z,12Z)-3-(((2-(dimethylamino)ethoxy)carbonyl)oxy)-2-(((3-octylundecanoyl)oxy)methyl)propyl octadeca-9,12-dienoate;

2-((((3-(diethylamino)propoxy)carbonyl)oxy)methyl) propane-1,3-diyl bis(3-octylundecanoate);

(9Z,12Z)-3-(((3-(diethylamino)propoxy)carbonyl)oxy)-2-(((3-octylundecanoyl)oxy)methyl)propyl octadeca-9,12-dienoate;

(9Z,12Z)-3-(((3-(diethylamino)propoxy)carbonyl)oxy)-2-(((7-hexyltridecaonoyl)oxy)methyl)propyl octadeca-9,12-dienoate;

(9Z,12Z)-3-(((3-(diethylamino)propoxy)carbonyl)oxy)-2-(((9-pentyltetradecanoyl)oxy)methyl)propyl octadeca-9,12-dienoate;

(9Z,12Z)-3-(((3-(diethylamino)propoxy)cabonyl)oxy)-2-(((5-heptyldodecanoyl)oxy)methyl)propyl octadeca-9,12-dienoate;

(9,12Z)-3-(2,2-bis(heptyloxy)acetoxy)-2-((((2-(dimethylamino)ethoxy)carbonyl)oxy)methyl)propyl octadeca-9,12-dienoate;

(9Z,12Z)-3-((6,6-bis(octyloxy)hexanoyl)oxy)-2-((((3-(diethylamino)propoxy)carbonyl)oxy)methyl)propyl octadeca-9,12-dienoate;

2-(3-ethyl-11-(((9Z,12Z)-octadeca-9,12-dienoyloxy) methyl)-8,14-dioxo-7,9,13-trioxa-3-azaheptadecan-17-yl)propane-1,3-diyl dioctanoate;

(9Z,9'Z,12Z,12Z)-2-((((3-(dimethylamino)propoxy)carbonyl)oxy)methyl)propane-1,3-diyl bis(octadeca-9,12-dienoate);

(9Z,9'Z,12Z,12'Z)-2-((((3-(diethylamino)propoxy)carbonyl)oxy)methyl)propane-1,3-diyl bis(octadeca-9,12-dienoate);

(9Z,9'Z,12Z,12'Z)-2-((((2-(dimethylamino)ethoxy)carbonyl)oxy)methyl)propane-1,3-diyl bis(octadeca-9,12-dienoate);

3-((4,4-bis(octyloxy)butanoyl)oxy)-2-(((9Z,12Z)-octadeca-9,12-dienoyloxy)methyl)propyl 1-isopropylpiperidine-4-carboxylate;

3-((4,4-bis(octyloxy)butanoyl)oxy)-2-(((9Z,12Z)-octadeca-9,12-dienoyloxy)methyl)propyl 1-(cyclopropylmethyl)piperidine-4-carboxylate;

3-((4,4-bis(octyl oxy)butanoyl)oxy)-2-(((9Z,12Z)-octadeca-9,12-dienoyloxy)methyl)propyl 1-methylpyrrolidine-3-carboxy late;

(9Z,9'Z,12Z,12Z)-2-(((((3-(diethylamino)propoxy)carbonyl)oxy)methyl)-2-(((9Z,12Z)-octadeca-9,12-dienoyloxy)methyl)propane-1,3-diyl bis(octadeca-9,12-dienoate);

(2S)-3-((4,4-bis(octyloxy)butanoyl)oxy)-2-(((9Z,12Z)-octadeca-9,12-dienoyloxy)methyl)propyl 1-methylpyrrolidine-2-carboxylate;

(2R)-3-((4,4-bis(octyloxy)butanoyl)oxy)-2-(((9Z,12Z)-octadeca-9,12-dienoyloxy)methyl)propyl 1-methylpyrrolidine-2-carboxylate;

3-((4,4-bis(octyloxy)butanoyl)oxy)-2-(((9Z,12Z)-octadeca-9,12-dienoyloxy)methyl)propyl 4-methylmorpholine-2-carboxylate;

3-((4,4-bis(octyloxy)butanoyl)oxy)-2-(((9Z,12Z)-octadeca-9,12-di enoyl oxy)methyl)propyl 1,4-dimethylpiperidine-4-carboxylate;

3-((4,4-bis(octyloxy)butanoyl)oxy)-2-(((9Z,12Z)-octadeca-9,12-dienoyloxy)methyl)propyl 1-methylpiperidine-4-carboxylate;

(9Z,12Z)-3-((4,4-bis(octyloxy)butanoyl)oxy)-2-(((((1-methylpyrrolidin-3-yl)oxy)carbonyl)oxy)methyl)propyl octadeca-9,12-dienoate;

(9Z,12Z)-3-((4,4-bis(octyloxy)butanoyl)oxy)-2-(((((1-methylpiperidin-4-yl)oxy)carbonyl)oxy)methyl)propyl octadeca-9,12-dienoate;

(9Z,12Z)-3-((4,4-bis(octyloxy)butanoyl)oxy)-2-(((((1-methylazetidin-3-yl)oxy)carbonyl)oxy)methyl)propyl octadeca-9,12-dienoate;

(9Z,12Z)-3-((4,4-bis(octyloxy)butanoyl)oxy)-2-(((((1-ethylpiperidin-4-yl)oxy)carbonyl)oxy)methyl)propyl octadeca-9,12-dienoate;

(9Z,12Z)-3-((4,4-bis(octyloxy)butanoyl)oxy)-2-(((((1-methylpiperidin-4-yl)methoxy)carbonyl)oxy)methyl) propyl octadeca-9,12-dienoate;

(9Z,12Z)-3-((4,4-bis(octyloxy)butanoyl)oxy)-2-(((((1,2,2,6,6-pentamethylpiperidin-4-yl)oxy)carbonyl)oxy) methyl)propyl octadeca-9,12-dienoate;

(9Z,12Z)-3-((4,4-bis(octyloxy)butanoyl)oxy)-2-((((3-(dimethylamino)propyl)carbamoyl)oxy)methyl)propyl octadeca-9,12-dienoate;

3-((4,4-bis((2-propylpentyl)oxy)butanoyl)oxy)-2-(((9Z,12Z)-octadeca-9,12-dienoyloxy)methyl)propyl 1,4-dimethylpiperidine-4-carboxylate;

3-((6,6-bis((2-propylpentyl)oxy)hexanoyl)oxy)-2-(((9Z,12Z)-octadeca-9,12-dienoyloxy)methyl)propyl 1,4-dimethylpiperidine-4-carboxylate;

2-(((1-methylpyrrolidine-3-carbonyl)oxy)methyl)propane-1,3-diyl bis(4,4-bis(octyloxy)butanoate);

2-(((1-methylpyrrolidine-3-carbonyl)oxy)methyl)propane-1,3-diyl bis(6,6-bis(octyloxy)hexanoate);

2-(((1-methylpyrrolidine-3-carbonyl)oxy)methyl)propane-1,3-diyl bis(6,6-bis((2-propylpentyl)oxy)hexanoate);

2-(5-(3-(dodecanoyloxy)-2-(((1-methylpyrrolidine-3-carbonyl)oxy)methyl)propoxy)-5-oxopentyl)propane-1,3-diyl dioctanoate;

2-(5-(3-((1-methylpyrrolidine-3-carbonyl)oxy)-2-((palmitoyloxy)methyl)propoxy)-5-oxopentyl)propane-1,3-diyl dioctanoate;

2-(S-(3-((1-methylpyrrolidine-3-carbonyl)oxy)-2-((tetradecanoyloxy)methyl)propoxy)-S-oxopentyl)propane-1,3-diyl dioctanoate;

3-((4,4-bis(octyl oxy)butanoyl)oxy)-2-((dodecanoyloxy) methyl)propyl 1-methylpyrrolidine-3-carboxylate;

3-((4,4-bis(octyloxy)butanoyl)oxy)-2-((tetradecanoyloxy)methyl)propyl 1-methylpyrrolidine-3-3-((4,4-bis (octyloxy)butanoyl)oxy)-2-((palmitoyloxy)methyl) propyl 1-methylpyrrolidine-3-carboxylate;

1-(3-((4,4-bis(octyloxy)butanoyl)oxy)-2-(((1-methylpyrrolidine-3-carbonyl)oxy)methyl)propyl) 8-methyl octanedioate;

1-(3-((4,4-bis(octyloxy)butanoyl)oxy)-2-(((1-methylpyr-rolidine-3-carbonyl)oxy)methyl)propyl) 10-octyl decanedioate;

1-(3-((6,6-bis((2-propylpentyl)oxy)hexanoyl)oxy)-2-(((1,4-dimethylpiperidine-4-carbonyl)oxy)methyl)propyl) 10-octyl decanedioate;

1-(3-((6,6-bis((2-propylpentyl)oxy)hexanoyl)oxy)-2-(((1,4-dimethylpiperidine-4-carbonyl)oxy)methyl)propyl) 8-methyl octanedioate; and 8-dimethyl O'1,O1-(2-(((1-methylpyrrolidine-3-carbonyl)oxy)methyl)propane-1,3-diyl) dioctanedioate.

6. A compound:

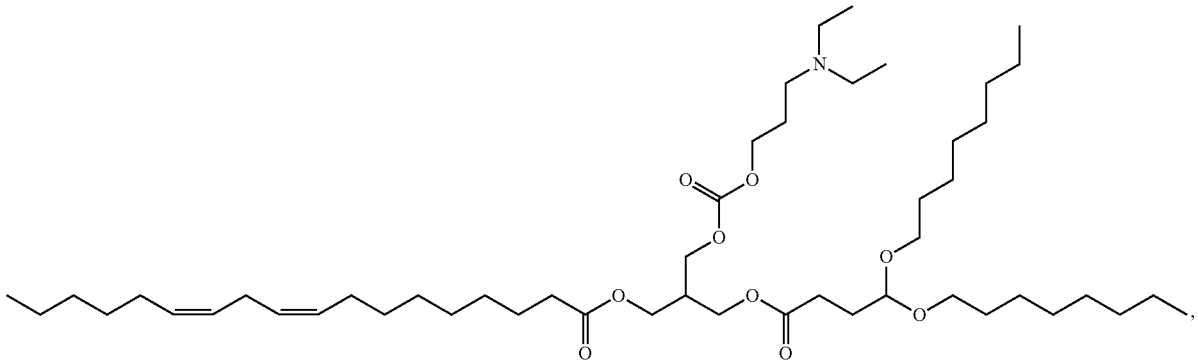 [SMILES: CCCCC/C=C\C/C=C\CCCCCCCC(=O)OCC(COC(=O)CCC(OCCCCCCCC)OCCCCCCCC)COC(=O)OCCCN(CC)CC]

(9Z,12Z)-3-((4,4-bis(octyloxy)butanoyl)oxy)-2-((((3-(diethylamino)propoxy)carbonyl)oxy)methyl)propyl octadeca-9,12-dienoate or a pharmaceutically acceptable salt thereof.

7. A compound:

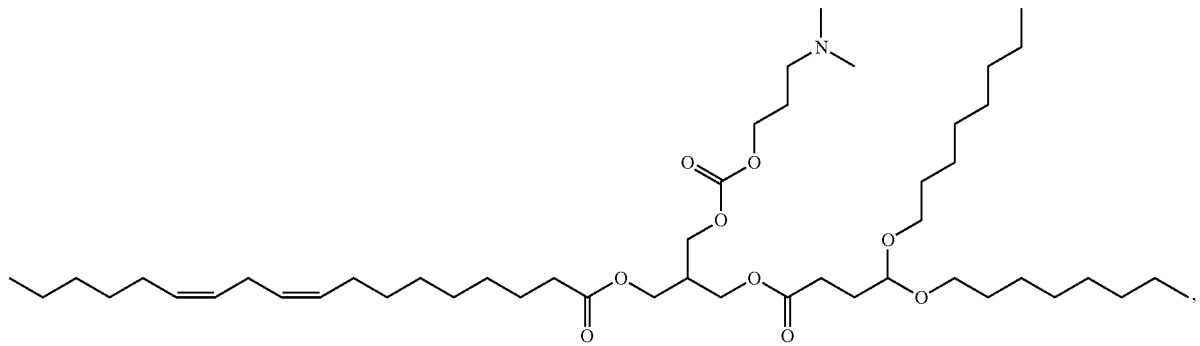 [SMILES: CCCCC/C=C\C/C=C\CCCCCCCC(=O)OCC(COC(=O)CCC(OCCCCCCCC)OCCCCCCCC)COC(=O)OCCCN(C)C]

(9Z,12Z)-3-((4,4-bis(octyloxy)butanoyl)oxy)-2-((((3-(dimethylamino)propoxy)carbonyl)oxy)methyl)propyl octadeca-9,12-dienoate; or a pharmaceutically acceptable salt thereof.

8. A compound:

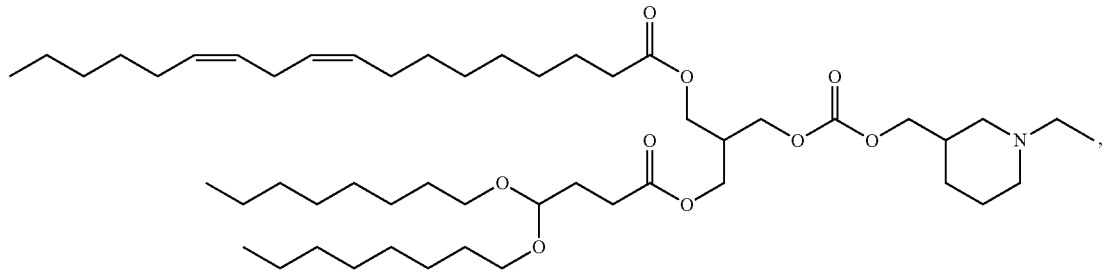 [SMILES: CCCCC/C=C\C/C=C\CCCCCCCC(=O)OCC(COC(=O)CCC(OCCCCCCCC)OCCCCCCCC)COC(=O)OCC1CCCN(CC)C1]

(9Z,12)-3-((4,4-bis(octyloxy)butanoyl)oxy)-2-(((((1-ethylpiperidin-3-yl)methoxy)carbonyl)oxy)methyl)propyl octadeca-9,12-dienoate; or a pharmaceutically acceptable salt thereof.

9. A compound:

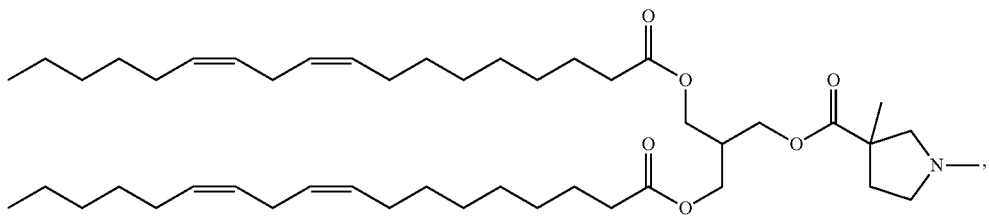 [SMILES: CCCCC/C=C\C/C=C\CCCCCCCC(=O)OCC(COC(=O)CCCCCCC/C=C\C/C=C\CCCCC)COC(=O)C1(C)CCN(C)C1]

(9Z,9'Z,12Z,12'Z)-2-(((1,3-dimethylpyrrolidine-3-carbonyl)oxy)methyl)propane-1,3-diyl bis(octadeca-9,12-dienoate); or a pharmaceutically acceptable salt thereof.

10. The compound according to claim 1 or a pharmaceutically acceptable salt thereof, wherein $R^1$ is

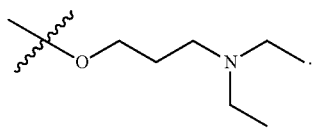 [SMILES: *OCCCN(CC)CC]

11. The compound according to claim 1 or a pharmaceutically acceptable salt thereof, wherein $R^2$ is

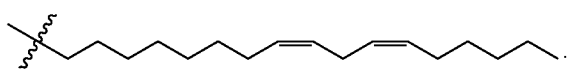

12. The compound according to claim 1 or a pharmaceutically acceptable salt thereof, wherein $R^3$ is

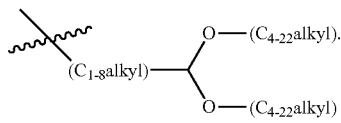

13. The compound according to claim 1 or a pharmaceutically acceptable salt thereof, wherein $R^2$ and $R^3$ are each independently selected from the group consisting of $C_{12-12}$ alkenyl and

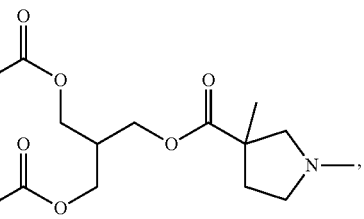

14. The compound according to claim 1 or a pharmaceutically acceptable salt thereof, wherein one of $R^2$ and $R^3$ is $C_{12-22}$ alkenyl and the other is

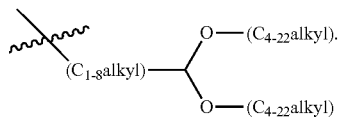

15. The compound according to claim 1 or a pharmaceutically acceptable salt thereof, wherein one of $R^2$ and $R^3$ is

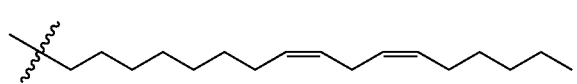 [SMILES: *CCCCCCC/C=C\C/C=C\CCCCC]

and the other is

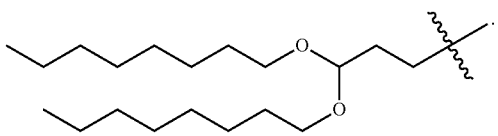 [SMILES: *CCC(OCCCCCCCC)OCCCCCCCC]

* * * * *

UNITED STATES PATENT AND TRADEMARK OFFICE
CERTIFICATE OF CORRECTION

PATENT NO. : 10,059,655 B2
APPLICATION NO. : 15/104736
DATED : August 28, 2018
INVENTOR(S) : Luis Brito et al.

Page 1 of 1

It is certified that error appears in the above-identified patent and that said Letters Patent is hereby corrected as shown below:

In the Claims

Claim 5, Column 218, Line 62, delete "(9Z,9Z,12Z,2'Z)" and insert in place thereof --(9Z,9'Z,12Z,12'Z)--

Claim 5, Column 219, Line 37, delete "(9,12Z)" and insert in place thereof --(9Z,12Z)--

Claim 5, Column 219, Line 46, delete "(9Z,9'Z,12Z,12Z)" and insert in place thereof --(9Z,9'Z,12Z,12'Z)--

Claim 5, Column 220, Line 11, delete "12-di enoyl oxy)" and insert in place thereof --12-dienoyloxy)--

Claim 5, Column 220, Line 56, delete "2-(S-3-(" and insert in place thereof --2-(5-(3-(--

Claim 5, Column 220, Line 59, delete "3-((4,4bis(octyl oxy)" and insert in place thereof --3-((4,4bis (octyloxy)--

Claim 9, Column 222, Line 64, delete "(9Z,12)" and insert in place thereof --(9Z,12Z)--

Signed and Sealed this
Fourth Day of December, 2018

Andrei Iancu
*Director of the United States Patent and Trademark Office*

SEQUENCE LISTING

<160> NUMBER OF SEQ ID NOS: 13

<210> SEQ ID NO 1
<211> LENGTH: 21
<212> TYPE: RNA
<213> ORGANISM: Artificial Sequence
<220> FEATURE:
<223> OTHER INFORMATION: Synthetic oligonucleotide

```
<220> FEATURE:
<221> NAME/KEY: modified_base
<222> LOCATION: (3)..(3)
<223> OTHER INFORMATION: 2'-O-methyl-nucleotide
<220> FEATURE:
<221> NAME/KEY: modified_base
<222> LOCATION: (13)..(13)
<223> OTHER INFORMATION: 2'-O-methyl-nucleotide
<220> FEATURE:
<221> NAME/KEY: modified_base
<222> LOCATION: (18)..(18)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotide

<400> SEQUENCE: 1
uuuaauugaa accaagacau u                                              21

<210> SEQ ID NO 2
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1)..(1)
<223> OTHER INFORMATION: 2'-O-methyl-nucleotide
<220> FEATURE:
<221> NAME/KEY: modified_base
<222> LOCATION: (3)..(6)
<223> OTHER INFORMATION: 2'-O-methyl-nucleotide
<220> FEATURE:
<221> NAME/KEY: modified_base
<222> LOCATION: (9)..(12)
<223> OTHER INFORMATION: 2'-O-methyl-nucleotide
<220> FEATURE:
<221> NAME/KEY: modified_base
<222> LOCATION: (15)..(16)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotide

<400> SEQUENCE: 2
ugucuugguu ucaauuaaau u                                              21

<210> SEQ ID NO 3
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (8)..(8)
<223> OTHER INFORMATION: 2'-O-methyl-nucleotide
<220> FEATURE:
<221> NAME/KEY: modified_base
<222> LOCATION: (17)..(17)
<223> OTHER INFORMATION: 2'-O-methyl-nucleotide
<220> FEATURE:
<221> NAME/KEY: modified_base
<222> LOCATION: (20)..(21)
<223> OTHER INFORMATION: 2'-O-methyl-nucleotide

<400> SEQUENCE: 3
uauuuaagga gggugaucuu u                                              21
```

```
<210> SEQ ID NO 4
<211> LENGTH: 21
<212> TYPE: RNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (5)..(7)
<223> OTHER INFORMATION: 2'-O-methyl-nucleotide
<220> FEATURE:
<221> NAME/KEY: modified_base
<222> LOCATION: (11)..(14)
<223> OTHER INFORMATION: 2'-O-methyl-nucleotide
<220> FEATURE:
<221> NAME/KEY: modified_base
<222> LOCATION: (19)..(21)
<223> OTHER INFORMATION: 2'-O-methyl-nucleotide

<400> SEQUENCE: 4
agaucacccu ccuuaaauau u                                        21

<210> SEQ ID NO 5
<211> LENGTH: 5427
<212> TYPE: DNA
<213> ORGANISM: Artificial Sequence
<220> FEATURE:
<223> OTHER INFORMATION: Synthetic oligonucleotide

<400> SEQUENCE: 5
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca caaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta caactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaacgg gccctctaga ctcgagcggc cgccactgtg ctggatatct gcagaattcc   960
accacactgg actagtggat ccgagctcgg taccaagctt aagtttaaac cgctgatcag  1020
cctcgactgt gccttctagt tgccagccat ctgttgtttg ccctcccc gtgccttcct   1080 tgaccctgga aggtgccact cccactgtcc tttcctaata aaatgaggaa attgcatcgc  1140
attgtctgag taggtgtcat tctattctgg gggtggggt gggcaggac agcaagggg    1200 aggattggga agacaatagc aggcatgctg gggatgcggt gggctctatg gcttctgagg  1260
cggaaagaac cagctgggc tctaggggt atccccacgc gccctgtagc ggcgcattaa   1320
gcgcggcggg tgtggtggtt acgcgcagcg tgaccgctac acttgccagc gccctagcgc  1380
```

```
ccgctcctttcgctttcttcccttcctttctcgccacgttcgccggctttccccgtcaag    1440
ctctaaatcggggctcccttagggttccgatttagtgctttacggcactcgaccccca     1500
aaaaacttgattagggtgatggttcacgtagtgggccatcgccctgatagacggttttc    1560
gcccttgtgacgttggagtccacgttcttttaatagtggactcttgttccaaactggaacaa 1620
cactcaaccctatctcggtctattcttttgatttataaggattttgccgatttcggcct   1680
attggttaaaaaatgagctgatttaacaaaatttaacgcgaattaattctgtgaatgt    1740
gtgtcagttagggtgtggaaagtccccaggctccccagcaggcagaagtatgcaaagcat   1800
gcatctcaattagtcagcaaccaggtgtggaaagtccccaggctcccagcaggcagaag    1860
tatgcaaagcatgcatctcaattagtcagcaaccatagtccgcccctaactccgcccat   1920
cccgcccctaactccgcccagttccgcccattctccgcccatggctgactaattttttt   1980
tatttatgcagaggccgaggccgcctctgcctctgagctattccagaagtagtgaggagg   2040
cttttttggaggcctaggctttgcaaaaagctcccgggagcttgtatatccattttcgg    2100
atctgatcaagagacaggatgaggatcgtttcgcatgattgaacaagatggattgcacgc   2160
aggttctccgccgcttgggtggagaggctattcggctatgactgggcacaacagacaat    2220
cggctgctctgatgccgccgtgttccggctgtcagcgcagggcgcccggttcttttttgt   2280
caagaccgacctgtccggtgccctgaatgaactgcaggacgaggcagcgcggctatcgtg   2340
gctggccacgcgggcgttccttgcgcagctgtgctcgacgttgtcactgaagcgggaag    2400
ggactggctgctattgggcgaagtgccgggcaggatctcctgtcatctcaccttgctcc    2460
tgccgagaaagtatccatcatggctgatgcaatgcggcggctgcatacgcttgatccggc   2520
tacctgcccattcgaccaccaagcgaaacatcgcatcgagcgagcacgtactcggatgga   2580
agccggtcttgtcgatcaggatgatctggacgaagagcatcaggggctcgcgccagccga   2640
actgttcgccaggctcaaggcgcgcatgcccgacggcgaggatctcgtcgtgacccatgg   2700
cgatgcctgcttgccgaatatcatggtggaaaatggccgcttttctggattcatcgactg   2760
tggccggctgggtgtggcggaccgctatcaggacatagcgttggctacccgtgatattgc   2820
tgaagagcttggcggcgaatgggctgaccgcttcctcgtgctttacggtatcgccgctcc   2880
cgattcgcagcgcatcgccttctatcgccttcttgacgagttcttctgagcgggactctg   2940
gggttcgaaatgaccgaccaagcgacgcccaacctgccatcacgagatttcgattccacc   3000
gccgccttctatgaaaggttgggcttcggaatcgttttccgggacgccggctggatgatc   3060
ctccagcgcgggatctcatgctggagttcttcgcccaccccaacttgtttattgcagct   3120
tataatggttacaaataaagcaatagcatcacaaatttcacaaataaagcatttttttca   3180
ctgcattctagttgtggtttgtccaaactcatcaatgtatcttatcatgtctgtataccg   3240
tcgacctctagctagagcttggcgtaatcatggtcatagctgtttcctgtgtgaaattgt   3300
tatccgctcacaattccacaacatacgagccggaagcataaagtgtaaagcctggggt    3360
gcctaatgagtgagctaactcacattaattgcgttgcgctcactgcccgctttccagtcg   3420
ggaaacctgtcgtgccagctgcattaatgaatcggccaacgcgcggggagaggcggtttg   3480
cgtattgggcgctcttccgcttcctcgctcactgactcgctgcgctcggtcgttcggctg   3540
cggcgagcggtatcagctcactcaaaggcggtaatacggttatccacagaatcaggggat   3600
aacgcaggaaagaacatgtgagcaaaaggccagcaaaaggccaggaaccgtaaaaaggcc   3660
gcgttgctggcgtttttccataggctccgcccccctgacgagcatcacaaaaatcgacgc   3720
tcaagtcagaggtggcgaaacccgacaggactataaagataccaggcgttccccctgga   3780
```

```
agctccctcg tgcgctctcc tgttccgacc ctgccgctta ccggatacct gtccgccttt    3840
ctcccttcgg gaagcgtggc gctttctcat agctcacgct gtaggtatct cagttcggtg    3900
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaagaacag tatttggtat ctgcgctctg    4140
ctgaagccag ttaccttcgg aaaaagagtt ggtagctctt gatccggcaa acaaaccacc    4200
gctggtagcg gtttttttgt ttgcaagcag cagattacgc gcagaaaaaa aggatctcaa    4260
gaagatcctt tgatcttttc tacggggtct gacgctcagt ggaacgaaaa ctcacgttaa    4320
gggattttgg tcatgagatt atcaaaaagg atcttcacct agatcctttt aaattaaaaa    4380
tgaagtttta aatcaatcta agtatatat  gagtaaactt ggtctgacag ttaccaatgc    4440
ttaatcagtg aggcacctat ctcagcgatc tgtctatttc gttcatccat agttgcctga    4500
ctccccgtcg tgtagataac tacgatacgg gagggcttac catctggccc cagtgctgca    4560
atgataccgc gagacccacg ctcaccggct ccagatttat cagcaataaa ccagccagcc    4620
ggaagggccg agcgcagaag tggtcctgca actttatccg cctccatcca gtctattaat    4680
tgttgccggg aagctagagt aagtagttcg ccagttaata gtttgcgcaa cgttgttgcc    4740
attgctacag gcatcgtggt gtcacgctcg tcgtttggta tggcttcatt cagctccggt    4800
tcccaacgat caaggcgagt tacatgatcc cccatgttgt gcaaaaaagc ggttagctcc    4860
ttcggtcctc cgatcgttgt cagaagtaag ttggccgcag tgttatcact catggttatg    4920
gcagcactgc ataattctct tactgtcatg ccatccgtaa gatgcttttc tgtgactggt    4980
gagtactcaa ccaagtcatt ctgagaatag tgtatgcggc gaccgagttg ctcttgcccg    5040
gcgtcaatac gggataatac cgcgccacat agcagaactt taaaagtgct catcattgga    5100
aaacgttctt cggggcgaaa actctcaagg atcttaccgc tgttgagatc cagttcgatg    5160
taacccactc gtgcacccaa ctgatcttca gcatctttta ctttcaccag cgtttctggg    5220
tgagcaaaaa caggaaggca aaatgccgca aaaaagggaa taagggcgac acggaaatgt    5280
tgaatactca tactcttcct ttttcaatat tattgaagca tttatcaggg ttattgtctc    5340
atgagcggat acatatttga atgtatttag aaaaataaac aataggggt  tccgcgcaca    5400
tttccccgaa aagtgccacc tgacgtc                                        5427
```

<210> SEQ ID NO 6
<211> LENGTH: 4523
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (1203)..(1203)
<223> OTHER INFORMATION: a, c, t, g, unknown or other
<220> FEATURE:
<221> NAME/KEY: misc_feature
<222> LOCATION: (1203)..(1203)
<223> OTHER INFORMATION: n is a, c, g, or t
<220> FEATURE:
<221> NAME/KEY: modified_base
<222> LOCATION: (1224)..(1225)
<223> OTHER INFORMATION: a, c, t, g, unknown or other
<220> FEATURE:
<221> NAME/KEY: misc_feature
<222> LOCATION: (1224)..(1225)
<223> OTHER INFORMATION: n is a, c, g, or t

<400> SEQUENCE: 6

```
gatccggagg ccggagaatt gtaatacgac tcactatagg gagacgcgtg ttaaataaca      60
aatctcaaca caacatatac aaaacaaacg aatctcaagc aatcaagcat tctacttcta     120
ttgcagcaat ttaaatcatt tcttttaaag caaaagcaat tttctgaaaa ttttcaccat     180
ttacgaacga tagccgccac catgcactgg ggaaccctgt gcggattcct gtggctgtgg     240
ccctacctgt tctatgtgca agccgtgccc atccagaagg tgcaggacga caccaagacc     300
ctgatcaaga ccatcgtgac ccggatcaac gacatcagcc acacccagag cgtgtccagc     360
aagcagaaag tgaccggcct ggacttcatc cccggcctgc acctatcct gaccctgtcc      420
aagatggacc agaccctggc cgtgtaccag cagatcctga ccagcatgcc cagccggaac     480
gtgatccaga tcagcaacga cctggaaaac ctgcgggacc tgctgcacgt gctggccttc     540
agcaagagct gccatctgcc ttgggccagc ggcctggaaa ccctggattc tctgggcgga     600
gtgctggaag ccagcggcta ctctacagag gtggtggccc tgagcagact gcagggcagc     660
ctgcaggata tgctgtggca gctggatctg agccccggct gctaatagcg gaccggcgat     720
agatgaagct cgctttcttg ctgtccaatt tctattaaag gttcctttgt tccctaagtc     780
caactactaa actgggggat attatgaagg gccttgagca tctggattct gcctaataaa     840
aaacatttat tttcattgca gctcgctttc ttgctgtcca atttctatta aaggttcctt     900
tgttccctaa gtccaactac taaactgggg gatattatga agggccttga gcatctggat     960
tctgcctaat aaaaaacatt tattttcatt gcggccgcaa aaaaaaaaaa aaaaaaaaa    1020
aaaaaaaaaa aaaaaaaaaa aaaaaaaaaa aaaaaaaaa aaaaaaaaa aaaaaaaaaa    1080
aaaaaaaaaa aaaaaaaaaa aaaaaaaaaa aaaaaaaga agagcaagct tcgatagcg     1140
ctgttcgtag aaaaaaaga agtaaataat tactacttgc catatagact aaatagctgc    1200
gcntaataca tctacacttt ctannattga caagtgatac gttgcaaaag gagcaacacc    1260
ccacagactc gatgactgcg cagtcataca gtgaaattgc cctaatgtct tacctctgaa    1320
agggctaaac gaaagtagag cactattccg cgtagctatt tagtgcgatc ttttagaaat    1380
atcagcccag agagctgggc tgataaatat tttatccgac aagacgaatt ttgctcaaat    1440
gagttaaaac gatgctacca ctatctgctg cttttacgag atcagcccac cattgcatca    1500
tcggacgacg ttgctcaaga taatcactgc ggttataagc gcgacgcacc tcattttgt     1560
ctacatgagc aagcgctgct tcaatgacat caggtggaaa tccttcctca ttgagtgccg    1620
tactggcgat agaacgcaag ccgtgtgaaa caagtacacc tcctaagcca gcacgcttga    1680
gtgctgcatt cactgttggg ctattcattg gttggttggg cttgatacgg ctaggaaaga    1740
taaattctcg gccaccactg agaggcttca tcatttccag aatagcaaga gccccatcag    1800
atagtggaac cgtatggtcc cggttcatct tcattcgagc tgcaggaatt ttccattcgc    1860
tagcattgaa atcgatctca tcccatcgag cctcagcagc ttcggcaggg cgggtgatgg    1920
ttagaagttg ccacatgaac aggcatcttg tggacatgct gatacttgcc gtacgcatgg    1980
tgtgcattag ctgcggaagt tgatccggcc ggatgcttgg catgttttc ttttgcggtt     2040
tctcgaaagc ttgagtattc tatagtgtca cctaaatagc ttggcgtaat catggtcata    2100
gctgtttcct gtgtgaaatt gttatccgct cacaattcca cacaacatac gagccggaag    2160
cataaagtgt aaagcctggg gtgcctaatg agtgagctaa ctcacattaa ttgcgttgcg    2220
ctcactgccc gctttccagt cgggaaacct gtcgtgccag ctgcattaat gaatcggcca    2280
acgcgcgggg agaggcggtt tgcgtattgg gcgctattcc gcttcctcgc tcactgactc    2340
```

```
gctgcgctcg gtcgttcggc tgcggcgagc ggtatcagct cactcaaagg cggtaatacg    2400
gttatccaca gaatcagggg ataacgcagg aaagaacatg tgagcaaaag gccagcaaaa    2460
ggccaggaac cgtaaaaagg ccgcgttgct ggcgtttttc gataggctcc gcccccctga    2520
cgagcatcac aaaaatcgac gctcaagtca gaggtggcga acccgacag  gactataaag    2580
ataccaggcg tttccccctg gaagctccct cgtgcgctct cctgttccga ccctgccgct    2640
taccggatac ctgtccgcct ttctcccttc gggaagcgtg gcgctttctc atagctcacg    2700
ctgtaggtat ctcagttcgg tgtaggtcgt tcgctccaag ctgggctgtg tgcacgaacc    2760
ccccgttcag cccgaccgct gcgccttatc cggtaactat cgtcttgagt ccaacccggt    2820
aagacacgac ttatcgccac tggcagcagc cactggtaac aggattagca gagcgaggta    2880
tgtaggcggt gctacagagt tcttgaagtg gtggcctaac tacggctaca ctagaaggac    2940
agtatttggt atctgcgctc tgctgaagcc agttaccttc ggaaaaagag ttggtagctc    3000
ttgatccggc aaacaaacca ccgctggtag cggtggtttt tttgtttgca agcagcagat    3060
tacgcgcaga aaaaaggat  ctcaagaaga tcctttgatc ttttctacgg ggtctgacgc    3120
tcagtggaac gaaaactcac gttaagggat tttggtcatg agattatcaa aaaggatctt    3180
cacctagatc cttttaaatt aaaaatgaag ttttaaatca atctaaagta tatatgagta    3240
aacttggtct gacagttacc aatgcttaat cagtgaggca cctatctcag cgatctgtct    3300
atttcgttca tccatagttg cctgactccc cgtcgtgtag ataactacga tacgggaggg    3360
cttaccatct ggccccagtg ctgcaatgat accgcgagac ccacgctcac cggctccaga    3420
tttatcagca ataaaccagc cagccggaag ggccgagcgc agaagtggtc ctgcaacttt    3480
atccgcctcc atccagtcta ttaattgttg ccgggaagct agagtaagta gttcgccagt    3540
taatagtttg cgcaacgttg ttggcattgc tacaggcatc gtggtgtcac gctcgtcgtt    3600
tggtatggct tcattcagct ccggttccca acgatcaagg cgagttacat gatccccat    3660
gttgtgcaaa aaagcggtta gctccttcgg tcctccgatc gttgtcagaa gtaagttggc    3720
cgcagtgtta tcactcatgg ttatggcagc actgcataat tctcttactg tcatgccatc    3780
cgtaagatgc ttttctgtga ctggtgagta ctcaaccaag tcattctgag aatagtgtat    3840
gcggcgaccg agttgctctt gcccggcgtc aatacgggat aataccgcgc cacatagcag    3900
aactttaaaa gtgctcatca ttggaaaacg ttcttcgggg cgaaaactct caaggatctt    3960
accgctgttg agatccagtt cgatgtaacc cactcgtgca cccaactgat cttcagcatc    4020
ttttactttc accagcgttt ctgggtgagc aaaaacagga aggcaaaatg ccgcaaaaaa    4080
gggaataagg gcgacacgga aatgttgaat actcatactc ttcctttttc aatattattg    4140
aagcatttat cagggttatt gtctcatgag cggatacata tttgaatgta tttagaaaaa    4200
taaacaaata ggggttccgc gcacatttcc ccgaaaagtg ccacctgacg tctaagaaac    4260
cattattatc atgacattaa cctataaaaa taggcgtatc acgaggccct ttcgtctcgc    4320
gcgtttcggt gatgacggtg aaaacctctg acacatgcag ctcccggaga cggtcacagc    4380
ttgtctgtaa gcggatgccg ggagcagaca gcccgtcag  ggcgcgtcag cgggtgttgg    4440
cgggtgtcgg ggctggctta actatgcggc atcagagcag attgtactga gagtgcacca    4500
taaattcgag ctcggtaccc ggg                                            4523
```

<210> SEQ ID NO 7
<211> LENGTH: 1080
<212> TYPE: RNA
<213> ORGANISM: Artificial Sequence

```
<220> FEATURE:
<223> OTHER INFORMATION: Synthetic oligonucleotide

<400> SEQUENCE: 7
gggagacgcg uguuaaauaa caaaucucaa cacaacauau acaaaacaaa cgaaucucaa      60
gcaaucaagc auucuacuuc uauugcagca auuuaaauca uuucuuuuaa agcaaaagca     120
auuuucugaa aauuuucacc auuuacgaac gauagccgcc accaugcacu ggggaacccu     180
gugcggauuc cuguggcugu ggcccuaccu guucuaugu g caagccgugc ccauccagaa    240
ggugcaggac gacaccaaga cccugaucaa gaccaucgug acccggauca acgacaucag     300
ccacacccag agcguguc ca gcaagcagaa agugaccggc cuggacuuca uccccggccu    360
gcacccuauc cugacccugu ccaagaugga ccagacccug gccguguacc agcagauccu    420
gaccagcaug cccagccgga acgugauc ca gaucagcaac gaccuggaaa accugcggga    480
ccugcugcac gugcuggccu ucagcaagag cugccaucug ccuugggcca gcggccugga    540
aacccuggau ucucugggcg gagugcugga agccagcggc uacucuacag agguggu gg c    600
ccugagcaga cugcagggca gccugcagga uaugcugugg cagcuggauc ugagccccgg    660
cugcuaauag cggaccggcg auagaugaag cucgcuuucu ugcugccaa uuucuauuaa     720
agguuccuuu guccccuaag uccaacuacu aaacggggg auauuaugaa gggccuugag     780
caucuggauu cugccaaaua aaaaacauuu auuuucauug cagcucgcuu ucuugcuguc    840
caauuucuau uaaagguucc uuuguucccu aaguccaacu acuaaacugg gggauauuau    900
gaagggccuu gagcaucugg auucugccua auaaaaaaca uuuauuuuca uugcggccgc    960
aaaaaaaaaa aaaaaaaaaa aaaaaaaaaa aaaaaaaaaa aaaaaaaaaa aaaaaaaaaa   1020
aaaaaaaaaa aaaaaaaaaa aaaaaaaaaa aaaaaaaaaa aaaaaaaaaa aaaaaaaaaa   1080

<210> SEQ ID NO 8
<211> LENGTH: 1128
<212> TYPE: RNA
<213> ORGANISM: Artificial Sequence
<220> FEATURE:
<223> OTHER INFORMATION: Synthetic oligonucleotide

<400> SEQUENCE: 8
gggagacgcg uguuaaauaa caaaucucaa cacaacauau acaaaacaaa cgaaucucaa      60
gcaaucaagc auucuacuuc uauugcagca auuuaaauca uuucuuuuaa agcaaaagca     120
auuuucugaa aauuuucacc auuuacgaac gauagccgcc accaugggcg ugcccgaaag    180
accuacacuc cugcugcugc ugucacugcu gcugauccc u cugggccugc cugugcugug    240
ugccccccu agacugaucu cgacagcag agugcuggaa cgguacaucc uggaagccaa    300
agaggccgag aacgugacga ugggaugug c cgagggcccc agacugagcg agaacaucac    360
cgugcccgac accaaaguga acuucuacgc cuggaagcgg auggaaguggg aagaacaggc    420
caucgaagug uggcagggcc ugagccugcu gagcgaggcu auucugcagg cacaggcucu    480
gcuggccaac agcagccagc cuccugagac acugcagcug cacaucgaca aggccaucag    540
cggccugaga agccugaccu ccccugcugag ggugcuggga gccagaaaag aacugaugag    600
cccccccugac accacccccc cugcuccucu gagaacucug accguggaca ccuucugcaa    660
gcuguuccgg guguacgcca acuucccgcg gggcaagcug aagcuguaca ccggcgaagu    720
gugcagacgg ggcgacagau gaagcucgcu uucuugcugu ccaauuucua uuaaagguuc    780
cuuuguuccc uaaguccaac acuaaacug g gggauauua ugaagggccu ugagcaucug    840
```

| | |
|---|---|
| gauucugccu aauaaaaaac auuuauuuuc auugcagcuc gcuucuugc uguccaauuu | 900 |
| cuauuaaagg uuccuuuguu cccuaagucc aacuacuaaa cuggggaua uuaugaaggg | 960 |
| ccuugagcau cuggauucug ccuaauaaaa aacauuuauu uucauugcaa aaaaaaaaa | 1020 |
| aaaaaaaaaa aaaaaaaaaa aaaaaaaaaa aaaaaaaaaa aaaaaaaaaa aaaaaaaaaa | 1080 |
| aaaaaaaaaa aaaaaaaaaa aaaaaaaaaa aaaaaaaaa aaaaaaa | 1128 |

<210> SEQ ID NO 9
<211> LENGTH: 1962
<212> TYPE: RNA
<213> ORGANISM: Artificial Sequence
<220> FEATURE:
<223> OTHER INFORMATION: Synthetic oligonucleotide

<400> SEQUENCE: 9

| | |
|---|---|
| gggagacgcg uguuaaauaa caaaucucaa cacaacauau acaaaacaaa cgaaucucaa | 60 |
| gcaaucaagc auucuacuuc uauugcagca auuuaaauca uuucuuuuaa agcaaaagca | 120 |
| auuuucugaa aauuuucacc auuuacgaac gauagccgcc accaugcagc gcgugaacau | 180 |
| gauuauggcc gagagcccug ccugaucac caucugccug cugggcuacc ugcugagcgc | 240 |
| cgagugcacc uguuucugg accacgagaa cgccaacaag auccugaacc ggcccaagcg | 300 |
| guacaacagc ggcaagcugg aagaguucgu gcagggcaac cuggaacgcg agugcaugga | 360 |
| agagaagugc agcuucgaag aggccagaga ggguucgag aacaccgagc ggaccaccga | 420 |
| guucuggaag caguacgugg acggcgacca gugcgagagc aaccccuguc ugaauggcgg | 480 |
| cagcugcaag gacgacauca acagcuacga gugcuggugu cccuucggcu ucagggcaa | 540 |
| gaacugcgag cuggacguga ccugcaacau caagaacggc agaugcgagc aguucugcaa | 600 |
| gaacagcgcc gacaacaagg ucgugugcuc cugcaccgag ggcuacagac uggccgagaa | 660 |
| ccagaagucc ugcgagcccg ccgugccuuu cccaugugga agagugugccg uguccagac | 720 |
| cagcaagcug accagagccg agacaguguu ccccgacgug gacuacguga acagcaccga | 780 |
| ggccgagaca auccuggaca acaucaccca gagcacccag uccuucaacg acuucaccag | 840 |
| agucgugggc ggcgaggaug ccaagccugg acaguucccg uggcagguug ucugaacgg | 900 |
| aaaggugac gccuuuugcg gcggcagcau cgugaacgag aaguggaucg ugacagccgc | 960 |
| ccacugcgug gaaaccggcg ugaagauuac aguguggcc ggcgagcaca acaucgagga | 1020 |
| aaccgagcac acagagcaga acggaacgu gaucagaauc uccccacc acaacuacaa | 1080 |
| cgccgccauc aacaaguaca accacgauau cgcccugcug gaacuggacg agccccuggu | 1140 |
| gcugaauagc uacgugaccc ccaucuguau cgccgacaaa gaguacacca acaucuuucu | 1200 |
| gaaguucggc agcggcuacg uguccggcug gggcagagug uuucacaagg cagauccgc | 1260 |
| ucuggugcug caguaccuga gaugccucu gguggaccgg gccaccuguc ugagaagcac | 1320 |
| caaguucacc aucuacaaca caugguucug cgccggcuuu cacgagggcg gcagagauag | 1380 |
| cugucagggc gauucuggcg gcccucacgu gacagaggug gaaggcacca gcuuucugac | 1440 |
| cggcaucauc agcuggggcg aggaaugcgc caugaagggg aaguacggca ucuacaccaa | 1500 |
| ggugccaga uacgugaacu ggaucaaaga aaagaccaag cugacauaau gacgaccgg | 1560 |
| cgauagauga agcucgcuuu cugcugcucc aauuucuauu aaagguuccu uguucccua | 1620 |
| aguccaacua cuaaacuggg ggauauuaug aagggccuug agcaucgga uucugccuaa | 1680 |
| uaaaaaacau uauuuucau ugcagcucgc uuucuugcug uccaauuucu auuaagguu | 1740 |
| ccuuuguucc cuaaguccaa cuacuaaacu ggggauauu augaagggcc uugagcaucu | 1800 |

| | |
|---|---|
| ggauucugcc uaauaaaaaa cauuuauuuu cauugcggcc gcaaaaaaaa aaaaaaaaaa | 1860 |
| aaaaaaaaaa aaaaaaaaaa aaaaaaaaaa aaaaaaaaaa aaaaaaaaaa aaaaaaaaaa | 1920 |
| aaaaaaaaaa aaaaaaaaaa aaaaaaaaaa aaaaaaaaaa aa | 1962 |

<210> SEQ ID NO 10
<211> LENGTH: 2226
<212> TYPE: RNA
<213> ORGANISM: Artificial Sequence
<220> FEATURE:
<223> OTHER INFORMATION: Synthetic oligonucleotide

<400> SEQUENCE: 10

| | |
|---|---|
| gggagacgcg uguuaaauaa caaaucucaa cacaacauau acaaaacaaa cgaaucucaa | 60 |
| gcaaucaagc auucuacuuc uauugcagca auuuaaauca uuucuuuuaa agcaaaagca | 120 |
| auuuucugaa aauuuucacc auuuacgaac gauagccgcc accauggaag acgccaaaaa | 180 |
| cauaaagaaa ggcccggcgc cauucuaucc gcuggaagau ggaaccgcug gagagcaacu | 240 |
| gcauaaggcu augaagagau acgcccuggu uccuggaaca auugcuuuua cagaugcaca | 300 |
| uaucgaggug gacaucacuu acgcugagua cuucgaaaug uccguucggu uggcagaagc | 360 |
| uaugaaacga uaugggcuga auacaaauca cagaaucguc guaugcagug aaaacucucu | 420 |
| ucaauucuuu augccggugu ugggcgcguu auuuaucgga guugcaguug cgcccgcgaa | 480 |
| cgacauuuau aaugaacgug aauugcucaa caguaugggc auuucgcagc uaccguggu | 540 |
| guucguuucc aaaaaggggu ugcaaaaaau uuugaacgug caaaaaaagc ucccaaucau | 600 |
| ccaaaaaauu auuaucaugg auucuaaaac ggauuaccag ggauuucagu cgauguacac | 660 |
| guucgucaca ucucaucuac cucccgguuu aaugaauac gauuuugugc cagaguccuu | 720 |
| cgauagggac aagacaauug cacugaucau gaacccucu ggaucuacug gucugccuaa | 780 |
| agguguucgcu cugccucaua gaacugccug cgugagauuc ucgcaugcca gagauccuau | 840 |
| uuuuggcaau caaaucauuc cggauacgc gauuuuaagu guuguccau uccaucacgg | 900 |
| uuuuggaaug uuuacuacac ucggauauu gauaugugga uucgagucg cuuaaugua | 960 |
| uagauuugaa gaggagcugu uucugaggag ccuucaggau acaagauuc aaagugcgcu | 1020 |
| gcuggugcca acccuauucu ccuucuucgc caaaagcacu cugauugaca aauacgauuu | 1080 |
| aucuaauuua cacgaaauug cuucggugg cgcucccuc ucuaaggaag ucgggggaagc | 1140 |
| gguugccaag agguuccauc ugccagguau caggcaagga uauggcuca cugagacuac | 1200 |
| aucagcuauu cugauuacac ccgaggggga ugauaaaccg ggcgcggucg guaaaguugu | 1260 |
| uccauuuuuu gaagcgaagg uuguggaucu ggauaccggg aaaacgcugg gcguuaauca | 1320 |
| aagaggcgaa cuguguguga gagguccuau gauuaugucc gguuauguaa caauccgga | 1380 |
| agcgaccaac gccuugauug acaaggaugg auggcuacau ucuggagaca uagcuuacug | 1440 |
| ggacgaagac gaacacuucu ucaucguuga ccgccugaag ucucugauua aguacaaagg | 1500 |
| cuaucaggug gcucccgcug aauuggaauc caucuugcuc caacaccccca acaucuucga | 1560 |
| cgcaggguc gcaggucuuc ccgacgauga cgccggugaa cucccgccg cguuguugu | 1620 |
| uuuggagcac ggaaagacga ugacggaaaa agagaucgug gauuacgucg ccagucaagu | 1680 |
| aacaaccgcg aaaaaguugc gcggaggagu uguuugug gacgaaguac cgaaaggucu | 1740 |
| uaccggaaaa cucgacgcaa gaaaaaucag agagauccuc auaaaggcca agaagggcgg | 1800 |
| aaagaucgcc gugugacgga ccggcgauag augaagcucg cuucuuugcu guccaauuuc | 1860 |

| | |
|---|---:|
| uauuaaaggu uccuuuguuc ccuaaguccu acuacuaaac uggggauau uaugaagggc | 1920 |
| cuugagcauc uggauucugc cuaauaaaaa acauuuauuu ucauugcagc ucgcuuucuu | 1980 |
| gcuguccaau uucauuaaa gguuccuuug uucccuaagu ccaacuacua aacuggggga | 2040 |
| uauuaugaag ggccuugagc aucuggauuc ugccuaauaa aaacauuua uuuucauugc | 2100 |
| ggccgcaaaa aaaaaaaaaa aaaaaaaaaa aaaaaaaaaa aaaaaaaaaa aaaaaaaaaa | 2160 |
| aaaaaaaaaa aaaaaaaaaa aaaaaaaaaa aaaaaaaaaa aaaaaaaaaa aaaaaaaaaa | 2220 |
| aaaaaa | 2226 |

<210> SEQ ID NO 11
<211> LENGTH: 1010
<212> TYPE: RNA
<213> ORGANISM: Artificial Sequence
<220> FEATURE:
<223> OTHER INFORMATION: Synthetic oligonucleotide

<400> SEQUENCE: 11

| | |
|---|---:|
| gggagacgcg uguuucugac auccggcgga auucugacau ccggcggaau ucgacauuc | 60 |
| ggcggaauuc ugacauccgg cggaauucug acauccggcg gaagacucac aaccccagaa | 120 |
| acagacagcc accaugggag ucaaaguucu guuugcccug aucugcaucg cuguggccga | 180 |
| ggccaagccc accgagaaca acgaagacuu caacaucgug gccguggcca gcaacuucgc | 240 |
| gaccacggau cucgaugcug accgcgggaa guugcccggc aagaagcugc cgcuggaggu | 300 |
| gcucaaagag auggaagcca augcccggaa agcuggcugc accaggggcu gucugaucug | 360 |
| ccugucccac aucaagugca cgcccaagau gaagaaguuc aucccaggac gcugccacac | 420 |
| cuacgaaggc gacaaagagu ccgcacaggg cggcauaggc gaggcgaucg ucgacauuc | 480 |
| ugagauuccu ggguucaagg acuuggagcc aauggagcag uucaucgcac aggucgaucu | 540 |
| guguguggac ugcacaacug gcugccucaa agggcuugcc aacgucagu guucugaccu | 600 |
| gcucaagaag uggcugccgc aacgcugugc gaccuuugcc agcaagaucc agggccaggu | 660 |
| ggacaagauc aagggggccg guggugacua acggaccgaa aacucaaugu auuucugagg | 720 |
| aagcguggug cauaaugcca cgcagugucu acauaaucaa uuuauuauuu ucuuuuauuu | 780 |
| uauucacaua aaaacucaau guauuucuga ggaagcgugg ugcauaauge cacgcagugu | 840 |
| cuacauaauc aauuuauuau uuucuuuuau uuuauucaca uagcggccgc aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa | 1010 |

<210> SEQ ID NO 12
<211> LENGTH: 250
<212> TYPE: RNA
<213> ORGANISM: Artificial Sequence
<220> FEATURE:
<223> OTHER INFORMATION: Synthetic oligonucleotide

<400> SEQUENCE: 12

| | |
|---|---:|
| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa aaaaaaaaaa aaaaaaaaaa | 120 |
| aaaaaaaaaa aaaaaaaaaa aaaaaaaaaa aaaaaaaaaa aaaaaaaaaa aaaaaaaaaa | 180 |
| aaaaaaaaaa aaaaaaaaaa aaaaaaaaaa aaaaaaaaaa aaaaaaaaaa aaaaaaaaaa | 240 |
| aaaaaaaaaa | 250 |

```
<210> SEQ ID NO 13
<211> LENGTH: 120
<212> TYPE: RNA
<213> ORGANISM: Artificial Sequence
<220> FEATURE:
<223> OTHER INFORMATION: Synthetic oligonucleotide

<400> SEQUENCE: 13
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
```